(12) United States Patent
Wadia et al.

(10) Patent No.: US 11,472,869 B2
(45) Date of Patent: *Oct. 18, 2022

(54) ANTIBODIES AND ANTIGEN-BINDING FRAGMENTS THAT SPECIFICALLY BIND TO MICROTUBULE-ASSOCIATED PROTEIN TAU

(71) Applicant: Janssen Vaccines & Prevention B.V., Leiden (NL)

(72) Inventors: Jehangir Wadia, San Diego, CA (US); Gabriel Pascual, San Diego, CA (US); Robert Anthony Williamson, Leiden (NL); Katarina Radosevic, Nootdorp (NL); Jaap Goudsmit, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,770

(22) Filed: Jul. 17, 2019

(65) Prior Publication Data

US 2020/0399350 A1   Dec. 24, 2020

Related U.S. Application Data

(63) Continuation of application No. 15/321,918, filed as application No. PCT/EP2015/064533 on Jun. 26, 2015, now Pat. No. 10,400,034.

(60) Provisional application No. 62/017,789, filed on Jun. 26, 2014, provisional application No. 62/017,812, filed on Jun. 26, 2014, provisional application No. 62/017,807, filed on Jun. 26, 2014, provisional application No. 62/017,746, filed on Jun. 26, 2014.

(30) Foreign Application Priority Data

Aug. 4, 2014 (EP) .................................. 1417699
Aug. 4, 2014 (EP) .................................. 14178706
Aug. 4, 2014 (EP) .................................. 14179719
Aug. 4, 2014 (EP) .................................. 14179739

(51) Int. Cl.
*C07K 16/18* (2006.01)
*A61K 39/395* (2006.01)
*G01N 33/68* (2006.01)

(52) U.S. Cl.
CPC ............ *C07K 16/18* (2013.01); *A61K 39/395* (2013.01); *G01N 33/6896* (2013.01); *C07K 2317/21* (2013.01); *C07K 2317/24* (2013.01); *C07K 2317/30* (2013.01); *C07K 2317/34* (2013.01); *C07K 2317/52* (2013.01); *C07K 2317/56* (2013.01); *C07K 2317/565* (2013.01); *C07K 2317/567* (2013.01); *C07K 2317/72* (2013.01); *C07K 2317/94* (2013.01); *G01N 2333/47* (2013.01); *G01N 2800/2821* (2013.01)

(58) Field of Classification Search
CPC ................ C07K 16/18; C07K 2317/21; C07K 2317/24; C07K 2317/30; C07K 2317/34; C07K 2317/52; C07K 2317/56; C07K 2317/565; C07K 2317/567; C07K 2317/72; C07K 2317/94
See application file for complete search history.

(56) References Cited

U.S. PATENT DOCUMENTS

| | | |
|---|---|---|
| 5,585,250 A | 12/1996 | Garrity et al. |
| 5,693,762 A | 12/1997 | Queen et al. |
| 5,853,724 A | 12/1998 | Garrity et al. |
| 5,939,598 A | 8/1999 | Kucherlapati |
| 6,531,313 B1 | 3/2003 | Goudsmit et al. |
| 6,881,537 B1 | 4/2005 | Goudsmit et al. |
| 7,238,530 B2 | 7/2007 | Goudsmit et al. |
| 7,425,437 B2 | 9/2008 | UytdeHaag et al. |
| 7,696,330 B2 | 4/2010 | Meulen et al. |
| 8,012,467 B2 | 9/2011 | Havenga et al. |
| 8,101,739 B2 | 1/2012 | Sullivan et al. |
| 8,106,170 B2 | 1/2012 | Ter Meulen et al. |
| 8,241,863 B2 | 8/2012 | Pascual et al. |
| 8,273,867 B2 | 9/2012 | Dowdy et al. |
| 8,568,719 B2 | 10/2013 | Williamson et al. |
| 8,697,352 B2 | 4/2014 | Goudsmit et al. |
| 8,747,856 B2 | 6/2014 | Abadie et al. |
| 9,012,618 B2 | 4/2015 | Sullivan et al. |
| 9,074,262 B2 | 7/2015 | Goudsmit et al. |
| 9,119,813 B2 | 9/2015 | Radosevic et al. |
| 9,125,870 B2 | 9/2015 | Radosevic et al. |
| 9,139,642 B2 | 9/2015 | Williamson et al. |
| 9,168,292 B2 | 10/2015 | Rodriguez-Munoz et al. |

(Continued)

FOREIGN PATENT DOCUMENTS

| | | |
|---|---|---|
| CN | 104080806 A | 10/2014 |
| WO | 9505466 | 2/1995 |

(Continued)

OTHER PUBLICATIONS

Van Cauwenberghe et al. The genetic landscape of Alzheimer disease: clinical implications and perspectives. Genet Med 18, 421-430 (2016).*

(Continued)

*Primary Examiner* — Gregory S Emch
(74) *Attorney, Agent, or Firm* — Kramer & Amado, P.C.

(57) ABSTRACT

The invention relates to antibodies and antigen-binding fragments that specifically bind to microtubule-associated protein tau. The invention also relates to diagnostic, prophylactic and therapeutic methods using anti-tau antibodies.

18 Claims, 21 Drawing Sheets

Specification includes a Sequence Listing.

(56) References Cited

U.S. PATENT DOCUMENTS

| | | | |
|---|---|---|---|
| 9,365,638 | B2 | 6/2016 | Williamson et al. |
| 9,403,900 | B2 | 8/2016 | Williamson et al. |
| 9,452,211 | B2 | 9/2016 | Meijberg et al. |
| 2001/0021518 | A1 | 9/2001 | Goudsmit et al. |
| 2003/0008275 | A1 | 1/2003 | Goudsmit et al. |
| 2003/0170211 | A1 | 9/2003 | Goudsmit et al. |
| 2005/0015819 | A1 | 1/2005 | Jurgen et al. |
| 2005/0019759 | A1 | 1/2005 | Goudsmit et al. |
| 2005/0186222 | A1 | 8/2005 | UytdeHaag et al. |
| 2005/0239118 | A1 | 10/2005 | Goudsmit et al. |
| 2006/0110803 | A1 | 5/2006 | Ter Meulen et al. |
| 2006/0121580 | A1 | 6/2006 | Ter Meulen et al. |
| 2006/0154243 | A1 | 7/2006 | Ter Meulen et al. |
| 2006/0222657 | A1 | 10/2006 | Dowdy et al. |
| 2006/0223056 | A1 | 10/2006 | Goudsmit et al. |
| 2006/0223057 | A1 | 10/2006 | Goudsmit et al. |
| 2006/0228699 | A1 | 10/2006 | Goudsmit et al. |
| 2006/0263802 | A1 | 11/2006 | Bakker et al. |
| 2007/0128217 | A1 | 6/2007 | ter Meulen et al. |
| 2008/0014204 | A1 | 1/2008 | Ter Meulen et al. |
| 2008/0027025 | A1 | 1/2008 | Dowdy et al. |
| 2008/0131461 | A1 | 6/2008 | Pau et al. |
| 2008/0182778 | A1 | 7/2008 | Pascual et al. |
| 2008/0206279 | A9 | 8/2008 | UytdeHaag et al. |
| 2009/0017068 | A1 | 1/2009 | UytdeHaag et al. |
| 2009/0093026 | A1 | 4/2009 | Dowdy et al. |
| 2009/0110695 | A1 | 4/2009 | Havenga et al. |
| 2009/0123438 | A1 | 5/2009 | Havenga et al. |
| 2009/0285879 | A1 | 11/2009 | Pau et al. |
| 2010/0081575 | A1 | 4/2010 | Williamson et al. |
| 2010/0093563 | A1 | 4/2010 | Williamson et al. |
| 2010/0172917 | A1 | 7/2010 | Ter Meulen et al. |
| 2011/0033389 | A1 | 2/2011 | Chen et al. |
| 2011/0076268 | A1 | 3/2011 | Williamson et al. |
| 2011/0189183 | A1 | 8/2011 | Williamson et al. |
| 2011/0256166 | A1 | 10/2011 | Havenga et al. |
| 2011/0281347 | A1 | 11/2011 | Havenga et al. |
| 2012/0014994 | A1 | 1/2012 | Pau et al. |
| 2012/0156239 | A1 | 6/2012 | Sullivan et al. |
| 2012/0165512 | A1 | 6/2012 | Abadie et al. |
| 2013/0122038 | A1 | 5/2013 | Radosevic et al. |
| 2013/0177573 | A1 | 7/2013 | Williamson et al. |
| 2013/0216580 | A1 | 8/2013 | Rodriguez-Munoz et al. |
| 2013/0236494 | A1 | 9/2013 | Radosevic et al. |
| 2014/0017278 | A1 | 1/2014 | Sullivan et al. |
| 2014/0044719 | A1 | 2/2014 | Williamson et al. |
| 2014/0147463 | A1 | 5/2014 | Radosevic et al. |
| 2014/0186391 | A1 | 7/2014 | Radosevic et al. |
| 2014/0199687 | A1 | 7/2014 | Goudsmit et al. |
| 2014/0357845 | A1 | 12/2014 | Meijberg et al. |
| 2014/0363427 | A1 | 12/2014 | Williamson et al. |
| 2015/0196632 | A1 | 7/2015 | Radosevic et al. |
| 2015/0292043 | A1 | 10/2015 | Goudsmit et al. |
| 2015/0320854 | A1 | 11/2015 | Radosevic et al. |
| 2016/0136262 | A1 | 5/2016 | Meijberg et al. |
| 2016/0145321 | A1 | 5/2016 | Wadia et al. |
| 2016/0145322 | A1 | 5/2016 | Wadia et al. |
| 2016/0194383 | A1 | 7/2016 | Williamson et al. |
| 2016/0281162 | A1 | 9/2016 | Dawkins et al. |
| 2016/0355553 | A1 | 12/2016 | Meijberg et al. |

FOREIGN PATENT DOCUMENTS

| | | | |
|---|---|---|---|
| WO | 2009/033743 | A1 | 3/2009 |
| WO | 2010144711 | | 12/2010 |
| WO | 2013041962 | | 3/2013 |
| WO | 2013/050567 | A1 | 4/2013 |
| WO | 2013050567 | | 4/2013 |
| WO | 2014100600 | | 6/2014 |
| WO | 2015197820 | | 12/2015 |
| WO | 2015197823 | | 12/2015 |

OTHER PUBLICATIONS

Abhinandan et al., Mol Immunol, 45:3832-9, 2008.
Almagro J.et al., Mol Recognit, 17:132-43, 2004.
Aluise et al., Biochim. Biophys. Acta. 1782 (2008), 549-558.
Arriagada et al., Neurology. Mar. 1992;42(3 Pt 1 ):631-9.
Asuni AA, et al, J Neurosci. 2007;27(34):9115-9129.
Bancher et al., Neurosci Lett 1993; 162:179-182.
Barghorn et al., 2004, Meth Mol Biol, 35-51.
Boimel M, et al, Exp Neurol. 2010;224(2): 472-485.
Boutajangout A, et al, J Neurochem. 2011;118(4):658-667.
Boutajangout A, et al, J Neurosci. 2010;30(49):16559-16566.
Braak et al., Acta Neuropathol, Berl, 82, 239, 1991.
Braak, H. and Braak, E, Neurobiol Aging. Jul.-Aug. 1997;18(4):351-7.
Cairns et al, Am J Pathol, 2007; 171: 227-40.
Castellani et al, Acta Neuropathol (Berl) 111, 503(2006.
Chai X, et al. J Biol Chem. 2011;286(39):34457-34467.
Chothia et al., Mol Biol, 96:901-17, 1987.
Chou and Talalay (Adv Enzyme Regul., 22:27-55, 1984).
Cragg et al., Blood, 2011, 118 2: pp. 219-220.
De Silva, R. et al, Neuropath and Appl Neurobio (2003) 29(3)288-302.
Drechsel et al., Mol Biol Cell 1992; 3:1141-1154.
Frost et al., J. Biol. Chem. 284 (2009), 12845-12852.
Gendron et al., Mol. Neurodegener, 4:13 , 2009.
Goedert et. al., 1994, Biochem J, 301: pp. 871-877.
Gomez-Isla, et al, Ann Neurol 1997; 41:17-24.
Götz, Brain. Res. Rev. 35 (2001), 266-286.
Hanger, et al. Trends Mol Med 15:112-9, 2009.
Jeganathan et al., Biochemistry 2008; 47:10526-10539.
Jicha, G., 1997, 48(2):128-32.
Spittaels, et al, Am J Pathology 155(6) 2153-2165, 1999.
Khlistunova et al., J. Biol. Chem. 281, 2006, 1205-1214.
Kosik, K. S., et al. (1986) PNAS USA 83, 4044-4048.
Lee et al., Annu. Rev. Neurosci. 24 (2001), 1121-1159.
Lefranc, et al. Dev Camp Immunol27:55-77, 2003.
Mandelkow et al., Cold Spring Harbor, Perspect Med 2, 2012.
Mercken et al, 1992, Acta Neuropatho, 84:265-272.
Nicholson et al.,, J Neurosci 2009; 29:4640-4651.
Oakley et al., Neurosci, 2006, 26(40):10129-10140.
Polydoro et al., J. Neoroscience 2009; 29:10741-10749.
Raj et.al. Neuron 2012; 73:1204-1215.
Rapoport, M, PNAS, 2002; 99:9, 6364-6369.
Reed et al J Neuropathol Exp Neurol. 1998 (6):588-601.
Roberson ED, et al, Science, 2007; 316:750-754.
Rosenmann H, et al. Arch Neurol. 2006;63(10):1459-1467.
Rostagna et al., Protoc Cell Biol. Sep. 2009; Chapter: Unit-3. 3333.
Rubenstein et al., 1986, Brain Res. 372, 80-88.
Seeley et.al. Neuron 2009; 62: 42-52.
Sigurdsson et al., Alzheimer Res. ,2009 ;6(5):446-450.
Small and Duff, Neuron. Nov. 26, 2008;60(4):534-42).
Spillantini et al., Trends Neurosci, 21:428-33, 1998.
Winblad et al., World Alzheimer Report 2010.
Vaccaro et al., 2005.
Zheng et al., J. Cell. Biochem. 109 (2010), 26-29.
Zheng-Fischhofer et al., 1998 Eur J Biochem, 252:542-552.
Zhou et.al., Neuron 2012; 73:1216-1227.
Binder et al., The distribution of Tau in the Mammalian Central Nervous System, The Journal of Cell Biology, Oct. 1, 1985, pp. 1371-1376, vol. 101, The Rockefeller University Press.
Ghoshal et al., Tau Conformational Changes Correspond to Impairments to Episodic Memory in Mild Cognitive Impairment and Alzheimer's Disease, Experimental Neurology, 2002, pp. 475-493, vol. 177, Elsevier Science.
Goedert et al., Monoclonal antibody AT8 recognises tau protein phosphorylated at both serine 202 and threonine 205, Neuroscience Letters, 1995, pp. 167-170, vol. 189, Elsevier Science Ltd.
Gupta et al., A novel human-derived antibody against NY-ESO-1 improves the efficacy of chemotherapy, Cancer Immunity, Jan. 15, 2013, 9 pages, vol. 13, p. 3, Maries van den Broek.
Horowitz et al., Early N-Terminal Changes and Caspase-6 Cleavage of Tau in Alzheimer's Disease, The Journal of Neuroscience, Sep. 8, 2004, pp. 7895-7902, vol. 24, No. 36.

(56) References Cited

OTHER PUBLICATIONS

Mercken et al., Monoclonal antibodies with selective specificity for Alzheimer Tau are directed against phosphatase-sensitive epitopes, Acta Neuropathol, 1992, pp. 265-272, vol. 84, Springer-Verlag.

Nelson et al., Development trends for human monoclonal antibody therapeutics, Nature Reviews, Oct. 2010, pp. 767-774, vol. 9.

PCT International Search Report, dated Dec. 23, 2015, PCT/EP2015/064533.

PCT Written Opinion, dated Dec. 23, 2015, PCT/EP2015/064533.

Porzig et al., Epitope mapping of mAbs AT8 and Tau5 directed against hyperphosphorylated regions of the human tau protein, Biochemical and Biophysical Research Communications, 2007, pp. 644-649, vol. 358, Elsevier Inc.

Van Dijk et al., Human antibodies as next generation therapeutics, Current Opinion in Chemical Biology, 2001, pp. 368-374, vol. 5, Elsevier Science Ltd.

Louis M. Weiner, Fully Human Therapeutic Monoclonal Antibodies, J Immunother, Jan. 2006, pp. 1-9, vol. 29, No. 1.

PCT International Search Report, dated Sep. 21, 2015, PCT/EP2015/064529.

PCT Written Opinion, dated Sep. 21, 2015, PCT/EP2015/064529.

"Japanese Office Action dated Jul. 16, 2019 in JPA 2016-575162", (English Translation provided).

Arai, et al., "Different immunoreactivities of the microtubule-binding region of tau and its molecular basis in brains from patients with Alzheimer's disease, Pick's disease, progressive supranuclear palsy and corticobasal degeneration", Acta Neuopathol. (2003) 105: 489-498.

Kayoko Tomizawa et al., "Tau-tubulin Kinase Phosphorylates Tau at Ser-208 and Ser-210, Sites Found in Paired Helical Filament-tau"; FEBS 24693—FEBS Letters 492, Mar. 2, 2001, pp. 221-227.

* cited by examiner

ANTIBODIES AND ANTIGEN-BINDING FRAGMENTS THAT SPECIFICALLY BIND TO MICROTUBULE-ASSOCIATED PROTEIN TAU

CROSS-REFERENCE TO RELATED APPLICATIONS

This application is a continuation of application Ser. No. 15/321,918, filed on Dec. 23, 2016, which is the national phase entry under 35 U.S.C. § 371 of International Patent Application PCT/EP2015/064533, filed Jun. 26, 2015, designating the United States of America and published in English as International Patent Publication WO 2015/197823 A1 on Dec. 30, 2015, which claims the benefit under Article 8 of the Patent Cooperation Treaty to European Patent Application Serial Nos. 14179739.9, 14179719.1, 14179706.8 and 14179699.5, all filed on Aug. 4, 2014, and under 35 U.S.C. § 119 to U.S. Provisional Patent Application Ser. Nos. 62/017,746, 62/017,807, 62/017,789, and 62/017,812, all filed on Jun. 26, 2014. The entire disclosures of the prior applications are hereby incorporated by reference herein in their entirety.

STATEMENT ACCORDING TO 37 C.F.R. § 1.821(c) OR (e)—SEQUENCE LISTING SUBMITTED AS ASCII TEXT FILE

Pursuant to 37 C.F.R. § 1.821(c) or (e), this application contains a sequence listing, which is contained on an ASCII text file entitled "Sequence Listing" (SYT 3017-CON_Corrected_PatentIn Seq 535_ST25.txt, created Jul. 14, 2020, having a size of 262,774 bytes), which is herein incorporated by reference.

TECHNICAL FIELD

The application relates to medicine. The disclosure, in particular, relates to antibodies and antigen-binding fragments that specifically bind to microtubule-associated protein tau. The disclosure also relates to diagnostic, prophylactic and therapeutic methods using anti-tau antibodies.

BACKGROUND

Dementia is a syndrome that can be caused by a number of progressive disorders that affect memory, thinking, behavior and the ability to perform everyday activities. About 36 million people worldwide are suffering from dementia today. The number of people with dementia is projected to double by 2030, and more than triple to 115.4 million people by 2050. Alzheimer's disease (AD) is the most common type of dementia. Currently, one in nine people age 65 and older (11 percent) and nearly half of those over age 85 have Alzheimer's disease. According to Alzheimer's Disease International, current global costs of caring for these patients exceeds $600 billion annually. These costs are likely to rise even faster than the prevalence of disease, especially in the developing world, as more formal social care systems emerge, and rising incomes lead to higher opportunity costs (B. Winblad and L Jonsson, World Alzheimer Report 2010).

The brains of AD patients have an abundance of two abnormal structures, amyloid plaques and neurofibrillary tangles. This is especially true in certain regions of the brain that are important in memory. There is also a substantial loss of neurons and synapses in the cerebral cortex and certain subcortical regions. Both neurofibrillary tangles and neuronal loss increase in parallel with the duration and severity of illness (T. Gomez-Isla et al., Ann. Neurol. 1997; 41:17-24) and neurofibrillary load has been shown to correlate with cognitive decline (H. Braak and E. Braak, Neurobiol. Aging 1997 July-August; 18(4):351-7).

Neurofibrillary tangles are intraneuronal lesions that are composed of hyperphosphorylated and insoluble accumulations of the microtubule-associated protein, tau. These accumulations are a histopathological feature of many neurodegenerative diseases, which are collectively known as tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD). In human tauopathies, pathology progresses from one brain region to another in disease-specific patterns (H. Braak and E. Braak, Neurobiol. Aging 1997 July-August; 18(4):351-7; Raj et al., Neuron. 2012; 73:1204-1215; Seeley et al., Neuron. 2009; 62:42-52; and Zhou et al. Neuron. 2012; 73:1216-1227), the underlying mechanism of which is not yet clear.

Tau pathology is involved in and may be a cause of many tauopathies. In its normal form, tau is a highly soluble microtubule-associated protein (Jeganathan et al., Biochemistry 2008, 47:10526-10539) that binds and promotes the assembly of microtubules (Drechsel et al., Mol. Biol. Cell. 1992, 3:1141-1154). However, in tauopathies, tau becomes hyperphosphorylated, causing detachment from microtubules, and ultimately accumulation as neurofibrillary tangles that are visualized within dystrophic neurites and cell bodies (Mandelkow and Mandelkow, Cold Spring Harbor, Perspect. Med. 2, 2012: a006247). The amount of tau pathology correlates with progressive neuronal dysfunction, synaptic loss, and functional decline in humans and transgenic mouse models (Arriagada et al., Neurology 1992 March; 42(3 Pt 1):631-9; Bancher et al., Neurosci. Lett. 1993, 162:179-182; Polydoro et al., J. Neuroscience 2009, 29:10741-10749; and Small and Duff, Neuron. 2008 Nov. 26; 60(4):534-42). While there have been no tau mutations observed in Alzheimer's disease, mutations in the tau gene appear to cause some forms of frontotemporal dementia (Cairns et al., Am. J. Pathol. 2007, 171:227-40), presenting with tau-positive inclusions and signifying that tau dysfunction is sufficient to cause neurodegeneration. Moreover, pathological tau appears to be an integral part of AP-induced neurotoxicity in cell culture and transgenic animal models (M. Rapoport, PNAS 2002, 99:9, 6364-6369; E. D. Roberson et al., Science 2007, 316:750-754; A. M. Nicholson and A. Ferreira, J. Neurosci. 2009, 29:4640-4651; H. Oakley, J. Neurosci. 2006, 26(40):10129-10140).

Passive and active immunizations against tau have been analyzed in mice using several different mouse models, including different phospho-tau peptides for active immunizations and anti-tau antibodies for passive immunotherapy (A. A. Asuni et al., J. Neurosci. 2007, 27(34):9115-9129; E. M. Sigurdsson, Curr. Alzheimer Res. 2009, 6(5):446-450; A. Boutajangout et al., J. Neurosci. 2010, 30(49):16559-16566; H. Rosenmann et al., Arch. Neurol. 2006, 63(10):1459-1467; M. Boimel et al., Exp. Neurol. 2010, 224(2):472-485). In the first report describing immunizations with a 30-amino acid phosphorylated tau peptide, an effect on the ratios of soluble and insoluble tau, reduction of tangle formation in the immunized mice, and functional benefits observed in behavior testing for these mice were shown (A. Boutajangout et al., J. Neuroscience 2010, 30:16559-16566). Passive immunization with well-characterized anti-tau antibodies, which react with phosphorylated Ser396 and Ser404 of the hyperphosphorylated tau protein at an early pathologic conformational epitope on tau, confirmed the results seen in active immunization studies. Mice treated with these antibodies showed marked reductions in tau pathology, which was measured by biochemical methods and histology, as well as a significant delay in loss of motor-function decline that was assessed in behavioral testing (A. Boutajangout et al., J. Neurochem. 2011, 118(4):658-667; X. Chai et al., J. Biol. Chem. 2011, 286(39):34457-34467).

Tau-based therapies have only been analyzed in mouse models to date. But in view of the severity of tauopathies in general, and to the cost to society of Alzheimer's disease specifically, there is an ongoing need for effective means to diagnose, monitor, prevent and treat tauopathies.

BRIEF SUMMARY

Provided are antibodies comprising an antigen-binding variable region that binds specifically to tau. Provided in particular, are anti-tau antibodies, and antigen-binding fragments thereof, that detect tau in normal human brain tissue, or detect tau deposits in human Alzheimer's Disease (AD) and Progressive Supranuclear Palsy (PSP) brain tissue. In certain embodiments, the anti-tau antibodies, and antigen-binding fragments thereof, bind to recombinant tau and/or paired helical filament ("PHF")-tau by Western assay.

Further provided are chimeric antibodies comprising an antigen-binding variable region from a naturally occurring human antibody that binds specifically to tau, and a recombinant constant region of a human IgG1, wherein the constant region of the chimeric antibody is different from the naturally occurring antibody.

In certain embodiments, provided are chimeric anti-tau antibodies, and antigen-binding fragments thereof, that detect tau in normal human brain tissue, but do not detect tau deposits in human Alzheimer's Disease (AD) and Progressive Supranuclear Palsy (PSP) brain tissue.

In certain embodiments, the (chimeric) anti-tau antibodies, and antigen-binding fragments thereof, bind to recombinant tau and/or PHF-tau by Western assay. In certain embodiments, the anti-tau antibodies, and antigen-binding fragments thereof, do not bind to recombinant tau or PHF-tau in an ELISA. The antibodies and antigen-binding fragments are preferentially capable of specifically binding to a tau peptide. In some embodiments, the antibodies and antigen-binding fragments are preferentially capable of specifically binding to a tau phospho-peptide but do not bind the peptide when it is not phosphorylated.

In certain embodiments, the anti-tau antibodies are not naturally occurring. Preferably, the antibodies are human.

The antibodies and antigen-binding fragments of the disclosure are useful as diagnostic, prophylactic and/or therapeutic agents, both alone and in combination with other diagnostics, prophylactic and/or therapeutic agents.

In one aspect, the disclosure relates to an anti-tau antibody comprising an antigen-binding site of a heavy chain CDR1 region of SEQ ID NO:163, a heavy chain CDR2 region of SEQ ID NO:164, and a heavy chain CDR3 region of SEQ ID NO:165, a light chain CDR1 region of SEQ ID NO:166, a light chain CDR2 region of SEQ ID NO:167 and a light chain CDR3 region of SEQ ID NO:168.

Another embodiment of the disclosure relates to an anti-tau antibody comprising an antigen-binding site of a heavy chain CDR1 region of SEQ ID NO:169, a heavy chain CDR2 region of SEQ ID NO:170, and a heavy chain CDR3 region of SEQ ID NO:171, a light chain CDR1 region of SEQ ID NO:172, a light chain CDR2 region of SEQ ID NO:173 and a light chain CDR3 region of SEQ ID NO:174.

In one aspect, the disclosure relates to an anti-tau antibody comprising an antigen-binding site of a heavy chain CDR1 region of SEQ ID NO:175, a heavy chain CDR2 region of SEQ ID NO:176, and a heavy chain CDR3 region of SEQ ID NO:177, a light chain CDR1 region of SEQ ID NO:178, a light chain CDR2 region of SEQ ID NO:179 and a light chain CDR3 region of SEQ ID NO:180.

Another embodiment of the disclosure relates to an anti-tau antibody comprising an antigen-binding site of a heavy chain CDR1 region of SEQ ID NO:181, a heavy chain CDR2 region of SEQ ID NO:182, and a heavy chain CDR3 region of SEQ ID NO:183, a light chain CDR1 region of SEQ ID NO:172, a light chain CDR2 region of SEQ ID NO:173 and a light chain CDR3 region of SEQ ID NO:184.

Another embodiment of the disclosure relates to an anti-tau antibody comprising an antigen-binding site of a heavy chain CDR1 region of SEQ ID NO:185, a heavy chain CDR2 region of SEQ ID NO:186, and a heavy chain CDR3 region of SEQ ID NO:187, a light chain CDR1 region of SEQ ID NO:188, a light chain CDR2 region of SEQ ID NO:173 and a light chain CDR3 region of SEQ ID NO:189.

Yet another aspect of the disclosure relates to an anti-tau antibody, comprising an antigen-binding site of a heavy chain CDR1 region of SEQ ID NO:190, a heavy chain CDR2 region of SEQ ID NO:191, and a heavy chain CDR3 region of SEQ ID NO:192, a light chain CDR1 region of SEQ ID NO:193, a light chain CDR2 region of SEQ ID NO:194 and a light chain CDR3 region of SEQ ID NO:195.

Yet another aspect of the disclosure relates to an anti-tau antibody comprising an antigen-binding site of a heavy chain CDR1 region of SEQ ID NO:196, a heavy chain CDR2 region of SEQ ID NO:197, and a heavy chain CDR3 region of SEQ ID NO:198, a light chain CDR1 region of SEQ ID NO:199, a light chain CDR2 region of SEQ ID NO:173 and a light chain CDR3 region of SEQ ID NO:200.

Yet another aspect of the disclosure relates to an anti-tau antibody comprising an antigen-binding site of heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:216, a light chain CDR2 region of SEQ ID NO:173 and a light chain CDR3 region of SEQ ID NO:217.

A further aspect of the disclosure relates to an anti-tau antibody comprising an antigen-binding site of a heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:218, a light chain CDR2 region of SEQ ID NO:174 and a light chain CDR3 region of SEQ ID NO:217.

A further aspect of the disclosure relates to an anti-tau antibody comprising an antigen-binding site of a heavy chain CDR1 region of SEQ ID NO:219, a heavy chain CDR2 region of SEQ ID NO:220, and a heavy chain CDR3 region of SEQ ID NO:221, a light chain CDR1 region of SEQ ID NO:218, a light chain CDR2 region of SEQ ID NO:173 and a light chain CDR3 region of SEQ ID NO:217.

The disclosure further relates to antigen-binding fragments of the above antibodies.

In another aspect, the disclosure relates to an anti-tau antibody comprising an antigen-binding site of a heavy chain variable region (VH) of SEQ ID NOS:87, 91, 95, 99, 103, 107, 111, 123, 127 or 131, and an antigen-binding site of a light chain variable region (VL) of SEQ ID NOS:88, 92, 96, 100, 104, 108, 112, 124, 128 or 132, and to antigen-binding fragments thereof.

In a further aspect, the disclosure relates to an anti-tau antibody comprising a heavy chain variable region comprising the amino acid sequence of SEQ ID NO:87 and a light chain variable region comprising an amino acid sequence of SEQ ID NO:88 and to antigen-binding fragments thereof. In a further aspect, the disclosure relates to an anti-tau antibody comprising a heavy chain variable region comprising the amino acid sequence of SEQ ID NO:91 and a light chain variable region comprising an amino acid sequence of SEQ ID NO:92 and to antigen-binding fragments thereof. In a further aspect, the disclosure relates to an anti-tau antibody comprising a heavy chain variable region comprising the amino acid sequence of SEQ ID NO:95 and a light chain variable region comprising an amino acid sequence of SEQ ID NO:96 and to antigen-binding fragments thereof. In a further aspect, the disclosure relates to an anti-tau antibody comprising a heavy chain variable region comprising the amino acid sequence of SEQ ID NO:99 and a light chain variable region comprising an amino acid sequence of SEQ ID NO:100 and to antigen-binding fragments thereof. In a further aspect, the disclosure relates to an anti-tau antibody comprising a heavy chain variable region comprising the amino acid sequence of SEQ ID NO:103 and a light chain variable region comprising an amino acid sequence of SEQ ID NO:104 and to antigen-binding fragments thereof. In a further aspect, the disclosure relates to an anti-tau antibody comprising a heavy chain variable region comprising the amino acid sequence of SEQ ID NO:107 and a light chain variable region comprising an amino acid sequence of SEQ ID NO:108 and to antigen-binding fragments thereof. In a further aspect, the disclosure relates to an anti-tau antibody comprising a heavy chain variable region comprising the amino acid sequence of SEQ ID NO:111 and a light chain variable region comprising an amino acid sequence of SEQ ID NO:112 and to antigen-binding fragments thereof. In a further aspect, the disclosure relates to an anti-tau antibody comprising a heavy chain variable region comprising the amino acid sequence of SEQ ID NO:123 and a light chain variable region comprising an amino acid sequence of SEQ ID NO:124 and to antigen-binding fragments thereof. In a further aspect, the disclosure relates to an anti-tau antibody comprising a heavy chain variable region comprising the amino acid sequence of SEQ ID NO:127 and a light chain variable region comprising an amino acid sequence of SEQ ID NO:128 and to antigen-binding fragments thereof. In a further aspect, the disclosure relates to an anti-tau antibody comprising a heavy chain variable region comprising the amino acid sequence of SEQ ID NO:131 and a light chain variable region comprising an amino acid sequence of SEQ ID NO:132 and to antigen-binding fragments thereof.

In one embodiment, the IgG1 heavy chain constant region is comprised of the amino acid sequence of SEQ ID NO:83. In another embodiment, the IgG1 light chain constant region is comprised of the amino acid sequence of SEQ ID NO:84.

The disclosure also provides nucleic acid molecules encoding the antibodies or antigen-binding fragments thereof. Another aspect of the disclosure is a vector comprising the nucleic acid molecules of the disclosure. A further feature of the disclosure is a host cell comprising the vector of the disclosure.

The disclosure also provides a method of producing an anti-tau antibody comprising culturing the host cell of the disclosure and recovering the antibody produced by the host cell.

The disclosure further provides for functional variants of the antibodies and immunoconjugates comprising the antibody and/or antigen-binding fragment thereof The disclosure further provides compositions and kits that comprise one or more antibodies of the disclosure and/or antigen-binding fragments thereof. The disclosure additionally provides diagnostic, prophylactic and therapeutic methods that employ the anti-tau antibodies. Prophylactic and therapeutic methods include administering to human subjects the anti-tau antibodies and/or antigen-binding fragments thereof for the prevention or treatment of a tauopathy and/or tau-mediated diseases or conditions, and/or amelioration of one or more symptoms of a tauopathy. Combinations of a plurality of different anti-tau antibodies and/or antigen-binding fragments thereof and/or with other anti-tau antibodies can be used for combination therapy. Compositions comprising the anti-tau antibodies and/or antigen-binding fragments thereof in combination with other prophylactic or therapeutic agents are also provided.

In some embodiments, the antibodies of the disclosure are unique in that the variable regions are recovered from anti-tau-specific memory B-cells from healthy individuals and detect tau deposits in human Alzheimer's brain, but do not detect tau in normal human brain, and are phospho-dependent and bind to tau peptide ptau 194-212 (SEQ ID NO:315) or ptau 200-217 (SEQ ID NO:319) or ptau 59-78 (SEQ ID NO:323) or ptau 406429 (SEQ ID NO:326). In other embodiments, the antibodies are unique in that the variable regions are recovered from anti-tau-specific memory B-cells from healthy individuals and detect tau deposits in human Alzheimer's brain, and detect tau in normal (i.e., healthy) human brain and are predominantly phospho-independent and bind to tau peptide tau 204-221 (SEQ ID NO:318) or tau 221-253 (SEQ ID NO:367). In still other embodiments, the antibodies of the disclosure are unique in that the variable regions are recovered from anti-tau-specific memory B-cells from individuals with Alzheimer's disease and are phospho-dependent and bind to phosphorylated tau peptide ptau 406429 (SEQ ID NO:326) and do not bind to unphosphorylated tau peptide tau 389-441 (SEQ ID NO:327).

BRIEF DESCRIPTION OF THE DRAWINGS

FIGS. 5A and 5B show the immunostaining of CBTAU-7.1, 8.1, 16.1, 18.1, 20.1, 22.1, 24.1, 27.1, and 28.1 on non-AD versus AD hippocampal and cortical tissue sections, respectively. FIG. 5C shows the immunostaining of CBTAU-7.1, 8.1, 16.1, 18.1, 20.1, 22.1, and 24.1 on non-PSP and PSP cortical tissue sections. FIG. 5D shows the immunostaining of CBTAU43.1, 46.1, 47.2, and 49.1 against non-AD and AD cortical tissue sections.

DETAILED DESCRIPTION OF THE INVENTION

Definitions

Figure 1A:
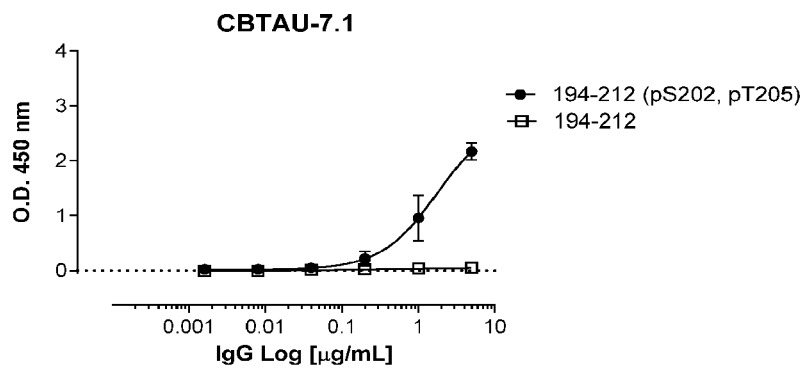
FIGS. 1A-1T show the reactivity of CBTAU-7.1, 8.1, 16.1, 18.1, 20.1, 22.1, 24.1, 27.1, 28.1, 41.1, 41.2, 42.1, 43.1, 44.1, 45.1, 46.1, 47.1, 47.2, and 49.1 against corresponding cognate and non-cognate peptide.
Figure 1B:
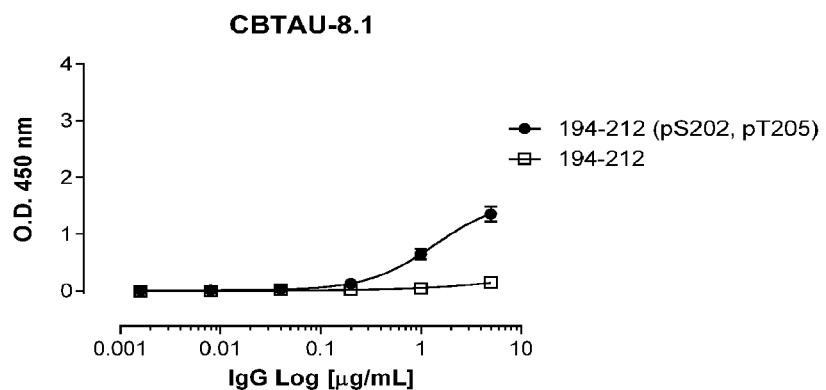
Figure 1C:
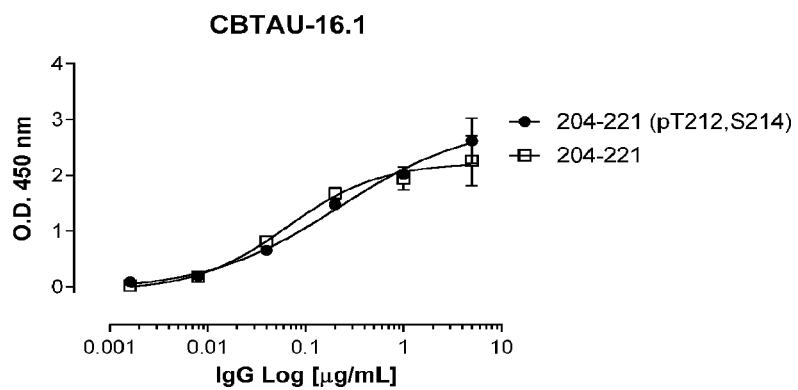
Figure 1D:
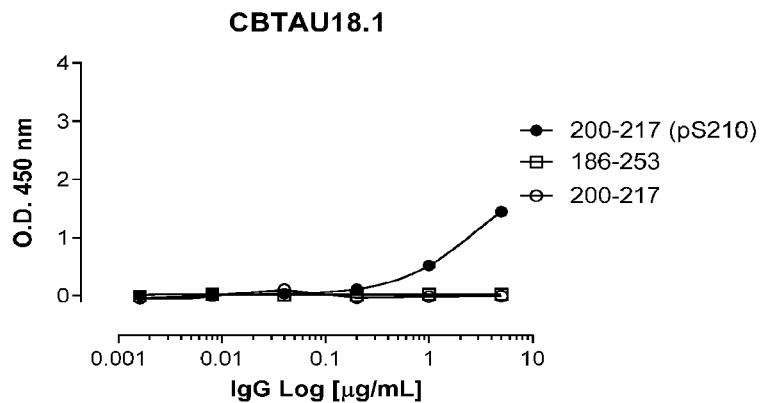
Figure 1E:
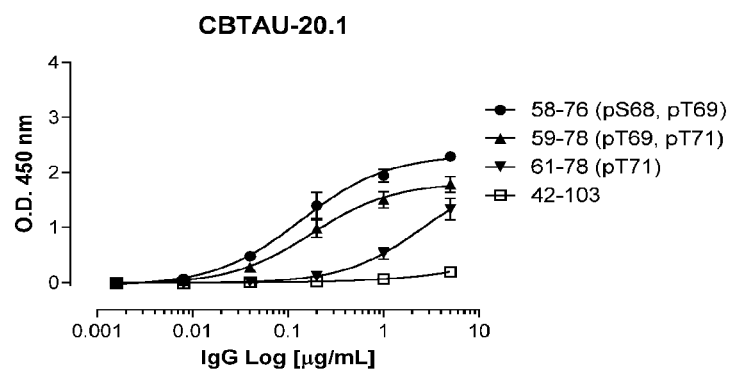
Figure 1F:
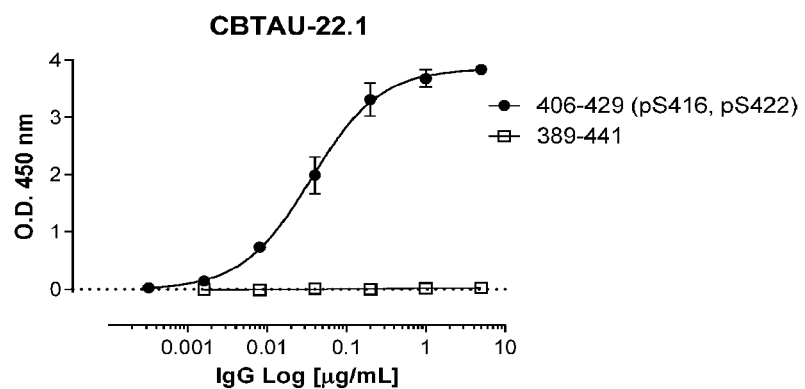
Figure 1G:
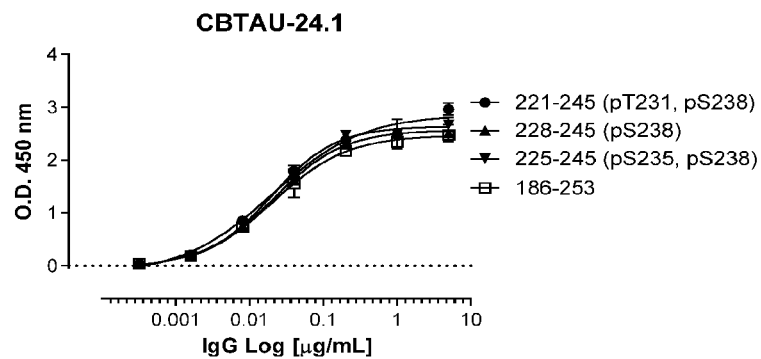

The term "included" or "including" as used herein is deemed to be followed by the words "without limitation."

The term "tau" as used herein, is used interchangeably to specifically refer to the native monomer form of tau. The term "tau" is also used to generally identify other conformers of tau, for example, oligomers or aggregates of tau. The term "tau" is also used to refer collectively to all types and forms of tau. Due to alternative splicing, six tau isoforms are present in the human brain. These isoforms differ by the absence or presence of one or two 29-amino acid inserts encoded by exon 2 and 3 in the amino-terminal part, in combination with either three (R1, R3 and R4) or four (R1-R4) repeat-regions in the carboxy-terminal part. The microtubule-binding domain is encoded by exon 10. The adult tau isoforms include the longest 441-amino acid component (SEQ ID NO:1), or 4R/2N, the 410-amino acids component (SEQ ID NO:2), or 3R/2N, the 412-amino acids component (SEQ ID NO:3), or 4R/1N, the 381-amino acids component (SEQ ID NO:4), or 3R/1N and the 383-amino acids component (SEQ ID NO:5) or 4R/0N. The shortest 352-amino acids isoform (SEQ ID NO:6), or 3R/0N, is found in the fetal brain, and thus is referred to as fetal tau isoform.

The "wild type" tau amino acid sequence is represented by the 441 amino acid isoform (SEQ ID NO:1) also referred to as "tau441," "4R/2N," "hTau40," "TauF," "Tau-4" or "full-length tau."

The term "recombinant tau" herein, refers to the longest isoform of human brain Tau (SEQ ID NO:1) expressed in *E. coli* and purified to homogeneity or near homogeneity (S. Barghorn, Meth. Mol. Biol. 2004 299:35-51). Recombinant tau is soluble and is not phosphorylated.

The term "neurofibrillary tangle" (NFT) refers to the pathological structures first described by Alzheimer in the brain of dementia patients. NFT are composed of orderly arranged subunits called paired helical filament aggregates of hyperphosphorylated tau protein that are most commonly known as a primary marker of Alzheimer's Disease.

The term "paired helical filament-tau" or "PHF-tau" as used herein refers to well-known tau aggregates that make up the pathological structures called neurofibrillary tangles (NFT), first described by Alzheimer in the brain of dementia patients. Their presence is also found in numerous other diseases known as tauopathies.

"Enriched PHF-tau" or "ePHF-tau," is prepared according to the protocol of Greenberg and Davies as detailed in the Examples. PHF-tau is enriched from 27,200×g supernatants containing 0.8 M NaCl by taking advantage of their insolubility in zwitterionic detergents (K. S. Kosik et al. (1986) PNAS USA 83:4044-4048; R. Rubenstein et al. (1986) Brain Res. 372:80-88) and mercaptoethanol. PHFs isolated with zwitterionic detergents appear to maintain antigenic sites that may be lost during the isolation of SDS-insoluble NeuroFibular Tangles and are similar in structure and contain many antigenic properties to PHF in NFTs. "Immunopurified PHF-tau" or "iPHF-tau" is affinity purified with an anti-tau monoclonal antibody. Such protocols have provided PHF-tau preparations that retain the classical paired helical filament structure by electron microscopy and are completely soluble in low concentrations of SDS (G. Jicha, 1997, 48(2):128-32). PHF-tau is also formed from recombinant tau by induction of polymerization in vitro with heparin (Mandelkow, et al., Methods in Molecular Biology 299:35-51(2004). Alternatively, PHF-tau is isolated by various other methods from brains of patients having AD using protocols, such as described in Rostagna and Ghiso (A. Rostagna and J. Ghiso, Curr. Protoc. Cell. Biol. September 2009; CHAPTER: Unit-3.3333). The isolated PHF-tau is characterized for its purity and hyperphosphorylation status with antibodies known to react with PHF-tau. In a typical PHF-tau preparation, the hyperphosphorylated bands migrating at about 60, 64, 68 and 72 kDa in Western blot (Spillantini and Goedert, Trends Neurosci. 21:428-33, 1998) are detected by an AT8 antibody that specifically binds hyperphosphorylated PHF-tau but not dephosphorylated PHF-tau.

The term "antibodies" as used herein is meant in a broad sense and includes immunoglobulin or antibody molecules including polyclonal antibodies, monoclonal antibodies including murine, human, human-adapted, humanized and chimeric monoclonal antibodies, bispecific or multi-specific antibodies and antibody fragments. In general, antibodies are proteins or peptide chains that exhibit binding specificity to a defined antigen. Antibody structures are well known. Immunoglobulins can be assigned to five major classes, namely IgA, IgD, IgE, IgG and IgM, depending on the heavy chain constant domain amino acid sequence. IgA and IgG are further sub-classified as the isotypes IgA1, IgA2, IgG1, IgG2, IgG3 and IgG4. Antibody light chains of any vertebrate species can be assigned to one of two clearly distinct types, namely kappa (K) and lambda (X), based on the amino acid sequences of their constant domains.

The term "antigen-binding fragments" means a portion of an intact antibody. Examples of antibody fragments include Fab, Fab', F(ab')2 and Fv fragments, CDR, antigen-binding site, heavy or light chain variable region, diabodies, triabodies single chain antibody molecules (scFv) and multi-specific antibodies formed from at least two intact antibodies or fragments thereof or (poly) peptides that contain at least a fragment of an immunoglobin that is sufficient to confer antigen binding to the (poly) peptide, etc. An antigen-binding fragment may comprise a peptide or polypeptide comprising an amino acid sequence of at least 2, 5, 10, 15, 20, 25, 30, 35, 40, 50, 60, 70, 80, 90, 100, 125, 150, 175, 200, or 250 contiguous amino acid residues of the amino acid sequence of the antibody. The antigen-binding fragments may be produced synthetically or by enzymatic or chemical cleavage of intact immunoglobulins or they may be genetically engineered by recombinant DNA techniques.

The methods of production are well known in the art and are described, for example, in Antibodies: A Laboratory Manual, edited by E. Harlow and D. Lane (1988), Cold Spring Harbor Laboratory, Cold Spring Harbor, N.Y., which is incorporated herein by reference. An antibody or antigen-binding fragment thereof may have one or more binding sites. If there is more than one binding site, the binding sites may be identical to one another or they may be different.

An immunoglobulin light or heavy chain variable region consists of a "framework" region interrupted by "antigen-binding sites." The antigen-binding sites are defined using various terms as follows: (i) Complementarity-Determining Regions (CDRs) are based on sequence variability (Wu and Kabat, J. Exp. Med. 132:211-50, 1970). Generally, the antigen-binding site has three CDRs in each variable region (HCDR1, HCDR2 and HCDR3 in heavy chain variable region (VH) and LCDR1, LCDR2 and LCDR3 in light chain variable region (VL)) (Kabat et al., Sequences of Proteins of Immunological Interest, 5th Ed. Public Health Service, National Institute of Health, Bethesda, Md., 1991). (ii) The term "hypervariable region," "HVR," or "HV" refers to the regions of an antibody variable domain that are hypervariable in structure as defined by Chothia and Lesk (Chothia and Lesk, J. Mol. Biol. 96:901-17, 1987). Generally, the antigen-binding site has three hypervariable regions in each VH (H1, H2, H3) and VL (L1, L2, L3). Chothia and Lesk refer to structurally conserved HVs as "canonical structures." Numbering systems as well as annotation of CDRs and HVs have recently been revised by Abhinandan and Martin (Abhinandan and Martin, Mol. Immunol. 45:3832-9, 2008). (iii) Another definition of the regions that form the antigen-binding site has been proposed by Lefranc (Lefranc, et al., Dev. Camp. Immunol. 27:55-77, 2003) based on the comparison of V domains from immunoglobulins and T-cell receptors. The International ImMunoGeneTics (IMGT) database (http:_//www_imgt_org) provides a standardized numbering and definition of these regions. The correspondence between CDRs, HVs and IMGT delineations is described in Lefranc et al. The antigen-binding site can also be delineated based on Specificity-Determining Residue Usage (SDRU) (Almagro, J. Mol. Recognit. 17:13243, 2004), where Specificity-Determining Residues (SDR), refers to amino acid residues of an immunoglobulin that are directly involved in antigen contact.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody or antigen-binding fragment, variant, or derivative thereof of the present disclosure are according to the Kabat numbering system, which, however, is theoretical and may not equally apply every antibody of the present disclosure. For example, depending on the position of the first CDR, the following CDRs might be shifted in either direction.

"Framework" or "framework sequence" are the remaining sequences within the variable region of an antibody other than those defined to be antigen-binding site sequences. Because the exact definition of an antigen-binding site can be determined by various delineations as described above, the exact framework sequence depends on the definition of the antigen-binding site.

The term "monoclonal antibody" (mAb) as used herein means an antibody (or antibody fragment) obtained from a population of substantially homogeneous antibodies. Monoclonal antibodies are highly specific, typically being directed against a single antigenic determinant.

In one aspect, the antibody of the present disclosure is a chimeric human antibody. Thus, in accordance with the present disclosure, the terms "human chimeric antibody" or "human recombinant antibody" and the like are used to denote a binding molecule, which antigen-binding features originated from a human cell, i.e., which antigen-binding site is derived from nucleic acids produced from a human cell such as a B cell, or the partial cDNA of which has been cloned from mRNA of a human cell, for example, a human memory B cell. A chimeric antibody is still "human" even if amino acid substitutions are made in the antibody, e.g., to improve biophysical or pharmacokinetic characteristics. Compared to artificially generated human-like antibodies such as single chain antibody fragments (scFvs) from a phage displayed antibody library or xenogeneic mice, the chimeric human antibody of the present disclosure is characterized by (i) the antigen-binding region being obtained using the human immune response rather than that of animal surrogates, i.e., the antigen-binding region has been generated in response to natural tau in its relevant conformation in the human body, and/or (ii) having protected the individual or is at least significant for the presence of tau.

Antibodies originating from human immunoglobulin libraries or from animals transgenic for one or more human immunoglobulins and that do not express endogenous immunoglobulins, as described infra and, for example, in, U.S. Pat. No. 5,939,598 by Kucherlapati et al., are denoted human-like antibodies in order to distinguish them from human-derived antibodies of the present disclosure.

For example, the pairing of heavy and light chains of human-like antibodies such as synthetic and semi-synthetic antibodies typically isolated from phage display do not necessarily reflect the original paring as it occurred in the original human B cell. Accordingly, Fab and scFv fragments obtained from recombinant expression libraries as commonly used in the prior art can be considered as being artificial with all possible associated effects on immunogenicity and stability. In contrast, the present disclosure provides antigen-binding regions of affinity-matured anti-tau antibodies from selected human subjects, which, in certain embodiments, are recombinantly expressed as chimeras with a common IgG1 constant region.

The term "functional variant," as used herein, refers to an antibody that comprises a nucleotide and/or amino acid sequence that is altered by one or more nucleotides and/or amino acids compared to the nucleotide and/or amino acid sequences of a reference antibody and that is capable of competing for specific binding to the binding partner, i.e., tau, with the reference antibody. In other words, the modifications in the amino acid and/or nucleotide sequence of the reference antibody do not significantly affect or alter the binding characteristics of the antibody encoded by the nucleotide sequence or containing the amino acid sequence, i.e., the antibody is still able to specifically recognize and bind its target. The functional variant may have conservative sequence modifications including nucleotide and amino acid substitutions, additions and deletions. Examples of functional variants include de-risking a free Cysteine or amino acid with potential post-translational modification in the hypervariable region, as well as Fc engineering to increase/decrease the binding affinity of IgG antibodies to FcRn, and increase/decrease serum half-life. A functional variant can also be generation of the antibody as a human chimeric or non-chimeric IgG2, IgG3 or IgG4 isotype, or as a chimeric or non-chimeric isotype of a different species. A functional variant can also be a mutation or mutations of the constant regions for enhancement of bispecific antibody formation. These modifications can be introduced by standard techniques known in the art, such as PCR, site-directed mutagenesis and random PCR-mediated mutagenesis, and may comprise natural as well as non-natural nucleotides and amino acids.

The term "specifically binding" or "specifically recognize," as used herein, in reference to the interaction of an antibody and its binding partner, e.g., an antigen, means that the interaction is dependent upon the presence of a particular amino acid sequence or structure, e.g., an antigenic determinant or epitope, on the binding partner. In other words, the antibody preferentially binds or recognizes the binding partner, even when the binding partner is present in a mixture of other molecules or organisms. The binding may be mediated by covalent or noncovalent interactions or a combination of both. In yet other words, the term "specifically binding" or "specifically recognizes" means that the antibody is specifically immunoreactive with an antigenic determinant or epitope and is not immunoreactive with other antigenic determinants or epitopes. An antibody that (immuno)specifically binds to an antigen may bind to other peptides or polypeptides with lower affinity as determined by, e.g., radioimmunoassays (MA), enzyme-linked immunosorbent assays (ELISA), BIACORE, or other assays known in the art. Antibodies or fragments thereof that specifically bind to an antigen may be cross-reactive with related antigens, carrying the same epitope. Preferably, antibodies or fragments thereof that specifically bind to an antigen do not cross-react with other antigens.

The term "epitope" as used herein means that part of the antigen that is contacted by the CDR loops of antibody. A "structural epitope" comprises about 15-22 contact residues on the antigen surface and involves many amino acid residues that make contact with a large group of residues on CDRs collectively referred to as the paratope of antibody. Direct contact between epitope and paratope residues is established through electrostatic forces such as hydrogen bonds, salt bridges, van der Waals forces of hydrophobic surfaces and shape complementarity. The interface has also bound water molecules or other co-factors that contribute to the specificity and affinity of antigen-antibody interactions. The binding energy of an antigen-antibody complex is primarily mediated by a small subset of contact residues in the epitope-paratope interface. These "energetic residues" are often located in the center of the epitope-paratope interface and make up the functional epitope. Contact residues in the periphery of the interface make generally minor contributions to the binding energy; their replacements have frequently little effect on the binding with antigen. Thus, the binding or functional activity of an epitope involves a small subset of energetic residues centrally located in the structural epitope and contacted by the specificity-determining CDRs. The assignment of a functional epitope on an antigenic protein can be made using several methods including Alanine scan mutagenesis or by solving the crystal structure of the antigen with the antibody.

An epitope can be linear in nature or can be a discontinuous epitope, e.g., a conformational epitope, which is formed by a spatial relationship between non-contiguous amino acids of an antigen rather than a linear series of amino acids. A conformational epitope includes epitopes resulting from folding of an antigen, where amino acids from differing portions of the linear sequence of the antigen come in close proximity in three-dimensional space. For discontinuous epitopes, it may be possible to obtain binding of one or more linear peptides with decreased affinity to a so-called partial epitope, e.g., dispersed at different regions of the protein sequence (M. S. Cragg, (2011) Blood 118 (2):219-20).

As used herein, the term "affinity" refers to a measure of the strength of the binding of an individual epitope or partial epitope with the CDRs of a binding molecule, e.g., an immunoglobulin molecule; see, e.g., Harlow et al., Antibodies: A Laboratory Manual, Cold Spring Harbor Laboratory Press, 2nd ed. (1988) at pages 27-28. As used herein, the term "avidity" refers to the overall stability of the complex between a population of immunoglobulins and an antigen, that is, the functional combining strength of an immunoglobulin mixture with the antigen; see, e.g., Harlow at pages 29-34. Avidity is related to both the affinity of individual immunoglobulin molecules in the population with specific epitopes, and also the valences of the immunoglobulins and the antigen. For example, the interaction between a bivalent monoclonal antibody and an antigen with a highly repeating epitope structure, such as a polymer, would be one of high avidity. The affinity or avidity of an antibody for an antigen can be determined experimentally using any suitable method; see, for example, Berzofsky et al., "Antibody-Antigen Interactions" in Fundamental Immunology, W. E. Paul, Ed., Raven Press New York, N.Y. (1984); J. Kuby, Immunology, W.H. Freeman and Company New York, N.Y. (1992), and methods described herein. General techniques for measuring the affinity of an antibody for an antigen include ELISA, RIA, and surface plasmon resonance. The measured affinity of a particular antibody-antigen interaction can vary if measured under different conditions, e.g., salt concentration, pH. Thus, measurements of affinity and other antigen-binding parameters, e.g., KD, IC50, are preferably made with standardized solutions of antibody and antigen, and a standardized buffer.

Antibodies or antigen-binding fragments or variants thereof of the disclosure may also be described or specified in terms of their ability to specifically detect the presence of antigen. The term "detect" or "detecting" is used in the broadest sense to include quantitative, semi-quantitative or qualitative measurements of a target molecule. In one aspect, antibodies described herein may only determine the presence or absence of tau polypeptide in a biological sample, e.g., by immunohistochemistry and, thus, the tau polypeptide is detectable or, alternatively, undetectable in the sample as determined by the method.

The term "phospho-specific antibody" or "phospho-dependent antibody" herein used means a specific antibody in which at least part or the entire epitope relies on a phosphorylated amino acid residue. A phospho-specific or phospho-dependent antibody does not detect un-phosphorylated antigen. The term "phospho-selective antibody" means a specific antibody that preferentially binds to the phosphorylated residue and has higher affinity to the phosphorylated versus the non-phosphorylated antigen. The term "non-phospho-selective antibody" or "phospho-independent" means a specific antibody that preferentially binds to the non-phosphorylated residue and has higher affinity to the non-phosphorylated versus the phosphorylated antigen. In certain embodiments, the anti-tau antibodies of the disclosure, or antigen-binding fragments thereof, are phospho-dependent. In certain other embodiments, the anti-tau antibodies of the disclosure, or antigen-binding fragments thereof, are phospho-independent.

The term "polynucleotide" is intended to encompass a singular nucleic acid as well as plural nucleic acids, and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid molecule" refers to any one or more nucleic acid segments, e.g., DNA or RNA fragments, present in a polynucleotide. By "isolated" nucleic acid or polynucleotide is intended a nucleic acid molecule, DNA or RNA that has been removed from its native environment. For example, a recombinant polynucleotide encoding an antibody contained in a vector is considered isolated for the purposes of this disclosure.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example, enhancers, operators, repressors, and transcription termination signals, can be operably associated with the polynucleotide to direct cell-specific transcription. Suitable promoters and other transcription control regions are disclosed herein.

As used herein, the terms "treat" or "treatment" refer to both therapeutic treatment and prophylactic or preventative measures, wherein the object is to prevent or slow down (lessen) an undesired physiological change or disorder, such as the development of Parkinsonism or Alzheimer's Disease. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the manifestation of the condition or disorder is to be prevented. A "medicament" as used herein, is an agent used in the treatment of an undesirable physiological change or disorder.

By "subject" or "individual" or "animal" or "patient" or "mammal" is meant any subject, particularly a mammalian subject, e.g., a human patient, for whom diagnosis, prognosis, prevention, or therapy is desired.

DESCRIPTION

Tau is an abundant central and peripheral nervous system protein having multiple well-known isoforms. In the human CNS, six major tau isoforms ranging in size from 352 to 441 exist due to alternative splicing (Hanger, et al., Trends Mol. Med. 15:112-9, 2009). These isoforms differ from each other by the regulated inclusion of 0-2 N-terminal inserts, and 3 or 4 tandemly arranged microtubule-binding repeats, and are referred to as ON3R (SEQ ID NO:6), 1N3R (SEQ ID NO:4), 2N3R (SEQ ID NO:2), ON4R (SEQ ID NO:5), 1N4R (SEQ ID NO:3) and 2N4R (SEQ ID NO:1). The term "recombinant tau" as used herein refers to the tau isoform of SEQ ID NO:1 that is devoid of phosphorylation and other post-translational modifications. The tau protein can be recombinantly expressed in high quantities, for example, in E. coli, baculovirus, mammalian or cell-free systems. "Recombinant tau" may be recombinantly expressed and purified using standard methods. (Barghorn, et al. 2004, Meth. Mol. Biol. 35-51).

Tau binds microtubules and regulates transport of cargo through cells, a process that can be modulated by tau phosphorylation that occurs at many of the 79 potential serine (Ser) and threonine (Thr) phosphorylation sites. Tau is highly phosphorylated during brain development. The degree of phosphorylation declines in adulthood. Some of the phosphorylation sites are located within the microtubule binding domains of tau, and it has been shown that an increase of tau phosphorylation negatively regulates the binding of microtubules. For example, Ser262 and Ser396, which lie within or adjacent to microtubule binding motifs, are hyperphosphorylated in the tau proteins of the abnormal paired helical filaments (PHFs), a major component of the neurofibrillary tangles (NFTs) in the brain of AD patients. PHFs are filamentous aggregates of tau proteins that are abnormally hyperphosphorylated and can be stained with specific anti-tau antibodies and detected by light microscopy. The same holds true for so-called straight tau filaments. PHFs form twisted ribbons consisting of two filaments twisted around one another with a periodicity of about 80 nm.

These pathological features are commonly referred to as "tau-pathology," "tauopathology" or "tau-related pathology." For a more detailed description of neuropathological features of tauopathies, refer to Le et al., Annu. Rev. Neurosci. 24 (2001), 1121-1159, and Gotz, Brain. Res. Rev. 35 (2001), 266-286, the disclosure content of which is incorporated herein by reference. Physiological tau protein stabilizes microtubules in neurons. Pathological phosphorylation leads to abnormal tau localization and aggregation, which causes destabilization of microtubules and impaired cellular transport. Aggregated tau is neurotoxic in vitro (Khlistunova et al., J. Biol. Chem. 281 (2006), 1205-1214). The exact neurotoxic species remains unclear, however, as do the mechanism(s) by which they lead to neuronal death. Aggregates of tau can be observed as the main component of neurofibrillary tangles (NFT) in many tauopathies, such as Alzheimer's disease (AD), Frontotemporal dementias, supranuclear palsy, Pick's disease, Argyrophilic grain disease (AGD), corticobasal degeneration, FTDP-17, Parkinson's disease, Dementia pugilistica (reviewed in Gendron and Petrucelli, Mol. Neurodegen. 4:13 (2009)). Besides these observations, evidence emerges that tau-mediated neuronal death can occur even in the absence of tangle formation. Soluble phospho-tau species are present in CSF (Aluise et al., Biochim. Biophys. Acta. 1782 (2008), 549-558). Tau aggregates can transmit a misfolded state from the outside to the inside of a cell and transfer between co-cultured cells (Frost et al., J. Biol. Chem. 284 (2009), 12845-12852).

In addition to the involvement in neurodegenerative tauopathies, observed alterations in tau phosphorylation during and after ischemia/reperfusion and after concussive head injury suggest tau plays a crucial role in neuronal damage and clinical pathophysiology of neurovascular disorders such as ischemic stroke (Zheng et al., J. Cell. Biochem. 109 (2010), 26-29), as well as changes in tau found in chronic traumatic encephalopathy, a tauopathy in concussed athletes and military veterans with Traumatic Brain Injury (BI).

This disclosure provides monoclonal antibodies, wherein the antibodies bind tau deposits in human AD brain tissue.

In certain embodiments, the antibodies a) bind tau deposits in human AD brain tissue and b) do not bind tau in normal brain tissue.

In certain embodiments, the antibodies a) bind tau deposits in human AD brain tissue, b) do not bind tau in normal human brain tissue, and c) do not bind tau deposits in Progressive Supranuclear Palsy (PSP) brain tissue.

In certain embodiments, the antibodies a) form an immunological complex with tau deposits in human AD brain tissue and b) do not form an immunological complex with tau in normal human brain tissue.

In certain embodiments, the antibodies are chimeric antibodies.

In certain embodiments, the antibodies are chimeric antibodies comprising an antigen-binding variable region from a human antibody that binds specifically to tau and a recombinant constant region of a human IgG1, and wherein the chimeric antibodies are different from the human antibody.

In certain embodiments, the antibodies are chimeric antibodies comprising an antigen-binding variable region from a human antibody that binds specifically to tau and a recombinant constant region of a human IgG1, wherein the constant region of the chimeric antibody differs from the constant region of the human antibody.

In certain embodiments, the antibodies are chimeric antibodies comprising a naturally occurring human antigen-binding variable region that binds specifically to tau and a recombinant constant region of a human IgG1 antibody.

In certain embodiments, the antibodies are chimeric antibodies comprising naturally occurring human light and heavy chain variable regions from a human antibody and recombinant human IgG1 heavy and light chain constant regions.

In certain embodiments, the antibodies are chimeric antibodies comprising heavy and light chain variable regions from a naturally occurring human antibody and recombinant human IgG1 heavy and light chain constant regions.

In certain embodiments, the antibodies are chimeric antibodies comprising heavy and light chain variable regions from a human antibody and recombinant human IgG1 heavy and light chain constant regions.

In certain embodiments, the antibodies are not naturally occurring.

The human anti-tau antibodies disclosed herein specifically bind tau and epitopes thereof and to various conformations of tau and epitopes thereof. For example, disclosed herein are antibodies that specifically bind pathologically modified tau isoforms and tau aggregates. In one example, a tau antibody disclosed herein binds to tau or an epitope thereof and shows no binding above about three times background for other proteins. An antibody that "specifically binds" or "selectively binds" a tau conformer refers to an antibody that does not bind all conformations of tau, i.e., does not bind at least one other tau conformer such as recombinant tau.

The variable domains of the chimeric anti-tau monoclonal antibodies of this disclosure may have origin from a pool of healthy human subjects exhibiting a tau-specific immune response or from subject affected with Alzheimer's Disease. The tau antibodies of this disclosure may also be called "human-derived antibodies" in order to emphasize that those antibody antigen-binding regions were indeed expressed by the subjects and have not been isolated from, for example, a human immunoglobulin-expressing phage library, which hitherto represented one common method for trying to provide human-like antibodies. For example, the antibodies of this disclosure differ from mAb AT8, MC1, and AT100, in that they are human-derived antibodies.

The anti-tau antibodies of this disclosure can be characterized by their binding properties to recombinant tau in an ELISA. Recombinant tau purified from *E. coli* is highly soluble owing to its hydrophilic character. It lacks phosphorylation of Ser, Thr and Tyr residues characteristic of tau found in tauopathies. In one embodiment of the disclosure, the anti-tau monoclonal antibodies disclosed herein do not specifically bind recombinant tau in an ELISA. In another embodiment of the disclosure, the anti-tau monoclonal antibodies bind to recombinant tau in an ELISA.

In an embodiment, the anti-tau antibody of the disclosure has been shown to specifically bind to a phosphorylated-tau peptide of SEQ ID NO:315 or SEQ ID NO:365. In another embodiment, the anti-tau antibody of the disclosure has been shown to bind to both phosphorylated tau peptide of SEQ ID NO:317 and non-phosphorylated peptide of tau SEQ ID NO:318 or phosphorylated peptide of SEQ ID NO:329 and non-phosphorylated tau peptide of SEQ ID NO:367.

The anti-tau antibodies disclosed herein in certain embodiments specifically bind tau peptide in a peptide ELISA. In one embodiment, an anti-tau antibody binds to a tau peptide, e.g., GTPGSRSRTPSLPTPPTR (SEQ ID NO:318), corresponding to amino acids 204-221 of tau441. In another embodiment, an anti-tau antibody binds to a tau peptide, e.g., GEPPK SGDRSGYS SP GSP GTP GSRSRTP SLP TPPTREPKKVAVVRTPPK SP S SAKSRLQTAPVP MPDL (SEQ ID NO:367), corresponding to amino acids 221-253 of tau441. The anti-tau antibody of the disclosure is unlike previously disclosed human anti-tau monoclonal antibodies (US 2013/0295021), which have been reported to bind to different tau peptides. Monoclonal antibodies NI-105.4E4, NI-105.4A3 and NI-105.4E4 bind to peptides 329-351+387-397, 337-343, and 35-49 of tau441, respectively.

Anti-tau antibodies of the disclosure can be characterized by their binding properties to PHF-tau in an ELISA. Anti-PHF-tau antibody clone AT8 binds to PHF-tau and has been used extensively to detect PHF-tau in neurofibrillary tangles in samples from Alzheimer's patients. AT8 is a phospho-specific monoclonal antibody and binds to phosphorylated Ser202 and Thr 205 of PHF-tau and is well-published for use in ELISA, immunohistochemistry, immunoblot, Western blot, and related applications. Clone AT8 recognizes Alzheimer Disease tau, as well as PHF-tau by ELISA and does not bind non-phosphorylated-tau from healthy individuals or recombinant tau. In one example, the anti-tau antibody of the disclosure does not bind to PHF-tau by ELISA. In another example, the anti-tau antibody of the disclosure binds to PHF-tau by ELISA.

Anti-tau antibodies of the disclosure can be characterized by their binding properties to PHF-tau and recombinant tau by Western blot. In neurodegenerative disorders, several mechanisms (phosphorylation, ubiquitination, oxidation, glycation) are involved in the aggregation of tau proteins into PHF. These pathological tau proteins are visualized by Western blotting as three major bands between 55 and 69 kDa, and a minor band at 74 kDa. Tau 55 results from the phosphorylation of the shortest isoform (SEQ ID NO:6), tau 64 from the phosphorylation of tau variants with one cassette exon (SEQ ID NO:4 and/or SEQ ID NO:5), tau 69 from the phosphorylation of tau variants with two cassette exons (SEQ ID NO:2 and/or SEQ ID NO:3). Phosphorylation of the longest tau isoform (SEQ ID NO:1) induces the formation of the additional hyperphosphorylated tau74 variant. In certain embodiments, the anti-tau antibodies bind to PHF-tau by Western analysis.

Anti-tau antibodies can be utilized in and characterized by immunohistochemistry (IHC) of tissue sections from normal or AD brain. Phospho-tau antibodies, in particular, highlight neurofibrillary pathology with a high degree of sensitivity and specificity, whereas, no detection of tau in normal healthy brain is observed. Clinicopathological studies have demonstrated that phospho-tau deposits or accumulations correspond more closely to clinical signs compared to amyloid-f3 accumulations, and progress in a stepwise fashion from transentorhinal, to limbic, to isocortical areas, forming the basis for AD staging [R. J. Castellani, et al., Acta Neuropathol. (Berl) 111:503(2006); H. Braak and E. Braak, Acta Neuropathol. (Berl) 82:239 (1991 Tau monoclonal antibodies that are commonly used in immunohistochemistry include AT8 (p202/p205 tau), AT180 (p231 tau), AT270 (p181 tau), AT100 (pT212 and S214), and MC-1, (M. Mercken et al., 1992 Acta Neuropathol. 84:265-272; Zheng-Fischhofer 1998 Eur. I Biochem. 252:542-552, M. Goedert et. al., 1994 Biochem. 1301:871-877). In one embodiment, the anti-tau monoclonal antibodies of the disclosure detect tau in normal (i.e., healthy) human brain tissue and detect tau deposits in human AD brain tissue. In another example, the anti-tau antibodies of the disclosure detect tau deposits in human AD brain but do not detect tau in normal human brain.

Anti-tau antibodies of the disclosure can also be utilized in and characterized by immunohistochemistry of additional tauopathies, including Progressive Supranuclear Palsy, Pick's Disease and others. The pathological filamentous-tau inclusions in PSP are composed of aberrantly phosphorylated-tau proteins, but there is a preferential accumulation of abnormal 4R tau isoforms. A panel of anti-tau monoclonal antibodies, including Alz50, Tau-2, T46, PHF-1, PHF-6, 12E8, PHF-1, RD4 and ATB, has been used to characterize PSP deposits (J. Neuropathol. Exp. Neurol. 1998 (6):588-601). All of the monoclonal antibodies stained intraneuronal and glial inclusions, however, 12E8 and PHF-6 stained with less intensity. These antibodies detect different epitopes of tau, e.g., phospho-specific, isoform-specific, and also detect tau deposits in AD brain. RD3, an anti-tau monoclonal antibody that specifically detects the 3-repeat tau isoform, shows limited IHC detection of PSP, yet intensely stains tau deposits in human AD brain tissue. The limited detection of PSP by this antibody is due to reduced levels of the 3-repeat tau isoform in PSP (R. De Silva et al., Neuropath. and Appl. Neurobio. (2003) 29(3)288-302). In one embodiment, the anti-tau antibodies of the disclosure detect tau deposits in human AD brain but do not detect tau in normal human brain and do not detect tau deposits in human PSP brain.

In certain embodiments, the antibody comprises a heavy chain comprising a) a heavy chain CDR1 region of SEQ ID NO:163, a heavy chain CDR2 region of SEQ ID NO:164, and a heavy chain CDR3 region of SEQ ID NO:165, b) a heavy chain CDR1 region of SEQ ID NO:169, a heavy chain CDR2 region of SEQ ID NO:170, and a heavy chain CDR3 region of SEQ ID NO:171, c) a heavy chain CDR1 region of SEQ ID NO:175, a heavy chain CDR2 region of SEQ ID NO:176, and a heavy chain CDR3 region of SEQ ID NO:177, d) a heavy chain CDR1 region of SEQ ID NO:181, a heavy chain CDR2 region of SEQ ID NO:182, and a heavy chain CDR3 region of SEQ ID NO:183, e) a heavy chain CDR1 region of SEQ ID NO:185, a heavy chain CDR2 region of SEQ ID NO:186, and a heavy chain CDR3 region of SEQ ID NO:187, f a heavy chain CDR1 region of SEQ ID NO:190, a heavy chain CDR2 region of SEQ ID NO:191, and a heavy chain CDR3 region of SEQ ID NO:192, g) a heavy chain CDR1 region of SEQ ID NO:196, a heavy chain CDR2 region of SEQ ID NO:197, and a heavy chain CDR3 region of SEQ ID NO:198, h) a heavy chain CDR1 region of SEQ ID NO:213, a heavy chain CDR2 region of SEQ ID NO:214, and a heavy chain CDR3 region of SEQ ID NO:215, i) a heavy chain CDR1 region of SEQ ID NO:219, a heavy chain CDR2 region of SEQ ID NO:220, and a heavy chain CDR3 region of SEQ ID NO:221.

In certain embodiments, the antibody comprises a light chain comprising: a) a light chain CDR1 region of SEQ ID NO:166, a light chain CDR2 region of SEQ ID NO:167, and a light chain CDR3 region of SEQ ID NO:168, b) a light chain CDR1 region of SEQ ID NO:172, a light chain CDR2 region of SEQ ID NO:173, and a light chain CDR3 region of SEQ ID NO:174, c) a light chain CDR1 region of SEQ ID NO:178, a light chain CDR2 region of SEQ ID NO:179, and a light chain CDR3 region of SEQ ID NO:180, d) a light chain CDR1 region of SEQ ID NO:172, a light chain CDR2 region of SEQ ID NO:173, and a light chain CDR3 region of SEQ ID NO:184, e) a light chain CDR1 region of SEQ ID NO:188, a light chain CDR2 region of SEQ ID NO:173, and a light chain CDR3 region of SEQ ID NO:189, f a light chain CDR1 region of SEQ ID NO:193, a light chain CDR2 region of SEQ ID NO:194, and a light chain CDR3 region of SEQ ID NO:195, g) a light chain CDR1 region of SEQ ID NO:199, a light chain CDR2 region of SEQ ID NO:173, and a light chain CDR3 region of SEQ ID NO:200, h) a light chain CDR1 region of SEQ ID NO:216, a light chain CDR2 region of SEQ ID NO:173, and a light chain CDR3 region of SEQ ID NO:217, and i) a light chain CDR1 region of SEQ ID NO:218, a light chain CDR2 region of SEQ ID NO:173, and a light chain CDR3 region of SEQ ID NO:217.

In certain embodiments, the antibody is selected from the group consisting of a) an antibody comprising a heavy chain CDR1 region of SEQ ID NO:163, a heavy chain CDR2 region of SEQ ID NO:164, and a heavy chain CDR3 region of SEQ ID NO:165, a light chain CDR1 region of SEQ ID NO:166, a light chain CDR2 region of SEQ ID NO:167 and a light chain CDR3 region of SEQ ID NO:168; b) an antibody comprising a heavy chain CDR1 region of SEQ ID NO:169, a heavy chain CDR2 region of SEQ ID NO:170, and a heavy chain CDR3 region of SEQ ID NO:171, a light chain CDR1 region of SEQ ID NO:172, a light chain CDR2 region of SEQ ID NO:173, and a light chain CDR3 region of SEQ ID NO:174; c) an antibody comprising a heavy chain CDR1 region of SEQ ID NO:175, a heavy chain CDR2 region of SEQ ID NO:176, and a heavy chain CDR3 region of SEQ ID NO:177, a light chain CDR1 region of SEQ ID NO:178, a light chain CDR2 region of SEQ ID NO:179, and a light chain CDR3 region of SEQ ID NO:180; d) a heavy chain CDR1 region of SEQ ID NO:181, a heavy chain CDR2 region of SEQ ID NO:182, and a heavy chain CDR3 region of SEQ ID NO:183, a light chain CDR1 region of SEQ ID NO:172, a light chain CDR2 region of SEQ ID NO:173, and a light chain CDR3 region of SEQ ID NO:184; e) an antibody comprising a heavy chain CDR1 region of SEQ ID NO:185, a heavy chain CDR2 region of SEQ ID NO:186, and a heavy chain CDR3 region of SEQ ID NO:187, a light chain CDR1 region of SEQ ID NO:188, a light chain CDR2 region of SEQ ID NO:173, and a light chain CDR3 region of SEQ ID NO:189; f) an antibody comprising a heavy chain CDR1 region of SEQ ID NO:190, a heavy chain CDR2 region of SEQ ID NO:191, and a heavy chain CDR3 region of SEQ ID NO:192, a light chain CDR1 region of SEQ ID NO:193, a light chain CDR2 region of SEQ ID NO:194 and a light chain CDR3 region of SEQ ID NO:195; g) an antibody comprising a heavy chain CDR1 region of SEQ ID NO:196, a heavy chain CDR2 region of SEQ ID NO:197, and a heavy chain CDR3 region of SEQ ID NO:198, a light chain CDR1 region of SEQ ID NO:199, a light chain CDR2 region of SEQ ID NO:173 and a light chain CDR3 region of SEQ ID NO:200; h) an antibody comprising a heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:216, a light chain CDR2 region of SEQ ID NO:173, and a light chain CDR3 region of SEQ ID NO:217; i) an antibody comprising a heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:218, a light chain CDR2 region of SEQ ID NO:174, and a light chain CDR3 region of SEQ ID NO:217; j) an antibody comprising a heavy chain CDR1 region of SEQ ID NO:219, a heavy chain CDR2 region of SEQ ID NO:220, and a heavy chain CDR3 region of SEQ ID NO:221, a light chain CDR1 region of SEQ ID NO:218, a light chain CDR2 region of SEQ ID NO:173, and a light chain CDR3 region of SEQ ID NO:217.

In certain embodiments, the antibody comprises a heavy chain variable region selected from the group consisting of the amino acid sequence of SEQ ID NOS:87, 91, 95, 99, 103, 107, 111, 123, 127 and 131. In certain embodiments, the antibody comprises a light chain variable region selected from the group consisting of the amino acid sequence of SEQ ID NOS:88, 92, 96, 100, 104, 108, 112, 124, 128, 132.

In certain embodiments, antigen-binding fragments of the above-described antibodies are provided. The antigen-binding fragments preferably bind to the same epitope. The anti-tau monoclonal antibodies and antigen-binding fragments of the present disclosure bind to different epitopes as compared to the epitopes of known human anti-tau antibodies, such as, e.g., NI-105.4E4, and NI-105.4A3. With "binding to a different epitope," it is meant that the antibody binds to different critical amino acid residues as compared to known antibodies.

In certain embodiments, the antibodies act synergistically when used in combination with other antibodies binding to tau protein. As used herein, the term "synergistic" means that the combined effect of the antibodies or antigen-binding fragments when used in combination is greater than their additive effects when used individually. A way of calculating synergy is by means of the combination index. The concept of the combination index (CI) has been described by Chou and Talalay (Adv. Enzyme Regul. 22:27-55, 1984).

In certain embodiments, the antibodies and antigen-binding fragments are for use as a medicament, and preferably for use in the diagnostic, therapeutic and/or prophylactic treatment of neurodegenerative diseases. Human anti-tau antibodies of the disclosure or fragments thereof, including Fab, (Fab')2, scFv fragments, or antibodies comprising antigen-binding sites of the antibodies of the disclosure can be used to treat, reduce or prevent symptoms in patients having a neurodegenerative disease that involves accumulation of tau or pathological tau or tau aggregation within the brain, such as patients suffering from AD, as well as any other tauopathy or other tau-related pathologies in which tau may be overexpressed. While not wishing to be bound by any particular theory, the antibodies of the disclosure may exert their beneficial effect by reducing or eliminating pathological tau or tau aggregation and hence the amount of PHF-tau in the brain. The antibodies of the disclosure may be used to treat an animal patient belonging to any classification. Examples of such animals include mammals such as humans, rodents, dogs, cats and farm animals. For example, the antibodies of the disclosure are useful in the preparation of a medicament for treatment of AD wherein the medicament is prepared for administration in dosages defined herein.

Another embodiment of the disclosure is a method of reducing aggregation of tau in patients in need thereof comprising administering to the patient a therapeutically effective amount of the isolated antibody of the disclosure for a time sufficient to reduce the aggregation of tau. Another embodiment of the disclosure is a method of treating or reducing symptoms of a neurodegenerative disease that involves aggregation of tau in a patient comprising administering to the patient a therapeutically effective amount of the isolated antibody of the disclosure for a time sufficient to treat or reduce symptoms of the neurodegenerative disease. Another embodiment of the disclosure is a method of reducing tau in patients in need thereof comprising administering to the patient a therapeutically effective amount of the isolated antibody of the disclosure for a time sufficient to reduce tau.

In any of the embodiments above, the neurodegenerative disease that involves aggregation of tau is a tauopathy. As used herein, a "tauopathy" encompasses any neurodegenerative disease that involves the pathological aggregation of tau within the brain. In addition to familial and sporadic AD, other exemplary tauopathies are frontotemporal dementia with Parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis, Parkinsonism-dementia complex, Down syndrome, Gerstmann-Straussler Scheinker disease, Hallervorden-Spatz disease, inclusion body myositis, Creutzfeld-Jakob disease, multiple system atrophy, Niemann-Pick disease type C, prion protein cerebral amyloid angiopathy, subacute sclerosing panencephalitis, myotonic dystrophy, nonguanamian motor neuron disease with neurofibrillary tangles, post-encephalitic Parkinsonism, and chronic traumatic encephalopathy, such as dementia pugilistica (boxing disease) (Morris, et al., Neuron. 70:410-26, 2011).

A tauopathy-related behavioral phenotype includes cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsion, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

Patients amenable to treatment include asymptomatic individuals at risk of AD or other tauopathy, as well as patients presently showing symptoms. Patients amenable to treatment include individuals who have a known genetic risk of AD, such as a family history of AD or presence of genetic risk factors in the genome. Exemplary risk factors are mutations in the amyloid precursor protein (APP), especially at position 717 and positions 670 and 671 (Hardy and Swedish mutations, respectively). Other risk factors are mutations in the presenilin genes, PS1 and PS2, and ApoE4, family history of hypercholesterolemia or atherosclerosis. Individuals presently suffering from AD can be recognized from characteristic dementia by the presence of risk factors described above. In addition, a number of diagnostic tests are available to identify individuals who have AD. These include measurement of cerebrospinal fluid tau and Aβ342 levels. Elevated tau and decreased Aβ342 levels signify the presence of AD. Individuals suffering from AD can also be diagnosed by AD and Related Disorders Association criteria.

Another embodiment of the disclosure is a method of reducing tau in patients in need thereof comprising administering to the patient a therapeutically effective amount of the isolated anti-tau antibody of the disclosure for a time sufficient to reduce tau. Patients amenable to treatment may suffer from an ailment associated with overexpression of tau. Some mutations, including mutations in intron 10, induce increased levels of the functionally normal four-repeat tau protein isoform, leading to neurodegeneration. Overexpression of the four-repeat human tau protein isoform specifically in neurons in a transgenic mouse led to development of axonal degeneration in brain and spinal cord. In the model, axonal dilations with accumulation of neurofilaments, mitochondria, and vesicles were documented. The axonopathy and the accompanying dysfunctional sensorimotor capacities were transgene-dosage related. These findings proved that merely increasing the concentration of the four-repeat tau protein isoform is sufficient to injure neurons in the central nervous system, without formation of intraneuronal neurofibrillary tangles (Spittaels, et al., Am. J. Pathology 155(6):2153-2165, 1999).

Administration/Pharmaceutical Compositions

Anti-tau antibodies of the disclosure are suitable, both as therapeutic and prophylactic agents for treating or preventing neurodegenerative diseases that involves accumulation of tau, and/or pathological aggregation of tau, such as AD or other tauopathies or tau-associated ailments. In asymptomatic patients, treatment can begin at any age (e.g., at about 10, 15, 20, 25, 30 years). Usually, however, it is not necessary to begin treatment until a patient reaches about 40, 50, 60, or 70 years. Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions or medicaments are administered to a patient susceptible to, or otherwise at risk of, AD or other ailments involving tau, in an amount sufficient to eliminate or reduce the risk, lessen the severity, or delay the outset of the disease, including biochemical, histologic and/or behavioral symptoms of a disease, its complications and intermediate pathological phenotypes presented during development of the disease. In therapeutic applications, compositions or medicaments are administered to a patient suspected of, or already suffering from, such a disease in an amount sufficient to reduce, arrest, or delay any of the symptoms of the disease (biochemical, histologic and/or behavioral). Administration of a therapeutic may reduce or eliminate mild cognitive impairment in patients that have not yet developed characteristic Alzheimer's pathology. An amount adequate to accomplish therapeutic or prophylactic treatment is defined as a therapeutically or prophylactically effective dose. In both prophylactic and therapeutic regimes, compositions or medicaments are usually administered in several dosages until a sufficient immune response has been achieved.

Anti-tau antibodies or fragments thereof of the disclosure may be administered in combination with other agents that are effective for treatment of related neurodegenerative diseases. In the case of AD, antibodies of the disclosure may be administered in combination with agents that reduce or prevent the deposition of amyloid beta (A(3). It is possible that PHF-tau and AP pathologies are synergistic. Therefore, combination therapy targeting the clearance of both PHF-tau and AP-elated pathologies at the same time may be more effective than targeting each individually.

In the case of Parkinson's Disease and related neurodegenerative diseases, immune modulation to clear aggregated forms of the a-synuclein protein is also an emerging therapy. A combination therapy that targets the clearance of both tau and a-synuclein proteins simultaneously may be more effective than targeting either protein individually. In the methods of the disclosure, the "therapeutically effective amount" of the antibody in the treatment or ameliorating symptoms of a tauopathy can be determined by standard research techniques. For example, the dosage of the antibody can be determined by administering the agent to relevant animal models well known in the art.

In addition, in vitro assays can be optionally employed to help identify optimal dosage ranges. Selection of a particular effective dose can be determined (e.g., via clinical trials) by those skilled in the art based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the severity of disease, and should be decided according to the judgment of the practitioner and each patient's circumstances. Effective doses can be extrapolated from dose-response curves derived from in vitro or animal model test systems. The mode of administration for therapeutic use of the antibodies of the disclosure may be any suitable route that delivers the agent to the host. Pharmaceutical compositions of these antibodies are useful for parenteral administration, e.g., intradermal, intramuscular, intraperitoneal, intravenous, subcutaneous, intranasal or intracranial, or they can be administered into the cerebrospinal fluid of the brain or spine.

The antibodies of the disclosure may be prepared as pharmaceutical compositions containing an effective amount of the antibody as an active ingredient in a pharmaceutically acceptable carrier. The term "carrier" refers to a diluent, adjuvant, excipient, or vehicle with which the antibody is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the antibodies of the disclosure in such pharmaceutical formulation can vary widely, i.e., from less than about 0.5%, usually at or at least about 1% to as much as 15% or 20% by weight and will be selected primarily based on required dose, fluid volumes, viscosities, etc., according to the particular mode of administration selected.

The treatment may be given in a single dose schedule, or as a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease. Thus, a pharmaceutical composition of the disclosure for intramuscular injection could be prepared to contain 1 ml sterile buffered water, and between about 1 ng to about 100 mg, about 50 ng to about 30 mg or about 5 mg to about 25 mg of an antibody of the disclosure. Similarly, a pharmaceutical composition of the disclosure for intravenous infusion could be made up to contain about 250 ml of sterile Ringer's solution, and about 1 mg to about 30 mg or about 5 mg to about 25 mg of an antibody of the disclosure. Actual methods for preparing parenterally administrable compositions are well known and are described in more detail in, for example, Remington's Pharmaceutical Science, 15th ed., Mack Publishing Company, Easton, Pa.

The antibodies of the disclosure can be lyophilized for storage and reconstituted in a suitable carrier prior to use. This technique has been shown to be effective with antibody and other protein preparations and known lyophilization and reconstitution techniques can be employed.

Diagnostic Methods and Kits

Antibodies of the disclosure may be used in methods of diagnosing AD or other tauopathy in a subject. This method involves detecting, in the subject, the presence of tau using a diagnostic reagent such as an antibody or a fragment thereof of this disclosure. Tau may be detected in a biological sample from a subject (e.g., blood, urine, cerebral spinal fluid) by contacting the biological sample with the diagnostic antibody reagent, and detecting binding of the diagnostic antibody reagent to PHF-tau in the sample from the subject. Assays for carrying out the detection include well-known methods such as ELISA, immunohistochemistry, Western blot, or in vivo imaging. Exemplary diagnostic antibodies are antibodies CBTAU-7.1, CBTAU-8.1, CBTAU-16.1, CBTAU-18.1, CBTAU-20.1, CBTAU-22.1, CBTAU-24.1, CBTAU-41.1, CBTAU-41.2, and CBTAU-42.1 of the disclosure, and are of IgG1, K type.

Diagnostic antibodies or similar reagents can be administered by intravenous injection into the body of the patient, or directly into the brain by any suitable route that delivers the agent to the host as exemplified above. The dosage of antibody should be within the same ranges as for treatment methods. Typically, the antibody is labeled, although in some methods, the primary antibody with affinity for tau is not labeled and a secondary labeling agent is used to bind to the primary antibody. The choice of label depends on the means of detection. For example, a fluorescent label is suitable for optical detection. Use of paramagnetic labels is suitable for tomographic detection without surgical intervention. Radioactive labels can also be detected using PET or SPECT.

Diagnosis is performed by comparing the number, size, and/or intensity of labeled tau, tau accumulation, tau aggregates, and/or neurofibrillary tangles in a sample from the subject or in the subject, to corresponding baseline values. The baseline values can represent the mean levels in a population of non-diseased individuals. Baseline values can also represent previous levels determined in the same subject.

The diagnostic methods described above can also be used to monitor a subject's response to therapy by detecting the presence of tau in a subject before, during or after the treatment. A change in values relative to baseline signals a response to treatment. Values can also change temporarily in biological fluids as pathological tau is being cleared from the brain.

The present disclosure is further directed to a kit for performing the above-described diagnostic and monitoring methods. Typically, such kits contain a diagnostic reagent such as the antibodies of the disclosure and, optionally, a detectable label. The diagnostic antibody itself may contain the detectable label (e.g., fluorescent molecule, biotin, etc.), which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for measuring tau in a biological sample, the antibodies of the kit may be supplied pre-bound to a solid phase, such as to the wells of a microtiter dish.

The contents of all cited references (including literature references, issued patents, published patent applications, and co-pending patent applications) cited throughout this application are hereby expressly incorporated by reference.

EXAMPLES

Example 1

Tau Peptide Design and Labeling

Hyperphosphorylation of tau protein resulting in release from microtubules and leading to depolymerization is a pathological hallmark occurring in Alzheimer's disease (AD) and other related tauopathies. As the equilibrium of free tau to microtubule-bound tau shifts in favor of the former, unassociated tau protein is thought to accumulate in a misfolded, aggregated state. During the disease process, tau is thought to adopt a variety of conformations, progressing from soluble dimeric and oligomeric forms to higher-order insoluble aggregates such as paired helical filaments (PHFs) and neurofibrillary tangles (NFTs). However, the exact forms of tau that contribute to pathology and, hence, optimal for therapeutic targeting, remain unknown. Consequently, attempts to target disease-promoting tau are often limited by the choice of target. In an effort to prepare novel anti-tau binding molecules, antibody variable regions to tau were recovered from human memory B-cells using phosphorylated and non-phosphorylated-tau peptides as bait antigens using a single-cell-based approach.

Human memory B-cells to tau are likely rare in the human repertoire; therefore, it was decided to label the tau baits with the brightest fluorophores. All tau peptides were synthesized with an amino-terminal biotin group to aid labeling with two bright fluorophores, streptavidin-APC or streptavidin-PE (aka, tau peptide tetramers). Each tau peptide was labeled with both fluorophores to increase the signal-to-noise during the screening of human memory B-cells (detailed in Example 2) from donor samples. Labeled tau peptide tetramers were prepared by mixing biotinylated peptide at a 35:1 molar ratio of peptide to streptavidin label overnight at 4° C. with gentle mixing. Free peptide was removed by separation over a BioSpin 30 column (Biorad). All tau peptide tetramers were stored at 4° C. for up to 2 months.

Example 2

Recovery of Anti-Tau-Specific Memory B-cells by Facs Sorting With Labelled Peptide Tetramers Monoclonal antibodies against tau were recovered from memory B-cells (CD22+CD19+CD27+IgG+) isolated from peripheral blood mononuclear cells (PBMCs) obtained from presumably asymptomatic (non-AD) human blood donors obtained from San Diego Blood Bank and TSRI Normal Blood Donor Services. In addition, AD patient blood samples were obtained through the CRO, Quintiles, from which three antibodies detailed here were recovered. PBMCs were isolated on FICOLL-PAQUE PLUS® (GE Healthcare) and cryopreserved at 50 million cells per ml in 90% FBS and 10% DMSO. An aliquot of plasma was heat inactivated at 56° C. and stored at −20° C. for downstream assessment of plasma reactivity.

For each sorting experiment, PBMCs from three to four donors were thawed and transferred to tubes containing pre-warmed RPMI complete (RPMI, 10% heat inactivated FBS and 1% penicillin/streptomycin), washed and incubated separately at 37° C. for 16 hours. Pooled PBMCs were enriched for mature B-cells by positive selection using CD22+magnetic beads (Miltenyi Biotec). Cells were resuspended in Tris-buffered saline pH 7.4, containing 2 mM EDTA and 0.25% bovine serum albumin Fraction V (TBS Buffer). The cells were stained with the extracellular markers IgG-FITC, CD19-PerCPCy5.5 and CD27-PECy7 (all from BD Biosciences) to label B-cells. Ten million cells were removed and as a negative control, biotin streptavidin-labeled conjugates were used. The remaining cells were incubated with a pool of ten dual-labeled tau peptide tetramers (SA-APC and SA-PE) at 16.8 nM each. Cells were incubated for 60 minutes at 4° C. with gentle mixing, washed twice and re-suspended at 20 million cells per ml in TBS buffer. Prior to sorting, DAPI (Thermo Fisher) was added as a live cell marker and cells were sorted on a Beckman Coulter MoFlo XDP. Negative control samples were used to determine nonspecific binding and signal-to-noise ratio. CD19+, IgG+, CD27hi, and antigen double-positive cells were collected and deposited into individual wells of a 96-well PCR plate and stored at −80° C.

Example 3

Recovery of Heavy and Light Chain Genes from Tau-Specific Single B-Cells

As detailed in Example 2, memory B-cells with reactivity to tau peptide tetramers were identified, isolated and sorted into individual microtiter wells. Heavy and light chain cDNAs were then recovered by a two-step PCR approach from individual B-cells, and variable domain sequences were cloned and expressed in vitro as full-length recombinant IgG1 antibodies and are thus human chimeric antibodies.

First Strand cDNA Synthesis

First-strand complementary DNA (cDNA) was generated from single sorted cells according to manufacturer's protocol (Superscript III, Invitrogen Corp.) with the following modifications: to each well containing a single B-cell, 0.5 µl of 10% NP-40, 1.0 µl of oligo dT, 1.0 µl of dNTP was added and samples were incubated at 65° C. for 5 minutes. After incubation, samples were placed on ice for 1 minute. The following was then added to each well: 2.0 µl of DTT, 4.0 µl of MgCl2, 1.0 µl of SUPERSCRIPT® RT, and 0.5 µl of RNaseOut. Samples were incubated at 50° C. for 50 minutes, followed by incubation at 85° C. for 5 minutes.

Step I Amplification

For the initial PCR (Step I), 2.5 µl of cDNA preparation was used as a template to amplify heavy and kappa or lambda light chains. Primer pools specific to the leader regions of antibody heavy (CB-5'LVH primers, Table 1), kappa light chain (CB-5'LVk primers, Table 2), and lambda light chain (CB-5' LVlam primers, Table 3) were used. A single reverse primer specific to the CH1 region, CK, and CL regions of the heavy, kappa light and lambda light chains, respectively, were used in the Step I PCR reaction.

TABLE 1

VH STEP I FORWARD PRIMERS

| Primer ID | DNA SEQUENCE (5'-3') | SEQ ID NO: |
|---|---|---|
| CB-5'LVH1a | ATGGACTGGACCTGGAGGTTCCTC | 7 |
| CB-5'LVH1b | ATGGACTGGACCTGGAGGATCCTC | 8 |
| CB-5'LVH1c | ATGGACTGGACCTGGAGGGTCTTC | 9 |
| CB-5'LVH1d | ATGGACTGGACCTGGAGCATCC | 10 |
| CB-5'LVH2 | GGACATACTTTGTTCCACGCTCCTGC | 11 |
| CB-5'LVH3a | AGGTGTCCAGTGTCAGGTGCAGC | 12 |
| CB-5'LVH3b | AGGTGTCCAGTGTGAGGTGCAGC | 13 |
| CB-5'LVH3c | AGGTGTCCAGTGTCAGGTACAGC | 14 |
| CB-5'LVH4 | GCAGCTCCCAGATGGGTCCTG | 15 |
| CB-5'LVH5 | TCAACCGCCATCCTCGCCCTC | 16 |
| CB-5'LVH6 | GTCTGTCTCCTTCCTCATCTTCCTGC | 17 |
| 3'CgCH1 | GGAAGGTGTGCACGCCGCTGGTC | 18 |

TABLE 2

VK STEP I FORWARD PRIMERS

| Primer ID | DNA SEQUENCE (5'-3') | SEQ ID NO: |
|---|---|---|
| CB-5'LVk1a | ATGAGGGTCCCCGCTCAGCTC | 19 |
| CB-5'LVk1b | ATGAGGGTCCCTGCTCAGCTC | 20 |
| CB-5'LVk1c | ATGAGAGTCCTCGCTCAGCTC | 21 |
| CB-5'LVk2 | TGGGGCTGCTAATGCTCTGG | 22 |
| CB-5'LVk3 | CCTCCTGCTACTCTGGCTCCCAG | 23 |
| CB-5'LVk4 | TCTCTGTTGCTCTGGATCTCTGGTGC | 24 |
| CB-5'LVk5 | CTCCTCAGCTTCCTCCTCCTTTGG | 25 |
| CB-5'LVk6 | AACTCATTGGGTTTCTGCTGCTCTGG | 26 |
| 3'Ck-Rev543 | GTTTCTCGTAGTCTGCTTTGCTCAGC | 27 |
| 3'Ck-Rev494 | GTGCTGTCCTTGCTGTCCTGCTC | 28 |
| 3'Ck-Rev | GCACTCTCCCCTGTTGAAGCTCTTTG | 29 |

TABLE 3

VL STEP I FORWARD PRIMERS (5'-3')

| Primer ID | DNA SEQUENCE (5'-3') | SEQ ID NO: |
|---|---|---|
| CB-5'L Vlam1 | CTCCTCGCTCACTGCACAGG | 30 |
| CB-5'L Vlam2 | CTCCTCTCTCACTGCACAGG | 31 |
| CB-5'L Vlam3 | CTCCTCACTCGGGACACAGG | 32 |
| CB-5'L Vlam4 | ATGGCCTGGACCCCTCTCTG | 33 |
| CB-5'L Vlam5 | ATGGCATGGATCCCTCTCTTCCTC | 34 |
| 3'Cl-Rev | CACTAGTGTGGCCTTGTTGGCTTG | 35 |

Step II Amplification

For Step II, 2.5 μl of Step I PCR product was used as a template to amplify heavy, and kappa or lambda light chain variable regions. A pool of forward and reverse primers specifically designed to the framework 1 region of antibody heavy chain (pCB-IgG-VH and 3'SalIJH primers, Table 4), kappa light chain (pCB-IgG-VK and 3'Jk primers, Table 5), and lambda light chain (CB-VL and 3'Clam-Step II primers, Table 6) were used to prepare DNA from the variable regions. Furthermore, Step II primers were designed to introduce XbaI (VK and VL forward primers) and XhoI (3'SalIJH primers) restriction sites for downstream cloning. Following the Step II amplification reactions, heavy and light chain variable domain PCR products were run on a 1% agarose gel. Heavy and light chain variable region fragments were purified according to the manufacturer's protocol (Qiagen) and used in the Step III PCR reaction.

TABLE 4

VH Step II Forward and Reverse Primers

| Primer ID | DNA SEQUENCE (5' - 3') | SEQ ID NO: |
|---|---|---|
| pCB-IgG-VH1a | CCTGTCTGGAATTCAGCATGGCCCAGGTGCAGCTGGTGCAGTC | 36 |
| pCB-IgG-VH1b | CCTGTCTGGAATTCAGCATGGCCCAGGTCCAGCTGGTGCAGTC | 37 |
| pCB-IgG-VH1c | CCTGTCTGGAATTCAGCATGGCCCAGGTTCAGCTGGTGCAGTC | 38 |
| pCB-IgG-VH1d | CCTGTCTGGAATTCAGCATGGCCCAGGTCCAGCTTGTGCAGTC | 39 |
| pCB-IgG-VH2a | CCTGTCTGGAATTCAGCATGGCCCAGGTCACCTTGAGGGAGTCTGG | 40 |
| pCB-IgG-VH2b | CCTGTCTGGAATTCAGCATGGCCCAGGTCACCTTGAAGGAGTCTGG | 41 |
| pCB-IgG-VH3a | CCTGTCTGGAATTCAGCATGGCCCAGGTGCAGCTGGTGGAGTC | 42 |
| pCB-IgG-VH3b | CCTGTCTGGAATTCAGCATGGCCGAGGTGCAGCTGTTGGAGTC | 43 |
| pCB-IgG-VH3c | CCTGTCTGGAATTCAGCATGGCCGAGGTGCAGCTGGTGGAGTC | 44 |
| pCB-IgG-VH3d | CCTGTCTGGAATTCAGCATGGCCCAGGTACAGCTGGTGGAGTCTG | 45 |
| pCB-IgG-VH4a | CCTGTCTGGAATTCAGCATGGCCCAGSTGCAGCTGCAGGAG | 46 |
| pCB-IgG-VH4b | CCTGTCTGGAATTCAGCATGGCCCAGGTGCAGCTACAGCAGTGG | 47 |
| pCB-IgG-VH5 | CCTGTCTGGAATTCAGCATGGCCGAGGTGCAGCTGGTGCAGTC | 48 |
| pCB-IgG-VH6 | CCTGTCTGGAATTCAGCATGGCCCAGGTACAGCTGCAGCAGTCAG | 49 |
| pCB-IgG-VH7 | CCTGTCTGGAATTCAGCATGGCCCAGGTGCAGCTGGTGCAATCTG | 50 |
| 3'SalIJH 1/2/4/5 | TCGGGCCTCGAGACTCACCTGAGGAGACGGTGACCAG | 51 |
| 3'SalIJH3 | TCGGGCCTCGAGACTCACCTGAAGAGACGGTGACCATTG | 52 |
| 3'SalIJH6 | TCGGGCCTCGAGACTCACCTGAGGAGACGGTGACCGTG | 53 |

TABLE 5

VK STEP II FORWARD and REVERSE PRIMERS

| Primer ID | DNA SEQUENCE (5'-3') | SEQ ID NO: |
|---|---|---|
| pCB-IgG-VK1a | CCGGTCTAGAGTTTTCCATGGCGGACATCCAGATGACCCAGTCTCC | 54 |
| pCB-IgG-VK1b | CCGGTCTAGAGTTTTCCATGGCGGACATCCAGTTGACCCAGTCTCC | 55 |
| pCB-IGG-VK1c | CCGGTCTAGAGTTTTCCATGGCGGCCATCCAGTTGACCCAGTCTCC | 56 |

TABLE 5-continued

VK STEP II FORWARD and REVERSE PRIMERS

| Primer ID | DNA SEQUENCE (5'-3') | SEQ ID NO: |
|---|---|---|
| pCB-IGG-VK2a | CCGGTCTAGAGTTTTCCATGGCGGATRTTGTGATGACTCAGTCTCCACTC | 57 |
| pCB-IgG-VK3a | CCGGTCTAGAGTTTTCCATGGCGGAAATTGTGTTGACGCAGTCTCCAG | 58 |
| pCB-IgG-VK3b | CCGGTCTAGAGTTTTCCATGGCGGAAATTGTGTTGACACAGTCTCCAG | 59 |
| pCB-IgG-VK3c | CCGGTCTAGAGTTTTCCATGGCGGAAATAGTGATGACGCAGTCTCCAG | 60 |
| pCB-IgG-VK4 | CCGGTCTAGAGTTTTCCATGGCGGACATCGTGATGACCCAGTCTCC | 61 |
| pCB-IgG-VK5 | CCGGTCTAGAGTTTTCCATGGCGGAAACGACACTCACGCAGTCTCC | 62 |
| pCB-IgG-VK6 | CCGGTCTAGAGTTTTCCATGGCGGAAATTGTGCTGACTCAGTCTCCAG | 63 |
| 3'Jk1 Rev IL | CGCAAAGTGCACTTACGTTTGATTTCCACCTTGGTCCCTTGGC | 64 |
| 3'Jk2 Rev IIb | CGCAAAGTGCACTTACGTTTGATCTCCAGCTTGGTCCCCTGGC | 65 |
| 3'Jk4 Rev IIc | CGCAAAGTGCACTTACGTTTGATATCCACTTTGGTCCCAGGGC | 66 |
| 3'Jk3 Rev IIc | CGCAAAGTGCACTTACGTTTGATCTCCACCTTGGTCCCTCCGC | 67 |
| 3'Jk5 Rev IId | CGCAAAGTGCACTTACGTTTAATCTCCAGTCGTGTCCCTTGGC | 68 |

TABLE 6

VL STEP II FORWARD and REVERSE PRIMERS

| Primer ID | DNA SEQUENCE (5'-3') | SEQ ID NO: |
|---|---|---|
| CB-VL1 | CCGGTCTAGAGTTTTCCATGGCGAATTTTATGCTGACTCAGCCCCACTC | 69 |
| CB-VL2 | CCGGTCTAGAGTTTTCCATGGCGTCCTATGTGCTGACTCAGCC | 70 |
| CB-VL3 | CCGGTCTAGAGTTTTCCATGGCGCAGTCTGTGCTGACGCAGCC | 71 |
| CB-VL4 | CCGGTCTAGAGTTTTCCATGGCGCAGTCTGTCGTGACGCAGCC | 72 |
| CB-VL5 | CCGGTCTAGAGTTTTCCATGGCGCAGTCTGCCCTGACTCAGCC | 73 |
| CB-VL6 | CCGGTCTAGAGTTTTCCATGGCGTCTTCTGAGCTGACTCAGGACC | 74 |
| CB-VL7 | CCGGTCTAGAGTTTTCCATGGCGTCCTATGAGCTGACTCAGCCACC | 75 |
| 3'Clam-Step II | CTCAGAGGAGGGYGGGAACAGAGTGAC | 76 |

Step III Amplification: Overlap Extension PCR

For Step III, the heavy and light chain variable region DNA fragments produced in Step II were linked into a single cassette via overlap extension PCR using 1) a kappa linker or lambda linker (see linker preparation method below), which anneals to the 3' end of the light chain Step II fragment and the 5' end of the heavy chain Step II fragment, and contains either the kappa or lambda constant region, 2) a forward overlap primer containing an XbaI restriction site, and 3) a reverse primer containing an XhoI restriction site. This reaction results in an approximate 2400 bp or 2200 bp amplicon (i.e., cassette) for the kappa or lambda chains, respectively, consisting of the light chain variable region, linker, and heavy chain variable region. Following amplification, the overlap extension PCR reaction product was PCR-purified according to the manufacturer's instructions (Qiagen PCR Purification Kit).

Linker Preparation

The linker fragment was amplified using pCB-IgG, a dual-CMV promoter vector generated in house and used to express both heavy and light chain genes, as template and the primers listed in Table 7. The linker fragment is 1765 or 1536 base pairs in length for kappa or lambda linker, respectively. The kappa linker contains from a 5' to 3' intron sequence followed by the kappa constant region, poly(A) termination sequence, and cytomegalovirus promoter sequence, allowing for one vector expression of the recombinant antibodies. The lambda linker contains the lambda constant region, poly(A) termination sequence, and cytomegalovirus promoter sequence. A common reverse primer (Linker VH_HAVT20_pCB-IgG-R) and kappa-specific forward primer (Linker_CK_intronpCB-IgG-F) were used (Table 7). The amplified fragment was separated on a 1% agarose gel and purified according to the manufacturer's protocol (Qiagen Gel Extraction Kit).

TABLE 7

LINKER AND OVERLAP PRIMERS

| Primer ID | SEQUENCE (5'-3') | SEQ ID NO: |
|---|---|---|
| Linker_VH_HAVT20_pCB-IgG-R | GGCCATGCTGAATTCCAGACAGG | 78 |
| Linker_CK_intron_pCB-IgG-F | AAACGTAAGTGCACTTTGCGGCCGCTAGG | 79 |
| Linker_CL_intron_pCB-IgG-F_opt | ACTCTGTTCCCRCCCTCCTCTGAGG | 80 |
| pCB-overlap F | CCGGTCTAGAGTTTTCCATGGCG | 81 |
| pCB-overlap R | TCGGGCCTCGAGACTCACC | 82 |

Cloning into Mammalian Expression Vector

Following purification of the overlap extension PCR product, the fragment was digested with XhoI and XbaI and subsequently separated on a 1% agarose gel. The band corresponding to the overlap cassette (~2.4 kb) was purified and ligated into an IgG1 expression vector, pCB-IgG. Antibody variable genes were subcloned into this vector and antibodies were recombinantly expressed as IgG1, regardless of their original (native) isotype. (An example of an IgG1 heavy chain constant region amino acid sequence is shown in SEQ ID NO:83 and light chain kappa constant region amino acid sequence is shown in SEQ ID NO:84.) All transformations were carried out using DH5a Max Efficiency cells (Invitrogen Corp.) and recovered in 250 IA of SOC for 1 hour at 37° C. Approximately 100 µl of recovered cells were plated onto a carbenicillin plate supplemented with 20 mM glucose. Plates were incubated overnight at 37° C. to allow for colony growth. The remaining recovered cell mixture was cultured with 4 ml of Super Broth (SB) media supplemented with 50 µg/ml carbenicillin and incubated overnight at 37° C. with shaking at 250 rpm. The following day, five colonies were picked per plate and grown in 3 ml of SB media supplemented with 50 µg/ml carbenicillin overnight at 37° C. Overnight cultures were used for DNA plasmid preparation (Qiagen).

Example 4

Antibody Sequencing, Germline Identification and Confirmation of Anti-Tau Peptide Reactivity in Transfection Supernatant To express IgG1 s, DNA plasmid minipreps of the aforementioned 4 ml cultures were prepared (Qiagen) and used to transfect 293Expi cells using EXPIFECTAMINE® according to the manufacturer's instructions (Invitrogen, Corp.). Transfections were carried out for a minimum of 72 hours in 10 ml cultures to allow for sufficient IgG expression. Cell media was harvested post-transfection and centrifuged to remove the cells and debris. Supernatants were quantified using Protein A sensor tips on an Octet Red system (ForteBio). Each supernatant was subsequently tested by ELISA with the bait peptide in order to confirm the presence of anti-tau reactive antibodies. Plasmid MINIPREP™ DNA (Qiagen) from the four individually picked cultures in Example 3 was prepared and heavy and light chains were sequenced with primers pC9_seq_HC-R (5'CATGT-CACCGGGGTGTGG 3') (SEQ ID NO:85) and pC9_seq_LC-R (5'TCACAGGGGATGTTAGGGACA3') (SEQ ID NO:86). One clone of the four was selected for subsequent experiments.

Heavy and Light chain variable region protein and nucleic acid sequences of antibody clones CBTAU-7.1 (SEQ ID NOS:87, 88, 89, 90), CBTAU-8.1 (SEQ ID NOS:91, 92, 93, 94), CBTAU-16.1 (SEQ ID NOS:95, 96, 97, 98), CBTAU-18.1 (SEQ ID NOS: 99, 100, 101, 102), CBTAU-20.1 (SEQ ID NOS:103, 104, 105, 106), CBTAU-22.1 (SEQ ID NOS: 107, 108, 109, 110), CBTAU-24.1 (SEQ ID NO:111, 112, 113, 114), CBTAU-27.1 (SEQ ID NOS:115, 116, 117, 118), CBTAU-28.1 (SEQ ID NOS:119, 120, 121, 122), CBTAU-41.1 (SEQ ID NOS:123, 124, 125, 126), CBTAU-41.2 (SEQ ID NOS:127, 128, 129, 130), CBTAU-42.1 (SEQ ID NOS: 131, 132, 133, 134), CBTAU-43.1 (SEQ ID NOS:135, 136, 137, 138), CBTAU-44.1 (SEQ ID NOS:139, 140, 141, 142), CBTAU-45.1 (SEQ ID NOS:143, 144, 145, 146), CBTAU-46.1 (SEQ ID NOS:147, 148, 149, 150), CBTAU-47.1 (SEQ ID NOS:151, 152, 153, 154), CBTAU-47.2 (SEQ ID NOS: 155, 156, 157, 158), and CBTAU-49.1 (SEQ ID NOS:159, 160, 161, 162) define novel CDRs for the selected anti-tau antibodies (Table 8).

An anti-tau antibody CBTAU-7.1 was generated comprising the VH of SEQ ID NO:87 and the VL of SEQ ID NO:88 and a human IgG1 constant region. An anti-tau antibody CBTAU-8.1 was generated comprising the VH of SEQ ID NO:91 and the VL of SEQ ID NO:92 and a human IgG1 constant region. An anti-tau antibody CBTAU-16.1 was generated comprising the VH of SEQ ID NO:95 and the VL of SEQ ID NO:96 and a human IgG1 constant region. An anti-tau antibody CBTAU-18.1 was generated comprising the VH of SEQ ID NO:99 and the VL of SEQ ID NO:100 and a human IgG1 constant region. An anti-tau antibody CBTAU-20.1 was generated comprising the VH of SEQ ID NO:103 and the VL of SEQ ID NO:104 and a human IgG1 constant region. An anti-tau antibody CBTAU-22.1 was generated comprising the VH of SEQ ID NO:107 and the VL of SEQ ID NO:108 and a human IgG constant region. An anti-tau antibody CBTAU-24.1 was generated comprising the VH of SEQ ID NO:111 and the VL of SEQ ID NO:112 and a human IgG1 constant region. An anti-tau antibody CBTAU-27.1 was generated comprising the VH of SEQ ID NO:115 and the VL of SEQ ID NO:116 and a human IgG1 constant region. An anti-tau antibody CBTAU-28.1 was generated comprising the VH of SEQ ID NO:119 and the VL of SEQ ID NO:120 and a human IgG1 constant region. An anti-tau antibody CBTAU-41.1 was generated comprising the VH of SEQ ID NO:123 and the VL of SEQ ID NO:124 and a human IgG1 constant region. An anti-tau antibody CBTAU-41.2 was generated comprising the VH of SEQ ID NO:127 and the VL of SEQ ID NO:128 and a human IgG1 constant region. An anti-tau antibody CBTAU-42.1 was generated comprising the VH of SEQ ID NO:131 and the VL of SEQ ID NO:132 and a human IgG1 constant region. An anti-tau antibody CBTAU-43.1 was generated comprising the VH of SEQ ID NO:135 and the VL of SEQ ID NO:136 and a human IgG1 constant region. An anti-tau antibody CBTAU-44.1 was generated comprising the VH of SEQ ID NO:139 and the VL of SEQ ID NO:140 and a human IgG1 constant region. An anti-tau antibody CBTAU-45.1 was generated comprising the VH of SEQ ID NO:143 and the VL of SEQ ID NO:144 and a human IgG1 constant region. An anti-tau antibody CBTAU-46.1 was generated comprising the VH of SEQ ID NO:147 and the VL of SEQ ID NO:148 and a human IgG1 constant region. An anti-tau antibody CBTAU-47.1 was generated comprising the VH of SEQ ID NO:151 and the VL of SEQ ID NO:152 and a human IgG1 constant region. An anti-tau antibody CBTAU-47.2 was generated comprising the VH of SEQ ID NO:155 and the VL of SEQ ID NO:156 and a human IgG1 constant region. An anti-tau antibody CBTAU-49.1 was generated comprising the VH of SEQ ID NO:159 and the VL of SEQ ID NO:160 and a human IgG1 constant region.

TABLE 8

Amino acid sequences of heavy and light chain variable region CDRs

| Clone | Tau aa region | CDR1 (SEQ ID NO:) | CDR2 (SEQ ID NO:) | CDR3 (SEQ ID NO:) |
|---|---|---|---|---|
| CBTAU 7.1 | 194-212 | SYWMH (163) | RINSDGSDTNYAD SVKG (164) | GRSYGFFDY (165) |
|  |  | RASQIISSNYLA (166) | GASSRAT (167) | QQYGTSPRT (168) |
| CBTAU 8.1 | 194-212 | TYGMH (169) | VIWFDGNNKYYA DSVKG (170) | DWWEAGCRPCYFF DY (171) |
|  |  | KSSQSVLYSSNNK NYLA (172) | WASTRES (173) | QQYYSPPLT (174) |
| CBTAU 16.1 | 204-221 | DYWMS (175) | NINQDGSAAYYVD SVRG (176) | DAHYYDRNRNNYY YYFDF (177) |
|  |  | RASQSVGANLA (178) | SASTRAT (179) | QQYNNWPRT (180) |
| CBTAU 18.1 | 200-217 | SGNYYWS (181) | RMSSSGSTNYNPSL KS (182) | ESGSSWQNHYYYG MDV (183) |
|  |  | KSSQSVLYSSNNK NYLA (172) | WASTRES (173) | QQYYSTPLT (184) |
| CBTAU 20.1 | 58-78 | NYAMS (185) | GISSDGNTFYADSV KG (186) | ESGRWGGGTLYGA HY (187) |
|  |  | KSSQSLLYNSNNK NYLT (188) | WASTRES (173) | QQYYSSPLT (189) |
| CBTAU 22.1 | 406-429 | DYNVH (190) | RISPNSGGTKYAQ KFQG (191) | GHCDGTTCSRAY (192) |
|  |  | RSSQSLLHRSGHK YLH (193) | LGSNRAS (194) | MQTLQTPWT (195) |
| CBTAU 24.1 | 221-245 | GYYLH (196) | WVNPRSGGTSYPP KFQG (197) | GRIPDVTAFDI (198) |
|  |  | KSSESLLYDSNNK NYLA (199) | WASTRES (173) | QQYFSTPWT (200) |
| CBTAU 27.1 | 299-328 | DYWTA (201) | IIYSGDSDTRYHPS VQG (202) | LDARVDAGWQLDS (203) |
|  |  | KSSQSVFSRDNNK NYLA (204) | WASSRES (205) | QHYFNTPHN (206) |
| CBTAU 28.1 | 52-71 | NYWIG (207) | IIYPGDSDTRYSPPF QG (208) | VGRPSKGGWFDP (209) |
|  |  | ESSQTLLYSSNEK NYLA (210) | WASTPES (211) | QQYYNSPYT (212) |
| CBTAU 41.1 | 406-429 | DSYMS (213) | YISRSSSHTNYADS VKG (214) | VQTTMIEGKTKLNY FDY (215) |
|  |  | ESSHSLLYRSNNR NYLA (216) | WASTRES (173) | QQFYTTPYT (217) |
| CBTAU 41.2 | 406-429 | DSYMS (213) | YISRSSSHTNYADS VKG (214) | VQTTMIEGKTKLNY FDY (215) |
|  |  | ESSHSLLYRSNNK NYLA (218) | WASTRES (173) | QQFYTTPYT (217) |

TABLE 8-continued

Amino acid sequences of heavy and light chain variable region CDRs

| Clone | Tau aa region | CDR1 (SEQ ID NO:) | CDR2 (SEQ ID NO:) | CDR3 (SEQ ID NO:) |
|---|---|---|---|---|
| CBTA U 42.1 | 406-429 | KAWMS (219) | RIKSKVDGETTDY AAPVRG (220) | LIHCDLSACLPHF (221) |
| | | ESSHSLLYRSNNK NYLA (218) | WASTRES (173) | QQFYTTPYT (217) |
| CBTA U 43.1 | 299-328 | NYWIA (222) | IIYPGDSDTTYSPSF QG (223) | LPRTDGDNSIGYFEY (224) |
| | | KSSQSVLYSSNSE NYLA (225) | WASTRES (173) | QQYYSTPFT (226) |
| CBTA U 44.1 | 406-429 | SYSMN (227) | YISSSTTTIYYADSV KG (228) | VPAPRLGGSYTY (229) |
| | | RASQSVSSSYLA (230) | GASSRAT (167) | QQYGTSPLT (231) |
| CBTA U 45.1 | 406-429 | DAWMS (232) | RIKSKNVGEIIDY AEHVRG (233) | GLGGGTYG (234) |
| | | RSSAGLRNNDGDI LLS (235) | RVSRRDS (236) | MRGPY (237) |
| CBTA U 46.1 | 82-103 | IYEMN (238) | YITNRGSTIYYADS VKG (239) | PRIGARVFDV (240) |
| | | KSSQTLLYKSNNE NYLA (241) | WASTRES (173) | QQYFTTALT (242) |
| CBTA U 47.1 | 52-71 | DHWIG (243) | IIFPEDSDTRYSGSF EG (244) | VSVVRKGGWFDP (245) |
| | | KSSQSLLYTSNNK NYLA (246) | WASTRES (173) | QQYYNSPYT (212) |
| CBTA U 47.2 | 52-71 | DHWIG (243) | IIFPGDSDIRYSPSF EG (247) | VAVVRKGGWFDS (248) |
| | | KSTQSLLWSANNK NYLA (249) | WASTRES (173) | QQYYNSPYT (212) |
| CBTA U 49.1 | 52-71 | SYWIG (250) | IIYPDDSDTRYNAS LEG (251) | RDRNCSGTTCYPRW FDS (252) |
| | | KSSQSLFYSGNSK DFLA (253) | WASTRDS (254) | HQYHSTPLS (255) |

CBTAU-7.1 antibody comprises a heavy chain CDR region of SEQ ID NO:163, a heavy chain CDR2 region of SEQ ID NO:164, and a heavy chain CDR3 region of SEQ ID NO:165, a light chain CDR1 region of SEQ ID NO:166, a light chain CDR2 region of SEQ ID NO:167 and a light chain CDR3 region of SEQ ID NO:168. CBTAU-8.1 antibody comprises a heavy chain CDR1 region of SEQ ID NO:169, a heavy chain CDR2 region of SEQ ID NO:170, and a heavy chain CDR3 region of SEQ ID NO:171, a light chain CDR1 region of SEQ ID NO:172, a light chain CDR2 region of SEQ ID NO:173 and a light chain CDR3 region of SEQ ID NO:174. CBTAU-16.1 antibody comprises a heavy chain CDR1 region of SEQ ID NO:175, a heavy chain CDR2 region of SEQ ID NO:176, and a heavy chain CDR3 region of SEQ ID NO:177, a light chain CDR1 region of SEQ ID NO:178, a light chain CDR2 region of SEQ ID NO:179 and a light chain CDR3 region of SEQ ID NO:180.

CBTAU-18.1 antibody comprises a heavy chain CDR1 region of SEQ ID NO:181, a heavy chain CDR2 region of SEQ ID NO:182, and a heavy chain CDR3 region of SEQ ID NO:183, a light chain CDR1 region of SEQ ID NO:172, a light chain CDR2 region of SEQ ID NO:173 and a light chain CDR3 region of SEQ ID NO:184. CBTAU-20.1 antibody comprises a heavy chain CDR1 region of SEQ ID NO:185, a heavy chain CDR2 region of SEQ ID NO:186, and a heavy chain CDR3 region of SEQ ID NO:187, a light chain CDR1 region of SEQ ID NO:188, a light chain CDR2 region of SEQ ID NO:173 and a light chain CDR3 region of SEQ ID NO:189. CBTAU-22.1 antibody comprises a heavy chain CDR1 region of SEQ ID NO:190, a heavy chain CDR2 region of SEQ ID NO:191, and a heavy chain CDR3 region of SEQ ID NO:192, a light chain CDR1 region of SEQ ID NO:193, a light chain CDR2 region of SEQ ID NO:194 and a light chain CDR3 region of SEQ ID NO:195.

CBTAU-24.1 antibody comprises a heavy chain CDR1 region of SEQ ID NO:196, a heavy chain CDR2 region of SEQ ID NO:197, and a heavy chain CDR3 region of SEQ ID NO:198, a light chain CDR1 region of SEQ ID NO:199, a light chain CDR2 region of SEQ ID NO:173 and a light chain CDR3 region of SEQ ID NO:200. CBTAU-27.1 antibody comprises a heavy chain CDR1 region of SEQ ID NO:201, a heavy chain CDR2 region of SEQ ID NO:202, and a heavy chain CDR3 region of SEQ ID NO:203, a light chain CDR1 region of SEQ ID NO:204, a light chain CDR2 region of SEQ ID NO:205 and a light chain CDR3 region of SEQ ID NO:206. CBTAU-28.1 antibody comprises a heavy chain CDR1 region of SEQ ID NO:207, a heavy chain CDR2 region of SEQ ID NO:208, and a heavy chain CDR3 region of SEQ ID NO:209, a light chain CDR1 region of SEQ ID NO:210, a light chain CDR2 region of SEQ ID NO:211 and a light chain CDR3 region of SEQ ID NO:212. CBTAU-41.1 antibody comprises a heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:216, a light chain CDR2 region of SEQ ID NO:173 and a light chain CDR3 region of SEQ ID NO:217. CBTAU-41.2 antibody comprises a heavy chain CDR1 region of SEQ ID NO:213, a heavy chain CDR2 region of SEQ ID NO:214, and a heavy chain CDR3 region of SEQ ID NO:215, a light chain CDR1 region of SEQ ID NO:218, a light chain CDR2 region of SEQ ID NO:174 and a light chain CDR3 region of SEQ ID NO:217. CBTAU-42.1 antibody comprises a heavy chain CDR1 region of SEQ ID NO:219, a heavy chain CDR2 region of SEQ ID NO:220, and a heavy chain CDR3 region of SEQ ID NO:221, a light chain CDR1 region of SEQ ID NO:218, a light chain CDR2 region of SEQ ID NO:173 and a light chain CDR3 region of SEQ ID NO:217. CBTAU-43.1 antibody comprises a heavy chain CDR1 region of SEQ ID NO:222, a heavy chain CDR2 region of SEQ ID NO:223, and a heavy chain CDR3 region of SEQ ID NO:224, a light chain CDR1 region of SEQ ID NO:225, a light chain CDR2 region of SEQ ID NO:173 and a light chain CDR3 region of SEQ ID NO:226. CBTAU-44.1 antibody comprises a heavy chain CDR1 region of SEQ ID NO:227, a heavy chain CDR2 region of SEQ ID NO:228, and a heavy chain CDR3 region of SEQ ID NO:229, a light chain CDR1 region of SEQ ID NO:230, a light chain CDR2 region of SEQ ID NO:167 and a light chain CDR3 region of SEQ ID NO:231. CBTAU-45.1 antibody comprises a heavy chain CDR1 region of SEQ ID NO:232, a heavy chain CDR2 region of SEQ ID NO:233, and a heavy chain CDR3 region of SEQ ID NO:234, a light chain CDR1 region of SEQ ID NO:235, a light chain CDR2 region of SEQ ID NO:236 and a light chain CDR3 region of SEQ ID NO:237. CBTAU-46.1 antibody comprises a heavy chain CDR1 region of SEQ ID NO:238, a heavy chain CDR2 region of SEQ ID NO:239, and a heavy chain CDR3 region of SEQ ID NO:240, a light chain CDR1 region of SEQ ID NO:241, a light chain CDR2 region of SEQ ID NO:173 and a light chain CDR3 region of SEQ ID NO:242. CBTAU-47.1 antibody comprises a heavy chain CDR1 region of SEQ ID NO:243, a heavy chain CDR2 region of SEQ ID NO:244, and a heavy chain CDR3 region of SEQ ID NO:245, a light chain CDR1 region of SEQ ID NO:246, a light chain CDR2 region of SEQ ID NO:173 and a light chain CDR3 region of SEQ ID NO:212. CBTAU-47.2 antibody comprises a heavy chain CDR1 region of SEQ ID NO:243, a heavy chain CDR2 region of SEQ ID NO:247, and a heavy chain CDR3 region of SEQ ID NO:248, a light chain CDR1 region of SEQ ID NO:249 a light chain CDR2 region of SEQ ID NO:173 and a light chain CDR3 region of SEQ ID NO:212. CBTAU-49.1 antibody comprises a heavy chain CDR1 region of SEQ ID NO:250, a heavy chain CDR2 region of SEQ ID NO:251, and a heavy chain CDR3 region of SEQ ID NO:252, a light chain CDR1 region of SEQ ID NO:254, a light chain CDR2 region of SEQ ID NO:254 and a light chain CDR3 region of SEQ ID NO:255.

Nucleic acid sequences of heavy and light chain variable regions of the anti-tau monoclonal antibodies were compared to known germline sequences using IgBLAST, an immunoglobulin variable domain sequence analysis tool, available at the NCBI (Nucleic Acids Res. 2013 July; 41 (Web Server issue):W34-40). Sequence alignment of heavy and light chain framework H1 and L1 regions, aligned with their respective proposed germline sequence and PCR primer, are shown in Table 9. Confirmed sequences were scaled up for expression and purification (detailed in Example 5). Selected clones were expanded into a 50 ml culture and plasmid midiprep DNA was prepared (Machery Nagel Midi Prep kit). Plasmid DNA was then used to transfect a 30 ml culture of 293Expi cells as detailed in Example 5.

TABLE 9

Framework nucleic acids of H1 and L1 aligned with germline and primer (Amino acids above) Differences marked in lower case lettering. Native refers to the antibody

| mAb | SEQ ID NO | Amino Terminal Protein and N-terminal Nucleic Acid Sequences |
|---|---|---|
| CBTAU-7.1 | | |
| VH | 87 | (Q V Q L V E S) |
| pCB-IgG-VH1b | 37 | CAGGTCCAGCTGGTGCAGTC |
| CBTAU-7.1VH | 89 | CAGGTCCAGCTGGTGGAGTCCGGGGGAGGCTTAGTTCAGCC TGGGGGGTCCCTGAGACTCTCCT |
| IGHV3-74*01. | 256 | gAGGTgCAGCTGGTGGAGTCCGGGGGAGGCTTAGTTCAGCCTG GGGGGTCCCTGAGACTCTCCT |
| Native 7.1 VH | 257 | (e V Q L V E) |
| VL | 88 | (D I V M T Q S P) |
| pCB-IgG-Vk4 | 61 | GACATCGTGATGACCCAGTCTCC |
| CBTAU-7.1 VL | 90 | GACATCGTGATGACCCAGTCTCCAGACACCCTGTCTTTGTCTC CAGGGGAGAGAGCCACCCTCT |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|
| IGKV3-NL5*01 | 258 | GAaATtGTGtTGACgCAGTCTCCAGcCACCCTGTCTTTGTCTCC AGGGGAaAGAGCCACCCTCT |
| Native 7.1 VL | 259 | (e I V l T Q S P) |

CBTAU-8.1

| VH pCB-IgG-VH3a | 91 42 | (Q V A L V E S) CAGGTGCAGCTGGTGGAGTC |
| CBTAU-8.1 VH | 93 | CAGGTGCAGCTGGTGGAGTCGAGGGGAGGCGTGGTCCAGCCTGGG ACGTCCCTGAGACTCTCCT |
| IGHV3-33*01 | 260 | CAGGTGCAGCTGGTGGAGTCtgGGGGAGGCGTGGTCCAGCCTGGG ACGTCCCTGAGACTCTCCT |
| Native 8.1 VH | 261 | (Q V A L V E S) |
| VL pCB-IgG-Vk5 | 92 62 | (E T T L T Q S P) GAAACGACACTCACGCAGTCTCC |
| CBTAU-8.1 VL | 94 | GAAACGACACTCACGCAGTCTCCAGACTCCCTGGCTGTGTCTCTGGG CGAGAGGGCCACCATCA |
| IGKV4-1*01 | 262 | GAcAtcgtgaTgACcCAGTCTCCAGACTCCCTGGCTGTGTCTCTGGGCGAGAGGG CCACCATCA |
| Native 8.1 VL | 263 | (d i v m T Q S P) |

CBTAU-16.1

| VH pCB-IgG-VH5 | 95 48 | (E V Q L V Q) GAGGTGCAGCTGGTGCAGTC |
| CBTAU-16.1 VH | 97 | GAGGTGCAGCTGGTGCAGTCTGGGGGAGGCTTGGTCCAGCCTGGG GGGTCCCTGAGACTCTCCT |
| IGHV3-64*01 | 264 | GAGGTGCAGCTGGTGgAGTCTGGGGGAGGCTTGGTCCAGCCTGGG GGGTCCCTGAGACTCTCCT |
| Native 16.1 VH | 265 | (E V Q L V e S) |
| VL pCB-IgG-VK3c | 96 60 | (E I V M T Q S P) GAAATAGTGATGACGCAGTCTCCGG |
| CBTAU-16.1VL | 98 | GAAATAGTGATGACGCAGTCTCCGGCCACCCTGTCTGTGTCTCCAGG GGAAAGAGCCACCCTCT |
| IGKV3-15*01 | 266 | GAAATAGTGATGACGCAGTCTCCaGCCACCCTGTCTGTGTCTCCAGG GGAAAGAGCCACCCTCT |
| Native 16.1 VL | 267 | (E I V M T Q S P) |

CBTAU-18.1

| VH | 99 | (Q V Q L L E S) No exact primer match |
| CBTAU-18.1 VH | 101 | CAGGTGCAGCTMIGGAGTCGGGCCCAGGACTGGTGAACCCTTCACAG ACCCTGTCCCTCACCT |
| IGHV4-31*05 | 268 | CAGGTGCAGCTGcaGGAGTCGGGCCCAGGACTGGTGAAGCCTTCACAGA CCCTGTCCCTCACCT |
| Native 18.1 VH | 269 | (Q V Q L q E S) |
| VL pCB-IgG-VK3b | 100 59 | (E I V L T Q S P) GAAATTGTGTTGACACAGTCTCCAG |
| CBTAU-18.1 VL | 102 | GAAATTGTGTTGACACAGTCTCCAGACTCCCTGGCTGTGTCTCTGGGCG AGAGGGCCAACATTA |
| IGKV4-1*01 | 262 | GAcATcGTGaTGACcCAGTCTCCAGACTCCCTGGCTGTGTCTCTGGGCGAG AGGGCCAcCATcA |
| Native 18.1 VL | 270 | (d I V m T Q S P) |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|
| | | CBTAU-20.1 |
| VH pCB-IgG-VH3d | 103 45 | (Q V Q L V E S) CAGGTACAGCTGGTGGAGTCTG |
| CBTAU-20.1 VH | 105 | CAGGTACAGCTGGTGGAGTCTGGGGGAGGCTTGGTACAGCCTGGG GGGTCCCTGAGACTCTCCT |
| IGHV3-23*04 | 271 | gAGGTgCAGCTGGTGGAGTCTGGGGGAGGCTTGGTACAGCCTGGG GGTCCCTGAGACTCTCCT |
| Native 20.1 VH | 272 | (e V Q L V E S) |
| VL pCB-IgG-VK1a | 104 54 | (D I Q M T Q S P) GACATCCAGATGACCCAGTCTCC |
| CBTAU-20.1 VL | 106 | GACATCCAGATGACCCAGTCTCCAGACTCCCTGGCTGTGTCTCTGGGCG AGAGGGCCACCATCA |
| IGKV4-1*01 | 262 | GACATCgtGATGACCCAGTCTCCAGACTCCCTGGCTGTGTCTCTGGGCGAG AGGGCCACCATCA |
| Native 20.1 VL | 273 | (D I v M T Q S P) |
| | | CBTAU-22.1 |
| VH pCB-IgG-VH1a | 107 36 | (Q V Q L V Q S) CAGGTGCAGCTGGTGCAGTC |
| CBTAU-22.1 VH | 109 | CAGGTGCAGCTGGTGCAGTCTGGGGCTGAGGTGAAGAAGCCTGGGG CCCCAGTGAAGGTCTC |
| IGHV1-2*02 | 274 | CAGGTGCAGCTGGTGCAGTCTGGGGCTGAGGTGAAGAAGCCTGGGG CCtCAGTGAAGGTCTC |
| Native 22.1 VH | 275 | (Q V Q L V Q S) |
| VL | 108 | (D V V M T Q S P L) No Exact Primer match |
| CBTAU-22.1 VL | 110 | GATGTTGTGATGACGCAGTCTCCACTCTCCCTGCCCGTCACCCCTGGAG AGCCGGCCTCCATC |
| IGKV2-28*01 | 276 | GATaTTGTGATGACtCAGTCTCCACTCTCCCTGCCCGTCACCCCTGGAGAG CCGGCCTCCATC |
| Native 22.1 VL | 277 | (D i V M T Q S P L) |
| | | CBTAU-24.1 |
| VH pCB-IgG-VH1d | 111 39 | (Q V Q L V S G) CAGGTCCAGCTTGTGCAGTC |
| CBTAU-24.1 VH | 113 | CAGGTCCAGCTTGTGCAGTCTGGGGCTGAGGTGAAGAAGCCTGGGG CCTCAGTGAAGGTCTCC |
| IGHV1-3*01 | 278 | CAGGTCCAGCTTGTGCAGTCTGGGGCTGAGGTGAAGAAGCCTGGGG CCTCAGTGAAGGTtTCC |
| Native 24.1 VH | 279 | (Q V Q L V S G) |
| VL pCB-IgG-VK1a | 112 54 | (D I Q M T Q S P) GACATCCAGATGACCCAGTCTCC |
| CBTAU-24.1 VL | 114 | GACATCCAGATGACCCAGTCTCCAGACTCCCTGGCTGTGTCTCTGGG CGAGAGGGCCACCATC |
| IGKV4-1*01 | 262 | GACATCgtGATGACCCAGTCTCCAGACTCCCTGGCTGTGTCTCTGGGCG AGAGGGCCACCATC |
| Native 24.1 VL | 280 | (D I v M T Q S P) |
| | | CBTAU27.1 |
| VH pCB-IgG-VH3a | 115 42 | (Q V Q L V E S) CAGGTGCAGCTGGTGGAGTC |
| CBTAU27.1 VH | 117 | CAGGTTCAGCTGGTGGAGTCTGGACCGGAGATGAGAAAGCCCGGGGAG TCTCTGAAAATTTCC |
| IGHV5-51*01 | 281 | gAGGTgCAGCTGGTGCAGTCTGGAgCaGAGgTGAaAAAGCCCGGGGAGTCTC TGAAgATcTCC |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|
| Native 27.1 VH | 282 | (e V Q L V q S) |
| VL | 116 | (D I Q L T Q S P) |
| pCB-IgG-VK1b | 55 | GACATCCAGTTGACCCAGTCTCC |
| CBTAU27.1 VL | 118 | GACATCCAGTTGACCCAGTCTCCAGATTCCCTGGCTGTGTCTCTGGG CGAGCGGGCCACCATC |
| IGKV4-1*01 | 262 | GACATCgtGATGACCCAGTCTCCAGACTCCCTGGCTGTGTCTCTGGG CGAGAGGGCCACCATC |
| Native 27.1 VL | 283 | (D I v m T Q S)P |

CBTAU28.1

| VH | 119 | (Q V Q L Q Q S) |
|---|---|---|
| pCB-IgG-VH6 | 49 | CAGGTaCAGCTgCAGCAGTCAG |
| CBTAU28.1 VH | 121 | CAGGTGCAGCTACAGCAGTCAGGAGCAGAAGTGAAAAAGCCCGGGG AGTCTCTGAAGATCTCC |
| IGHV5-51*01 | 281 | gAGGTGCAGCTggtGCAGTCtGGAGCAGAAGTGAAAAAGCCCGGGGAG TCTCTGAAGATCTCC |
| Native 28.1 VH | 284 | (e V Q L v Q S) |
| VL | 120 | (D I Q M T Q S P) |
| pCB-IgG-VK1a | 54 | GACATCCAGATGACCCAGTCTCC |
| CBTAU28.1 VL | 122 | GACATCCAGATGACCCAGTCTCCAGACTCCCTGGCTGTGTCTCTGGGCG AGAGGGCCACCATC |
| IGKV4-1*01 | 262 | GACATCgtGATGACCCAGTCTCCAGACTCCCTGGCTGTGTCTCTGGGCGAG AGGGCCACCATC |
| Native 28.1 VL | 285 | (D I v M T Q S P) |

CBTAU41.1

| VH | 123 | (E V Q L L E S) |
|---|---|---|
| pCB-IgG-VH3b | 43 | GAGGTGCAGCTGTTGGAGTC |
| CBTAU41.1 VH | 125 | GAGGTGCAGCTGTTGGAGTCTGGGGGAGGCTTGGTCAAGCCTGGAGG GTCCCTGAGACTCTCC |
| IGHV3-11*06 | 286 | cAGGTGCAGCTGgTGGAGTCTGGGGGAGGCTTGGTCAAGCCTGGAGG GTCCCTGAGACTCTCC |
| Native 41.1 VH | 287 | (q V Q L v E S) |
| VL | 124 | (D I Q M T Q S P) |
| pCB-IgG-VK1a | 54 | GACATCCAGATGACCCAGTCTCC |
| CBTAU41.1 VL | 126 | GACATCCAGATGACCCAGTCTCCAGACTCCCTGGCTGTGTCTCTGGG CGAGAGGGTCACCATC |
| IGKV4-101 | 262 | GACATCgtGATGACCCAGTCTCCAGACTCCCTGGCTGTGTCTCTGGGCG AGAGGGT cAccATc |
| Native 41.1 VL | 288 | (D I v M T Q S P) |

CBTAU41.2

| VH | 127 | (E V Q L V Q S) |
|---|---|---|
| pCB-IgG-VH3b | 43 | GAGGTGCAGCTGGTGCAGTC |
| CBTAU41.2 VH | 129 | GAGGTGCAGCTGGTGCAGTCTGGGGGAGGCTTGGTCAAGCCTGGAGGG TCCCTGAGACTCTCC |
| IGHV3-11*06 | 286 | cAGGTGCAGCTGGTGgAGTCTGGGGGAGGCTTGGTCAAGCCTGGAGGG TCCCTGAGACTCTCC |
| Native 41.2 VH | 289 | (q V Q L v E S) |
| VL | 128 | (A I Q L T Q S P) |
| pCB-IgG-VK1c | 56 | GCCATCCAGTTGACCCAGTCTCC |
| CBTAU41.2 VL | 130 | GCCATCCAGTTGACCCAGTCTCCAGACTCCCTGGCTGTGTCTCTGGGCGAG AGGGTCACCATC |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|
| IGKV4-1*01 | 262 | gaCATCgtGaTGACCCAGTCTCCAGACTCCCTGGCTGTGTCTCTGGGCGAGAG GGTCACCATC |
| Native 41.2 VL | 290 | (d I v m T Q S P) |

CBTAU42.1

| VH pCB-IgG-VH1a-c | 131 36 | (Q L V Q S E G) CAGCTGGTGCAGTC |
| CBTAU42.1 VH | 133 | CAGCTGGTGCAGTCTGAGGGAGGCCTGGCAGAGCCTGGGGGGTCCC TTAGACTC |
| IGHV3-15*01 | 291 | CAGGTGGTGgAGTCTGgGGGAGGCCTGGCAGAGCCTGGGGGGTCCC TTAGACTC |
| Native 42.1 VH | 292 | (Q L V e S g g) |
| VL pCB-IgG-VK3a | 132 58 | (E I V L T Q S P) GAAATTGTGTTGACGCAGTCTCCAG |
| CBTAU41.1 VL | 134 | GAAATTGTGTTGACGCAGTCTCCAGACTCCCTGGCTGTGTCTCTGGGCGA GAGGGTCACCATC |
| IGKV4-1*01 | 262 | GAcATcGTGaTGACCCAGTCTCCAGACTCCCTGGCTGTGTCTCTGGGCGAGA GGGTCACCATC |
| Native 42.1 VL | 293 | (d I V m T Q S P) |

CBTAU43.1

| VH pCB-IgG-VH1a | 135 36 | (Q V Q L V Q S) CAGGTGCAGCTGGTGCAGTC |
| CBTAU43.1 VH | 137 | CAGGTGCAGCTGGTGCAGTCTGGAGGAGAGGTGAAAAAGCCGGGGGAG TCTCTGAAGATCTCC |
| IGHV5-51*03 | 294 | gAGGTGCAGCTGGTGCAGTCTGGAGGAGAGGTGAAAAAGCCGGGGGAG TCTCTGAAGATCTCC |
| Native 43.1 VH | 295 | (e V Q L V Q S) |
| VL pCB-IgG-VK3b | 136 59 | (E I V L T Q S P) GAAATTGTGTTGACACAGTCTCCAG |
| CBTAU43.1 VL | 138 | GAAATTGTGTTGACACAGTCTCCAGCCTCCCTGGCTGTGTCTCTGGGCGAG AGGGCCACCATC |
| IGKV4-1*01 | 262 | GAcATcGTGaTGACCCAGTCTCCAGCCTCCCTGGCTGTGTCTCTGGGCGAGAG GGCCACCATC |
| Native 43.1 VL | 296 | (d I V m T Q S P) |

CBTAU44.1

| VH pCB-IgG-VH3c | 139 44 | (E V Q L V E S) GAGGTGCAGCTGGTGGAGTC |
| CBTAU44.1 VH | 141 | GAGGTGCAGCTGGTGGAGTCTGGGGGAGGCTTGGTACAGCCTGGGGGGTC CCTGAGACTCTCC |
| IGHV3-48*01 | 297 | GAGGTGCAGCTGGTGGAGTCTGGGGGAGGCTTGGTACAGCCTGGGGGGTC CCTGAGACTCTCC |
| Native 44.1 VH | 298 | (E V Q L V E S) |
| VL pCB-IgG-VK1a | 140 54 | (D I Q M T Q S) GACATCCAGATGACCCAGTCTCC |
| CBTAU44.1 VL | 142 | GACATCCAGATGACCCAGTCTCCAGGCACCCTGTCTTTGTCTCCAGGGGAAAG AG CCACCCTC |
| IGKV3-20*01 | 299 | GAaATtgtGtTgACgCAGTCTCCAGGCACCCTGTCTTTGTCTCCAGGGGAAAGAG CCACCCTC |
| Native 44.1 VL | 300 | (e I v L T Q S) |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|

CBTAU45.1

| VH pCB-IgG-VH3c | 143 44 | (E V Q L V E S) GAGGTGCAGCTGGTGGAGTC |
|---|---|---|
| CBTAU45.1 VH | 145 | GAAATTGTGTTGACACAGTCTCCACTCTCCCTGCCCGCCACCCTTGGACAGC CGGCCTCCATC |
| IGHV3-15*02 | 301 | GAGGTGCAGCTGGTGGAGTCTGGGGGAGACTTGGTAAAGCCTGGGGGGTC CCTTAGACTCTCC |
| Native 45.1 VH | 302 | (E V Q L V E S) |
| VL pCB-IgG-VK3b | 144 59 | (E I V L T Q S P) GAAATTGTGTTGACACAGTCTCCAG |
| CBTAU45.1 VL | 146 | GAAATTGTGTTGACACAGTCTCCACTCTCCCTGCCCGCCACCCTTGGACAG CCGGCCTCCATC |
| IGKV2-30*01 | 303 | GAtgTTGTGaTGACtCAGTCTCCACTCTCCCTGCCCGCCACCCTTGGACAGCC GGCCTCCATC |
| Native 45.1 VL | 304 | (d v V m T Q S P) |

CBTAU46.1

| VH pCB-IgG-VH3d | 147 45 | (Q V Q L V E S) CAGGTACAGCTGGTGGAGTCTG |
|---|---|---|
| CBTAU46.1 VH | 149 | CAGGTACAGCTGGTGGAGTCTGGGGGAGGCTTGGTACAGCCTGGAGAGT CCCTGAGACTCTCC |
| IGHV3-48*03 | 305 | gAGGTgCAGCTGGTGGAGTCTGGGGGAGGGTTGGTACAGCCTGGAGAGTC CCTGAGACTCTCC |
| Native 46.1 VH | 306 | (E V Q L V E S) |
| VL pCB-IgG-VK1b | 148 55 | (D I Q L T Q S P) GACATCCAGTTGACCCAGTCTCC |
| CBTAU46.1 VL | 150 | GACATCCAGTTGACCCAGTCTCCAGACTCCCTGGCTGTGTCTCTGGGCGAGA GGGCCACCATC |
| IGKV4-1*01 | 262 | GACATCgtGatGACCCAGTCTCCAGACTCCCTGGCTGTGTCTCTGGGCGAGAGG GCCACCATC |
| Native 46.1 VL | 307 | (D I v m T Q S P) |

CBTAU47.1

| VH pCB-IgG-VH1a | 151 36 | (Q V Q L V Q S) CAGGTGCAGCTGGTGCAGTC |
|---|---|---|
| CBTAU47.1 VH | 153 | CAGGTGCAGCTGGTGCAGTCTGGAGCAGTGGTGAAAAAGCCCGGGGAG TCTCTGAAGATCTC |
| IGHV5-51*01 | 308 | gAGGTGCAGCTGGTGCAGTCTGGAGCAGTGGTGAAAAAGCCCGGGGAGTC TCTGAAGATCTC |
| Native 47.1 VH | 309 | (E V Q L V Q S) |
| VL pCB-IgG-VK1c | 152 56 | (A I Q L T Q S P) GCCATCCAGTTGACCCAGTCTCC |
| CBTAU44.1 VL | 154 | GCCATCCAGTTGACCCAGTCTCCAGACTCCCTGGCTGTGTCTCTGGGCGAGA GGGCCACCATC |
| IGKV4-1*01 | 262 | GaCATCgtGatGACCCAGTCTCCAGACTCCCTGGCTGTGTCTCTGGGCGAGAG GGCCACCATC |
| Native 47.1 VL | 310 | (d I v m T Q S P) |

CBTAU47.2

| VH pCB-IgG-VH3d | 155 45 | (Q V Q L V E S) CAGGTACAGCTGGTGGAGTCTG |
|---|---|---|
| CBTAU47.1 VH | 157 | CAGGTACAGCTGGTGGAGTCTGGAGCAGAACTGAAAAAGCCCGGGGAGTCT CTGAAGATCTCC |

TABLE 9-continued

Framework nucleic acids of H1 and L1 aligned with germline and primer
(Amino acids above) Differences marked in lower case lettering. Native refers to the antibody

| mAb | SEQ ID NO | Amino Terminal Protein and N-terminal Nucleic Acid Sequences |
|---|---|---|
| IGHV5-51*01 | 281 | gAGGTgCAGCTGGTGcAGTCTGGAGCAGAACTGAAAAAGCCCGGGGAGTCTCTGAAGATCTCC |
| Native 47.2 VH | 311 | (e V Q L V q S) |
| VL | 156 | (E I V M T Q S P) |
| pCB-IgG-VK3c | 60 | GAAATAGTGATGACGCAGTCTCCAG |
| CBTAU44.1 VL | 158 | GAAATTGTGATGACCCAGTCTCCAGAGTCCCTGGCTGTGTCTCTGGGCGAGAGGGCCACCATC |
| IGKV4-1*01 | 262 | GAcATcGTGATGACCCAGTCTCCAGAGTCCCTGGCTGTGTCTCTGGGCGAGAGGGCCACCATC |
| Native 47.2 VL | 312 | (d I V M T Q S P) |

CBTAU49.1

| VH | 159 | (Q V Q L V Q S) |
|---|---|---|
| pCB-IgG-VH1a | 36 | CAGGTGCAGCTGGTGCAGTC |
| CBTAU49.1 VH | 161 | CAGGTGCAGCTGGTGCAGTCTGGGGCAGAGGTGAAAAAGCCGTGGGAGTCTCTGAAGATCTCC |
| IGHV5-51*03 | 294 | gAGGTGCAGCTGGTGCAGTCTGGGGCAGAGGTGAAAAAGCCGTGGGAGTCTCTGAAGATCTCC |
| Native 49.1 VH | 313 | (e V Q L V Q S) |
| VL | 160 | (E I V L T Q S P) |
| pCB-IgG-VK6 | 63 | GAAATTGTGCTGACTCAGTCTCCAG |
| CBTAU49.1 VL | 162 | GAAATTGTGCTGACTCAGTCTCCAGACTTCCTGGCTGTGTCTCTGGGCGAGAGGGCCACCATC |
| IGKV4-1*01 | 262 | GAcATcGTGaTGACcCAGTCTCCAGACTTCCTGGCTGTGTCTCTGGGCGAGAGGGCCACCATC |
| Native 49.1 VL | 314 | (d I V m T Q S P) |

Transfected IgG1 supernatants were assayed for reactivity to tau peptides by ELISA. First, 96 half-well ELISA plates (Costar) were coated with 50 IA of bovine actin (1 µg/ml, Sigma) as a negative control and Affinipure goat anti-human F(ab)2 (2 µg/ml, Jackson Immunoresearch) to confirm antibody production. Plates were coated in TBS overnight at 4° C. The following day, plates were washed five times with TBS/0.05% TWEEN® (TBS-T) and blocked with 150 IA of TBS-T plus 2.5% BSA (blocking buffer) for 2 hour. Tau peptides were captured on streptavidin-coated plates (Pierce) at a concentration of 0.43 µM in 100 µl of TBS. Tau peptides used to set up ELISA assays were the same used as baits in corresponding sorting experiment. Tau peptide-coated plates were then incubated at RT for 1.5 hours. All plates were then washed five times with TBS/0.05% TWEEN® and blocked with 150 µl and 300 µl (tau peptide plates only) of blocking buffer and incubated at RT for 2 hours. IgG transfection supernatants were diluted to 5 µg/ml (based on quantitation by Octet Red) and titrated five-fold in TBS/0.25% BSA. Mouse anti-actin (Sigma, Cat. No. A3853) was used at 1.25 µg/ml as a positive control for bovine actin-coated plates. Commercial grade antibodies were used at 1 µg/ml as positive controls for ELISA assays, including AT8 monoclonal antibody (Thermo, MN1020), AT100 monoclonal antibody (Thermo, MN1060) and AT180 monoclonal antibody (Thermo, MN1040). Primary antibodies were incubated for 2 hours at RT and washed five times in TBS-T. Finally, goat-anti human IgG Fab or goat anti-mouse HRP (Jackson Labs) was used at 1:2000 and 1:4000, respectively, and incubated for 1 hour at RT. Plates were washed five times in TBS-T and developed with SureBlue Reserve TMB Microwell Peroxidase Substrate (KPL). The reaction was halted by the addition of 50 µl and 100 µl (peptide plates) of TMB Stop Solution (KPL) and the absorbance at 450 nm was measured using an ELISA plate reader. Supernatants with the aforementioned binding activities were subsequently reconfirmed in an independent ELISA experiment. Once reconfirmed, a clone was selected for downstream IgG expression and purification (Example 5).

Example 5

IgG1 Expression and Purification of Cloned Anti-Tau Chimeric mAbs

After ELISA screening and confirmation of antibody reactivity, selected clones were expressed as IgG1 s as indicated in Example 4. Cell culture media was harvested and centrifuged to remove the cells after a minimum of 72 hours and up to a maximum of 168 hours. Clarified supernatants were subsequently passed twice through a Protein A Sepharose column (GE Healthcare Life Sciences) and washed with 50 ml of PBS. IgGs were subsequently eluted with 10 ml of IgG elution buffer (Pierce) and neutralized with Tris pH 8.0 and subsequently dialyzed overnight against PBS. Dialyzed samples were concentrated using a 10,000 MWCO ultra-centrifugal unit (Amicon) to a final volume of about 1 mL, and antibody concentrations were determined with Protein A sensor tips using a human IgG standard on the Octet Red384 (ForteBio). Purified antibodies were further quality controlled by performing SDS-PAGE under non-reducing and reducing conditions and by size exclusion chromatography.

Example 6

IgG Binding

Reactivity to Tau Peptides

IgG1s generated and quality controlled as described above were tested by ELISA for their ability to bind to specified cognate peptide(s), as well as non-cognate peptide (Table 10). 96-well ELISA plates (Costar) or streptavidin-coated plates (Pierce) were coated with antigen (bovine actin and affinipure goat anti-human F(ab)2) or tau peptides, respectively, as detailed in Example 4. Purified anti-tau IgGs were diluted to 5 μg/ml in TBS containing 0.25% BSA, and titrated five-fold. Antibody controls and secondary antibodies were used as detailed in Example 4. antibody reactivity at 1 μg/mL was determined by ELISA and scored as no binding (−), weak (−/+), moderate (+), or strong (++). (−) for average of two O.D. 450 nm readings <0.3; (−/+) for >0.5 and <1.0; (+) for >1.0 and <1.5; (++) for >1.5.

TABLE 10

Cognate and non-cognate peptides used in ELISAs

| mAb | Peptide | Peptide sequence (pX) denotes phosphorylated amino acid | SEQ ID NO | Results |
|---|---|---|---|---|
| CBTAU-7.1 | ptau 194-212 (pS202, pT205) | RSGYSSPG(pS)PG(pT)PGSRSRT | 315 | + |
|  | tau 194-212 | RSGYSSPGSPGTPGSRSRT | 316 | − |
| CBTAU-8.1 | ptau 194-212 (pS202, pT205) | RSGYSSPG(pS)PG(pT)PGSRSRT | 315 | −/+ |
|  | tau 194-212 | RSGYSSPGSPGTPGSRSRT | 316 | − |
| CBTAU-16.1 | ptau 204-221 (pT212, pS214) | GTPGSRSR(pT)P(pS)LPTPPTR | 317 | ++ |
|  | tau 204-221 | GTPGSRSRTPSLPTPPTR | 318 | ++ |
| CBTAU-18.1 | patu 200-217 (pS210) | PGSPGTPGSR(pS)RTPSLPT | 319 | −/+ |
|  | tau 200-217 | PGSPGTPGSRSRTPSLPT | 320 | − |
|  | tau 186-253 | GEPPKSGDRSGYSSPGSPGTPGSRSRTPSLPTPPTREPKKVAVVRTPPKSPSSAKSRLQTAPVPMPDL | 321 | − |
| CBTAU-20.1 | ptau 58-76 (pS68, pT69) | EPGSETSDAK(pS)(pT)PTAEDVT | 322 | ++ |
|  | ptau 59-78 (pT69, pT71) | PGSETSDAKS(pT)P(pT)AEDVTAP | 323 | ++ |
|  | ptau 61-78 (pT71) | SETSDAKSTP(pT)AEDVTAP | 324 | −/+ |
|  | tau 42-103 | GLKESPLQTPTEDGSEEPGSETSDAKSTPTAEDVTAPLVDEGAPGKQAAAQPHTEIPEGTTA | 325 | − |
| CBTAU-22.1 | ptau 406-429 (pS416, pS422) | RHLSNVSSTG(pS)IDMVD(pS)PQLATLA | 326 | ++ |
|  | tau 389-441 | GAEIVYKSPVVSGDTSPRHLSNVSSTGSIDMVDSPQLATLADEVSASLAKQGL | 327 | − |
| CBTAU-24.1 | ptau 221-245 (pT231, pS238) | REPKKVAVVR(pT)PPKSPS(pS)AKSRLQT | 328 | ++ |
|  | ptau 228-245 (pS238) | VVRTPPKSPS(pS)AKSRLQT | 329 | ++ |
|  | ptau 225-245 (pS235, pS238) | KVAVVRTPPK(pS)PS(pS)AKSRLQT | 330 | ++ |
|  | tau 186-253 | GEPPKSGDRSGYSSPGSPGTPGSRSRTPSLPTPPTREPKKVAVVRTPPKSPSSAKSRLQTAPVPMPDL | 321 | ++ |
| CBTAU-27.1 | tau 299-369 | HVPGGGSVQIVYKPVDLSKVTSKCGSLGNIHHKPGGGQVEVKSEKLDFKDRVQSKIGSLDNITHVPGGGNK | 331 | + |
|  | ptau 194-212 (pS202, pT205) | RSGYSSPG(pS)PG(pT)PGSRSRT | 315 | − |
| CBTAU-28.1 | tau 42-103 | GLKESPLQTPTEDGSEEPGSETSDAKSTPTAEDVTAPLVDEGAPGKQAAAQPHTEIPEGTTA | 325 | ++ |
|  | ptau 257-272 | KSKIG(pS)TENLKHQPGG | 332 | − |
| CBTAU-41.1 | ptau 406-429 (p416, p422) | RHLSNVSSTG(pS)IDMVD(pS)PQLATLA | 326 | + |
|  | tau 389-441 | GAEIVYKSPVVSGDTSPRHLSNVSSTGSIDMVDSPQLATLADEVSASLAKQGL | 327 | − |
| CBTAU-41.2 | ptau 406-429 (p416, p422) | RHLSNVSSTG(pS)IDMVD(pS)PQLATLA | 326 | + |
|  | tau 389-441 | GAEIVYKSPVVSGDTSPRHLSNVSSTGSIDMVDSPQLATLADEVSASLAKQGL | 327 | − |

TABLE 10-continued

Cognate and non-cognate peptides used in ELISAs

| mAb | Peptide | Peptide sequence (pX) denotes phosphorylated amino acid | SEQ ID NO | Results |
|---|---|---|---|---|
| CBTAU-42.1 | ptau 406-429 (p416, p422) | RHLSNVSSTG(pS)IDMVD(pS)PQLATLA | 326 | ++ |
| | tau 389-441 | GAEIVYKSPVVSGDTSPRHLSNVSSTGSIDMVDSPQLATLADEVSASLAKQGL | 327 | − |
| CBTAU-43.1 | tau 299-369 | HVPGGGSVQIVYKPVDLSKVTSKCGSLGNIHHKPGGGQVEVKSEKLDFKDRVQSKIGSLDNITHVPGGGNK | 331 | + |
| | ptau 194-212 (pS202, pT205) | RSGYSSPG(pS)PG(pT)PGSRSRT | 315 | − |
| CBTAU-44.1 | ptau 406-429 (p416, p422) | RHLSNVSSTG(pS)IDMVD(pS)PQLATLA | 326 | −/+ |
| | tau 389-441 | GAEIVYKSPVVSGDTSPRHLSNVSSTGSIDMVDSPQLATLADEVSASLAKQGL | 327 | − |
| CBTAU-45.1 | ptau 406-429 (p416, p422) | RHLSNVSSTG(pS)IDMVD(pS)PQLATLA | 326 | ++ |
| | tau 389-441 | GAEIVYKSPVVSGDTSPRHLSNVSSTGSIDMVDSPQLATLADEVSASLAKQGL | 327 | − |
| CBTAU-46.1 | tau 42-103 | GLKESPLQTPTEDGSEEPGSETSDAKSTPTAEDVTAPLVDEGAPGKQAAAQPHTEIPEGTTA | 325 | + |
| | ptau 224-241 (pT231, pS235) | KKVAVVR(pT)PPK(pS)PSSAKS | 333 | − |
| CBTAU-47.1 | tau 42-103 | GLKESPLQTPTEDGSEEPGSETSDAKSTPTAEDVTAPLVDEGAPGKQAAAQPHTEIPEGTTA | 325 | ++ |
| | ptau 257-272 (pS262) | KSKIG(pS)TENLKHQPGG | 332 | − |
| CBTAU-47.2 | tau 42-103 | GLKESPLQTPTEDGSEEPGSETSDAKSTPTAEDVTAPLVDEGAPGKQAAAQPHTEIPEGTTA | 325 | ++ |
| | ptau 257-272 (pS262) | KSKIG(pS)TENLKHQPGG | 332 | − |
| CBTAU-49.1 | tau 42-103 | GLKESPLQTPTEDGSEEPGSETSDAKSTPTAEDVTAPLVDEGAPGKQAAAQPHTEIPEGTTA | 325 | ++ |
| | ptau 224-241 (pT231, pS235) | KKVAVVR(pT)PPK(pS)PSSAKS | 333 | − |
| AT8 | ptau 194-121 (pS202, pT205) | RSGYSSPG(pS)PG(pT)PGSRSRT | 315 | ++ |
| | tau 194-212 | RSGYSSPGSPGTPGSRSRT | 316 | − |

*Amino acid region on human tau441 isoform

Figure 1H:
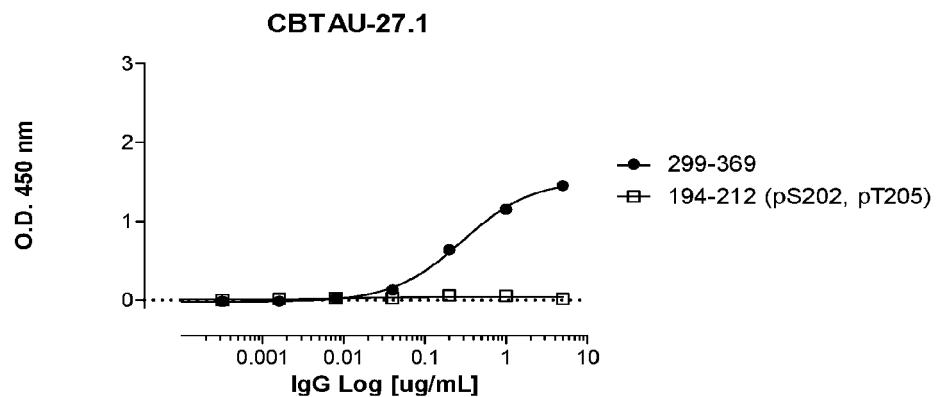
Figure 1I:
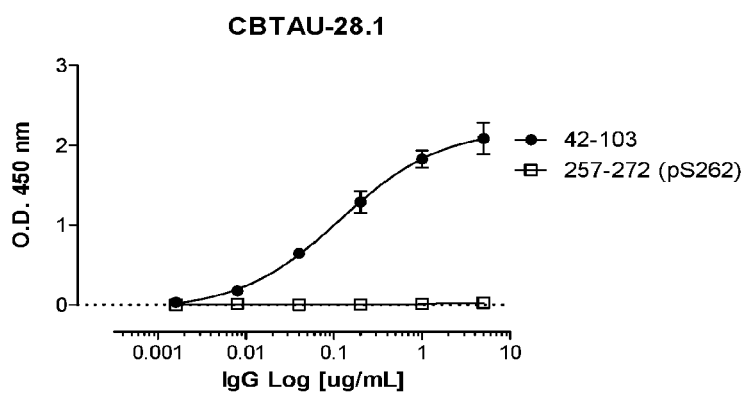
Figure 1J:
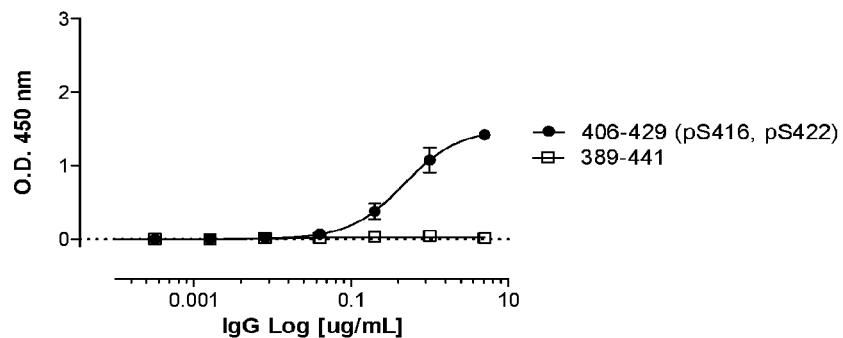
Figure 1K:
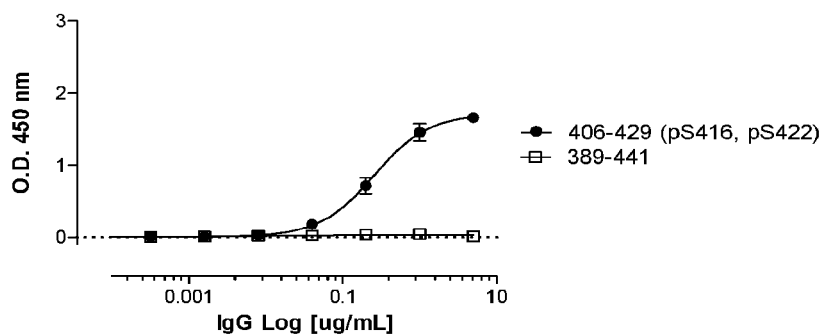
Figure 1L:
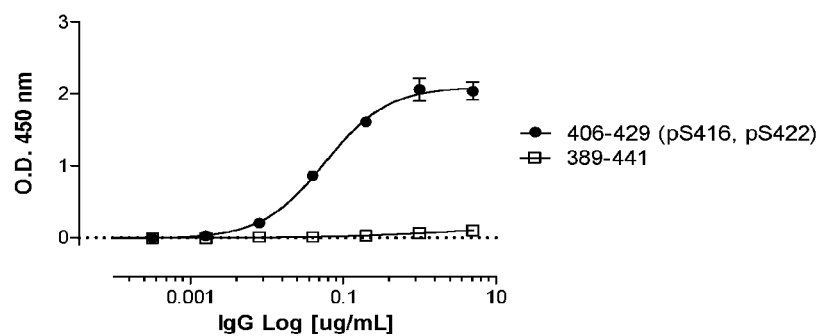
Figure 1M:
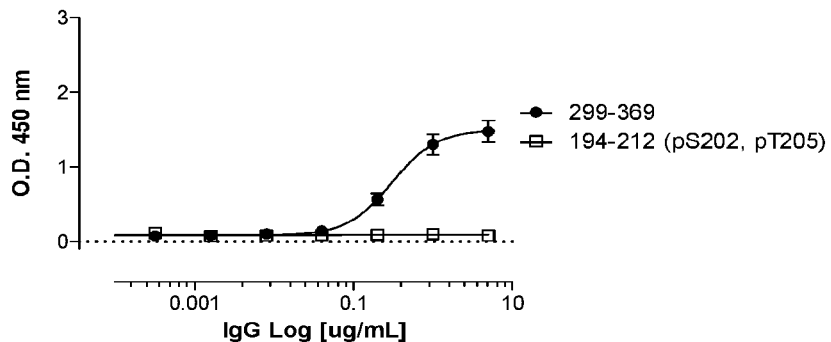
Figure 1N:
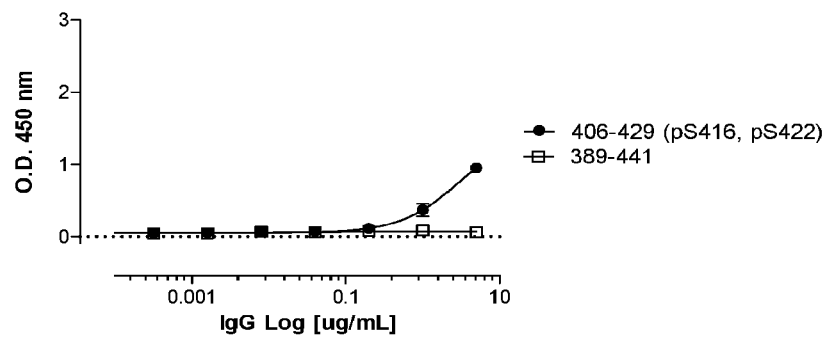
Figure 1O:
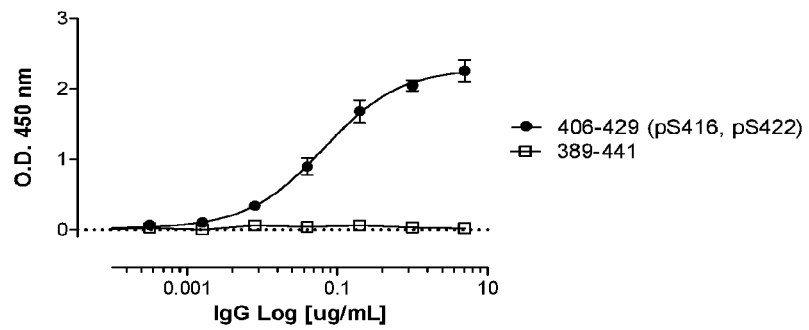
Figure 1P:
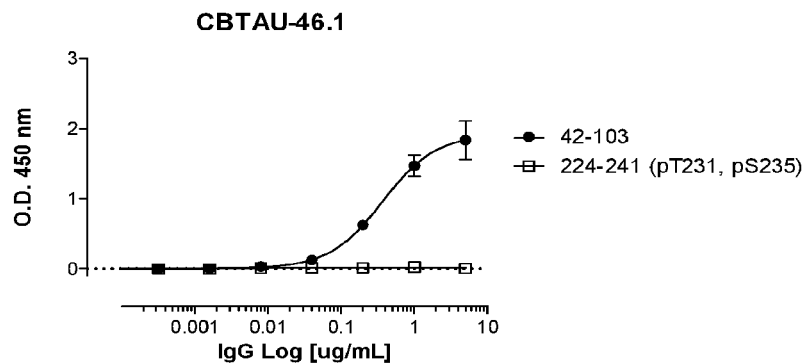
Figure 1Q:
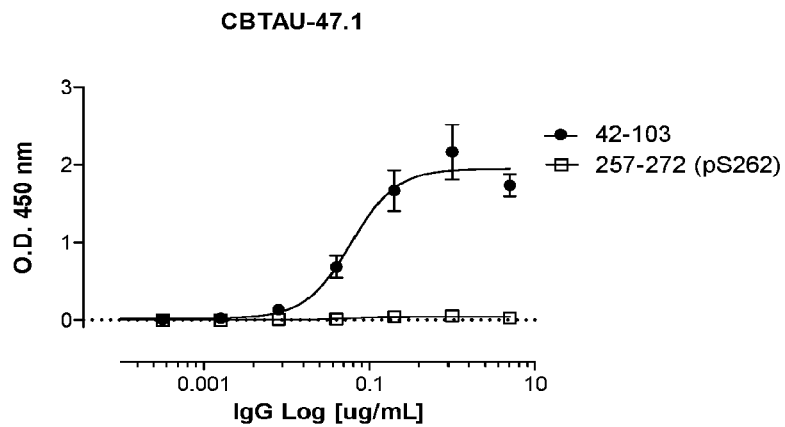
Figure 1R:
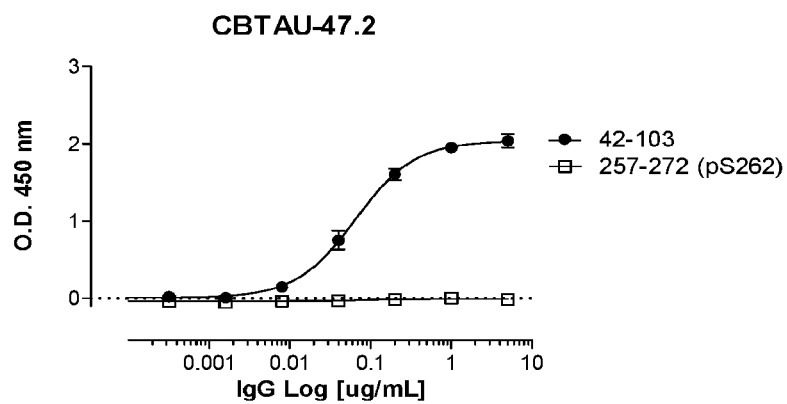
Figure 1S:
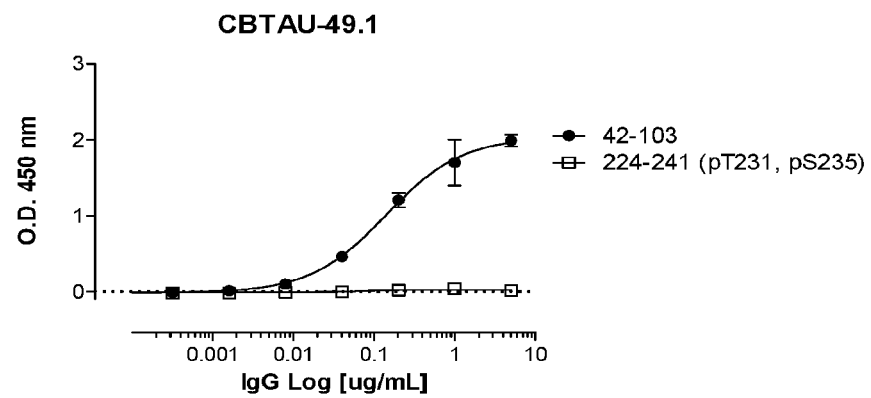
Figure 1T:
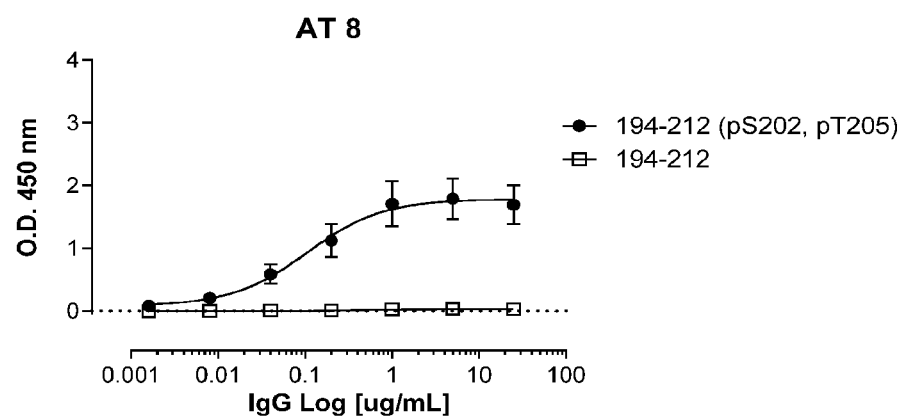

Results are shown in FIGS. 1A-1T. The anti-tau mAbs described herein can be classified into two main groups: those that react only to phosphorylated peptides (phospho-dependent mAbs) and those that react to both phosphorylated and non-phosphorylated peptides (phospho-independent mAbs). Anti-tau mAbs CBTAU-7.1, CBTAU-8.1, CBTAU-18.1, and CBTAU-22.1 were recovered from non-AD individuals using the approach detailed in Example 3. These mAbs are phospho-dependent and, as shown by ELISA (FIGS. 1A-1T), react only with the phosphorylated peptide but not to either a non-phosphorylated peptide spanning that region or a non-phosphorylated version of the peptide. Anti-tau mAbs CBTAU-7.1 and CBTAU-8.1 react specifically to a phosphorylated peptide containing the AT8-binding epitope. This peptide spans amino acids 194 to 212 and contains phosphorylated residues at positions 202 and 205. CBTAU-18.1 reacts to a phosphorylated peptide spanning amino acids 200-217 with a phosphorylated serine residue at position 210. Lastly, CBTAU-22.1 reacts to a peptide spanning amino acids 406-429, with two phosphorylated serines at positions 416 and 422.

Similarly, CBTAU-20.1 was identified from a non-AD individual and is predominately phospho-dependent as it reacts to three different phosphorylated peptides spanning amino acids 59-77. Two of these peptides are dually phosphorylated, one at positions 68 and 69, and the second at positions 69 and 71. CBTAU-20.1 also reacts to a third peptide that is singly phosphorylated at position 71, suggesting that phosphorylation at threonine 71 is sufficient and important for CBTAU-20.1 reactivity. CBTAU-20.1 shows weak reactivity to a non-phosphorylated peptide spanning region 42-103.

Like the aforementioned mAbs, CBTAU-16.1 and CBTAU-24.1 were also recovered from non-AD individuals; however, both mAbs are phospho-independent and, as observed by ELISA, react to both a phosphorylated and non-phosphorylated peptide spanning the specified region. CBTAU-16.1 reacts to amino acid region 204-221, whereas CABTAU-24.1 reacts to three different peptides spanning amino acids 221-245. In addition, two additional anti-tau mAbs (CBTAU-27.1 and CBTAU-28.1) were identified from screens conducted with non-AD donor samples using 60-70 amino acid-length non-phosphorylated peptides corresponding to amino acid regions 42-103 and 299-369, respectively; therefore, both mAbs are specific to non-phosphorylated-tau.

Finally, CBTAU mAbs 41.1, 41.2, 42.1, 43.1, 44.1, 45.1, 46.1, 47.1, 47.2, and 49.1 were identified from a small study where 25 young non-AD (18-27 y.o.), 25 non-AD (55+y.o.), and 25 AD (55+ y.o.) individuals were screened. The peptide set that was used for this study included eight phosphorylated peptides (including CBTAU-22.1 cognate peptide) and two non-phosphorylated peptides (CBTAU-27.1 and CBTAU-28.1 cognate peptides). CBTAU mAbs 41.1, 41.2, and 42.1 were recovered from AD donors and react with the CBTAU-22.1 cognate peptide. Similar to CBTAU-22.1, these mAbs are phospho-dependent as shown in FIGS. 1J-1L Two additional mAbs (CBTAU-44.1 and CBTAU-45.1) were identified from non-AD (55+y.o.) individuals with reactivity to the CBTAU-22.1 cognate peptide. As expected, these two were also phospho-dependent (FIGS. 1N and 1O). CBTAU-43.1 was also identified from screens conducted in non-AD (55+y.o.) individuals; however, the mAb was recovered with the CBTAU-27.1 cognate peptide and is specific to non-phosphorylated-tau (FIG. 1M). Lastly, CBTAU-46.1, 47.1, 47.2, and 49.1 were recovered from non-AD (18-27 y.o.) individuals with reactivity to the CBTAU-28.1 peptide and, similar to CBTAU-28.1, are specific to non-phosphorylated-tau (FIGS. 1P-1S).

Example 7

Reactivity to Paired Helical Filaments and Recombinant Tau by ELISA

To further characterize the specificity of some of the chimeric antibodies, their reactivity to recombinant tau, enriched and immunopurified paired helical filaments was tested by ELISA.

PHF-tau was immunopurified according to the protocol of Greenberg and Davies. Briefly, cortical tissues corresponding to Alzheimer's disease individuals were homogenized with 10 volumes of cold buffer (10 mM Tris, pH 7.4, 1 mM EGTA, 0.8 M NaCL and 10% sucrose) and centrifuged at 27,200×g for 20 minutes at 4° C. N-lauroylsarcosine and 2-mercaptoethanol were added to the supernatant to reach a final concentration of 1% (wt/vol) and 1% (vol/vol), respectively. The mixture was incubated at 37° C. for 2-2.5 hours with constant rocking, followed by centrifugation at 108,000×g for 30 minutes at room temperature. The pellet containing PHF-tau was washed three times with PBS and dissolved in PBS without protein inhibitors and further centrifuged at 12,000×g for 5 minutes. The recovered supernatant containing enriched PHF-tau (ePHF-tau) was immunoaffinity purified over an hTau10 affinity column and eluted with 3M or 4 M KSCN overnight at 4° C., followed by dialysis against 1 L PBS at 4° C. with three changes of buffer. hTau10 is an antibody generated in house by immunizing with recombinant tau. It binds to both recombinant and PHF-tau at an amino-terminal epitope. The immunopurified PHF-tau (iPHF-tau) was concentrated with a Sartorius centrifugal filtering device.

For the ELISA, half-area 96-well binding plates (Costar) were coated with 50 µl of antigen in TBS (2 µg/ml recombinant tau, 2 µg/ml bovine action affinipure goat anti-human F(ab)2, 1 µg/ml of affinity-purified paired helical filaments, and 1 µg/ml of monoclonal anti-tau antibody, HT7 (Thermo Scientific, MN1000). The next day, plates were washed with TBS-T and subsequently blocked with 150 µl of TBS plus 2.5% BSA for 2 hours at RT. Following blocking, ePHF-tau was captured for 2 hours at RT on the anti-tau antibody-coated plate. Purified anti-tau IgGs were diluted to 10 µg/ml in TBS plus 0.25% BSA, and IgGs were titrated five-fold at RT for 2 hours. AT8 (10 µg/ml) was used as a positive control for iPHF-tau and captured ePHF-tau. Plates were washed five times with TBS-T and secondary antibodies, diluted in TBS plus 0.25% BSA, were added and incubated at RT for 1 hour. Goat Anti-Human IgG F(ab')2 (Jackson Labs) was used at a 1:2000 dilution and goat anti-mouse HRP (Jackson Labs) was used at 1:4000 (used for anti-actin control). Following incubation, plates were washed four times in TBS-T and developed with SureBlue Reserve TMB Microwell Peroxidase Substrate (KPL) for approximately 2 minutes. The reaction was immediately halted by the addition of TMB Stop Solution (KPL) and the absorbance at 450 nm was measured using an ELISA plate reader.

Figure 2A:
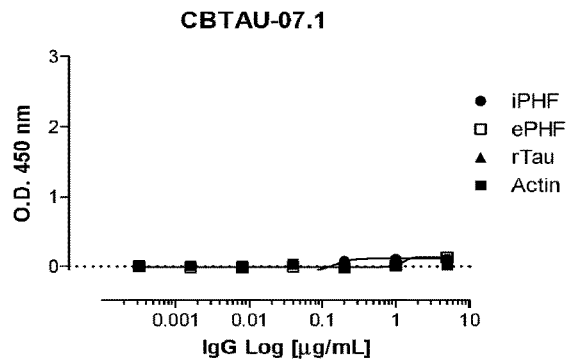
FIGS. 2A-2J show the reactivity of CBTAU-7.1, 8.1, 16.1, 18.1, 20.1, 22.1, 24.1, 27.1, and 28.1 against recombinant tau (rTau), enriched immunopurified paired helical filaments (ePHF), and immunopurified paired helical filaments (iPHF) by ELISA. Anti-tau mAb, ATB, was used as positive control.
Figure 2B:
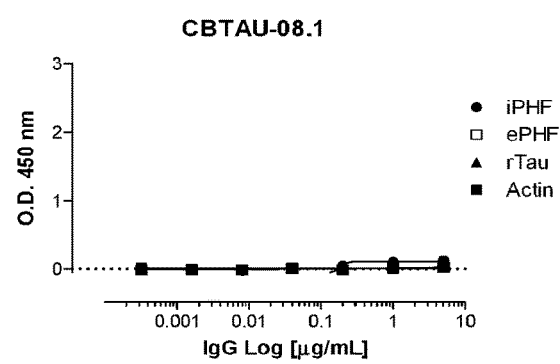
Figure 2C:
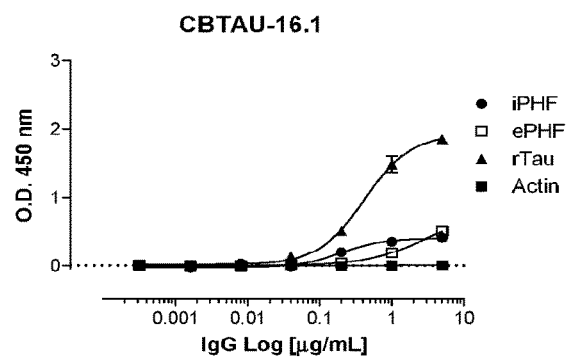
Figure 2D:
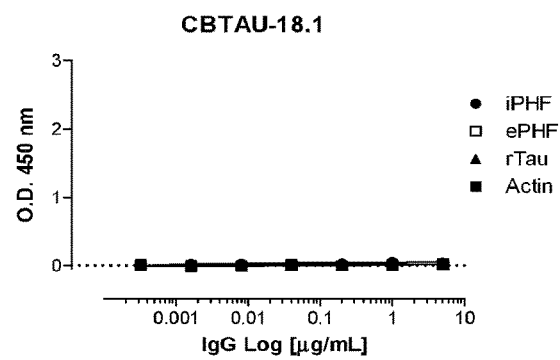
Figure 2E:
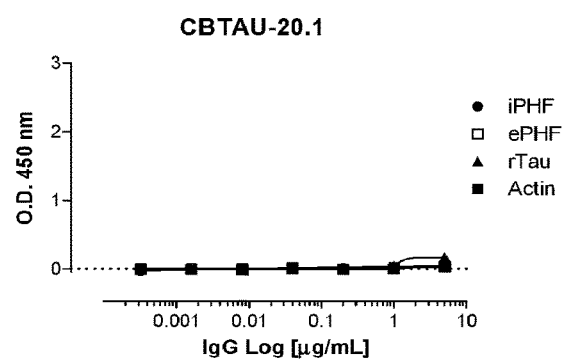
Figure 2F:
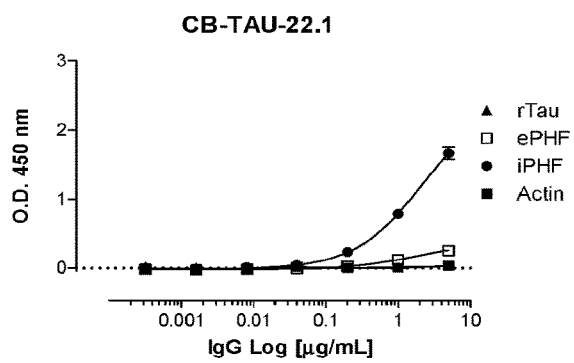

Results are shown in FIGS. 2A-2J. As expected, phospho-dependent mAbs CBTAU-7.1, CBTAU-8.1, and CBTAU-18.1 do not react to recombinant tau by ELISA (FIGS. 2A, 2B, and 2D). CBTAU-20.1 shows minor reactivity to recombinant tau consistent with its weak reactivity to a non-phosphorylated peptide spanning region 42-103. Interestingly, these phospho-dependent mAbs do not show any reactivity to paired helical filaments (i.e., ePHF-tau and iPHF-tau) with the exception of CBTAU-7.1, which shows minor reactivity to ePHF-tau at higher antibody concentrations. Lastly, phospho-dependent CBTAU-22.1 shows no reactivity to recombinant tau, but does react to both iPHF-tau and ePHF-tau (FIG. 2F).

Figure 2G:
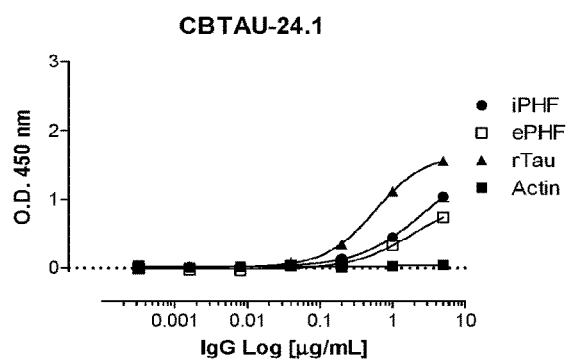
Figure 2H:
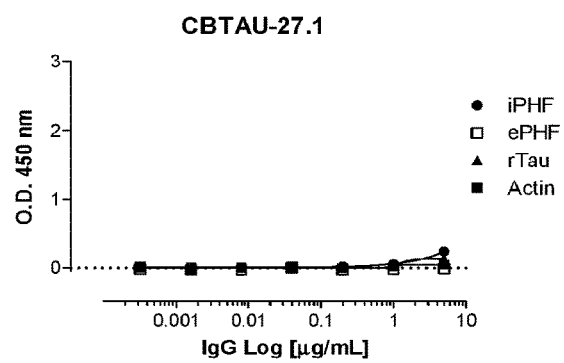
Figure 2I:
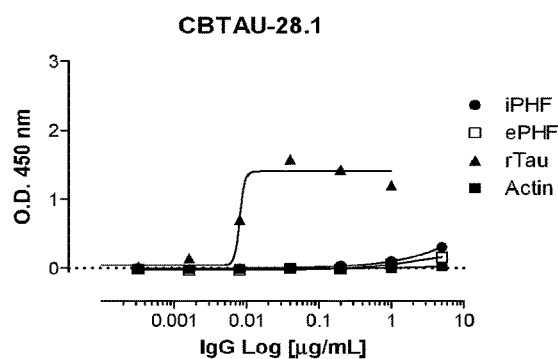
Figure 2J:
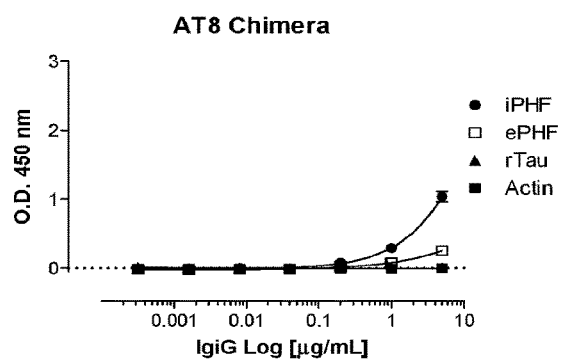

Phospho-independent anti-tau mAbs, CBTAU-16.1 and CBTAU-24.1 react to both recombinant tau and both formats of paired helical filaments (i.e., iPHF-tau and ePHF-tau; FIGS. 2C and 2G). CBTAU-28.1 shows strong binding to recombinant tau, with weak immunoreactivity to both PHF-tau formats (FIG. 2I). Finally, CBTAU-27.1 shows weak immunoreactivity to both recombinant tau and PHF-tau (FIG. 1H).

Example 8

Reactivity to Paired Helical Filaments and Recombinant Tau by Western Blot Analysis To extend the observations of the rTau- and PHF-binding ELISAs and to examine if secondary structure plays a role in reactivity, recombinant tau, enriched and immunopurified paired helical filaments were tested by Western blot analysis. Approximately 0.5 µg of iPHF, ePHF, and 1 µg of rTau at a final concentration of 1× NuPAGE® LDS Sample buffer (0.5% LDS final) (Novex, NP0007) was heated at 70° C. for 10 minutes. Samples were loaded onto a 26-well, 4-12% Bis-Tris NOVEX® NuPAGE® gel (Invitrogen) with MOPS SDS running buffer (Novagen, NP0001), and subsequently transferred onto a nitrocellulose membrane. Membrane was blocked overnight in 1× Tris Buffered Saline (TBS) with 0.05% TWEEN®-20 and 4% non-fat dry milk. CBTAU mAbs were used as primary at 25 µg/mL in 1×TBS with 0.05% TWEEN®-20 and 4% non-fat dry milk and incubated for 2 hours at room temperature. The membrane was then washed three times for 5 minutes each in 1×TBS with 0.05% TWEEN®-20. Peroxidase AffiniPure goat anti-human IgG, Fcy fragment specific (Jackson ImmunoResearch) was then used as secondary at a 1:2000 dilution in 1×TBS with 0.05% TWEEN®-20 and 4% non-fat dry milk and incubated for 45 minutes at RT. The membrane was washed three times for 5 minutes each and developed using the SUPERSIGNAL® West Pico kit (Pierce).

Figure 3:
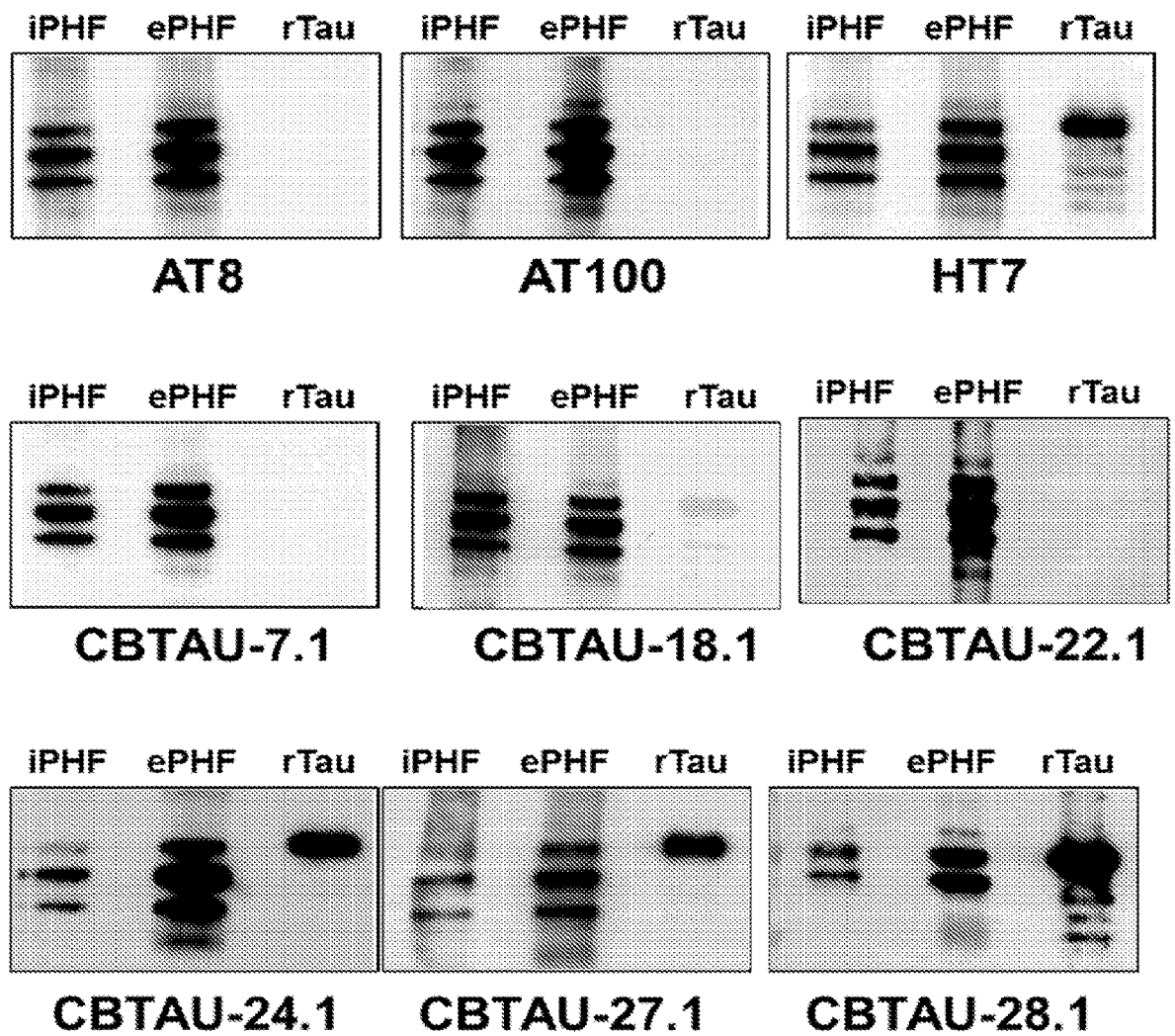
FIG. 3 shows the immunoreactivity of CBTAU-7.1, 18.1, 22.1, 24.1, 27.1, and 28.1 against rTau, ePHF, and iPHF by Western blot analysis.

The results for the Western blot analysis are shown in FIG. 3. FIG. 3 shows reactivity of three control antibodies, AT8, AT100, and HT7 (two phospho-tau-specific and total tau-specific, respectively). Both AT8 and AT100 show the triple bands characteristic of PHF-tau, which correspond to approximately 68, 64, and 60 kDa. Contrary to the ELISA results, phospho-dependent mAbs, CBTAU-7.1 and CBTAU-18.1 react to both iPHF-tau and ePHF-tau by Western blot, suggesting that the epitopes for these mAbs are not accessible when tau adopts higher order conformations present in PHF-tau. However, these epitopes become accessible under the strong denaturing conditions of SDS-PAGE. CBTAU-27.1 shows binding to recombinant tau and PHF by Western blot yet weak reactivity to each by ELISA, suggesting that the epitope for this antibody is only exposed under strong denaturing conditions. CBTAU-28.1 reacts strongly to recombinant tau by both Western blot and ELISA, and also shows reactivity to PHF-tau by both assays. CBTAU-28.1 reacts to the E1/E2 region of tau (amino acids 42-103), which is not present in all tau isoforms; therefore, only the 68 and 64 kDa bands on PHF-tau are detected by CBTAU-28.1. Finally, CBTAU-22.1 and CBTAU-24.1 show similar results to the ELISA assay, reacting to either PHF-tau but not recombinant tau and to both PHF-tau and recombinant tau, respectively.

Example 9

Reactivity to Tau Fragment Peptides by ELISA

To characterize the specificity of the recovered antibodies, their reactivity to tau phosphorylated and non-phosphorylated peptides (Tables 11-21, FIGS. 4A-4G) was tested by ELISA. Biotinylated tau peptides were synthesized commercially and dissolved in water at 1 mg/ml and frozen at −80° C. Briefly, 96-well streptavidin-binding plates (Thermo-Fisher) were coated with 2 µg/ml of tau peptides diluted in TBS and incubated overnight at 4° C. The following day, plates were washed with TBS-T and subsequently blocked with 2.5% BSA in TBS for 2 hours at RT. Following blocking, purified anti-tau IgGs were diluted to 2 µg/ml (or to 5 µg/ml and titrated five-fold for finer mapping of CBTAU-27.1, 28.1, 43.1, 46.1, 47.1, 47.2, and 49.1 using peptide sequences in Tables 15-20) in TBS plus 0.25% BSA and incubated at RT for 2 hours. The human-chimerized version of AT8 IgG (at 2 µg/ml) described in Example 11 was used as a positive control in each of the mapping experiments. Plates were washed five times with TBS-T followed by the addition of secondary antibody [goat Anti-Human IgG F(ab')2 (Jackson Labs) at 1:2000 dilution], diluted in TBS plus 0.25% BSA, and incubated at RT for 1 hour. Following incubation, plates were washed four times in TBS-T and developed with SureBlue Reserve TMB Microwell Peroxidase Substrate (KPL) for approximately 90 seconds. The reaction was immediately halted by the addition of TMB Stop Solution (KPL) and the absorbance at 450 nm was measured using an ELISA plate reader. Each experiment was conducted in triplicate across three different days. Reactivity was considered positive when values were equal to or higher than an OD of 0.4 in the ELISA assay. For determining the reactivity of each mAb to tau-phosphorylated and non-phosphorylated peptides, antibody reactivity at 2 µg/mL was determined by ELISA and scored as no binding (−), weak (−/+), moderate (+), or strong (++). (−) for average of two O.D. 450 nm readings <0.3; (−/+) for >0.5 and <1.0; (+) for >1.0 and <1.5; (++) for >1.5. For finer mapping of CBTAU-27.1, 28.1, 43.1, 46.1, 47.1, 47.2, and 49.1 (detailed on Tables 15-20), antibody reactivity at 1 µg/mL was determined by ELISA and scored as no binding (−), weak (−/+), moderate (+), or strong (++). (−) for average of three O.D. 450 nm readings <0.3; (−/+) for >0.5 and <1.0; (+) for >1.0 and <1.5; (++) for >1.5.

TABLE 11

CBTAU-7.1: Peptides for reactivity by ELISA

| Peptide | SEQ ID NO. | Peptide sequence (pX) denotes phosphorylated amino acid | Results |
|---|---|---|---|
| tau 186-253 | 321 | GEPPKSGDRSGYSSPGSPGTPGSRSRTPSLPTPPTREP KKVAVVRTPPKSPSSAKSRLQTAPVPMPDL | − |
| ptau 187-212 | 334 | EPPKSGDRSG(pY)SSPGSPG(pT)PGSRSRT | −/+ |
| ptau 188-205 | 335 | PPKSGDRSGY(pS)SPGSPGT | − |
| ptau 188-206 | 336 | PPKSGDRSGY(pS(pS)PGSPGTP | − |
| ptau 188-209 | 337 | PPKSGDRSGY(pS)SPG(pS)PGTPGSR | ++ |
| ptau 188-212 | 338 | PPKSGDRSGY(pS)SPGSPG(pT)PGSRSRT | −/+ |
| ptau 189-206 | 339 | PKSGDRSGYS(pS)PGSPGTP | − |
| ptau 189-209 | 340 | PKSGDRSGYS(pS)PG(pS)PGTPGSR | − |
| ptau 189-212 | 341 | PKSGDRSGYS(pS)PGSPG(pT)PGSRSRT | + |
| tau 190-209 | 342 | KSGDRSGYSSPGSPGTPGSR | − |
| ptau 192-209 | 343 | GDRSGYSSPG(pS)PGTPGSR | − |
| ptau 192-212 | 344 | GDRSGYSSPG(pS)PG(pT)PGSRSRT | + |
| ptau 192-215 | 345 | GDRSGYSSPG(pS)PGTPG(pS)RSRTPSL | − |
| ptau 192-217 | 346 | GDRSGYSSPG(pS)PGTPGSR(pS)RTPSLPT | − |
| ptau 194-212 | 315 | RSGYSSPG(pS)PG(pT)PGSRSRT | + |
| tau 194-212 | 316 | RSGYSSPGSPGTPGSRSRT | − |

TABLE 12

CBTAU-18.1: Peptides for reactivity by ELISA

| Peptide | SEQ ID NO. | Peptide sequence (pX) denotes phosphorylated amino acid | Results |
|---|---|---|---|
| ptau 186-253 | 321 | GEPPKSGDRSGYSSPGSPGTPGSRSRTPSLPTPPTREP KKVAVVRTPPKSPSSAKSRLQTAPVPMPDL | − |
| ptau 192-217 | 346 | GDRSGYSSPG(pS)PGTPGSR(pS)RTPSLPT | ++ |
| ptau 194-212 | 315 | RSGYSSPG(pS)PG(pT)GSRSRT | − |
| tau 194-212* | 316 | RSGYSSPGSPGTPGSRSRT | − |
| ptau 195-212 | 347 | SGYSSPGSPG(pT)PGSRSRT | − |
| ptau 195-215 | 348 | SGYSSPGSPG(pT)PG(pS)RSRTPSL | − |
| ptau 195-217 | 349 | SGYSSPGSPG(pT)PGSR(pS)RTPSLPT | ++ |
| ptau 195-219 | 350 | SGYSSPGSPG(pT)PGSRSR(pT)PSLPTPP | − |
| tau 195-214 | 351 | SGYSSPGSPGTPGSRSRTPS | − |
| ptau 198-215 | 352 | SSPGSPGTPG(pS)RSRTPSL | − |
| ptau 198-217 | 353 | SSPGSPGTPG(pS)R(pS)RTPSLPT | ++ |
| ptau 198-219 | 354 | SSPGSPGTPG(pS)RSR(pT)PSLPTPP | −/+ |
| ptau 198-221 | 355 | SSPGSPGTPG(pS)RSRTP(pS)LPTPPTR | − |
| tau 198-217 | 356 | SSPGSPGTPGSRSRTPSLPT | − |
| ptau 200-217 | 319 | PGSPGTPGSR(pS)RTPSLPT | + |
| tau 200-217 | 320 | PGSPGTPGSRSRTPSLPT | − |
| ptau 200-219 | 357 | PGSPGTPGSR(pS)R(pT)PSLPTPP | −/+ |
| ptau 200-221 | 358 | PGSPGTPGSR(pS)RTP(pS)LPTPPTR | − |
| ptau 200-224 | 359 | PGSPGTPGSR(pS)RTPSLP(pT)PPTREPK | − |

TABLE 13

CBTAU-22.1: Peptides for reactivity by ELISA

| Peptide | SEQ ID NO. | Peptide sequence (pX) denotes phosphorylated amino acid | Results |
|---|---|---|---|
| ptau 404-421 | 360 | SPRHLSNVSS(pT)GSIDMVD | − |
| ptau 404-429 | 361 | SPRHLSNVSS(pT)GSIDMVD(pS)PQLATLA | ++ |
| tau 405-423 | 362 | PRHLSNVSSTGSIDMVDSP | − |
| ptau 406-423 | 363 | RHLSNVSSTG(pS)IDMVDSP | − |
| ptau 406-429 | 326 | RHLSNVSSTG(pS)IDMVD(pS)PQLATLA | ++ |
| tau 409-428 | 364 | SNVSSTGSIDMVDSPQLATL | − |
| ptau 412-429 | 365 | SSTGSIDMVD(pS)PQLATLA | ++ |
| ptau 412-434 | 366 | SSTGSIDMVD(pS)PQLA(pT)LADEVSA | ++ |

TABLE 14

CBTAU-24.1: Peptides for reactivity by ELISA

| Peptide | SEQ ID NO. | Peptide sequence (pX) denotes phosphorylated amino acid | Results |
|---|---|---|---|
| tau 221-253 | 367 | GEPPKSGDRSGYSSPGSPGTPGSRSRTPSLPTPPTREP KKVAVVRTPPKSPSSAKSRLQTAPVPMPDL | ++ |
| ptau 221-238 | 368 | REPKKVAVVR(pT)PPKSPSS | − |
| ptau 221-242 | 369 | REPKKVAVVR(pT)PPK(pS)PSSAKSR | − |
| ptau 221-244 | 370 | REPKKVAVVR(pT)PPKSP(pS)SAKSRLQ | − |
| ptau 221-245 | 328 | REPKKVAVVR(pT)PPKSPS(pS)AKSRLQT | ++ |
| ptau 225-242 | 371 | KVAVVRTPPK(pS)PSSAKSR | − |
| ptau 225-244 | 372 | KVAVVRTPPK(pS)P(pS)SAKSRLQ | −/+ |
| ptau 225-245 | 330 | KVAVVRTPPK(pS)PS(pS)AKSRLQT | ++ |
| ptau 227-244 | 373 | AVVRTPPKSP(pS)SAKSRLQ | ++ |
| ptau 227-245 | 374 | AVVRTPPKSP(pS)(pS)AKSRLQT | ++ |
| ptau 228-245 | 329 | VVRTPPKSPS(pS)AKSRLQT | ++ |

TABLE 15

CBTAU-27.1: Peptides for reactivity by ELISA

| Peptide | SEQ ID NO. | Peptide sequence (pX) denotes phosphorylated amino acid | Results |
|---|---|---|---|
| Cluster 1 | | | |
| tau 299-369 | 331 | HVPGGGSVQIVYKPVDLSKVTSKCGSLGNIHH KPGGGQVEVKSEKIDFKDRVQSKIGSLDNIT HVPGGGNK | ++ |
| Cluster 2 | | | |
| ptau 404-421 p414 | 360 | SPRHLSNVSS(pT)GSIDMVD | − |
| ptau 404-429 p414, 422 | 361 | SPRHLSNVSS(pT)GSIDMVD(pS)PQLATLA | −/+ |
| ptau 406-423 p416 | 363 | RHLSNVSSTG(pS)DMVDSP | − |
| ptau 406-429 p416, 422 | 326 | RHLSNVSSTG(pS)IDMVD(pS)PQLATLA | −/+ |
| ptau 412-429 p422 | 365 | SSTGSIDMVD(pS)PQLATLA | −/+ |
| ptau 412-434 p422, 427 | 366 | SSTGSIDMVD(pS)PQLA(pT)LADEVSA | −/+ |
| tau 299-318 | 375 | HVPGGGSVQIVYKPVDLSKV | + |
| tau 309-328 | 376 | VYKPVDLSKVTSKCGSLGNI | −/+ |
| tau 319-338 | 377 | TSKCGSLGNIHHKPGGGQVE | − |
| tau 329-348 | 378 | HHKPGGGQVEVKSEKIDFKD | − |
| tau 339-358 | 379 | VKSEKIDFKDRVQSKIGSLD | − |
| tau 349-369 | 380 | RVQSKIGSLDNITHVPGGGNK | − |

TABLE 16

CBTAU-28.1: Peptides for reactivity by ELISA

| Peptide | SEQ ID NO. | Peptide sequence | Results |
|---|---|---|---|
| tau 42-103 | 325 | GLKFSPLQTPTEDGSEEPGSETSD AKSTPTAEDVTAPLVDEGAPGKQA AAQPHTEIPEGTTA | ++ |
| tau 42-61 | 381 | GLKFSPLQTPTEDGSEEPGS | − |
| tau 52-71 | 382 | TEDGSEEPGSETSDAKSTPT | ++ |
| ptau 58-75 | 383 | EPGSETSDAK(pS)TPTAEDV | − |
| tau 62-81 | 384 | ETSDAKSTPTAEDVTAPLVD | − |
| tau 72-91 | 385 | AEDVTAPLVDEGAPGKQAAA | − |
| tau 82-103 | 386 | EGAPGKQAAAQPHTEIPEGTTA | − |

TABLE 17

CBTAU-43.1: Peptides for reactivity by ELISA

| Peptide | SEQ ID NO. | Peptide sequence | Results |
|---|---|---|---|
| tau 299-369 | 331 | HVPGGGSVQIVYKPVDLSKVTSKCGSLGNIHHKPGGGQVEVKSEKIDFKDRVQSKIGSLDNITHVPGGGNK | ++ |
| tau 299-318 | 375 | HVPGGGSVQIVYKPVDLSKV | ++ |
| tau 309-328 | 376 | VYKPVDLSKVTSKCGSLGNI | ++ |
| tau 319-338 | 377 | TSKCGSLGNIHHKPGGGQVE | – |
| tau 329-348 | 378 | HHKPGGGQVEVKSEKIDFKD | – |
| tau 339-358 | 379 | VKSEKIDFKDRVQSKIGSLD | – |
| tau 349-369 | 380 | RVQSKIGSLDNITHVPGGGNK | – |

TABLE 18

CBTAU-46.1: Peptides for reactivity by ELISA

| Peptide | SEQ ID NO. | Peptide sequence | Results |
|---|---|---|---|
| tau 42-103 | 325 | GLKFSPLQTPTEDGSEEPGSETSDAKSTPTAEDVTAPLVDEGAPGKQAAAQPHTEIPEGTA | ++ |
| tau 42-61 | 381 | GLKFSPLQTPTEDGSEEPGS | – |
| tau 52-71 | 382 | TEDGSEEPGSETSDAKSTPT | – |
| tau 62-81 | 384 | ETSDAKSTPTAEDVTAPLVD | – |
| tau 72-91 | 385 | AEDVTAPLVDEGAPGKQAAA | – |
| tau 82-103 | 386 | EGAPGKQAAAQPHTEIPEGTTA | ++ |

TABLE 19

CBTAU-47.1 and CBTAU-47.2: Peptides for reactivity by ELISA

| Peptide | SEQ ID NO. | Peptide sequence | Results |
|---|---|---|---|
| tau 42-103 | 325 | GLKFSPLQTPTEDGSEEPGSETSDAKSTPTAEDVTAPLVDEGAPGKQAAAQPHTEIPEGTIA | ++ |
| tau 42-61 | 381 | GLKFSPLQTPTEDGSEEPGS | – |
| tau 52-71 | 382 | TEDGSEEPGSETSDAKSTPT | ++ |
| tau 62-81 | 384 | ETSDAKSTPTAEDVTAPLVD | – |
| tau 72-91 | 385 | AEDVTAPLVDEGAPGKQAAA | – |
| tau 82-103 | 386 | EGAPGKQAAAQPHTEIPEGTTA | – |

TABLE 20

CBTAU-49.1: Peptides for reactivity by ELISA

| Peptide | SEQ ID NO. | Peptide sequence | Results |
|---|---|---|---|
| tau 42-103 | 325 | GLKFSPLQTPTEDGSEEPGSETSDAKSTPTAEDVTAPLVDEGAPGKQAAAQPHTEIPEGTIA | ++ |
| tau 42-61 | 381 | GLKFSPLQTPTEDGSEEPGS | – |
| tau 52-71 | 382 | TEDGSEEPGSETSDAKSTPT | ++ |
| tau 62-81 | 384 | ETSDAKSTPTAEDVTAPLVD | – |
| tau 72-91 | 385 | AEDVTAPLVDEGAPGKQAAA | – |
| tau 82-103 | 386 | EGAPGKQAAAQPHTEIPEGTTA | – |

TABLE 20

AT8 Peptides for reactivity by ELISA

| Peptide | SEQ ID NO. | Peptide sequence (pX) denotes phosphorylated amino acid | Result |
|---|---|---|---|
| ptau 189-212 | 341 | PKSGDRSGYS(pS)PGSPG(pT)PGSRSRT | – |
| tau 192-211 | 387 | GDRSGYSSPGSPGTPGSRSR | – |
| ptau 192-209 | 343 | GDRSGYSSPG(pS)PGTPGSR | – |
| ptau 192-212 | 344 | GDRSGYSSPG(pS)PG(pT)PGSRSRT | ++ |
| ptau 192-215 | 345 | GDRSGYSSPG(pS)PGTPG(pS)RSRTPSL | – |
| ptau 192-217 | 346 | GDRSGYSSPG(pS)PGTPGSR(pS)RTPSLPT | – |
| ptau 194-212 | 315 | RSGYSSPG(pS)PG(pT)PGSRSRT | ++ |
| tau 194-212* | 316 | RSGYSSPGSPGTPGSRSRT | – |
| ptau 195-212 | 347 | SGYSSPGSPG(pT)PGSRSRT | – |

Although CBTAU-7.1 was recovered using a peptide that contains the AT8 epitope (Table 21; 192-212; pS202, pT205), the phospho-residues contributing to binding for CBTAU-7.1 appeared to be promiscuous involving positions S202+T205, but also combinations of S198+S202, S198+T205, S199+T205 and possibly Y197+T205. Unphosphorylated peptides showed no reactivity to CBTAU-7.1. For CBTAU-18.1, the minimal epitope was found to consist of amino acids 198-217 and dependent on pS210 but not when T212, S214 or T217 were also phosphorylated. CBTAU-22.1 reactivity was found to be dependent on pS422, while antibody CBTAU-24.1 revealed strong binding to its corresponding unphosphorylated peptide and, thus, unaffected by phosphorylation.

Figure 4A:
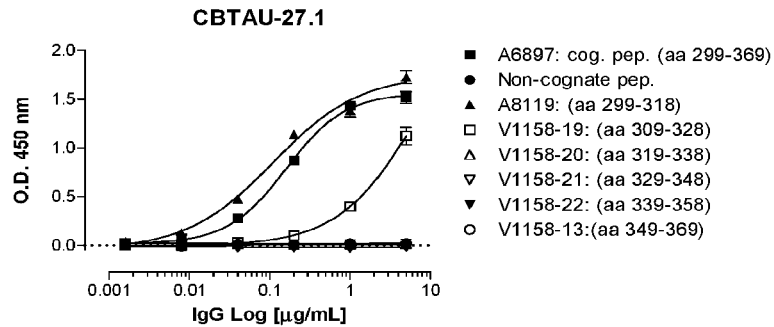
FIGS. 4A-4G show the epitope mapping of CBTAU-27.1, 28.1, 43.1, 46.1, 47.1, 47.2, and 49.1 using overlapping peptides that correspond to regions 42-103 and 299-369 on human tau441.
Figure 4B:
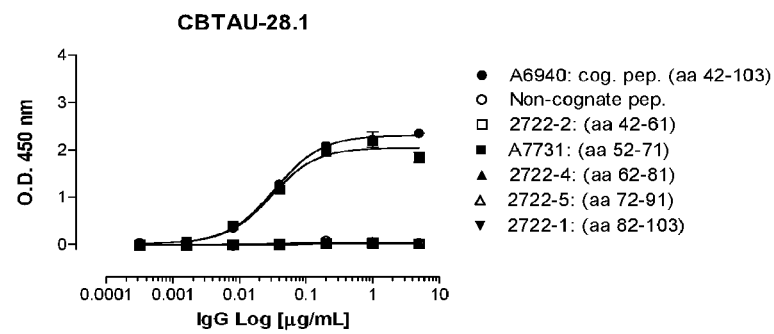
Figure 4C:
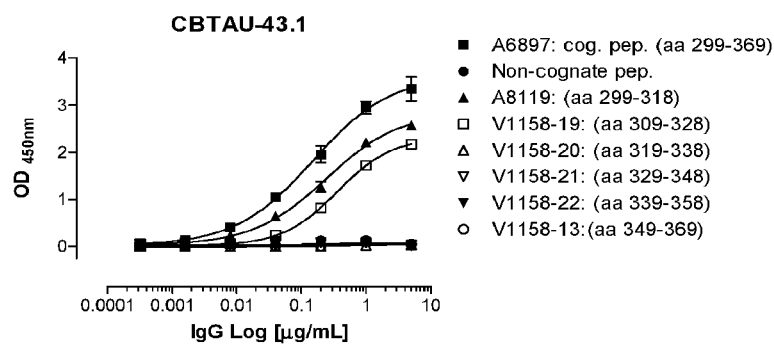
Figure 4D:
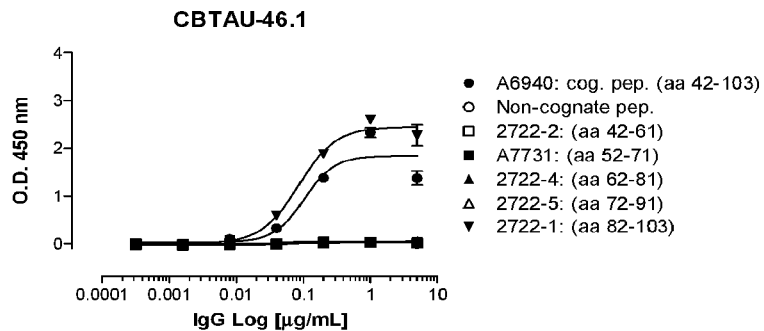
Figure 4E:
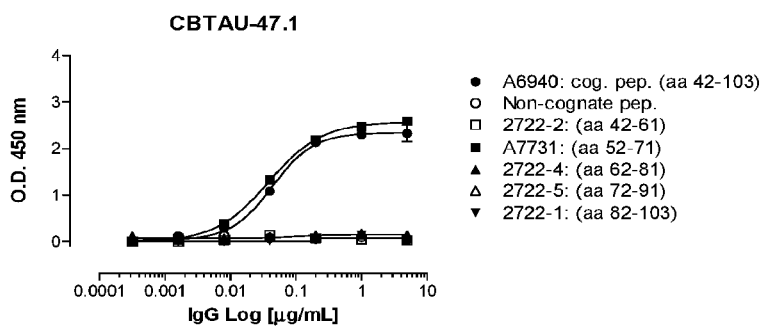
Figure 4F:
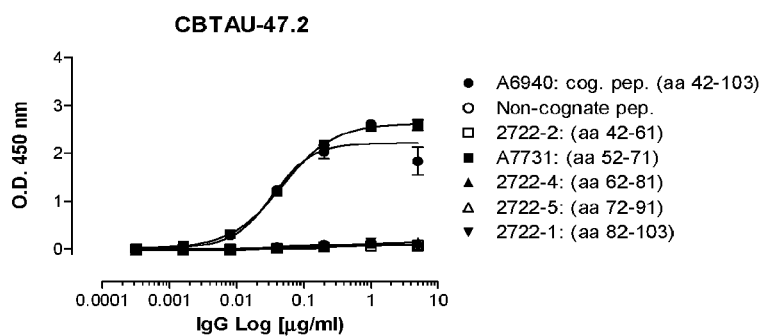
Figure 4G:
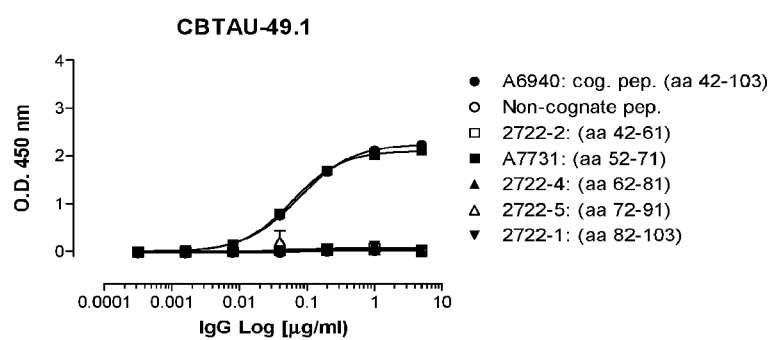

CBTAU-27.1 and CBTAU-43.1 were recovered using an unphosphorylated peptide spanning amino acids 299-369. Interestingly, overlapping peptides within this region revealed similar binding requirements for both mAbs (i.e., CBTAU-27.1 and CBTAU-43.1 reacted to peptides spanning amino acids 299-318 and 309-328, respectively), suggesting that the epitope for both mAbs is within regions 299-328 on tau441 (FIGS. 4A and 4C).

CBTAU-28.1, 46.1, 47.1, 47.2, and 49.1 were recovered from human donor samples using a peptide spanning regions 42-103 on tau441. Testing the reactivity of each mAb against a smaller overlapping set of peptides showed similar binding for CBTAU-47.1, 47.2, and 49.1 as CBTAU-28.1 (i.e., reactivity to a peptide spanning regions 52-71), suggesting comparable binding requirements; however, CBTAU-46.1 bound to a region C-terminal to the aforementioned mAbs (i.e., 82-1031; FIGS. 4B and 4D-4G).

Example 10

Alanine Scanning of Peptide Epitopes

To further characterize the specificity and amino acid contribution to binding of each of the recover mAbs, their reactivity to tau peptides with each position replaced with Alanine was tested by ELISA. All experimental protocols were identical to Example 9. Antibody reactivity at 1 µg/mL was determined by ELISA and scored as no binding (−), weak (−/+), moderate (+), or strong (++). (−) for average of two O.D. 450 nm readings <0.3; (−/+) for >0.5 and <1.0; (+) for >1.0 and <1.5; (++) for >1.5. Results for each antibody are shown in Tables 22-29.

TABLE 22

Alanine scanning results for CBTAU-7.1 and CBTAU-8.1

| Region (Tau441) | SEQ ID NO | Peptide sequence (pX) denotes phosphorylated amino acid | Results 7.1 | Results 8.1 |
|---|---|---|---|---|
| ptau 187-212 | 334 | EPPKSGDRSGYSSPG(pS)PG(pT)PGSRSRT | ++ | ++ |
| ptau 187-212 (A187) | 388 | APPKSGDRSGYSSPG(pS)PG(pT)PGSRSRT | + | ++ |
| ptau 187-212 (A18) | 389 | EAPKSGDRSGYSSPG(pS)PG(pT)PGSRSRT | + | ++ |
| ptau 187-212 (A19) | 390 | EPAKSGDRSGYSSPG(pS)PG(pT)PGSRSRT | + | ++ |
| ptau 187-212 (A10) | 391 | EPPASGDRSGYSSPG(pS)PG(pT)PGSRSRT | ++ | ++ |
| ptau 187-212 (A191) | 392 | EPPKAGDRSGYSSPG(pS)PG(pT)PGSRSRT | ++ | ++ |
| ptau 187-212 (A12) | 393 | EPPKSADRSGYSSPG(pS)PG(pT)PGSRSRT | ++ | ++ |
| ptau 187-212 (A193) | 394 | EPPKSGARSGYSSPG(pS)PG(pT)PGSRSRT | ++ | ++ |
| ptau 187-212 (A194) | 395 | EPPKSGDASGYSSPG(pS)PG(pT)PGSRSRT | ++ | ++ |
| ptau 187-212 (A195) | 396 | EPPKSGDRAGYSSPG(pS)PG(pT)PGSRSRT | ++ | ++ |
| ptau 187-212 (A196) | 397 | EPPKSGDRSAYSSPG(pS)PG(pT)PGSRSRT | ++ | ++ |
| ptau 187-212 (A197) | 398 | EPPKSGDRSGASSPG(pS)PG(pT)PGSRSRT | ++ | ++ |
| ptau 187-212 (A198) | 399 | EPPKSGDRSGYASPG(pS)PG(pT)PGSRSRT | ++ | ++ |
| ptau 187-212 (A199) | 400 | EPPKSGDRSGYSAPG(pS)PG(pT)PGSRSRT | + | ++ |
| ptau 187-212 (A200) | 401 | EPPKSGDRSGYSSAG(pS)PG(pT)PGSRSRT | + | ++ |
| ptau 187-212 (A201) | 402 | EPPKSGDRSGYSSPA(pS)PG(pT)PGSRSRT | ++ | ++ |

TABLE 22-continued

Alanine scanning results for CBTAU-7.1 and CBTAU-8.1

| Region (Tau441) | SEQ

TABLE 23-continued

Alanine scanning results for CBTAU-22.1

| Region (Tau441) | SEQ ID NO | Peptide sequence (pX) denotes phosphorylated amino acid | Results |
|---|---|---|---|
| ptau 406-429 (A421) | 429 | RHLSNVSSTG(pS)IDMVA(pS)PQLATLA | -/+ |
| ptau 406-429 (A422) | 430 | RHLSNVSSTG(pS)IDMVDAPQLATLA | - |
| ptau 406-429 (A423) | 431 | RHLSNVSSTG(pS)IDMVD(pS)AQLATLA | + |
| ptau 406-429 (A424) | 432 | RHLSNVSSTG(pS)IDMVD(pS)PALATLA | ++ |
| ptau 406-429 (A425) | 433 | RHLSNVSSTG(pS)IDMVD(pS)PQAATLA | + |
| ptau 406-429 (A427) | 434 | RHLSNVSSTG(pS)IDMVD(pS)PQLAALA | ++ |
| ptau 406-429 (A428) | 435 | RHLSNVSSTG(pS)IDMVD(pS)PQLATAA | ++ |

TABLE 24

CBTAU-24.1 Alanine Scan Results

| Region (Tau441) | SEQ ID NO | Peptide sequence (pX) denotes phosphorylated amino acid | Results |
|---|---|---|---|
| ptau 221-245 | 328 | REPKKVAVVR(pT)PPKSPS(pS)AKSRLQT | ++ |
| ptau 221-245 (A222) | 436 | RAPKKVAVVR(pT)PPKSPS(pS)AKSRLQT | ++ |
| ptau 221-245 (A223) | 437 | REAKKVAVVR(pT)PPKSPS(pS)AKSRLQT | ++ |
| ptau 221-245 (A224) | 438 | REPAKVAVVR(pT)PPKSPS(pS)AKSRLQT | ++ |
| ptau 221-245 (A225) | 439 | REPKAVAVVR(pT)PPKSPS(pS)AKSRLQT | ++ |
| ptau 221-245 (A226) | 440 | REPKKAAVVR(pT)PPKSPS(pS)AKSRLQT | ++ |
| ptau 221-245 (A228) | 441 | REPKKVAAVR(pT)PPKSPS(pS)AKSRLQT | ++ |
| ptau 221-245 (A229) | 442 | REPKKVAVAR(pT)PPKSPS(pS)AKSRLQT | ++ |
| ptau 221-245 (A230) | 443 | REPKKVAVVA(pT)PPKSPS(pS)AKSRLQT | ++ |
| ptau 221-245 (A231) | 444 | REPKKVAVVRAPPKSPS(pS)AKSRLQT | ++ |
| ptau 221-245 (A232) | 445 | REPKKVAVVR(pT)APKSPS(pS)AKSRLQT | ++ |
| ptau 221-245 (A233) | 446 | REPKKVAVVR(pT)PAKSPS(pS)AKSRLQT | ++ |
| ptau 221-245 (A234) | 447 | REPKKVAVVR(pT)PPASPS(pS)AKSRLQT | ++ |
| ptau 221-245 (A235) | 448 | REPKKVAVVR(pT)PPKAPS(pS)AKSRLQT | ++ |
| ptau 221-245 (A236) | 449 | REPKKVAVVR(pT)PPKSAS(pS)AKSRLQT | - |
| ptau 221-245 (A237) | 450 | REPKKVAVVR(pT)PPKSPA(pS)AKSRLQT | ++ |
| ptau 221-245 (A238) | 451 | REPKKVAVVR(pT)PPKSPSAAKSRLQT | ++ |
| ptau 221-245 (A240) | 452 | REPKKVAVVR(pT)PPKSPS(pS)AASRLQT | ++ |
| ptau 221-245 (A241) | 453 | REPKKVAVVR(pT)PPKSPS(pS)AKARLQT | ++ |
| ptau 221-245 (A242) | 454 | REPKKVAVVR(pT)PPKSPS(pS)AKSALQT | ++ |
| ptau 221-245 (A243) | 455 | REPKKVAVVR(pT)PPKSPS(pS)AKSRAQT | ++ |
| ptau 221-245 (A244) | 456 | REPKKVAVVR(pT)PPKSPS(pS)AKSRLAT | ++ |
| ptau 221-245 (A245) | 457 | REPKKVAVVR(pT)PPKSPS(pS)AKSRLQA | ++ |

TABLE 25

CBTAU-27.1 Alanine Scan Results

| Region (Tau441) | SEQ ID NO: | Peptide sequence | Results |
|---|---|---|---|
| tau 299-323 | 458 | HVPGGGSVQIVYKPVDLSKVTSKCG | ++ |
| tau 299-323 (A299) | 459 | AVPGGGSVQIVYKPVDLSKVTSKCG | ++ |
| tau 299-323 (A300) | 460 | HAPGGGSVQIVYKPVDLSKVTSKCG | ++ |
| tau 299-323 (A301) | 461 | HVAGGGSVQIVYKPVDLSKVTSKCG | ++ |
| tau 299-323 (A302) | 462 | HVPAGGSVQIVYKPVDLSKVTSKCG | ++ |
| tau 299-323 (A303) | 463 | HVPGAGSVQIVYKPVDLSKVTSKCG | ++ |

TABLE 25-continued

CBTAU-27.1 Alanine Scan Results

| Region (Tau441) | SEQ ID NO: | Peptide sequence | Results |
|---|---|---|---|
| tau 299-323 (A304) | 464 | HVPGGASVQIVYKPVDLSKVTSKCG | ++ |
| tau 299-323 (A305) | 465 | HVPGGGAVQIVYKPVDLSKVTSKCG | ++ |
| tau 299-323 (A306) | 466 | HVPGGGSAQIVYKPVDLSKVTSKCG | ++ |
| tau 299-323 (A307) | 467 | HVPGGGSVAIVYKPVDLSKVTSKCG | ++ |
| tau 299-323 (A308) | 468 | HVPGGGSVQAVYKPVDLSKVTSKCG | ++ |
| tau 299-323 (A309) | 469 | HVPGGGSVQIAYKPVDLSKVTSKCG | ++ |
| tau 299-323 (A310) | 470 | HVPGGGSVQIVAKPVDLSKVTSKCG | ++ |
| tau 299-323 (A311) | 471 | HVPGGGSVQIVYAPVDLSKVTSKCG | ++ |
| tau 299-323 (A312) | 472 | HVPGGGSVQIVYKAVDLSKVTSKCG | ++ |
| tau 299-323 (A313) | 473 | HVPGGGSVQIVYKPADLSKVTSKCG | ++ |
| tau 299-323 (A314) | 474 | HVPGGGSVQIVYKPVALSKVTSKCG | -/+ |
| tau 299-323 (A315) | 475 | HVPGGGSVQIVYKPVDASKVTSKCG | - |
| tau 299-323 (A316) | 476 | HVPGGGSVQIVYKPVDLAKVTSKCG | ++ |
| tau 299-323 (A317) | 477 | HVPGGGSVQIVYKPVDLSAVTSKCG | - |
| tau 299-323 (A318) | 478 | HVPGGGSVQIVYKPVDLSKATSKCG | ++ |
| tau 299-323 (A319) | 479 | HVPGGGSVQIVYKPVDLSKVASKCG | ++ |
| tau 299-323 (A320) | 480 | HVPGGGSVQIVYKPVDLSKVTAKCG | ++ |
| tau 299-323 (A321) | 481 | HVPGGGSVQIVYKPVDLSKVTSACG | ++ |
| tau 299-323 (A322) | 482 | HVPGGGSVQIVYKPVDLSKVTSKAG | ++ |
| tau 299-323 (A323) | 483 | HVPGGGSVQIVYKPVDLSKVTSKCA | ++ |

TABLE 26

CBTAU-28.1 Alanine Scan Results

| Region (Tau441) | SEQ ID NO | Peptide sequence | Results |
|---|---|---|---|
| tau 52-71 | 382 | TEDGSEEPGSETSDAKSTPT | ++ |
| tau 52-71 (A52) | 484 | AEDGSEEPGSETSDAKSTPT | ++ |
| tau 52-71 (A53) | 485 | TADGSEEPGSETSDAKSTPT | ++ |
| tau 52-71 (A54) | 486 | TEAGSEEPGSETSDAKSTPT | ++ |
| tau 52-71 (A55) | 487 | TEDASEEPGSETSDAKSTPT | ++ |
| tau 52-71 (A56) | 488 | TEDGAEEPGSETSDAKSTPT | ++ |
| tau 52-71 (A57) | 489 | TEDGSAEPGSETSDAKSTPT | ++ |
| tau 52-71 (A58) | 490 | TEDGSEAPGSETSDAKSTPT | ++ |
| tau 52-71 (A59) | 491 | TEDGSEEAGSETSDAKSTPT | -/+ |
| tau 52-71 (A60) | 492 | TEDGSEEPASETSDAKSTPT | ++ |
| tau 52-71 (A61) | 493 | TEDGSEEPGAETSDAKSTPT | ++ |
| tau 52-71 (A62) | 494 | TEDGSEEPGSATSDAKSTPT | - |
| tau 52-71 (A63) | 495 | TEDGSEEPGSEASDAKSTPT | -/+ |
| tau 52-71 (A64) | 496 | TEDGSEEPGSETADAKSTPT | ++ |
| tau 52-71 (A65) | 497 | TEDGSEEPGSETSAAKSTPT | - |
| tau 52-71 (A67) | 498 | TEDGSEEPGSETSDAASTPT | - |
| tau 52-71 (A68) | 499 | TEDGSEEPGSETSDAKATPT | ++ |
| tau 52-71 (A69) | 500 | TEDGSEEPGSETSDAKSAPT | ++ |
| tau 52-71 (A70) | 501 | TEDGSEEPGSETSDAKSTAT | ++ |
| tau 52-71 (A71) | 502 | TEDGSEEPGSETSDAKSTPA | ++ |

TABLE 27

CBTAU-43.1 Alanine Scan Results

| Region (Tau441) | SEQ ID NO: | Peptide sequence | Results |
|---|---|---|---|
| tau 299-323 | 458 | HVPGGGSVQIVYKPVDLSKVTSKCG | ++ |
| tau 299-323 (A299) | 459 | AVPGGGSVQIVYKPVDLSKVTSKCG | ++ |
| tau 299-323 (A300) | 460 | HAPGGGSVQIVYKPVDLSKVTSKCG | ++ |
| tau 299-323 (A301) | 461 | HVAGGGSVQIVYKPVDLSKVTSKCG | ++ |
| tau 299-323 (A302) | 462 | HVPAGGSVQIVYKPVDLSKVTSKCG | ++ |
| tau 299-323 (A303) | 463 | HVPGAGSVQIVYKPVDLSKVTSKCG | ++ |
| tau 299-323 (A304) | 464 | HVPGGASVQIVYKPVDLSKVTSKCG | ++ |
| tau 299-323 (A305) | 465 | HVPGGGAVQIVYKPVDLSKVTSKCG | ++ |
| tau 299-323 (A306) | 466 | HVPGGGSAQIVYKPVDLSKVTSKCG | ++ |
| tau 299-323 (A307) | 467 | HVPGGGSVAIVYKPVDLSKVTSKCG | ++ |
| tau 299-323 (A308) | 468 | HVPGGGSVQAVYKPVDLSKVTSKCG | ++ |
| tau 299-323 (A309) | 469 | HVPGGGSVQIAYKPVDLSKVTSKCG | ++ |
| tau 299-323 (A310) | 470 | HVPGGGSVQIVAKPVDLSKVTSKCG | ++ |

TABLE 27-continued

CBTAU-43.1 Alanine Scan Results

| Region (Tau441) | SEQ ID NO | Peptide sequence | Results |
|---|---|---|---|
| tau 299-323 (A311) | 471 | HVPGGGSVQIVYAPVDLSKVTSKCG | ++ |
| tau 299-323 (A312) | 472 | HVPGGGSVQIVYKAVDLSKVTSKCG | -/+ |
| tau 299-323 (A313) | 473 | HVPGGGSVQIVYKPADLSKVTSKCG | ++ |
| tau 299-323 (A314) | 474 | HVPGGGSVQIVYKPVALSKVTSKCG | ++ |
| tau 299-323 (A315) | 475 | HVPGGGSVQIVYKPVDASKVTSKCG | - |
| tau 299-323 (A316) | 476 | HVPGGGSVQIVYKPVDLAKVTSKCG | ++ |
| tau 299-323 (A317) | 477 | HVPGGGSVQIVYKPVDLSAVTSKCG | - |
| tau 299-323 (A318) | 478 | HVPGGGSVQIVYKPVDLSKATSKCG | ++ |
| tau 299-323 (A319) | 479 | HVPGGGSVQIVYKPVDLSKVASKCG | ++ |
| tau 299-323 (A320) | 480 | HVPGGGSVQIVYKPVDLSKVTAKCG | ++ |
| tau 299-323 (A321) | 481 | HVPGGGSVQIVYKPVDLSKVTSACG | ++ |
| tau 299-323 (A322) | 482 | HVPGGGSVQIVYKPVDLSKVTSKAG | ++ |
| tau 299-323 (A323) | 483 | HVPGGGSVQIVYKPVDLSKVTSKCA | ++ |

TABLE 28

CBTAU-47.1 and 47.2 Alanine Scan Results

| Region (Tau441) | SEQ ID NO | Peptide sequence | Results CBTAU-47.1 | Results CBTAU-47.2 |
|---|---|---|---|---|
| tau 52-71 | 382 | TEDGSEEPGSETSDAKSTPT | ++ | ++ |
| tau 52-71 (A52) | 484 | AEDGSEEPGSETSDAKSTPT | ++ | ++ |
| tau 52-71 (A53) | 485 | TADGSEEPGSETSDAKSTPT | ++ | ++ |
| tau 52-71 (A54) | 486 | TEAGSEEPGSETSDAKSTPT | ++ | ++ |
| tau 52-71 (A55) | 487 | TEDASEEPGSETSDAKSTPT | ++ | ++ |
| tau 52-71 (A56) | 488 | TEDGAEEPGSETSDAKSTPT | ++ | ++ |
| tau 52-71 (A57) | 489 | TEDGSAEPGSETSDAKSTPT | ++ | ++ |
| tau 52-71 (A58) | 490 | TEDGSEAPGSETSDAKSTPT | ++ | ++ |
| tau 52-71 (A59) | 491 | TEDGSEEAGSETSDAKSTPT | - | - |
| tau 52-71 (A60) | 492 | TEDGSEEPASETSDAKSTPT | ++ | ++ |
| tau 52-71 (A61) | 493 | TEDGSEEPGAETSDAKSTPT | -/+ | ++ |
| tau 52-71 (A62) | 494 | TEDGSEEPGSATSDAKSTPT | - | - |
| tau 52-71 (A63) | 495 | TEDGSEEPGSEASDAKSTPT | - | - |
| tau 52-71 (A64) | 496 | TEDGSEEPGSETADAKSTPT | ++ | ++ |
| tau 52-71 (A65) | 497 | TEDGSEEPGSETSAAKSTPT | - | - |
| tau 52-71 (A67) | 498 | TEDGSEEPGSETSDAASTPT | - | - |
| tau 52-71 (A68) | 499 | TEDGSEEPGSETSDAKATPT | ++ | ++ |
| tau 52-71 (A69) | 500 | TEDGSEEPGSETSDAKSAPT | ++ | ++ |
| tau 52-71 (A70) | 501 | TEDGSEEPGSETSDAKSTAT | ++ | ++ |
| tau 52-71 (A71) | 502 | TEDGSEEPGSETSDAKSTPA | ++ | ++ |

TABLE 29

CBTAU-49.1 Alanine Scan Results

| Region (Tau441) | SEQ ID NO | Peptide sequence | Results |
|---|---|---|---|
| tau 52-71 | 382 | TEDGSEEPGSETSDAKSTPT | ++ |
| tau 52-71 (A52) | 484 | AEDGSEEPGSETSDAKSTPT | ++ |
| tau 52-71 (A53) | 485 | TADGSEEPGSETSDAKSTPT | ++ |
| tau 52-71 (A54) | 486 | TEAGSEEPGSETSDAKSTPT | ++ |
| tau 52-71 (A55) | 487 | TEDASEEPGSETSDAKSTPT | ++ |
| tau 52-71 (A56) | 488 | TEDGAEEPGSETSDAKSTPT | ++ |
| tau 52-71 (A57) | 489 | TEDGSAEPGSETSDAKSTPT | ++ |
| tau 52-71 (A58) | 490 | TEDGSEAPGSETSDAKSTPT | ++ |
| tau 52-71 (A59) | 491 | TEDGSEEAGSETSDAKSTPT | - |
| tau 52-71 (A60) | 492 | TEDGSEEPASETSDAKSTPT | ++ |
| tau 52-71 (A61) | 493 | TEDGSEEPGAETSDAKSTPT | - |
| tau 52-71 (A62) | 494 | TEDGSEEPGSATSDAKSTPT | - |
| tau 52-71 (A63) | 495 | TEDGSEEPGSEASDAKSTPT | + |
| tau 52-71 (A64) | 496 | TEDGSEEPGSETADAKSTPT | + |
| tau 52-71 (A65) | 497 | TEDGSEEPGSETSAAKSTPT | - |
| tau 52-71 (A67) | 498 | TEDGSEEPGSETSDAASTPT | - |
| tau 52-71 (A68) | 499 | TEDGSEEPGSETSDAKATPT | + |
| tau 52-71 (A69) | 500 | TEDGSEEPGSETSDAKSAPT | + |
| tau 52-71 (A70) | 501 | TEDGSEEPGSETSDAKSTAT | + |
| tau 52-71 (A71) | 502 | TEDGSEEPGSETSDAKSTPA | + |

Although CBTAU-7.1 and CBTAU-8.1 were recovered using a tau phosphopeptide containing the AT8 epitope (i.e., pS202, pT205), both mAbs exhibited different epitope requirements according to the alanine scan results (Table 22). In addition to S202 and T205, substitutions at positions G204 and P206 resulted in reduced binding for CBTAU-7.1. In contrast, alanine substitutions at positions G204, T205, P206, and R209 reduced the reactivity of CBTAU-8.1 to the peptide, yet the S202A substitution had no effect. Like AT8, both mAbs are phospho-dependent, but require additional (non-phosphorylated residues) for binding. The alanine scan results for CBTAU-22.1 showed a dependency on phosphorylation at S422 (Table 23), as substitution at this position completed inhibited binding. Substitution at D421 resulted in a reduction but not a complete inhibition in binding. Finally, alanine scan results for CBTAU-24.1 showed P236 to be the only critical residue for binding (Table 24).

To map the critical contact residues for CBTAU-27.1 and 43.1, alanine scanning was also conducted within regions 299-323 of tau (Table 25 and Table 27, respectively). The critical contact residues for CBTAU-27.1 binding were shown to be D314, L315, and K317. The results suggest that residues D314 and K317 may form salt bridge interactions between the epitope and CDR residues on the mAb. While CBTAU-43.1 was recovered using the cognate peptide for CBAU-27.1, the critical residues according to the alanine scan were different. In addition to L315 and K317, the proline at position 312 was shown to be an important contact for CBTAU-43.1 binding. Lastly, alanine scanning was also conducted for CBTAU-28.1 as well as to CBTAU-47.1, 47.1, and 49.1 (Tables 26, 28, 29). As shown in Example 9, CBTAU mAbs 47.1, 47.2, 49.1 mapped to the same peptide region as CBTAU-28.1 (i.e., 52-71). Interestingly, all mAbs shared identical binding requirements as to CBTAU-28.1. The critical contact residues were shown to be P59, S61, E62, T63, D65, and K67. Several of these residues were found to be charged, implicating important salt bridge interactions between the epitope and the mAbs.

Example 11

Immunohistochemistry

Tau pathology is believed to initiate within the entorhinal cortex (EC) and spread along connected neuronal pathways in the hippocampus before progressing into the cortex. To determine the reactivity of the recovered IgGs to pathogenic deposits of tau along these neuronal pathways, hippocampal tissues were obtained from an 82-year-old, non-diseased (non-AD; Abcam, Cat No. ab4305) male and an 88-year-old Alzheimer's disease (AD; Abcam, Cat. No. ab4583) male (Abcam). Cortical tissues were obtained from a 71-year-old non-diseased (non-AD) and 71-year-old Alzheimer's disease (AD) individual (Banner Sun Health). In addition to AD, there are many neurological disorders that are characterized by tau pathology, also known as tauopathies. To extend the findings, the recovered mAbs were tested in tissues obtained from progressive supranuclear palsy (PSP) and non-progressive supranuclear palsy (non-PSP) frontal lobes obtained from a 73-year-old male and an 81-year-old female, respectively (Biochain). Brain tissues were de-paraffinized and rehydrated by washing twice for 10 minutes in xylene (VWR International), followed by washing twice for 3 minutes in 100% ethanol, twice for 3 minutes in 95% ethanol, twice for 3 minutes in 70% ethanol, and once for 30 seconds in distilled H2O using TISSUE-TEK® Slide Staining Set (VWR International). Tissue sections underwent heat-mediated antigen retrieval using citrate buffer (10 mM citric acid, pH 6.0) to expose antigenic sites. Sections were then incubated with blocking buffer [10% normal goat serum (Jackson ImmunoResearch, Inc.), 1% BSA and 0.3% TRITON® X-100 in PBS)] at RT for 1 hour. Excess water was removed and tissue sections were circled with an ImmEdge Hydrophobic Barrier Pen (Vector Labs). A humidified chamber was prepared by covering the bottom of a staining tray with H2O, and sections were then washed with PBS three times for 5 minutes by aspiration. Endogenous peroxidase activity was quenched in 10% H2O2 for 30 minutes at RT. Following quenching, slides were washed with PBS three times for 5 minutes by aspiration. Slides were then blocked for 1 hour at RT with a solution of 10% normal goat serum, 0.3% TRITON® X-100, 1% BSA in 1×PBS. Primary antibodies were labeled with biotin using the Zenon Human IgG Labeling Kit (Life Technologies) per manufacturer's instructions. As a negative control, a human anti-RSV-specific antibody was used. An Fc-region human-chimerized version of AT8 IgG was used as a positive control. After labeling, primary antibodies were diluted separately in blocking buffer at concentrations of 5 µg/ml and 20 µg/ml. For peptide competition experiments, 13.3 µM of cognate peptide (i.e., peptide used to recover the mAb in sorting experiments) was pre-incubated with the primary antibody for 30 minutes at RT prior to incubation with tissue sections. Tissue sections were incubated at RT for two hours with 100 µl of diluted biotin-labeled primary antibody or peptide competed antibody. After antibody was removed by aspiration, a second fixation of the tissue section was performed in 4% formaldehyde in PBS and incubated for 15 minutes at RT. The section was washed with PBS three times for 5 minutes by aspiration. Sections were then incubated for 30 minutes with streptavidin substrate VECTASTAIN® ABC Reagent (Vector Labs) before washing with PBS. Tissues were then developed with DAB substrate (Vector Labs) in the presence of nickel. Sections were then washed two times with ddH2O and allowed to completely dry at RT before mounting with 50 µl of VectaMount Permanent Mounting Medium (Vector Labs). Finally, tissue sections were counterstained with hematoxylin (Vector Labs). Representative images were acquired with Olympus BX-41 upright microscope using METAMORPH® software.

Figure 5A:
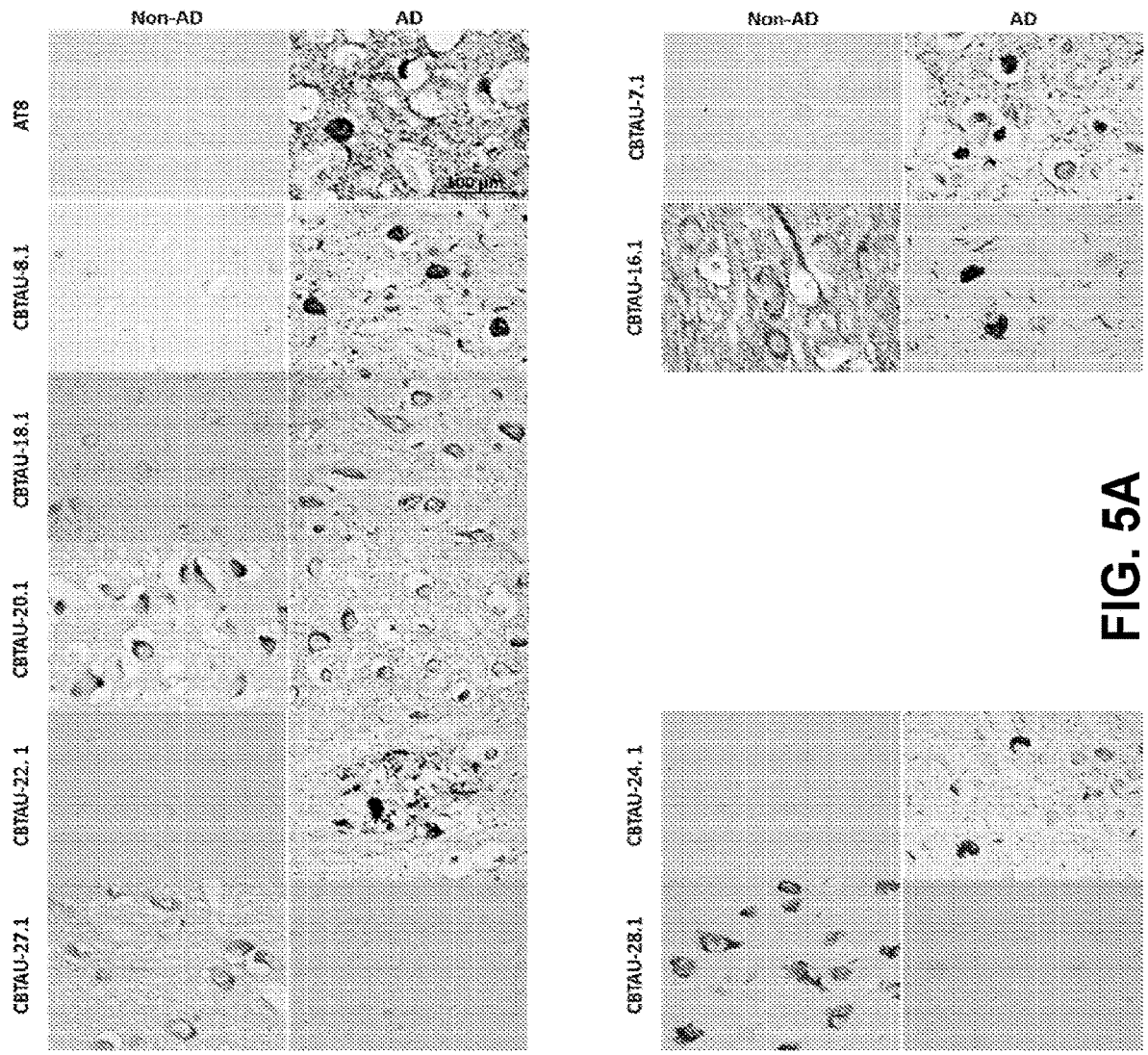
FIGS. 5A-5D show the immunohistochemical results for the CBTAU mAbs detailed in this application.
Figure 5B:
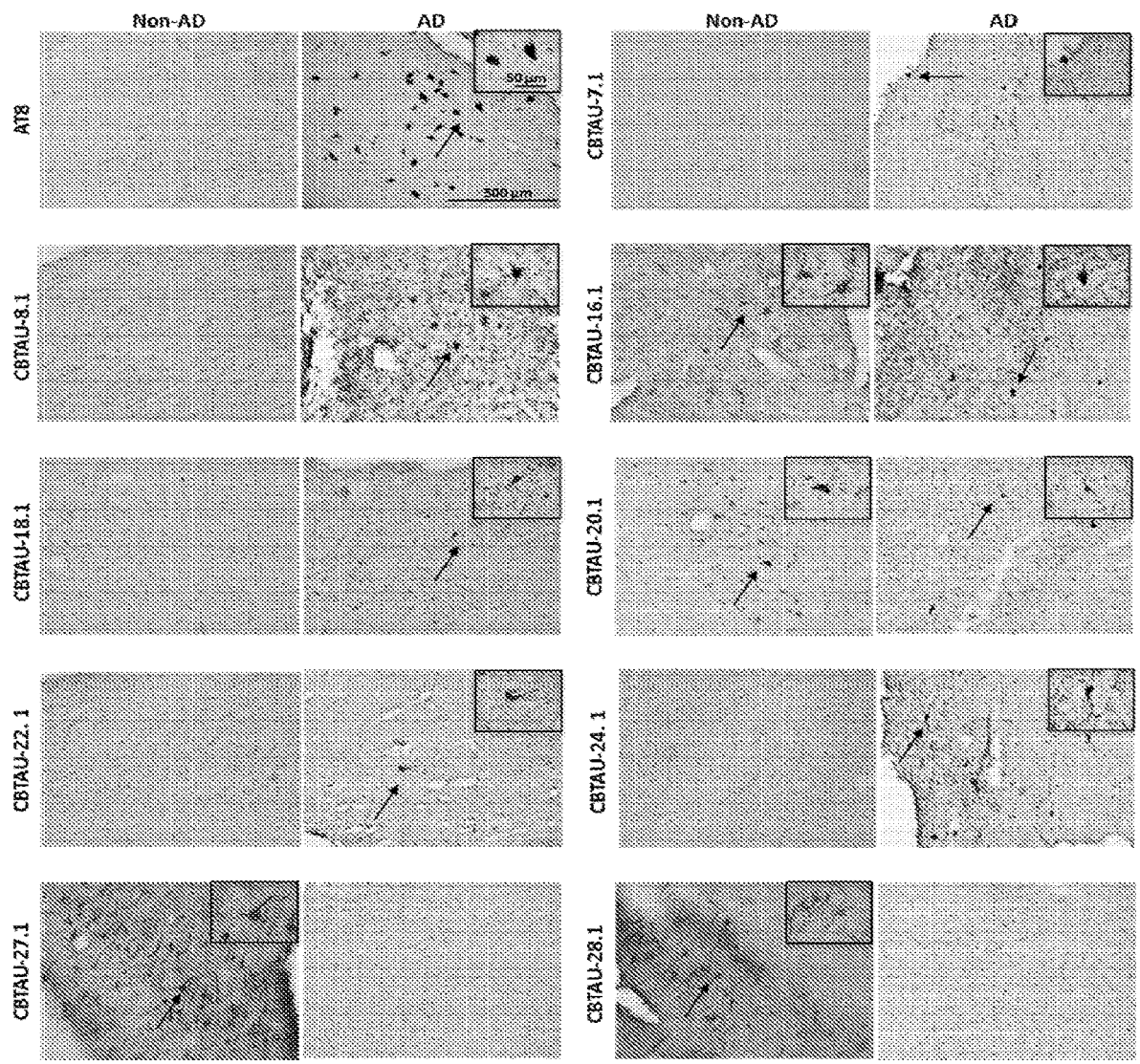

Results from the immunohistochemistry are shown in FIGS. 5A-5D. CBTAU-7.1 and CBTAU-8.1 showed positive immunoreactivity on AD brain tissues specifically, and not to healthy brain tissues, which suggests binding to pathogenic tau deposits present in diseased brain tissues. These antibodies recognize AT8-positive tau tangles and neutrophil threads in subregions of the hippocampus (FIG. 5A; entorhinal cortex) and cerebral cortex (FIG. 5B). Furthermore, the positive immunoreactivity was consistently found across multiple experiments in the neuronal cytoplasm and processes. In addition, CBTAU-18.1, 22.1, and 24.1 were also tested against hippocampal and cortical tissue sections (FIGS. 5A and 5B). Similar to CBTAU-7.1 and CBTAU-8.1, all mAbs reacted specifically to tau on AD tissue sections but not to tau on non-AD tissue sections. Of interest, CBTAU-24.1, which is not specific to phosphorylated tau, reacts specifically to diseased tau on AD tissue sections but not to tau on non-AD sections. Finally, CBTAU-16.1 and CBTAU-20.1 show reactivity to tau on both non-AD and AD tissue sections.

Figure 5C:
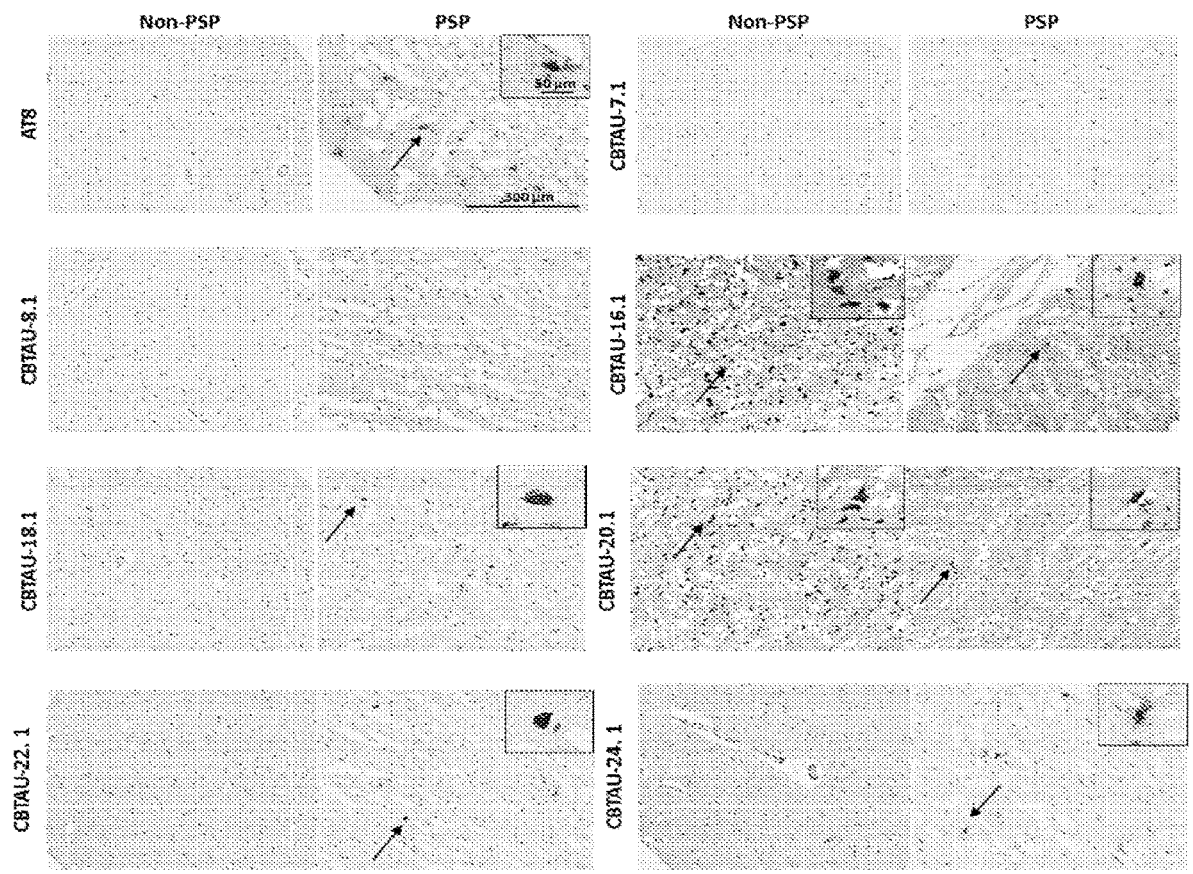

In addition, CBTAU-7.1, 8.1, 16.1, 18.1, 20.1, 22.1, and 24.1 were tested on cortical tissue sections corresponding to progressive supranuclear palsy (FIG. 5C). Unlike AT8, CBTAU-7.1 and CBTAU-8.1 failed to detect tau tangles in the human PSP brain, suggesting that the epitope for both mAbs is not present on PSP. CBTAU-16.1 and CBTAU-20.1 showed positive immunoreactivity to tau on non-PSP and PSP cortical brain sections, suggesting binding to both normal tau and pathogenic forms of tau. In non-AD brain sections, these antibodies showed positive immunostaining of tau in neuronal cytoplasm and processes (FIGS. 5A and 5B), yet both mAbs detected tangles and neutrophil threads in AD brain sections similar to AT8. Similar immunoreactivity as AT8 to tau tangles was also detected in PSP brain tissue sections, suggesting that both CBTAU-16.1 and CBTAU-20.1 recognize common pathogenic tau forms in other non-AD tauopathies. Furthermore, CBTAU-22.1 and CBTAU-24.1 showed immunoreactivity exclusively in AD brain tissues, with positive immunoreactivity to tangles and neutrophil threads. CBTAU-18.1 showed weak immunoreactivity in non-AD brain tissues, yet reacted stronger to AD tissue samples. CBTAU-18.1, CBTAU-22.1 and CBTAU-24.1 were also positive for tau tangles in PSP brain tissue sections (FIG. 5C).

Figure 5D:
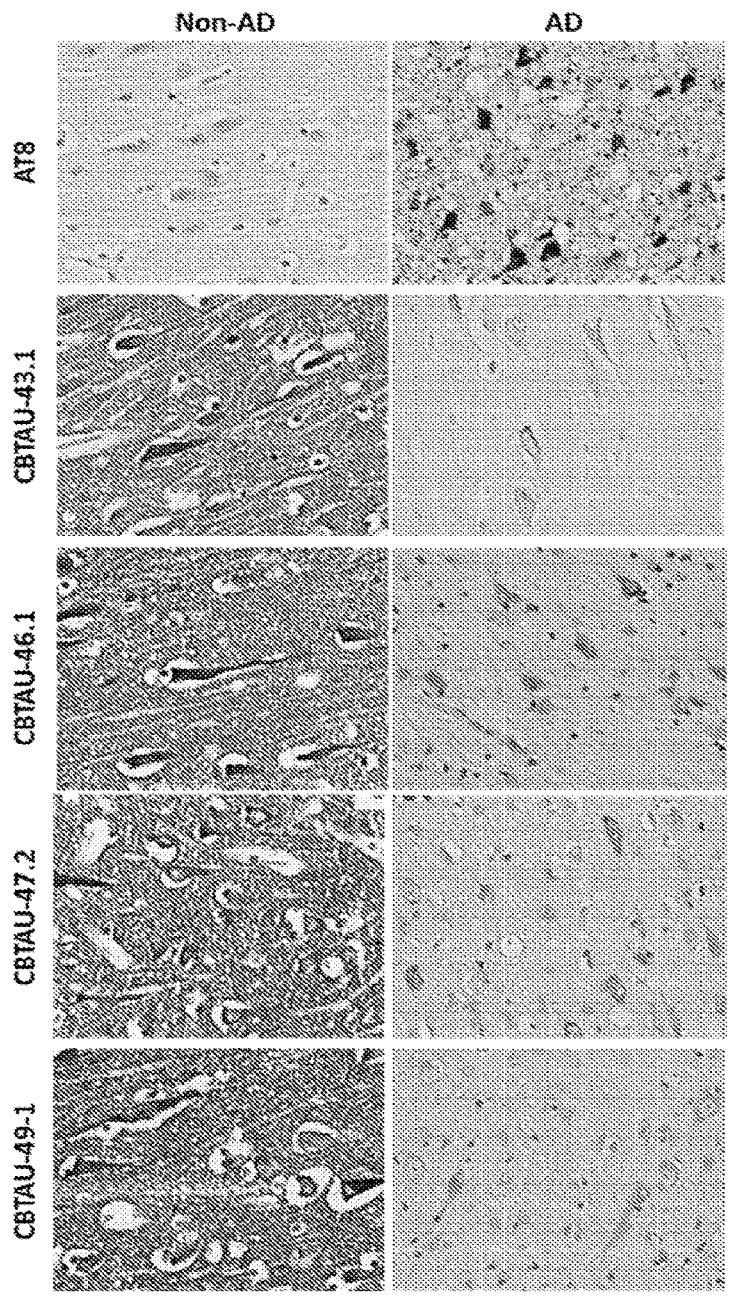

CBTAU-27.1 and CBTAU-28.1 showed selective immunostaining in non-AD tissue sections with diffuse immunostaining in neuronal cytoplasm and processes. Interestingly, both antibodies failed to show immunoreactivity in AD tissue sections (both hippocampal and cortical), defining a novel epitope that is lost during disease progression. Unlike the majority of the human anti-tau mAbs that were identified, CBTAU-27.1 and CBTAU-28.1 were recovered by screening donor samples using an unphosphorylated peptide set spanning the entire region of human tau441. These antibodies do not require phosphorylation for binding (FIGS. 1A-1T) and, as shown in FIGS. 2A-2J, do not react to PHF by ELISA. Therefore, the diffuse immunostaining pattern observed for these two mAbs was expected. In addition, CBTAU-43.1, which was originally recovered using the CBTAU-27.1 cognate peptide, was tested against cortical tissue sections. CBTAU-43.1 reacted similar to CBTAU-27.1, staining tau on non-AD but not tau on AD tissue sections. Likewise, CBTAU-46.1, 47.2 (only one variant tested), and 49.1, which were recovered using the CBTAU-28.1 cognate peptide, reacted specifically to tau on non-AD but not AD tissue sections (FIG. 5D). It is interesting to note that these mAbs all share common heavy and light chain germlines (i.e., VH5-51 and VK4-1), bind to the same regions on tau and, as shown in FIG. 5D, share similar immunohistochemical properties.

The immunohistochemistry results presented here for CBTAU-7.1, 8.1, 18.1, 22.1, 24.1, 27.1, and 28.1 have been confirmed on multiple regions of the brain and tissue samples corresponding to several non-AD and AD individuals. Immunoreactivity of CBTAU mAbs 43.1, 46.1, 47.2, and 49.1 has been confirmed once using the same tissue sample and has not yet been confirmed on samples corresponding to other AD and non-AD individuals.

Example 12

Dephosphorylation IHC

Given that the results of the IHC for CBTAU-28.1 showed immunoreactivity to tau on non-AD tissue sections but not to tau on AD tissue sections, it was hypothesized that the loss of this epitope during disease progression was a result of modification(s) (i.e., phosphorylation). To test this hypothesis, human brain tissue sections were dephosphorylated prior to assessing immunoreactivity of CBTAU-28.1. Paraffin-embedded human brain tissue sections (Abcam, cat #:ab4305, 54-year-old male, no clinical symptom vs. Abcam, cat #:ab4583, 93-year-old Hispanic female, Alzheimer disease) were deparaffinized and rehydrated by washing twice for 10 minutes in xylene (VWR International), followed by washing twice for 3 minutes in 100% ethanol, twice for 3 minutes in 95% ethanol, twice for 3 minutes in 70% ethanol, and once for 30 seconds in distilled H2O using TISSUE-TEK® Slide Staining Set (VWR International). To minimize non-specific antibody binding, tissues were never allowed to dry during washes. Tissue sections underwent heat-mediated antigen retrieval using citrate buffer {citric acid, pH 6.0) to expose antigenic sites. Excess water was removed and tissue sections were circled with an ImmEdge Hydrophobic Barrier Pen (Vector Labs). A humidified chamber was prepared by covering the bottom of a staining tray with H2O, and sections were then washed with PBS three times for 5 minutes by aspiration. Endogenous peroxidase activity was quenched in H2O2 for 15 minutes at RT. Following quenching, slides were washed with PBS three times for 5 minutes by aspiration. Sections were subsequently treated with 130 units/mL of calf intestinal alkaline phosphatase (CIAP) for 2.5 hours at 32 degrees. Slides were then blocked for 1 hour at RT with a solution of 10% normal goat serum, 0.3% TRITON® X-100, 1% BSA in 1×PBS. Murinized CBTAU-28.1 (Fc region murinized), and control mAbs AT8 and isotype control (anti-RSV mAb 4.1) were incubated overnight on hippocampal sections at a final concentration of 1 μg/mL Sections were washed and incubated with anti-mouse, Fcγ fragment-specific antibody for 2 hours at room temperature. Samples were developed with peroxidase substrate solution DAB in the presence of Nickel. Samples were counter-stained with hematoxylin (Vector Labs). Representative images were acquired with Olympus BX-41 upright microscope using METAMORPH® software.

Figure 6A:
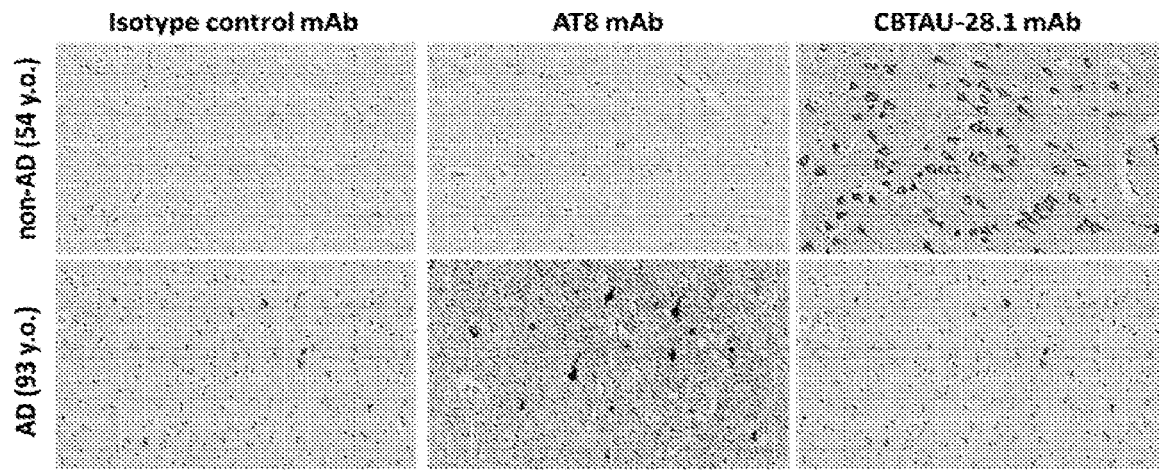
FIG. 6A shows immunoreactivity of CBTAU-28.1 and control mAbs against non-AD (54 y.o. male; no clinical symptoms) and AD (93 y.o. Hispanic female) hippocampal tissue sections.
Figure 6B:
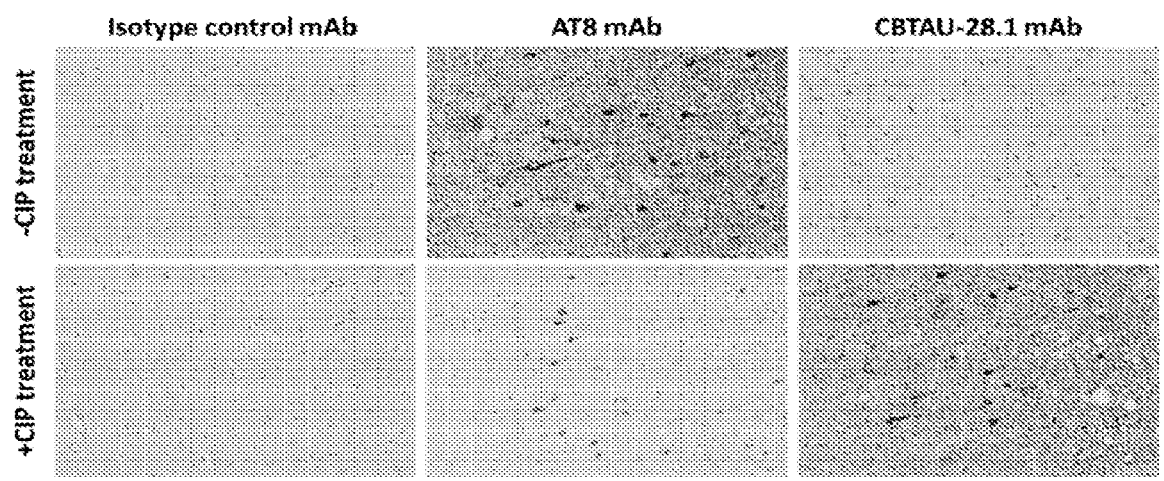
FIG. 6B shows reactivity of CBTAU-28.1 and control mAbs to AD (93 y.o. Hispanic female) hippocampal tissue sections with and without calf intestinal phosphatase treatment.

Results are shown in FIGS. 6A and 6B. As expected, CBTAU-28.1 reacts to tau present in the non-AD hippocampal tissue sections but does not react to tau in the AD tissue sections. In contrast, control mAb, AT8, does not react to tau in non-AD sections, but clearly reacts to pathogenic tau deposits present in the AD sections (FIG. 6A). However, pretreatment of AD tissue sections with phosphatase restores reactivity of CBTAU-28.1, allowing it to stain pathogenic tau deposits present in these sections. As expected, the reactivity of AT8 was reduced with pretreatment of the AD tissue sections with phosphatase (FIG. 6B).

Example 13

Dephosphorylation ELISA

To confirm the results of Example 12, dephosphorylation of paired helical filaments was tested for reactivity to CBTAU-28.1 by ELISA. Half-area 96-well binding plates (Costar) were coated with 50 μl of antigen in TBS (2 μg/ml bovine action affinipure goat anti-human F(ab)2, and 1 μg/ml of affinity-purified paired helical filaments, iPHF, pretreated with and without calf intestinal phosphatase, CIP). Phosphatase-treated iPHF was prepared as follows. iPHF samples were resuspended in 1×NEB buffer 4 (50 mM potassium acetate, 20 mM Tris-acetate, 10 mM magnesium acetate, and 1 mM DTT) at a final concentration of 0.05 μg/ml. One unit of CIP per μg of iPHF was added (CIP, NEB Cat. No. M0290S). iPHF samples were incubated with CIP for 90 minutes at 37° C. prior to coating on ELISA binding plates. Following antigen binding overnight, the plates were washed with TBS-T and subsequently blocked with 150 μl of TBS plus 2.5% BSA for 2 hours at RT. Purified control and anti-tau IgG, CBTAU-28.1), were titrated in five-fold dilutions starting at 25 μg/ml in TBS/0.25% BSA, and IgGs and incubated for 1.5 hours. Plates were washed four times with TBS-T and secondary antibody (anti-human Fab HRP, Jackson Immunoresearch, Cat. No. 109-036-097) was added and incubated at RT for 45 minutes. Following incubation, plates were washed four times in TBS-T and developed with SureBlue Reserve TMB Microwell Peroxidase Substrate (KPL) for approximately 2 minutes. The reaction was immediately halted by the addition of TMB Stop Solution (KPL) and the absorbance at 450 nm was measured using an ELISA plate reader. Each experimental point was performed in triplicate.

Figure 7:
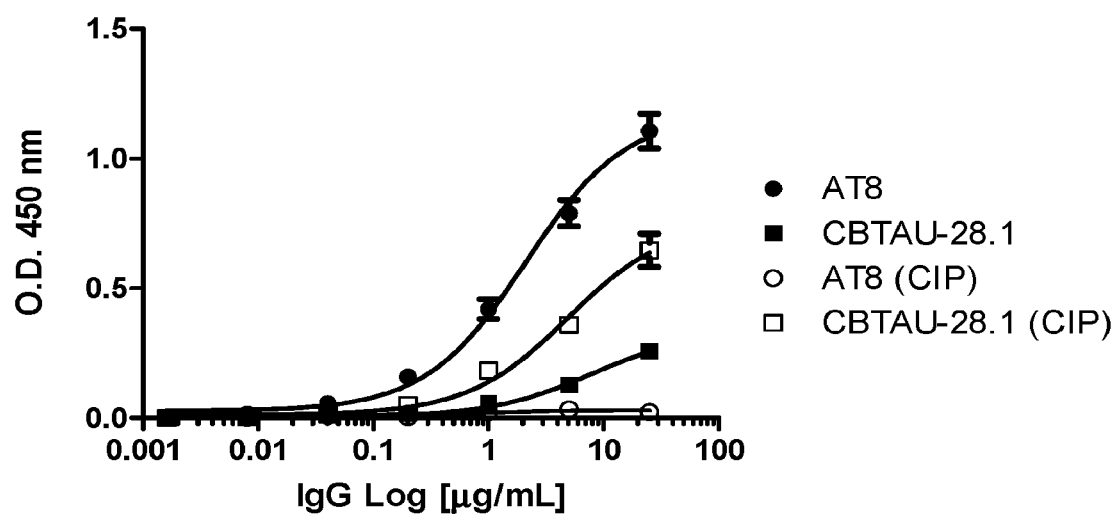
FIG. 7 shows reactivity of CBTAU-28.1 and phospho-tau mAb, ATB, against iPHF (immunopurified paired helical filaments) and calf intestinal phosphatase-treated iPHF samples.
Figure 8A:
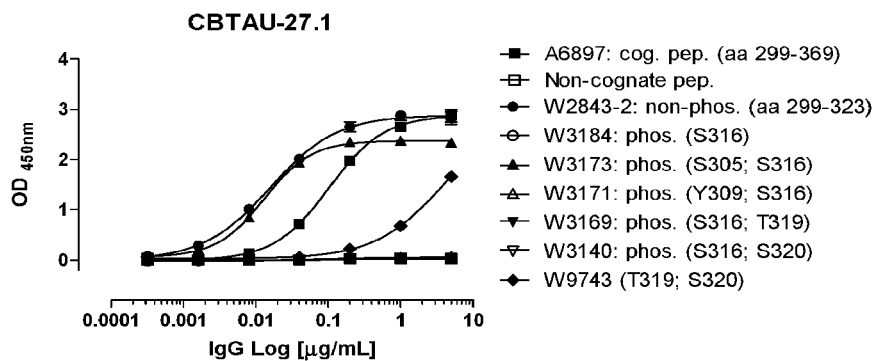
FIGS. 8A-8F show reactivity of CBTAU-27.1, 28.1, 43.1, 46.1, 47.1, 47.2, and 49.1 to the tau phosphopeptides detailed on Tables 30-34.
Figure 8B:
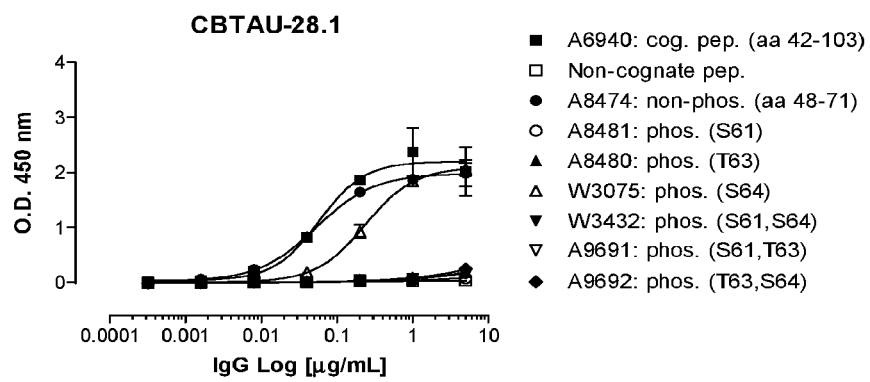
Figure 8C:
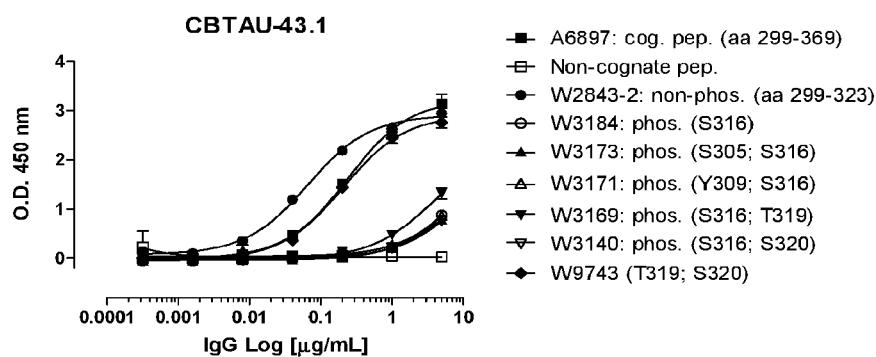
Figure 8D:
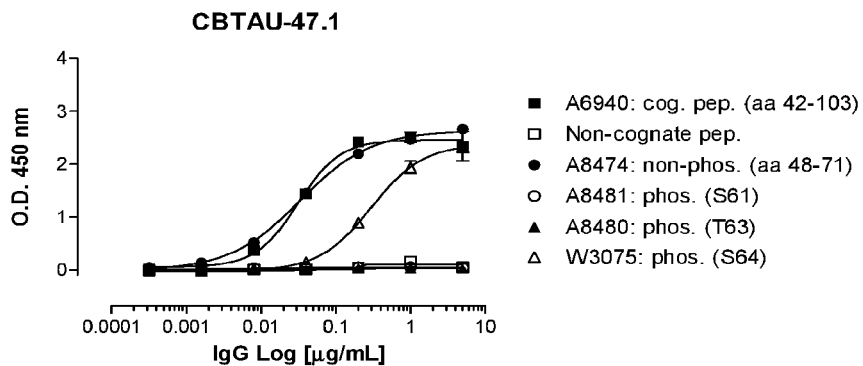
Figure 8E:
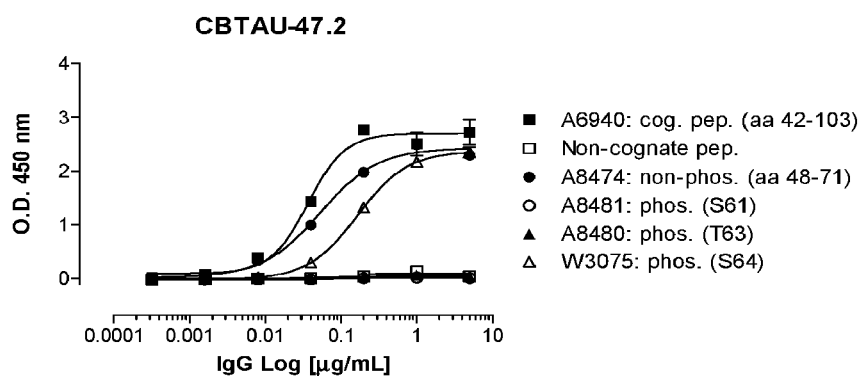
Figure 8F:
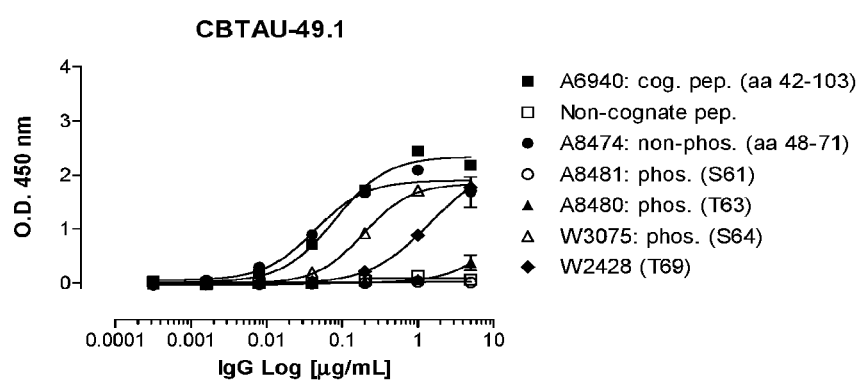

Results are shown in FIG. 7. As previously shown in Example 7, CBTAU-28.1 reacts poorly to iPHF by ELISA in contrast to AT8. However, dephosphorylation of iPHF with CIP restores the reactivity of CBTAU-28.1 to the filamentous sample. As expected, the reactivity of the phospho-tau control mAb, AT8, is abolished after dephosphorylation of iPHF with CIP.

Example 14

Reactivity of CBTAU-27.1, 28.1, 43.1, 47.1, 47.2 and 49.1 to Phosphopeptides

The immunohistochemical results for CBTAU-27.1 (and CBTAU-43.1) and CBTAU-28.1 (and CBTAU-46.1, 47.2, 49.1) suggest that these mAbs react with an epitope on tau that is present in normal, non-AD, tissue sections but is lost or masked during the disease setting (FIGS. 5A-5D). It was hypothesized that this was a result of a phosphorylation event within the region that results in masking of the epitope(s). The experiments highlighted in Examples 12 and 13 showed that this was indeed true for 28.1. Therefore, it was desired to specifically identify the site(s) that could potentially be targeted for phosphorylation and account for loss of reactivity for CBTAU-28.1. Because 47.1, 47.2, and 49.1 bound to the same region on tau as CBTAU-28.1 (i.e., 52-71), it was decided to test these mAbs as well in these experiments. In addition, the same exercise was carried out for CBTAU-43.1 and CBTAU-27.1 as they behave similarly to CBTAU-28.1 by IHC.

Singly and dually phosphorylated-tau peptides were designed to cover all potential phosphorylation sites with regions 52-71 and 299-323 (CBTAU-28.1 and CBTAU-27.1 binding region, respectively). CBTAU-27.1 and CBTAU-43.1 mAbs were tested against the peptides listed on Tables 30 and 32.96-well streptavidin-coated ELISA plates (Pierce) were coated with phosphorylated tau peptides as detailed in Example 9. Purified anti-tau IgGs were diluted to 5 µg/ml in TBS containing 0.25% BSA, and titrated five-fold. Antibody control and secondary antibodies were used as detailed in Example 9. Antibody reactivity at 1 µg/mL was determined by ELISA and scored as no binding (−), weak (−1+), moderate (+), or strong (++). (−) for average of two O.D. 450 nm readings <0.3; (−/+) for >0.5 and <1.0; (+) for >1.0 and <1.5; (++) for >1.5. Results for each antibody are shown in Tables 30-34 and FIGS. 8A-8F.

TABLE 30

CBTAU-27.1: Peptides for reactivity by ELISA

| Peptide | SEQ ID NO. | | Result |
|---|---|---|---|
| tau 299-369 | 331 | HVPGGGSVQIVYKPVDLSKVTSKCGSLGNIHHKPGGGQVEVKSEKLDFKDRVQSKIGSLDNITHVPGGGNK | ++ |

TABLE 30-continued

CBTAU-27.1: Peptides for reactivity by ELISA

| Peptide | SEQ ID NO. | | Result |
|---|---|---|---|
| tau 299-323 | 458 | HVPGGGSVQIVYKPVDLSKVTSKCG | ++ |
| ptau 299-323 p305 | 503 | HVPGGG(pS)VQIVYKPVDLSKVTSKCG | ++ |
| ptau 299-323 p310 | 504 | HVPGGGSVQIV(pY)KPVDLSKVTSKCG | ++ |
| ptau 299-323 p316 | 505 | HVPGGGSVQIVYKPVDL(pS)KVTSKCG | − |
| ptau 299-323 p319 | 506 | HVPGGGSVQIVYKPVDLSKV(pT)SKCG | ++ |
| ptau 299-323 p320 | 507 | HVPGGGSVQIVYKPVDLSKVT(pS)KCG | ++ |
| ptau 299-323 p305, 310 | 508 | HVPGGG(pS)VQIV(pY)KPVDLSKVTSKCG | ++ |
| ptau 299-323 p305, 316 | 509 | HVPGGG(pS)VQIVYKPVDL(pS)KVTSKCG | − |
| ptau 299-323 p305, 320 | 510 | HVPGGG(pS)VQIVYKPVDLSKV(pT)SKCG | ++ |
| ptau 299-323 p305, 321 | 511 | HVPGGG(pS)VQIVYKPVDLSKVT(pS)KCG | ++ |
| ptau 299-323 p310, 316 | 512 | HVPGGGSVQIV(pY)KPVDL(pS)KVTSKCG | − |
| ptau 299-323 p310, 320 | 513 | HVPGGGSVQIV(pY)KPVDLSKV(pT)SKCG | ++ |
| ptau 299-323 p310, 321 | 514 | HVPGGGSVQIV(pY)KPVDLSKVT(pS)KCG | ++ |
| ptau 299-323 p316, 320 | 515 | HVPGGGSVQIVYKPVDL(pS)KV(pT)SKCG | − |
| ptau 299-323 p316, 321 | 516 | HVPGGGSVQIVYKPVDL(pS)KVT(pS)KCG | − |
| ptau 299-323 p320, 321 | 517 | HVPGGGSVQIVYKPVDLSKV(pT)(pS)KCG | −/+ |

TABLE 31

CBTAU-28.1: Peptides for reactivity by ELISA

| Peptide | SEQ ID NO. | | Result |
|---|---|---|---|
| tau 42-103 | 325 | GLKESPLQTPTEDGSEEPGSETSDAKSTPTAEDVTAPLVDEGAPGKQAAAQPHTEIPEGTTA | ++ |
| tau 48-71 | 518 | LQTPTEDGSEEPGSETSDAKSTPT | ++ |
| ptau 48-71 (p71) | 519 | LQTPTEDGSEEPGSETSDAKSTP(pT) | ++ |
| ptau 48-71 (p63) | 520 | LQTPTEDGSEEPGSE(pT)SDAKSTPT | − |
| ptau 48-71 (p61) | 521 | LQTPTEDGSEEPG(pS)ETSDAKSTPT | − |

TABLE 31-continued

CBTAU-28.1: Peptides for reactivity by ELISA

| Peptide | SEQ ID NO. | | Result |
|---|---|---|---|
| ptau 48-71 (p56) | 522 | LQTPTEDG(pS)EEPGSETSDAKSTPT | ++ |
| ptau 48-71 (p52) | 523 | LQTP(pT)EDGSEEPGSETSDAKSTPT | ++ |
| ptau 48-71 (p68) | 524 | LQTPTEDGSEEPGSETSDAK(pS)TPT | ++ |
| ptau 48-71 (p69) | 525 | LQTPTEDGSEEPGSETSDAKS(pT)PT | ++ |
| ptau 48-71 (p64) | 526 | LQTPTEDGSEEPGSET(pS)DAKSTPT | ++ |
| ptau 48-71 (p61, p64) | 527 | LQTPTEDGSEEPG(pS)ET(pS)DAKSTPT | − |
| ptau 48-71 (p61, p63) | 528 | LQTPTEDGSEEPG(pS)E(pT)SDAKSTPT | − |
| ptau 48-71 (p63, p64) | 529 | LQTPTEDGSEEPGSE(pT)(pS)DAKSTPT | − |

TABLE 32

CBTAU-43.1: Peptides for reactivity by ELISA

| Peptide | SEQ ID NO. | | Result |
|---|---|---|---|
| tau 299-369 | 331 | HVPGGGSVQIVYKPVDLSKVTSKCGSLGNIHHKPGGGQVEVKSEKIDFKDRVQSKIGSLDNITHVPGGGNK | ++ |
| tau 299-323 | 458 | HVPGGGSVQIVYKPVDLSKVTSKCG | ++ |
| ptau 299-323 p305 | 503 | HVPGGG(pS)VQIVYKPVDLSKVTSKCG | ++ |
| ptau 299-323 p310 | 504 | HVPGGGSVQIV(pY)KPVDLSKVTSKCG | ++ |
| ptau 299-323 p316 | 505 | HVPGGGSVQIVYKPVDL(pS)KVTSKCG | − |
| ptau 299-323 p319 | 506 | HVPGGGSVQIVYKPVDLSKV(pT)SKCG | ++ |
| ptau 299-323 p320 | 507 | HVPGGGSVQIVYKPVDLSKVT(pS)KCG | ++ |
| ptau 299-323 p305, 310 | 508 | HVPGGG(pS)VQIV(pY)KPVDLSKVTSKCG | ++ |
| ptau 299-323 p305, 316 | 509 | HVPGGG(pS)VQIVYKPVDL(pS)KVTSKCG | − |
| ptau 299-323 p305, 320 | 510 | HVPGGG(pS)VQIVYKPVDLSKV(pT)SKCG | ++ |
| ptau 299-323 p305, 321 | 511 | HVPGGG(pS)VQIVYKPVDLSKVT(pS)KCG | ++ |
| ptau 299-323 p310, 316 | 512 | HVPGGGSVQIV(pY)KPVDL(pS)KVTSKCG | − |
| ptau 299-323 p310, 320 | 513 | HVPGGGSVQIV(pY)KPVDLSKV(pT)SKCG | ++ |

TABLE 32-continued

CBTAU-43.1: Peptides for reactivity by ELISA

| Peptide | SEQ ID NO. | | Result |
|---|---|---|---|
| ptau 299-323 p310, 321 | 514 | HVPGGGSVQIV(pY)KPVDLSKVT(pS)KCG | ++ |
| ptau 299-323 p316, 320 | 515 | HVPGGGSVQIVYKPVDL(pS)KV(pT)SKCG | −/+ |
| ptau 299-323 p316, 321 | 516 | HVPGGGSVQIVYKPVDL(pS)KVT(pS)KCG | − |
| ptau 299-323 p320, 321 | 517 | HVPGGGSVQIVYKPVDLSKV(pT)(pS)KCG | ++ |

TABLE 33

CBTAU-47.1 and CBTAU-47.2: Peptides for reactivity by ELISA

| Peptide | SEQ ID NO. | | Result CBTAU-47.1 | Result CBTAU-47.2 |
|---|---|---|---|---|
| tau 42-103 | 325 | GLKESPLQTPTEDGSEEPGSETSDAKSTPTAEDVTAPLVDEGAPGKQAAAQPHTIPEGTTA | ++ | ++ |
| tau 48-71 | 518 | LQTPTEDGSEEPGSETSDAKSTPT | ++ | ++ |
| ptau 48-71 (p71) | 519 | LQTPTEDGSEEPGSETSDAKSTP(pT) | ++ | ++ |
| ptau 48-71 (p63) | 520 | LQTPTEDGSEEPGSE(pT)SDAKSTPT | − | − |
| ptau 48-71 (p61) | 521 | LQTPTEDGSEEPG(pS)ETSDAKSTPT | − | − |
| ptau 48-71 (p56) | 522 | LQTPTEDG(pS)EEPGSETSDAKSTPT | ++ | ++ |
| ptau 48-71 (p52) | 523 | LQTP(pT)EDGSEEPGSETSDAKSTPT | ++ | ++ |
| ptau 48-71 (p68) | 524 | LQTPTEDGSEEPGSETSDAK(pS)TPT | ++ | ++ |
| ptau 48-71 (p69) | 525 | LQTPTEDGSEEPGSETSDAKS(pT)PT | ++ | ++ |
| ptau 48-71 (Ser64) | 526 | LQTPTEDGSEEPGSET(pS)DAKSTPT | ++ | ++ |
| ptau 48-71 (p61, Ser64) | 527 | LQTPTEDGSEEPG(pS)ET(pS)DAKSTPT | − | − |
| ptau 48-71 (p61, p63) | 528 | LQTPTEDGSEEPG(pS)E(pT)SDAKSTPT | − | − |

TABLE 33-continued

CBTAU-47.1 and CBTAU-47.2: Peptides for reactivity by ELISA

| Peptide | SEQ ID NO. | | Result CBTAU-47.1 | Result CBTAU-47.2 |
|---|---|---|---|---|
| ptau 48-71 (p63, p64) | 529 | LQTPTEDGSEEPGSE(pT)(pS) DAKSTPT | – | – |

TABLE 34

CBTAU-49.1: Peptides for reactivity by ELISA

| Peptide | SEQ ID NO. | | Result |
|---|---|---|---|
| tau 42-103 | 325 | GLKESPLQTPTEDGSEEPGSETSDA KSTPTAEDVTAPLVDEGAPGKQAA AQPHT EIPEGTTA | ++ |
| tau 48-71 | 518 | LQTPTEDGSEEPGSETSDAKSTPT | ++ |
| ptau 48-71 (p71) | 519 | LQTPTEDGSEEPGSETSDAKSTP(pT) | ++ |
| ptau 48-71 (p63) | 520 | LQTPTEDGSEEPGSE(pT)SDAKSTPT | – |
| ptau 48-71 (p61) | 521 | LQTPTEDGSEEPG(pS)ETSDAKSTPT | – |
| ptau 48-71 (p56) | 522 | LQTPTEDG(pS)EEPGSETSDAKSTPT | ++ |
| ptau 48-71 (p52) | 523 | LQTP(pT)EDGSEEPGSETSDAKSTPT | ++ |
| ptau 48-71 (p68) | 524 | LQTPTEDGSEEPGSETSDAK(pS)TPT | ++ |
| ptau 48-71 (p69) | 525 | LQTPTEDGSEEPGSETSDAKS(pT)PT | -/+ |
| ptau 48-71 (Ser64) | 526 | LQTPTEDGSEEPGSET(pS)DAKSTPT | ++ |
| ptau 48-71 (p61, Ser64) | 527 | LQTPTEDGSEEPG(pS)ET(pS)DAKSTPT | – |
| ptau 48-71 (p61, p63) | 528 | LQTPTEDGSEEPG(pS)E(pT)SDAKSTPT | – |
| ptau 48-71 (p63, p64) | 529 | LQTPTEDGSEEPGSE(pT)(pS)DAKSTPT | – |

The results for CBTAU-27.1 and CBTAU-43.1 show that phosphorylation at S316 is sufficient to completely inhibit reactivity (Table 30 and Table 32). This suggests that the loss in reactivity to tau on AD tissue sections (Example 11) may be due to phosphorylation at S316, an event that may occur early during the course of the disease. For CBTAU-28.1, 47.1, 47.2, 49.1, phosphorylation at either S61 or T63 is sufficient to completely inhibit reactivity. Taken together, the results for CBTAU-28.1, 47.1, 47.2, and 49.1 suggest that phosphorylation at S61 and/or T63 is a mechanism that accounts for loss of this epitope during the course of the disease.

Example 15

Generation of Anti-Tau mAb Mouse-Human Chimeras and Human Isotypes

To test the efficacy of the human anti-tau mAbs in a mouse model of tauopathy, mouse-human antibody chimeras were generated by replacing the human Fc region with a mouse IgG1 Fc. Briefly, the human IgG1 CH1 region was amplified from the pCB-IgG vector using primers Step1HMchim-Fwd and Step1HMchim-Rev (Table 35) to generate a 0.95 kb fragment containing a 5'-XhoI site (frag. 1). Mouse IgG1 CH2 and CH3 domains (Fc region) are amplified from a gene-synthesized construct using primers Step2HMchim-Fwd and Step2HMchim-Rev (Table 30) to generate a 0.82 kb fragment (frag. 2). A third fragment (frag. 3) was generated by amplifying the polyA region of the pCB-IgG vector using primers Step3HMchim-Fwd and Step3HMchim-Rev (Table 30), which includes a 3'-DraIII site. The three fragments were linked into a single cassette by overlap extension PCR to generate a 2.3 kb overlap fragment harboring the human CH1 followed by the mouse CH2-CH3 domains. The overlap fragment was subsequently cloned via the XhoI and DraIII sites into the pCB-IgG CBTAU-7.1 vector to generate a mouse-human chimera of CBTAU-7.1, containing the human variable, CH1, hinge and Ck regions followed by the mouse CH2 and CH3 regions. CBTAU-22.1, 24.1, 27.1, 28.1, 47.1, 47.2, 46.1, 49.1, and 43.1 chimeras were then generated by digesting the CBTAU-7.1 chimera construct and pCB-IgG CBTAU human mAb constructs with XhoI and XbaI, and the corresponding fragments were subcloned. Nucleotide sequences for all constructs are verified according to standard techniques known to the skilled artisan. Chimeric antibodies were subsequently expressed and purified as detailed in Example 5 using Protein G agarose instead of Protein A.

TABLE 35

PRIMERS FOR MOUSE-HUMAN CHIMERIZATION

| Primer ID | DNA SEQUENCE (5'-3') | SEQ ID NO: |
|---|---|---|
| Step1HMchim-Fwd | TCTCCGCCGGTGAGTCTCGAGGC | 530 |
| Step1HMchim-Rev | TGTCCCTGGATGCAGGCTACTCTAGG | 531 |
| Step2HMchim-Fwd | AGAGTAGCCTGCATCCAGGGACAG | 532 |
| Step2HMchim-Rev | TCTAGATCATTTACCAGGAGAGTGGGAGAG | 533 |
| Step3HMchim-Fwd | TCTCCTGGTAAATGATCTAGAGTTTAAACCGCTG | 534 |
| Step3HMchim-Rev | ATGGCCCACTACGTGAACCATCACC | 535 |

Example 16

Preparation of IgG2, 3 and 4 Isotypes

As mentioned in Example 3, all CBTAU mAbs were cloned and expressed as chimeric human IgG1 regardless of their native isotype. To generate additional human isotype versions (i.e., IgG2/3/4), the CH1 through CH3 region corresponding to each of the human IgG isotypes is PCR amplified from gene-synthesized constructs containing the corresponding constant regions, hinge, and intron sequences. The PCR amplicons contain 5'-XhoI and 3'-DraIII sites, which are used to subclone the fragments into the corresponding pCB-IgG CBTAU antibody construct. In this manner, human IgG2, 3 and 4 isotype versions are generated for each of the anti-tau mAbs.

Example 17

Generation of De-Risked and Fc-Engineered Anti-Tau Chimeric Monoclonal Antibody Variants The heavy and light chain variable regions (VH and VL) for each anti-tau antibody clone isolated in Example 3 are analyzed for the presence of free cysteines and potential post-translational modification sites, which include glycosylation, deamidation and oxidation sites. Amino acid mutations consisting of structurally conserved and/or germline-based substitutions are used to change these sites. Non-conserved cysteines in the variable regions are mutated to serine. For glycosylation sites, several mutations are used, including replacement of asparagine for the conservative glutamine or germline mutations. Modifications to the deamidation sites include replacement of aspartic acid for asparagine and serine or alanine for glycine. Sites of potential oxidation are not modified. To increase the binding affinity to FcRn and thus increase the half-life of IgG1 mAbs in vivo, several mutations located at the boundary between the CH2 and CH3 regions are generated. These mutations included M252Y/S254T/T256E plus H433K/N434F (C. Vaccaro et al., 2005) or T250Q/M428L (P. R. Hinton et al., 2004), which have been shown to increase IgG1 binding to FcRn. All substitutions are generated by site-directed mutagenesis per manufacturer's instructions (QuicKCHANGE™ II, Agilent Technologies, cat. no. 200521). Nucleotide sequences for all constructs are verified according to standard techniques known to the skilled artisan.

What is claimed is:

1. A monoclonal antibody,
wherein the antibody binds tau deposits in human AD brain tissue, but does not bind tau in normal human brain tissue and does not bind tau deposits in Progressive Supranuclear Palsy ("PSP") brain tissue; and
wherein the antibody comprises:
an antigen-binding site of a VH of SEQ ID NO:87 and an antigen-binding site of a VL of SEQ ID NO:88; or
an antigen-binding site of a VH of SEQ ID NO:99 and an antigen-binding site of a VL of SEQ ID NO:100.

2. The antibody of claim 1, wherein the antibody comprises:
a naturally occurring human antigen-binding variable region that binds specifically to tau, and
a recombinant constant region of a human IgG1 antibody.

3. The antibody of claim 1, wherein the antibody comprises:
naturally occurring human light and heavy chain variable regions from a human antibody, and
recombinant human IgG1 heavy and light chain constant regions.

4. The antibody of claim 1, wherein the antibody comprises:
heavy and light chain variable regions from a naturally occurring human antibody, and recombinant human IgG1 heavy and light chain constant regions.

5. The antibody of claim 1, wherein the antibody comprises:
heavy and light chain variable regions from a human antibody, and
recombinant human IgG1 heavy and light chain constant regions.

6. The antibody of claim 1, comprising an antigen-binding site of a VH of SEQ ID NO:87 and an antigen-binding site of a VL of SEQ ID NO:88.

7. A monoclonal antibody,
wherein the antibody binds tau deposits in human AD brain tissue, but does not bind tau in normal human brain tissue and does not bind tau deposits in Progressive Supranuclear Palsy ("PSP") brain tissue,
wherein the antibody is selected from the group consisting of
a) an antibody comprising a heavy chain CDR1 region comprising SEQ ID NO:175, a heavy chain CDR2 region comprising SEQ ID NO:176, and a heavy chain CDR3 region comprising SEQ ID NO:177, a light chain CDR1 region comprising SEQ ID NO:178, a light chain CDR2 region comprising SEQ ID NO:179 and a light chain CDR3 region comprising SEQ ID NO:180,
b) an antibody comprising a heavy chain CDR1 region comprising SEQ ID NO:181, a heavy chain CDR2 region comprising SEQ ID NO:182, and a heavy chain CDR3 region comprising SEQ ID NO:183, a light chain CDR1 region comprising SEQ ID NO:172, a light chain CDR2 region comprising SEQ ID NO:173 and a light chain CDR3 region comprising SEQ ID NO:184,
c) an antibody comprising a heavy chain CDR1 region comprising SEQ ID NO:185, a heavy chain CDR2 region comprising SEQ ID NO:186, and a heavy chain CDR3 region comprising SEQ ID NO:187, a light chain CDR1 region comprising SEQ ID NO:188, a light chain CDR2 region of comprising SEQ ID NO:173 and a light chain CDR3 region comprising SEQ ID NO:189,
d) an antibody comprising a heavy chain CDR1 region comprising SEQ ID NO:190, a heavy chain CDR2 region comprising SEQ ID NO:191, and a heavy chain CDR3 region comprising SEQ ID NO:192, a light chain CDR1 region comprising SEQ ID NO:193, a light chain CDR2 region comprising SEQ ID NO:194 and a light chain CDR3 region comprising SEQ ID NO:195,
e) an antibody comprising a heavy chain CDR1 region comprising SEQ ID NO:196, a heavy chain CDR2 region comprising SEQ ID NO:197, and a heavy chain CDR3 region comprising SEQ ID NO:198, a light chain CDR1 region comprising SEQ ID NO:199, a light chain CDR2 region comprising SEQ ID NO:173 and a light chain CDR3 region comprising SEQ ID NO:200,
f) an antibody comprising a heavy chain CDR1 region comprising SEQ ID NO:213, a heavy chain CDR2 region comprising SEQ ID NO:214, and a heavy chain CDR3 region comprising SEQ ID NO:215, a light chain CDR1 region comprising SEQ ID NO:216, a light chain CDR2 region comprising SEQ ID NO:173 and a light chain CDR3 region comprising SEQ ID NO:217; NO:217,
g) an antibody comprising a heavy chain CDR1 region comprising SEQ ID NO:213, a heavy chain CDR2 region comprising SEQ ID NO:214, and a heavy chain CDR3 region comprising SEQ ID NO:215, a light chain CDR1 region comprising SEQ ID NO:218, a light chain CDR2 region comprising SEQ ID NO:174 and a light chain CDR3 region comprising SEQ ID NO:217; NO:217, and
h) an antibody comprising a heavy chain CDR1 region comprising SEQ ID NO:219, a heavy chain CDR2 region comprising SEQ ID NO:220, and a heavy chain CDR3 region comprising SEQ ID NO:221, a light chain CDR1 region comprising SEQ ID NO:218, a light chain CDR2 region comprising SEQ ID NO:173 and a light chain CDR3 region comprising SEQ ID NO:217.

8. The antibody of claim 7, comprising an antigen-binding site of a VH of SEQ ID NO:95 and an antigen-binding site of a VL of SEQ ID NO:96.

9. The antibody of claim 1, comprising an antigen-binding site of a VH of SEQ ID NO:99 and an antigen-binding site of a VL of SEQ ID NO:100.

10. The antibody of claim 7, comprising an antigen-binding site of a VH of SEQ ID NO:103 and an antigen-binding site of a VL of SEQ ID NO:104.

11. The antibody of claim 7, comprising an antigen-binding site of a VH of SEQ ID NO:107 and an antigen-binding site of a VL of SEQ ID NO:108.

12. The antibody of claim 7, comprising an antigen-binding site of a VH of SEQ ID NO:111 and an antigen-binding site of a VL of SEQ ID NO:112.

13. The antibody of claim 7, comprising an antigen-binding site of a VH of SEQ ID NO:123 and an antigen-binding site of a VL of SEQ ID NO:124.

14. The antibody of claim 7, comprising an antigen-binding site of a VH of SEQ ID NO:127 and an antigen-binding site of a VL of SEQ ID NO:128.

15. The antibody of claim 7, comprising an antigen-binding site of a VH of SEQ ID NO:131 and an antigen-binding site of a VL of SEQ ID NO:132.

16. A method for treatment of a subject with Alzheimer's disease, or memory and/or cognitive disorders associated with tau, the method comprising administering the monoclonal antibody of claim 1 to the subject for treatment of Alzheimer's disease, or memory and/or cognitive disorders associated with tau.

17. A method for diagnosing a subject for Alzheimer's disease, or memory and/or cognitive disorders associated with tau, the method comprising:
   a) contacting a biological sample from the subject with the monoclonal antibody of claim 1: and
   b) detecting binding of tau antigen in the biological sample from the subject to the monoclonal antibody.

18. The method of claim 17, wherein the biological sample comprises peripheral blood, serum, plasma, urine, cerebrospinal fluid, tissue biopsy, surgical specimen, fine needle aspirates, autopsy material, cell culture supernatant, isolated cells, fermentation supernatant, or tissue homogenate.

\* \* \* \* \*

SEQUENCE LISTING

<160> NUMBER OF SEQ ID NOS: 535

<210> SEQ ID NO 1
<211> LENGTH: 441
<212> TYPE: PRT
<213> ORGANISM: Homo sapiens

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240
```

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
            275                 280                 285

Ser Lys Cys Gly Ser Lys Asp Asn Ile Lys His Val Pro Gly Gly Gly
            290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
            370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 2
<211> LENGTH: 410
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Pro Gly Ser Glu Thr Ser
            50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
            130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro

```
                  165                 170                 175
Pro Ala Pro Lys Thr Pro Pro Ser Ser Gly Glu Pro Lys Ser Gly
            180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
            290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
                405                 410

<210> SEQ ID NO 3
<211> LENGTH: 412
<212> TYPE: PRT
<213> ORGANISM: Homo sapiens

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
            85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125
```

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
        355                 360                 365

Val Val Ser Gly Asp Thr Ser Pro Arg His Leu Ser Asn Val Ser Ser
    370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 4
<211> LENGTH: 383
<212> TYPE: PRT
<213> ORGANISM: Homo sapiens

<400> SEQUENCE: 4

Thr Ala Met Ala Glu Pro Arg Gln Glu Phe Glu Val Met Glu Asp His
1               5                   10                  15

Ala Gly Thr Tyr Gly Leu Gly Asp Arg Lys Asp Gln Gly Gly Tyr Thr
            20                  25                  30

Met His Gln Asp Gln Glu Gly Asp Thr Asp Ala Gly Leu Lys Glu Ser
        35                  40                  45

Pro Leu Gln Thr Pro Thr Glu Asp Gly Ser Glu Pro Gly Ser Glu
    50                  55                  60

Thr Ser Asp Ala Lys Ser Thr Pro Thr Ala Glu Ala Glu Glu Ala Gly
65                  70                  75                  80

Ile Gly Asp Thr Pro Ser Leu Glu Asp Glu Ala Ala Gly His Val Thr
                85                  90                  95

```
Gln Ala Arg Met Val Ser Lys Ser Lys Asp Gly Thr Gly Ser Asp Asp
            100                 105                 110

Lys Lys Ala Lys Gly Ala Asp Gly Lys Thr Lys Ile Ala Thr Pro Arg
            115                 120                 125

Gly Ala Ala Pro Pro Gly Gln Lys Gly Gln Ala Asn Ala Thr Arg Ile
            130                 135                 140

Pro Ala Lys Thr Pro Ala Pro Lys Thr Pro Pro Ser Ser Gly Glu
145                 150                 155                 160

Pro Pro Lys Ser Gly Asp Arg Ser Gly Tyr Ser Ser Pro Gly Ser Pro
                165                 170                 175

Gly Thr Pro Gly Ser Arg Ser Arg Thr Pro Ser Leu Pro Thr Pro Pro
            180                 185                 190

Thr Arg Glu Pro Lys Lys Val Ala Val Val Arg Thr Pro Pro Lys Ser
            195                 200                 205

Pro Ser Ser Ala Lys Ser Arg Leu Gln Thr Ala Pro Val Pro Met Pro
210                 215                 220

Asp Leu Lys Asn Val Lys Ser Lys Ile Gly Ser Thr Glu Asn Leu Lys
225                 230                 235                 240

His Gln Pro Gly Gly Gly Lys Val Gln Ile Val Tyr Lys Pro Val Asp
            245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
            290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
            325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
            370                 375                 380

<210> SEQ ID NO 5
<211> LENGTH: 385
<212> TYPE: PRT
<213> ORGANISM: Homo sapiens

<400> SEQUENCE: 5

Thr Ala Met Ala Glu Pro Arg Gln Glu Phe Glu Val Met Glu Asp His
1               5                   10                  15

Ala Gly Thr Tyr Gly Leu Gly Asp Arg Lys Asp Gln Gly Gly Tyr Thr
            20                  25                  30

Met His Gln Asp Gln Glu Gly Asp Thr Asp Ala Gly Leu Lys Ala Glu
            35                  40                  45

Glu Ala Gly Ile Gly Asp Thr Pro Ser Leu Glu Asp Glu Ala Ala Gly
            50                  55                  60

His Val Thr Gln Ala Arg Met Val Ser Lys Ser Lys Asp Gly Thr Gly
65              70                  75                  80

Ser Asp Asp Lys Lys Ala Lys Gly Ala Asp Gly Lys Thr Lys Ile Ala
```

```
                85                  90                  95
Thr Pro Arg Gly Ala Pro Pro Gly Gln Lys Gly Gln Ala Asn Ala
            100                 105                 110
Thr Arg Ile Pro Ala Lys Thr Pro Pro Ala Pro Lys Thr Pro Ser
            115                 120                 125
Ser Gly Glu Pro Pro Lys Ser Gly Asp Arg Ser Gly Tyr Ser Ser Pro
130                 135                 140
Gly Ser Pro Gly Thr Pro Gly Ser Arg Ser Arg Thr Pro Ser Leu Pro
145                 150                 155                 160
Thr Pro Pro Thr Arg Glu Pro Lys Lys Val Ala Val Val Arg Thr Pro
            165                 170                 175
Pro Lys Ser Pro Ser Ser Ala Lys Ser Arg Leu Gln Thr Ala Pro Val
            180                 185                 190
Pro Met Pro Asp Leu Lys Asn Val Lys Ser Lys Ile Gly Ser Thr Glu
            195                 200                 205
Asn Leu Lys His Gln Pro Gly Gly Gly Lys Val Gln Ile Ile Asn Lys
            210                 215                 220
Lys Leu Asp Leu Ser Asn Val Gln Ser Lys Cys Gly Ser Lys Asp Asn
225                 230                 235                 240
Ile Lys His Val Pro Gly Gly Gly Ser Val Gln Ile Val Tyr Lys Pro
            245                 250                 255
Val Asp Leu Ser Lys Val Thr Ser Lys Cys Gly Ser Leu Gly Asn Ile
            260                 265                 270
His His Lys Pro Gly Gly Gly Gln Val Glu Val Lys Ser Glu Lys Leu
            275                 280                 285
Asp Phe Lys Asp Arg Val Gln Ser Lys Ile Gly Ser Leu Asp Asn Ile
            290                 295                 300
Thr His Val Pro Gly Gly Gly Asn Lys Lys Ile Glu Thr His Lys Leu
305                 310                 315                 320
Thr Phe Arg Glu Asn Ala Lys Ala Lys Thr Asp His Gly Ala Glu Ile
            325                 330                 335
Val Tyr Lys Ser Pro Val Val Ser Gly Asp Thr Ser Pro Arg His Leu
            340                 345                 350
Ser Asn Val Ser Ser Thr Gly Ser Ile Asp Met Val Asp Ser Pro Gln
            355                 360                 365
Leu Ala Thr Leu Ala Asp Glu Val Ser Ala Ser Leu Ala Lys Gln Gly
            370                 375                 380
Leu
385

<210> SEQ ID NO 6
<211> LENGTH: 352
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
Gln Asp Gln Glu Gly Asp Thr Asp Ala Gly Leu Lys Ala Glu Glu Ala
            35                  40                  45
Gly Ile Gly Asp Thr Pro Ser Leu Glu Asp Glu Ala Ala Gly His Val
        50                  55                  60
```

```
Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
            100                 105                 110

Ile Pro Ala Lys Thr Pro Ala Pro Lys Thr Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
        290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
            340                 345                 350

<210> SEQ ID NO 7
<211> LENGTH: 24
<212> TYPE: DNA
<213> ORGANISM: Artificial Sequence
<220> FEATURE:
<223> OTHER INFORMATION: synthetic construct

<400> SEQUENCE: 7
atggactgga cctggaggtt cctc                                            24

<210> SEQ ID NO 8
<211> LENGTH: 24
<212> TYPE: DNA
<213> ORGANISM: Artificial Sequence
<220> FEATURE:
<223> OTHER INFORMATION: synthetic construct

<400> SEQUENCE: 8
atggactgga cctggaggat cctc                                            24
```

```
<210> SEQ ID NO 9
<211> LENGTH: 24
<212> TYPE: DNA
<213> ORGANISM: Artificial Sequence
<220> FEATURE:
<223> OTHER INFORMATION: synthetic construct

<400> SEQUENCE: 9
atggactgga cctggagggt cttc                                          24

<210> SEQ ID NO 10
<211> LENGTH: 22
<212> TYPE: DNA
<213> ORGANISM: Unknown
<220> FEATURE:
<223> OTHER INFORMATION: synthetic construct

<400> SEQUENCE: 10
atggactgga cctggagcat cc                                            22

<210> SEQ ID NO 11
<211> LENGTH: 26
<212> TYPE: DNA
<213> ORGANISM: Artificial Sequence
<220> FEATURE:
<223> OTHER INFORMATION: synthetic construct

<400> SEQUENCE: 11
ggacatactt tgttccacgc tcctgc                                        26

<210> SEQ ID NO 12
<211> LENGTH: 23
<212> TYPE: DNA
<213> ORGANISM: Artificial Sequence
<220> FEATURE:
<223> OTHER INFORMATION: synthetic construct

<400> SEQUENCE: 12
aggtgtccag tgtcaggtgc agc                                           23

<210> SEQ ID NO 13
<211> LENGTH: 23
<212> TYPE: DNA
<213> ORGANISM: Artificial Sequence
<220> FEATURE:
<223> OTHER INFORMATION: synthetic construct

<400> SEQUENCE: 13
aggtgtccag tgtgaggtgc agc                                           23

<210> SEQ ID NO 14
<211> LENGTH: 23
<212> TYPE: DNA
<213> ORGANISM: Artificial Sequence
<220> FEATURE:
<223> OTHER INFORMATION: synthetic construct

<400> SEQUENCE: 14
aggtgtccag tgtcaggtac agc                                           23

<210> SEQ ID NO 15
<211> LENGTH: 21
<212> TYPE: DNA
<213> ORGANISM: Artificial Sequence
<220> FEATURE:
<223> OTHER INFORMATION: synthetic construct
```

<400> SEQUENCE: 15
gcagctccca gatgggtcct g                                              21

<210> SEQ ID NO 16
<211> LENGTH: 21
<212> TYPE: DNA
<213> ORGANISM: Artificial Sequence
<220> FEATURE:
<223> OTHER INFORMATION: synthetic construct

<400> SEQUENCE: 16
tcaaccgcca tcctcgccct c                                              21

<210> SEQ ID NO 17
<211> LENGTH: 26
<212> TYPE: DNA
<213> ORGANISM: Artificial Sequence
<220> FEATURE:
<223> OTHER INFORMATION: synthetic construct

<400> SEQUENCE: 17
gtctgtctcc ttcctcatct tcctgc                                         26

<210> SEQ ID NO 18
<211> LENGTH: 23
<212> TYPE: DNA
<213> ORGANISM: Artificial Sequence
<220> FEATURE:
<223> OTHER INFORMATION: synthetic construct

<400> SEQUENCE: 18
ggaaggtgtg cacgccgctg gtc                                            23

<210> SEQ ID NO 19
<211> LENGTH: 21
<212> TYPE: DNA
<213> ORGANISM: Artificial Sequence
<220> FEATURE:
<223> OTHER INFORMATION: synthetic construct

<400> SEQUENCE: 19
atgagggtcc ccgctcagct c                                              21

<210> SEQ ID NO 20
<211> LENGTH: 21
<212> TYPE: DNA
<213> ORGANISM: Artificial Sequence
<220> FEATURE:
<223> OTHER INFORMATION: synthetic construct

<400> SEQUENCE: 20
atgagggtcc ctgctcagct c                                              21

<210> SEQ ID NO 21
<211> LENGTH: 21
<212> TYPE: DNA
<213> ORGANISM: Artificial Sequence
<220> FEATURE:
<223> OTHER INFORMATION: synthetic construct

<400> SEQUENCE: 21
atgagagtcc tcgctcagct c                                              21

<210> SEQ ID NO 22
<211> LENGTH: 20

```
<212> TYPE: DNA
<213> ORGANISM: Artificial Sequence
<220> FEATURE:
<223> OTHER INFORMATION: synthetic construct

<400> SEQUENCE: 22
tggggctgct aatgctctgg                                              20

<210> SEQ ID NO 23
<211> LENGTH: 23
<212> TYPE: DNA
<213> ORGANISM: Artificial Sequence
<220> FEATURE:
<223> OTHER INFORMATION: synthetic construct

<400> SEQUENCE: 23
cctcctgcta ctctggctcc cag                                          23

<210> SEQ ID NO 24
<211> LENGTH: 26
<212> TYPE: DNA
<213> ORGANISM: Artificial Sequence
<220> FEATURE:
<223> OTHER INFORMATION: synthetic construct

<400> SEQUENCE: 24
tctctgttgc tctggatctc tggtgc                                       26

<210> SEQ ID NO 25
<211> LENGTH: 24
<212> TYPE: DNA
<213> ORGANISM: Artificial Sequence
<220> FEATURE:
<223> OTHER INFORMATION: synthetic construct

<400> SEQUENCE: 25
ctcctcagct tcctcctcct ttgg                                         24

<210> SEQ ID NO 26
<211> LENGTH: 26
<212> TYPE: DNA
<213> ORGANISM: Artificial Sequence
<220> FEATURE:
<223> OTHER INFORMATION: synthetic construct

<400> SEQUENCE: 26
aactcattgg gtttctgctg ctctgg                                       26

<210> SEQ ID NO 27
<211> LENGTH: 26
<212> TYPE: DNA
<213> ORGANISM: Artificial Sequence
<220> FEATURE:
<223> OTHER INFORMATION: synthetic construct

<400> SEQUENCE: 27
gtttctcgta gtctgctttg ctcagc                                       26

<210> SEQ ID NO 28
<211> LENGTH: 23
<212> TYPE: DNA
<213> ORGANISM: Artificial Sequence
<220> FEATURE:
<223> OTHER INFORMATION: synthetic construct

<400> SEQUENCE: 28
```

```
gtgctgtcct tgctgtcctg ctc                                              23

<210> SEQ ID NO 29
<211> LENGTH: 26
<212> TYPE: DNA
<213> ORGANISM: Artificial Sequence
<220> FEATURE:
<223> OTHER INFORMATION: synthetic construct

<400> SEQUENCE: 29
gcactctccc ctgttgaagc tctttg                                           26

<210> SEQ ID NO 30
<211> LENGTH: 20
<212> TYPE: DNA
<213> ORGANISM: Artificial Sequence
<220> FEATURE:
<223> OTHER INFORMATION: synthetic construct

<400> SEQUENCE: 30
ctcctcgctc actgcacagg                                                  20

<210> SEQ ID NO 31
<211> LENGTH: 20
<212> TYPE: DNA
<213> ORGANISM: Artificial Sequence
<220> FEATURE:
<223> OTHER INFORMATION: synthetic construct

<400> SEQUENCE: 31
ctcctctctc actgcacagg                                                  20

<210> SEQ ID NO 32
<211> LENGTH: 20
<212> TYPE: DNA
<213> ORGANISM: Artificial Sequence
<220> FEATURE:
<223> OTHER INFORMATION: synthetic construct

<400> SEQUENCE: 32
ctcctcactc gggacacagg                                                  20

<210> SEQ ID NO 33
<211> LENGTH: 20
<212> TYPE: DNA
<213> ORGANISM: Artificial Sequence
<220> FEATURE:
<223> OTHER INFORMATION: synthetic construct

<400> SEQUENCE: 33
atggcctgga ccctctctg                                                   20

<210> SEQ ID NO 34
<211> LENGTH: 24
<212> TYPE: DNA
<213> ORGANISM: Artificial Sequence
<220> FEATURE:
<223> OTHER INFORMATION: synthetic construct

<400> SEQUENCE: 34
atggcatgga tccctctctt cctc                                             24

<210> SEQ ID NO 35
<211> LENGTH: 24
<212> TYPE: DNA
<213> ORGANISM: Artificial Sequence
```

<220> FEATURE:
<223> OTHER INFORMATION: synthetic construct

<400> SEQUENCE: 35
cactagtgtg gccttgttgg cttg                                              24

<210> SEQ ID NO 36
<211> LENGTH: 43
<212> TYPE: DNA
<213> ORGANISM: Artificial Sequence
<220> FEATURE:
<223> OTHER INFORMATION: synthetic construct

<400> SEQUENCE: 36
cctgtctgga attcagcatg gcccaggtgc agctggtgca gtc                         43

<210> SEQ ID NO 37
<211> LENGTH: 43
<212> TYPE: DNA
<213> ORGANISM: Artificial Sequence
<220> FEATURE:
<223> OTHER INFORMATION: synthetic construct

<400> SEQUENCE: 37
cctgtctgga attcagcatg gcccaggtcc agctggtgca gtc                         43

<210> SEQ ID NO 38
<211> LENGTH: 43
<212> TYPE: DNA
<213> ORGANISM: Artificial Sequence
<220> FEATURE:
<223> OTHER INFORMATION: synthetic construct

<400> SEQUENCE: 38
cctgtctgga attcagcatg gcccaggttc agctggtgca gtc                         43

<210> SEQ ID NO 39
<211> LENGTH: 43
<212> TYPE: DNA
<213> ORGANISM: Artificial Sequence
<220> FEATURE:
<223> OTHER INFORMATION: synthetic construct

<400> SEQUENCE: 39
cctgtctgga attcagcatg gcccaggtcc agcttgtgca gtc                         43

<210> SEQ ID NO 40
<211> LENGTH: 46
<212> TYPE: DNA
<213> ORGANISM: Artificial Sequence
<220> FEATURE:
<223> OTHER INFORMATION: synthetic construct

<400> SEQUENCE: 40
cctgtctgga attcagcatg gcccaggtca ccttgaggga gtctgg                      46

<210> SEQ ID NO 41
<211> LENGTH: 46
<212> TYPE: DNA
<213> ORGANISM: Artificial Sequence
<220> FEATURE:
<223> OTHER INFORMATION: synthetic construct

<400> SEQUENCE: 41
cctgtctgga attcagcatg gcccaggtca ccttgaagga gtctgg                      46

```
<210> SEQ ID NO 42
<211> LENGTH: 43
<212> TYPE: DNA
<213> ORGANISM: Artificial Sequence
<220> FEATURE:
<223> OTHER INFORMATION: synthetic construct

<400> SEQUENCE: 42
cctgtctgga attcagcatg gcccaggtgc agctggtgga gtc                43

<210> SEQ ID NO 43
<211> LENGTH: 43
<212> TYPE: DNA
<213> ORGANISM: Artificial Sequence
<220> FEATURE:
<223> OTHER INFORMATION: synthetic construct

<400> SEQUENCE: 43
cctgtctgga attcagcatg gccgaggtgc agctgttgga gtc                43

<210> SEQ ID NO 44
<211> LENGTH: 43
<212> TYPE: DNA
<213> ORGANISM: Artificial Sequence
<220> FEATURE:
<223> OTHER INFORMATION: synthetic construct

<400> SEQUENCE: 44
cctgtctgga attcagcatg gccgaggtgc agctggtgga gtc                43

<210> SEQ ID NO 45
<211> LENGTH: 45
<212> TYPE: DNA
<213> ORGANISM: Artificial Sequence
<220> FEATURE:
<223> OTHER INFORMATION: synthetic construct

<400> SEQUENCE: 45
cctgtctgga attcagcatg gcccaggtac agctggtgga gtctg              45

<210> SEQ ID NO 46
<211> LENGTH: 41
<212> TYPE: DNA
<213> ORGANISM: Artificial Sequence
<220> FEATURE:
<223> OTHER INFORMATION: synthetic construct

<400> SEQUENCE: 46
cctgtctgga attcagcatg gcccagstgc agctgcagga g                  41

<210> SEQ ID NO 47
<211> LENGTH: 44
<212> TYPE: DNA
<213> ORGANISM: Artificial Sequence
<220> FEATURE:
<223> OTHER INFORMATION: synthetic construct

<400> SEQUENCE: 47
cctgtctgga attcagcatg gcccaggtgc agctacagca gtgg               44

<210> SEQ ID NO 48
<211> LENGTH: 43
<212> TYPE: DNA
<213> ORGANISM: Artificial Sequence
<220> FEATURE:
<223> OTHER INFORMATION: synthetic construct
```

<400> SEQUENCE: 48
cctgtctgga attcagcatg gccgaggtgc agctggtgca gtc         43

<210> SEQ ID NO 49
<211> LENGTH: 45
<212> TYPE: DNA
<213> ORGANISM: Artificial Sequence
<220> FEATURE:
<223> OTHER INFORMATION: synthetic construct

<400> SEQUENCE: 49
cctgtctgga attcagcatg gcccaggtac agctgcagca gtcag       45

<210> SEQ ID NO 50
<211> LENGTH: 45
<212> TYPE: DNA
<213> ORGANISM: Artificial Sequence
<220> FEATURE:
<223> OTHER INFORMATION: synthetic construct

<400> SEQUENCE: 50
cctgtctgga attcagcatg gcccaggtgc agctggtgca atctg       45

<210> SEQ ID NO 51
<211> LENGTH: 37
<212> TYPE: DNA
<213> ORGANISM: Artificial Sequence
<220> FEATURE:
<223> OTHER INFORMATION: synthetic construct

<400> SEQUENCE: 51
tcgggcctcg agactcacct gaggagacgg tgaccag                37

<210> SEQ ID NO 52
<211> LENGTH: 39
<212> TYPE: DNA
<213> ORGANISM: Artificial Sequence
<220> FEATURE:
<223> OTHER INFORMATION: synthetic construct

<400> SEQUENCE: 52
tcgggcctcg agactcacct gaagagacgg tgaccattg              39

<210> SEQ ID NO 53
<211> LENGTH: 38
<212> TYPE: DNA
<213> ORGANISM: Artificial Sequence
<220> FEATURE:
<223> OTHER INFORMATION: synthetic construct

<400> SEQUENCE: 53
tcgggcctcg agactcacct gaggagacgg tgaccgtg               38

<210> SEQ ID NO 54
<211> LENGTH: 46
<212> TYPE: DNA
<213> ORGANISM: Artificial Sequence
<220> FEATURE:
<223> OTHER INFORMATION: synthetic construct

<400> SEQUENCE: 54
ccggtctaga gttttccatg gcggacatcc agatgaccca gtctcc      46

<210> SEQ ID NO 55

<211> LENGTH: 46
<212> TYPE: DNA
<213> ORGANISM: Artificial Sequence
<220> FEATURE:
<223> OTHER INFORMATION: synthetic construct

<400> SEQUENCE: 55
ccggtctaga gttttccatg gcggacatcc agttgaccca gtctcc          46

<210> SEQ ID NO 56
<211> LENGTH: 46
<212> TYPE: DNA
<213> ORGANISM: Artificial Sequence
<220> FEATURE:
<223> OTHER INFORMATION: synthetic construct

<400> SEQUENCE: 56
ccggtctaga gttttccatg gcggccatcc agttgaccca gtctcc          46

<210> SEQ ID NO 57
<211> LENGTH: 50
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (7)..(7)
<223> OTHER INFORMATION: A or G
<220> FEATURE:
<221> NAME/KEY: misc_feature
<222> LOCATION: (7)..(7)
<223> OTHER INFORMATION: a or g

<400> SEQUENCE: 57
ccggtctaga gttttccatg gcggatrttg tgatgactca gtctccactc      50

<210> SEQ ID NO 58
<211> LENGTH: 48
<212> TYPE: DNA
<213> ORGANISM: Artificial Sequence
<220> FEATURE:
<223> OTHER INFORMATION: synthetic construct

<400> SEQUENCE: 58
ccggtctaga gttttccatg gcggaaattg tgttgacgca gtctccag        48

<210> SEQ ID NO 59
<211> LENGTH: 48
<212> TYPE: DNA
<213> ORGANISM: Artificial Sequence
<220> FEATURE:
<223> OTHER INFORMATION: synthetic construct

<400> SEQUENCE: 59
ccggtctaga gttttccatg gcggaaattg tgttgacaca gtctccag        48

<210> SEQ ID NO 60
<211> LENGTH: 48
<212> TYPE: DNA
<213> ORGANISM: Artificial Sequence
<220> FEATURE:
<223> OTHER INFORMATION: synthetic construct

<400> SEQUENCE: 60
ccggtctaga gttttccatg gcggaaatag tgatgacgca gtctccag        48

<210> SEQ ID NO 61
<211> LENGTH: 46
<212> TYPE: DNA
<213> ORGANISM: Artificial Sequence
<220> FEATURE:
<223> OTHER INFORMATION: synthetic construct

<400> SEQUENCE: 61
ccggtctaga gttttccatg gcggacatcg tgatgaccca gtctcc      46

<210> SEQ ID NO 62
<211> LENGTH: 46
<212> TYPE: DNA
<213> ORGANISM: Artificial Sequence
<220> FEATURE:
<223> OTHER INFORMATION: synthetic construct

<400> SEQUENCE: 62
ccggtctaga gttttccatg gcggaaacga cactcacgca gtctcc      46

<210> SEQ ID NO 63
<211> LENGTH: 48
<212> TYPE: DNA
<213> ORGANISM: Artificial Sequence
<220> FEATURE:
<223> OTHER INFORMATION: synthetic construct

<400> SEQUENCE: 63
ccggtctaga gttttccatg gcggaaattg tgctgactca gtctccag      48

<210> SEQ ID NO 64
<211> LENGTH: 43
<212> TYPE: DNA
<213> ORGANISM: Artificial Sequence
<220> FEATURE:
<223> OTHER INFORMATION: synthetic construct

<400> SEQUENCE: 64
cgcaaagtgc acttacgttt gatttccacc ttggtccctt ggc      43

<210> SEQ ID NO 65
<211> LENGTH: 43
<212> TYPE: DNA
<213> ORGANISM: Artificial Sequence
<220> FEATURE:
<223> OTHER INFORMATION: synthetic construct

<400> SEQUENCE: 65
cgcaaagtgc acttacgttt gatctccagc ttggtcccct ggc      43

<210> SEQ ID NO 66
<211> LENGTH: 43
<212> TYPE: DNA
<213> ORGANISM: Artificial Sequence
<220> FEATURE:
<223> OTHER INFORMATION: synthetic construct

<400> SEQUENCE: 66
cgcaaagtgc acttacgttt gatatccact ttggtcccag ggc      43

<210> SEQ ID NO 67
<211> LENGTH: 43
<212> TYPE: DNA
<213> ORGANISM: Artificial Sequence
<220> FEATURE:
<223> OTHER INFORMATION: synthetic construct

<400> SEQUENCE: 67
cgcaaagtgc acttacgttt gatctccacc ttggtccctc cgc  43

<210> SEQ ID NO 68
<211> LENGTH: 43
<212> TYPE: DNA
<213> ORGANISM: Artificial Sequence
<220> FEATURE:
<223> OTHER INFORMATION: synthetic construct

<400> SEQUENCE: 68
cgcaaagtgc acttacgttt aatctccagt cgtgtccctt ggc  43

<210> SEQ ID NO 69
<211> LENGTH: 49
<212> TYPE: DNA
<213> ORGANISM: Artificial Sequence
<220> FEATURE:
<223> OTHER INFORMATION: synthetic construct

<400> SEQUENCE: 69
ccggtctaga gttttccatg gcgaatttta tgctgactca gccccactc  49

<210> SEQ ID NO 70
<211> LENGTH: 43
<212> TYPE: DNA
<213> ORGANISM: Artificial Sequence
<220> FEATURE:
<223> OTHER INFORMATION: synthetic construct

<400> SEQUENCE: 70
ccggtctaga gttttccatg gcgtcctatg tgctgactca gcc  43

<210> SEQ ID NO 71
<211> LENGTH: 43
<212> TYPE: DNA
<213> ORGANISM: Artificial Sequence
<220> FEATURE:
<223> OTHER INFORMATION: synthetic construct

<400> SEQUENCE: 71
ccggtctaga gttttccatg gcgcagtctg tgctgacgca gcc  43

<210> SEQ ID NO 72
<211> LENGTH: 43
<212> TYPE: DNA
<213> ORGANISM: Artificial Sequence
<220> FEATURE:
<223> OTHER INFORMATION: synthetic construct

<400> SEQUENCE: 72
ccggtctaga gttttccatg gcgcagtctg tcgtgacgca gcc  43

<210> SEQ ID NO 73
<211> LENGTH: 43
<212> TYPE: DNA
<213> ORGANISM: Artificial Sequence
<220> FEATURE:
<223> OTHER INFORMATION: synthetic construct

<400> SEQUENCE: 73
ccggtctaga gttttccatg gcgcagtctg ccctgactca gcc  43

<210> SEQ ID NO 74
<211> LENGTH: 45

```
<212> TYPE: DNA
<213> ORGANISM: Artificial Sequence
<220> FEATURE:
<223> OTHER INFORMATION: synthetic construct

<400> SEQUENCE: 74
ccggtctaga gttttccatg gcgtcttctg agctgactca ggacc            45

<210> SEQ ID NO 75
<211> LENGTH: 46
<212> TYPE: DNA
<213> ORGANISM: Artificial Sequence
<220> FEATURE:
<223> OTHER INFORMATION: synthetic construct

<400> SEQUENCE: 75
ccggtctaga gttttccatg gcgtcctatg agctgactca gccacc           46

<210> SEQ ID NO 76
<211> LENGTH: 27
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (13)..(13)
<223> OTHER INFORMATION: c or t

<400> SEQUENCE: 76
ctcagaggag ggygggaaca gagtgac                                27

<210> SEQ ID NO 77
<211> LENGTH: 1766
<212> TYPE: DNA
<213> ORGANISM: Artificial Sequence
<220> FEATURE:
<223> OTHER INFORMATION: synthetic construct

<400> SEQUENCE: 77
aaacgtaagt gcactttgcg gccgctagga agaaactcaa aacatcaaga ttttaaatac    60
gcttcttggt ctccttgcta taattatctg ggataagcat gctgttttct gtctgtccct   120
aacatgccct gtgattatcc gcaaacaaca cacccaaggg cagaactttg ttacttaaac   180
accatcctgt ttgcttcttt cctcaggaac tgtggctgca ccatctgtct tcatcttccc   240
gccatctgat gagcagttga aatctggaac tgcctctgtt gtgtgcctgc tgaataactt   300
ctatcccaga gaggccaaag tacagtggaa ggtggataac gccctccaat cgggtaactc   360
ccaggagagt gtcacagagc aggacagcaa ggacagcacc tacagcctca gcagcaccct   420
gacgctgagc aaagcagact acgagaaaca caaagtctac gcctgcgaag tcacccatca   480
gggcctgagc tcgcccgtca caaagagctt caacagggga gagtgttagt aacggatcg    540 atccgagctc ggtaccaagc ttaagtttaa accgctgatc agcctcgact gtgccttcta   600
gttgccagcc atctgttgtt tgcccctccc ccgtgccttc cttgaccctg gaaggtgcca   660
ctcccactgt cctttcctaa taaaatgagg aaattgcatc gcattgtctg agtaggtgtc   720
attctattct ggggggtggg gtggggcagg acagcaaggg ggaggattgg gaagacaata   780
gcaggcatgc tggggatgcg gtaatctgct tagggttagg cgttttgcgc tgcttcgcta   840
ggtggtcaat attggccatt agccatatta ttcattggtt atatagcata aatcaatatt   900
ggctattggc cattgcatac gttgtatcca tatcataata tgtacattta tattggctca   960
```

```
tgtccaacat taccgccatg ttgacattga ttattgacta gttattaata gtaatcaatt   1020
acggggtcat tagttcatag cccatatatg gagttccgcg ttacataact tacggtaaat   1080
ggcccgcctg gctgaccgcc caacgacccc cgcccattga cgtcaataat gacgtatgtt   1140
cccatagtaa cgccaatagg gactttccat tgacgtcaat gggtggagta tttacggtaa   1200
actgcccact tggcagtaca tcaagtgtat catatgccaa gtacgccccc tattgacgtc   1260
aatgacggta aatggcccgc ctggcattat gcccagtaca tgaccttatg gactttcct   1320 acttggcagt acatctacgt attagtcatc gctattacca tggtgatgcg gttttggcag   1380
tacatcaatg ggcgtggata gcggtttgac tcacggggat ttccaagtct ccaccccatt   1440
gacgtcaatg ggagtttgtt ttggcaccaa aatcaacggg actttccaaa atgtcgtaac   1500
aactccgccc cattgacgca aatgggcggt aggcgtgtac ggtgggaggt ctatataagc   1560
agagctcgtt tagtgaaccg tcagatcgcc tggagacgcc atccacgctg ttttgacctc   1620
catagaagac accgggaccg atccagcctc cgcggccggg aacggtgcat tggaagcttg   1680
gtaccgagct cggatccgcc accatggcct gccccggatt tctgtgggcc ctggtcatca   1740
gcacctgtct ggaattcagc atggcc                                        1766
```

<210> SEQ ID NO 78
<211> LENGTH: 23
<212> TYPE: DNA
<213> ORGANISM: Artificial Sequence
<220> FEATURE:
<223> OTHER INFORMATION: synthetic construct

<400> SEQUENCE: 78
ggccatgctg aattccagac agg                                              23

<210> SEQ ID NO 79
<211> LENGTH: 29
<212> TYPE: DNA
<213> ORGANISM: Artificial Sequence
<220> FEATURE:
<223> OTHER INFORMATION: synthetic construct

<400> SEQUENCE: 79
aaacgtaagt gcactttgcg gccgctagg                                        29

<210> SEQ ID NO 80
<211> LENGTH: 25
<212> TYPE: DNA
<213> ORGANISM: Artificial Sequence
<220> FEATURE:
<223> OTHER INFORMATION: synthetic construct

<400> SEQUENCE: 80
actctgttcc crccctcctc tgagg                                            25

<210> SEQ ID NO 81
<211> LENGTH: 23
<212> TYPE: DNA
<213> ORGANISM: Artificial Sequence
<220> FEATURE:
<223> OTHER INFORMATION: synthetic construct

<400> SEQUENCE: 81
ccggtctaga gttttccatg gcg                                              23

<210> SEQ ID NO 82
<211> LENGTH: 19

<212> TYPE: DNA
<213> ORGANISM: Artificial Sequence
<220> FEATURE:
<223> OTHER INFORMATION: synthetic construct

<400> SEQUENCE: 82
tcgggcctcg agactcacc							19

<210> SEQ ID NO 83
<211> LENGTH: 330
<212> TYPE: PRT
<213> ORGANISM: Homo sapiens

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 84
<211> LENGTH: 107
<212> TYPE: PRT
<213> ORGANISM: Homo sapiens

<400> SEQUENCE: 84

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 85
<211> LENGTH: 18
<212> TYPE: DNA
<213> ORGANISM: Artificial Sequence
<220> FEATURE:
<223> OTHER INFORMATION: synthetic construct

<400> SEQUENCE: 85
catgtcaccg gggtgtgg                                                 18

<210> SEQ ID NO 86
<211> LENGTH: 21
<212> TYPE: DNA
<213> ORGANISM: Artificial Sequence
<220> FEATURE:
<223> OTHER INFORMATION: synthetic construct

<400> SEQUENCE: 86
tcacagggga tgttagggac a                                             21

<210> SEQ ID NO 87
<211> LENGTH: 117
<212> TYPE: PRT
<213> ORGANISM: Artificial Sequence
<220> FEATURE:
<223> OTHER INFORMATION: Combination of PCR-generated and human sequence

<400> SEQUENCE: 87

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asp Thr Asn Tyr Ala Asp Ser Val
    50                  55                  60

Lys Gly Arg Phe Thr Phe Ser Arg Asp Asn Ala Lys Asn Thr Leu Tyr
65                  70                  75                  80

```
Leu Gln Met Thr Ser Leu Arg Ala Glu Asp Thr Ala Ile Tyr Tyr Cys
            85                  90                  95

Thr Arg Gly Arg Ser Tyr Gly Phe Phe Asp Tyr Trp Gly Gln Gly Ala
        100                 105                 110

Leu Val Thr Val Ser
        115

<210> SEQ ID NO 88
<211> LENGTH: 108
<212> TYPE: PRT
<213> ORGANISM: Artificial Sequence
<220> FEATURE:
<223> OTHER INFORMATION: Combination of PCR-generated and human sequence

<400> SEQUENCE: 88

Asp Ile Val Met Thr Gln Ser Pro Asp Thr Leu Ser Leu Ser Pro Gly
1               5                   10                  15

Glu Arg Ala Thr Leu Ser Cys Arg Ala Ser Gln Ile Ile Ser Ser Asn
            20                  25                  30

Tyr Leu Ala Trp Tyr Gln Gln Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Ala Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Arg Thr Phe Gly Gln Gly Thr Lys Leu Glu Ile Lys
            100                 105

<210> SEQ ID NO 89
<211> LENGTH: 354
<212> TYPE: DNA
<213> ORGANISM: Artificial Sequence
<220> FEATURE:
<223> OTHER INFORMATION: Combination of PCR-generated and human sequence

<400> SEQUENCE: 89
caggtccagc tggtggagtc cggggggaggc ttagttcagc ctggggggtc cctgagactc      60
tcctgtgcag cgtctggatt caccttcagc agctactgga tgcactgggt ccgccaagct     120
ccagggaagg gctggtgtg gtctcccgt attaatagtg atgggagtga cacaaactac      180
gcggactccg tgaagggccg attcaccttc tccagagaca cgccaagaa cacattgtat     240 ctgcagatga ccagtctgcg agccgaggac acggctatat attactgtac aaggggggcgc    300 agttatggtt tctttgacta ctggggccag ggagccctgg tcaccgtctc ctca          354

<210> SEQ ID NO 90
<211> LENGTH: 324
<212> TYPE: DNA
<213> ORGANISM: Artificial Sequence
<220> FEATURE:
<223> OTHER INFORMATION: Combination of PCR-generated and human sequence

<400> SEQUENCE: 90
gacatcgtga tgacccagtc tccagacacc ctgtctttgt ctccagggga gagagccacc      60
ctctcctgca gggccagtca gattattagc agcaactact tagcctggta ccaacaacaa     120
cctggccagg ctcccaggct cctcatctat ggtgcatcca gcagggccac aggcatccca    180
gacaggttca gtggcagtgg gtctgcgaca gacttcactc tcaccatcag cagactggag    240
```

-continued

```
cctgaagatt ttgcagtgta ttactgtcag cagtatggta cctcacctcg gacgttcggc      300
caggggacca agctggagat caaa                                             324
```

<210> SEQ ID NO 91
<211> LENGTH: 124
<212> TYPE: PRT
<213> ORGANISM: Artificial Sequence
<220> FEATURE:
<223> OTHER INFORMATION: Combination of PCR-generated and human sequence

<400> SEQUENCE: 91

```
Gln Val Gln Leu Val Glu Ser Arg Gly Gly Val Val Gln Pro Gly Thr
1               5                   10                  15

Ser Leu Arg Leu Ser Cys Lys Ala Ser Gly Phe Thr Phe Ser Thr Tyr
            20                  25                  30

Gly Met His Trp Val Arg Gln Ala Pro Gly Lys Ala Leu Glu Trp Val
        35                  40                  45

Ala Val Ile Trp Phe Asp Gly Asn Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Gly Glu Asp Thr Ala Val Tyr Tyr Cys
                85                  90                  95

Ala Arg Asp Trp Trp Glu Ala Gly Cys Arg Pro Cys Tyr Phe Phe Asp
            100                 105                 110

Tyr Trp Gly Gln Gly Ser Leu Val Thr Val Ser Ser
        115                 120
```

<210> SEQ ID NO 92
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 92

```
Glu Thr Thr Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Pro Pro Leu Thr Phe Gly Gly Gly Thr Lys Leu Glu Ile
            100                 105                 110

Lys
```

<210> SEQ ID NO 93
<211> LENGTH: 372
<212> TYPE: DNA
<213> ORGANISM: Artificial Sequence
<220> FEATURE:
<223> OTHER INFORMATION: Combination of PCR-generated and human sequence

<400> SEQUENCE: 93

```
caggtgcagc tggtggagtc gaggggaggc gtggtccagc ctgggacgtc cctgagactc    60
tcctgtaaag cgtctggatt caccttcagc acttatggca tgcactgggt ccgccaggct   120
ccaggcaagg cgctggagtg ggtggcagtt atatggtttg atggaaataa caaatattat   180
gcagactccg tgaagggccg attcaccatc tccagagaca attccaagaa cacggtgtat   240
ctgcaaatga acagcctgag aggcgaggac acggctgttt attactgtgc gagagattgg   300
tgggaagccg ggtgccggcc ctgttatttc tttgactact ggggccaggg aagcctggtc   360
accgtctcct ca                                                       372
```

<210> SEQ ID NO 94
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 94

```
gaaacgacac tcacgcagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aaggtgctca tttactgggc ttctacccgg   180
gaatccgggg tccctgaccg attcagtggc agcgggtctg ggaccgattt cactctcacc   240
atcagcagcc tgcaggctga agatgtggca gtttattact gtcagcaata ttatagtcct   300
ccgctcactt tcggcggagg gaccaagctg gagatcaaa                          339
```

<210> SEQ ID NO 95
<211> LENGTH: 127
<212> TYPE: PRT
<213> ORGANISM: Artificial Sequence
<220> FEATURE:
<223> OTHER INFORMATION: Combination of PCR-generated and human sequence

<400> SEQUENCE: 95

```
Glu Val Gln Leu Val Gln Ser Gly Gly Gly Leu Val Gln Pro Gly Gly
  1               5                  10                  15
Ser Leu Arg Leu Ser Cys Ala Ala Ser Gly Phe Thr Phe Ser Asp Tyr
             20                  25                  30
Trp Met Ser Trp Val Arg Gln Ala Pro Gly Lys Gly Leu Glu Trp Val
         35                  40                  45
Ala Asn Ile Asn Gln Asp Gly Ser Ala Ala Tyr Tyr Val Asp Ser Val
     50                  55                  60
Arg Gly Arg Phe Thr Ile Ser Arg Asp Ser Ala Glu Asn Ser Leu Asn
 65                  70                  75                  80
Leu Gln Met Asn Ser Leu Arg Ala Glu Asp Thr Ala Val Tyr Tyr Cys
                 85                  90                  95
Ala Lys Asp Ala His Tyr Tyr Asp Arg Asn Arg Asn Asn Tyr Tyr Tyr
            100                 105                 110
Tyr Phe Asp Phe Trp Gly Gln Gly Thr Leu Val Thr Val Ser Ser
        115                 120                 125
```

<210> SEQ ID NO 96
<211> LENGTH: 107
<212> TYPE: PRT
<213> ORGANISM: Artificial Sequence
<220> FEATURE:

<223> OTHER INFORMATION: Combination of PCR-generated and human sequence

<400> SEQUENCE: 96

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ala Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys
            100                 105
```

<210> SEQ ID NO 97
<211> LENGTH: 381
<212> TYPE: DNA
<213> ORGANISM: Artificial Sequence
<220> FEATURE:
<223> OTHER INFORMATION: Combination of PCR-generated and human sequence

<400> SEQUENCE: 97

```
gaggtgcagc tggtgcagtc tgggggaggc ttggtccagc ctggggggtc cctgagactc    60
tcctgtgcag cctctggatt caccttcagt gactattgga tgagctgggt ccgccaggct   120
ccagggaagg ggctggagtg ggtggccaac ataaatcaag atggaagtgc tgcatactat   180
gtggactctg tgaggggccg attcaccatc tccagagaca cgccgagaa ctcactgaat    240
ctgcaaatga acagcctgag agccgaggac acggctgtgt attactgtgc gaaagatgca   300
cattactacg atcgtaatcg taataattat tactactact ttgacttctg gggccaggga   360
accctggtca ccgtctcctc a                                              381
```

<210> SEQ ID NO 98
<211> LENGTH: 321
<212> TYPE: DNA
<213> ORGANISM: Artificial Sequence
<220> FEATURE:
<223> OTHER INFORMATION: Combination of PCR-generated and human sequence

<400> SEQUENCE: 98

```
gaaatagtga tgacgcagtc tccggccacc ctgtctgtgt ctccagggga aagagccacc    60
ctctcctgca gggccagtca gagtgttggc gccaacttag cctggtacca gcagaaacct   120
gggcaggctc ccaggctcct catctattct gcatccacca gggccactgg tgtcccagcc   180
aggttcagtg gcagtgggtc tgggacagag ttcactctca ccatcagcag cctgcagtct   240
gaagattttg cagtttatta ctgtcagcag tataataact ggcctcggac gttcggccaa   300
gggaccaagg tggaaatcaa a                                              321
```

<210> SEQ ID NO 99
<211> LENGTH: 127
<212> TYPE: PRT
<213> ORGANISM: Artificial Sequence
<220> FEATURE:
<223> OTHER INFORMATION: Combination of PCR-generated and human sequence

<400> SEQUENCE: 99

| Gln | Val | Gln | Leu | Leu | Glu | Ser | Gly | Pro | Gly | Leu | Val | Asn | Pro | Ser | Gln |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Gly |
|---|---|---|---|---|---|---|---|---|---|---|---|---|---|---|---|
| | | | 20 | | | | | 25 | | | | | 30 | | |

| Asn | Tyr | Tyr | Trp | Ser | Trp | Ile | Arg | Gln | Pro | Ala | Gly | Lys | Gly | Leu | Glu |
|---|---|---|---|---|---|---|---|---|---|---|---|---|---|---|---|
| | | 35 | | | | | 40 | | | | | 45 | | | |

| Trp | Ile | Gly | Arg | Met | Ser | Ser | Gly | Ser | Thr | Asn | Tyr | Asn | Pro | Ser |
|---|---|---|---|---|---|---|---|---|---|---|---|---|---|---|
| 50 | | | | | 55 | | | | | 60 | | | | |

| Leu | Lys | Ser | Arg | Val | Thr | Met | Ser | Glu | Asp | Thr | Ser | Lys | Asn | Gln | Phe |
|---|---|---|---|---|---|---|---|---|---|---|---|---|---|---|---|
| 65 | | | | | 70 | | | | | 75 | | | | | 80 |

| Ser | Leu | Lys | Leu | Ser | Ser | Val | Thr | Ala | Ala | Asp | Thr | Ala | Val | Tyr | Tyr |
|---|---|---|---|---|---|---|---|---|---|---|---|---|---|---|---|
| | | | | 85 | | | | | 90 | | | | | 95 | |

| Cys | Ala | Arg | Glu | Ser | Gly | Ser | Ser | Trp | Gln | Asn | His | Tyr | Tyr | Tyr |
|---|---|---|---|---|---|---|---|---|---|---|---|---|---|---|
| | | | 100 | | | | | 105 | | | | | 110 | |

| Gly | Met | Asp | Val | Trp | Gly | Gln | Gly | Thr | Thr | Val | Thr | Val | Ser | Ser |
|---|---|---|---|---|---|---|---|---|---|---|---|---|---|---|
| | | 115 | | | | | 120 | | | | | 125 | | |

<210> SEQ ID NO 100
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 100

| Glu | Ile | Val | Leu | Thr | Gln | Ser | Pro | Asp | Ser | Leu | Ala | Val | Ser | Leu | Gly |
|---|---|---|---|---|---|---|---|---|---|---|---|---|---|---|---|
| 1 | | | | 5 | | | | | 10 | | | | | 15 | |

| Glu | Arg | Ala | Asn | Ile | Asn | Cys | Lys | Ser | Ser | Gln | Ser | Val | Leu | Tyr | Ser |
|---|---|---|---|---|---|---|---|---|---|---|---|---|---|---|---|
| | | | 20 | | | | | 25 | | | | | 30 | | |

| Ser | Asn | Asn | Lys | Asn | Tyr | Leu | Ala | Trp | Tyr | Gln | Gln | Lys | Ser | Gly | Gln |
|---|---|---|---|---|---|---|---|---|---|---|---|---|---|---|---|
| | | 35 | | | | | 40 | | | | | 45 | | | |

| Pro | Pro | Lys | Leu | Leu | Ile | Tyr | Trp | Ala | Ser | Thr | Arg | Glu | Ser | Gly | Val |
|---|---|---|---|---|---|---|---|---|---|---|---|---|---|---|---|
| | 50 | | | | | 55 | | | | | 60 | | | | |

| Pro | Asp | Arg | Phe | Ser | Gly | Ser | Gly | Ser | Gly | Thr | Asp | Phe | Thr | Leu | Thr |
|---|---|---|---|---|---|---|---|---|---|---|---|---|---|---|---|
| 65 | | | | | 70 | | | | | 75 | | | | | 80 |

| Ile | Ser | Ser | Leu | Gln | Ala | Glu | Asp | Val | Ala | Val | Tyr | Tyr | Cys | Gln | Gln |
|---|---|---|---|---|---|---|---|---|---|---|---|---|---|---|---|
| | | | | 85 | | | | | 90 | | | | | 95 | |

| Tyr | Tyr | Ser | Thr | Pro | Leu | Thr | Phe | Gly | Gly | Gly | Thr | Lys | Val | Asp | Ile |
|---|---|---|---|---|---|---|---|---|---|---|---|---|---|---|---|
| | | | 100 | | | | | 105 | | | | | 110 | | |

Lys

<210> SEQ ID NO 101
<211> LENGTH: 381
<212> TYPE: DNA
<213> ORGANISM: Artificial Sequence
<220> FEATURE:
<223> OTHER INFORMATION: Combination of PCR-generated and human sequence

<400> SEQUENCE: 101

| caggtgcagc tgttggagtc gggcccagga ctggtgaacc cttcacagac cctgtccctc | 60 |
| acctgcactg tctctggtgg ctccatcagc agtggtaatt actactggag ctggatccgg | 120 |
| cagcccgccg ggaagggact ggagtggatt gggcgtatgt ctagtagtgg gagcaccaac | 180 |
| tacaacccct ccctcaagag tcgagtcacc atgtcagaag acacgtccaa gaaccagttc | 240 |
| tccctgaagt tgagctctgt gaccgccgca gacacggccg tgtattactg tgccagagaa | 300 |

-continued

```
tcgggtagca gctggcaaaa tcactactac tactacggta tggacgtctg gggccaaggg    360
accacggtca ccgtctcctc a                                              381
```

<210> SEQ ID NO 102
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 102

```
gaaattgtgt tgacacagtc tccagactcc ctggctgtgt ctctgggcga gagggccaac    60
attaattgca agtccagcca gagtgtttta tacagctcca acaataagaa ctacttagct   120
tggtaccagc agaaatcagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctctcactt tcggcggagg gaccaaagtg gatatcaaa                           339
```

<210> SEQ ID NO 103
<211> LENGTH: 123
<212> TYPE: PRT
<213> ORGANISM: Artificial Sequence
<220> FEATURE:
<223> OTHER INFORMATION: Combination of PCR-generated and human sequence

<400> SEQUENCE: 103

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Gly Ile Ser Ser Asp Gly Asn Thr Phe Tyr Ala Asp Ser Val Lys
    50                  55                  60

Gly Arg Phe Thr Val Ser Arg Asp Asn Ser Lys Asn Thr Leu Tyr Leu
65                  70                  75                  80

Gln Val Asn Ser Leu Arg Ala Asp Asp Thr Ala Val Tyr Tyr Cys Ala
                85                  90                  95

Lys Glu Ser Gly Arg Trp Gly Gly Gly Thr Leu Tyr Gly Ala His Tyr
            100                 105                 110

Trp Gly Gln Gly Thr Pro Val Thr Val Ser Ser
        115                 120
```

<210> SEQ ID NO 104
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 104

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Asn
            20                  25                  30

Ser Asn Asn Lys Asn Tyr Leu Thr Trp Tyr Gln Gln Lys Pro Gly Gln
        35                  40                  45
```

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 105
<211> LENGTH: 369
<212> TYPE: DNA
<213> ORGANISM: Artificial Sequence
<220> FEATURE:
<223> OTHER INFORMATION: Combination of PCR-generated and human sequence

<400> SEQUENCE: 105
caggtacagc tggtggagtc tgggggaggc ttggtacagc ctggggggtc cctgagactc    60
tcctgtgcag cctctggatt cacctttagg aactatgcca tgagttgggt ccgccaggct   120
ccagggaagg ggctggagtg ggtctcaggc attagtagtg acggtaatac attctacgca   180
gactccgtga agggccggtt caccgtctcc agagacaatt ccaagaacac gttgtatctg   240
caagtgaaca gtctgagagc cgacgacacg gccgtatatt actgtgcgaa agagagtggc   300
cgttggggtg gtggaacctt atacggggcg cactactggg gccagggaac cccggtcacc   360
gtctcctca                                                           369

<210> SEQ ID NO 106
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 106
gacatccaga tgacccagtc tccagactcc ctggctgtgt ctctgggcga gagggccacc    60
atcaactgca agtccagcca gagtttgtta taactccca ataataagaa ctacttaact   120
tggtaccagc aaaaaccagg acagcctcct aagttgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtagt   300
cctctcactt tcggcggagg gaccaaggtg gagatcaaa                          339

<210> SEQ ID NO 107
<211> LENGTH: 121
<212> TYPE: PRT
<213> ORGANISM: Artificial Sequence
<220> FEATURE:
<223> OTHER INFORMATION: Combination of PCR-generated and human sequence

<400> SEQUENCE: 107

Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
                20                  25                  30

Asn Val His Trp Val Arg Gln Ala Pro Gly Gln Gly Pro Glu Trp Ile
            35                  40                  45

Gly Arg Ile Ser Pro Asn Ser Gly Gly Thr Lys Tyr Ala Gln Lys Phe
            50                  55                  60

Gln Gly Arg Val Thr Met Thr Arg Asp Met Ser Met Asn Thr Ala Tyr
 65                  70                  75                  80

Met Glu Leu Ser Gly Leu Arg Ser Asp Asp Thr Ala Val Tyr Tyr Cys
                 85                  90                  95

Val Arg Gly His Cys Asp Gly Thr Thr Cys Ser Arg Ala Tyr Trp Gly
                100                 105                 110

Gln Gly Thr Leu Val Thr Val Ser Ser
            115                 120

<210> SEQ ID NO 108
<211> LENGTH: 112
<212> TYPE: PRT
<213> ORGANISM: Artificial Sequence
<220> FEATURE:
<223> OTHER INFORMATION: Combination of PCR-generated and human sequence

<400> SEQUENCE: 108

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Arg
             20                  25                  30

Ser Gly His Lys Tyr Leu His Trp Tyr Leu Gln Arg Pro Gly Gln Ser
         35                  40                  45

Pro Gln Val Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln Thr
                 85                  90                  95

Leu Gln Thr Pro Trp Thr Phe Gly Gln Gly Thr Lys Val Glu Ile Lys
                100                 105                 110

<210> SEQ ID NO 109
<211> LENGTH: 363
<212> TYPE: DNA
<213> ORGANISM: Artificial Sequence
<220> FEATURE:
<223> OTHER INFORMATION: Combination of PCR-generated and human sequence

<400> SEQUENCE: 109
caggtgcagc tggtgcagtc tggggctgag gtgaagaagc ctggggcccc agtgaaggtc      60
tcctgcgaga cttctggata caggttcagc gactacaatg tacactgggt gcgacaggcc     120
cctggacaag ggcctgagtg gataggacgg atcagcccta acagcggtgg cacaaagtat     180
gcacagaagt ttcaaggcag ggtcaccatg accagggaca tgtccatgaa cacagcctac     240
atggagctga gcgggctgag atctgacgac acggccgtgt attattgtgt aagaggacat     300
tgtgatggta ccacttgctc tcgtgcctac tggggccagg gaaccctggt caccgtctcc     360
tca                                                                   363

<210> SEQ ID NO 110
<211> LENGTH: 336
<212> TYPE: DNA
<213> ORGANISM: Artificial Sequence
<220> FEATURE:
<223> OTHER INFORMATION: Combination of PCR-generated and human sequence

<400> SEQUENCE: 110

```
gatgttgtga tgacgcagtc tccactctcc ctgcccgtca ccctggaga gccggcctcc      60 atctcctgca ggtctagtca gagcctcctg catagaagtg acacaagta tttgcattgg     120 tacctgcaga ggccagggca gtctccacag gtcctgatct atttgggttc taatcgggcc    180
tccggggtcc ctgacaggtt cagtggcagt ggatcaggca cagattttac actgaaaatc    240
agcagagtgg aggctgagga tgttgggctt tattactgca tgcaaactct acaaacccc     300 tggacattcg gccaagggac caaggtggaa atcaaa                              336
```

<210> SEQ ID NO 111
<211> LENGTH: 120
<212> TYPE: PRT
<213> ORGANISM: Artificial Sequence
<220> FEATURE:
<223> OTHER INFORMATION: Combination of PCR-generated and human sequence

<400> SEQUENCE: 111

```
Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr Gly Tyr
                20                  25                  30

Tyr Leu His Trp Val Arg Gln Ala Pro Gly Gln Gly Leu Glu Trp Met
            35                  40                  45

Gly Trp Val Asn Pro Arg Ser Gly Gly Thr Ser Tyr Pro Pro Lys Phe
        50                  55                  60

Gln Gly Arg Val Thr Met Thr Arg Asp Thr Ser Ile Asn Thr Ala Tyr
65                  70                  75                  80

Met Asp Leu Thr Trp Leu Thr Ser Asp Thr Ala Val Tyr Tyr Cys
                85                  90                  95

Ala Val Gly Arg Ile Pro Asp Val Thr Ala Phe Asp Ile Trp Gly Gln
            100                 105                 110

Gly Thr Pro Val Thr Val Ser Ser
        115                 120
```

<210> SEQ ID NO 112
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 112

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser Glu Ser Leu Leu Tyr Asp
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Glu Thr Asp Phe Thr Leu Thr
65                  70                  75                  80

Ile Ser Ser Leu Gln Ala Glu Asp Val Ala Val Tyr His Cys Gln Gln
                85                  90                  95

Tyr Phe Ser Thr Pro Trp Thr Phe Gly Gln Gly Thr Lys Leu Glu Ile
            100                 105                 110

Lys
```

<210> SEQ ID NO 113
<211> LENGTH: 360
<212> TYPE: DNA
<213> ORGANISM: Artificial Sequence
<220> FEATURE:
<223> OTHER INFORMATION: Combination of PCR-generated and human sequence

<400> SEQUENCE: 113

```
caggtccagc ttgtgcagtc tgggctgag  gtgaagaagc tggggcctc  agtgaaggtc    60
tcctgtacgg cctctggata cactttcacc ggctattatt tacactgggt gcgacaggcc   120
cctggacaag gacttgagtg gatggggtgg gtcaaccta  ggagtggtgg cacaagctat   180
ccaccgaagt ttcagggcag ggtcaccatg accagggaca cgtccatcaa cacagcctac   240
atggacctga cctggctgac atctgacgac acggccgtct attattgtgc ggtcggaaga   300
atacctgatg taactgcttt cgatatctgg ggccagggga caccggtcac cgtctcctca   360
```

<210> SEQ ID NO 114
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 114

```
gacatccaga tgacccagtc tccagactcc ctggctgtgt ctctgggcga gagggccacc    60
atcaactgca gtccagcga  gagtcttta  tacgactcca acaataagaa ctacttagct   120
tggtaccagc agaaaccagg acagcctcct aagttgctca tttattgggc atctacccgg   180
gaatccgggg tccctgaccg attcagtggc agcgggtctg agacagattt cactctcacc   240
atcagcagcc tgcaggctga gatgtggca  gtttatcact gtcaacaata tttcagtact   300
ccttggacgt tcggccaggg gaccaagctg gagatcaaa                           339
```

<210> SEQ ID NO 115
<211> LENGTH: 122
<212> TYPE: PRT
<213> ORGANISM: Artificial Sequence
<220> FEATURE:
<223> OTHER INFORMATION: Combination of PCR-generated and human sequence

<400> SEQUENCE: 115

```
Gln Val Gln Leu Val Glu Ser Gly Pro Glu Met Arg Lys Pro Gly Glu
 1               5                  10                  15

Ser Leu Lys Ile Ser Cys Lys Thr Ser Gly Tyr Ile Phe Asp Tyr
            20                  25                  30

Trp Thr Ala Trp Val Arg Gln Leu Pro Gly Lys Gly Leu Gln Trp Met
        35                  40                  45

Gly Ile Ile Tyr Ser Gly Asp Ser Asp Thr Arg Tyr His Pro Ser Val
    50                  55                  60

Gln Gly His Val Thr Met Ser Thr Asp Ser Ser Leu Thr Thr Ala Tyr
65                  70                  75                  80

Leu Gln Trp Ser Ser Leu Lys Ala Ser Asp Thr Gly Ile Tyr Tyr Cys
                85                  90                  95

Ala Arg Leu Asp Ala Arg Val Asp Ala Gly Trp Gln Leu Asp Ser Trp
            100                 105                 110

Gly Gln Gly Thr Leu Val Thr Val Ser Ser
        115                 120
```

<210> SEQ ID NO 116
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 116

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Ser Arg
            20                  25                  30

Asp Asn Asn Lys Asn Tyr Leu Ala Trp Tyr Gln His Lys Ser Gly Gln
        35                  40                  45

Pro Pro Lys Leu Leu Phe Phe Trp Ala Ser Ser Arg Glu Ser Gly Val
    50                  55                  60

Ser Asp Arg Phe Ser Gly Ser Gly Ser Gly Thr Asp Phe Thr Leu Thr
65                  70                  75                  80

Ile Asp Asn Leu Gln Ala Glu Asp Val Ala Leu Tyr Tyr Cys Gln His
                85                  90                  95

Tyr Phe Asn Thr Pro His Asn Phe Gly Gln Gly Thr Lys Leu Glu Ile
            100                 105                 110

Lys

<210> SEQ ID NO 117
<211> LENGTH: 366
<212> TYPE: DNA
<213> ORGANISM: Artificial Sequence
<220> FEATURE:
<223> OTHER INFORMATION: Combination of PCR-generated and human sequence

<400> SEQUENCE: 117
caggttcagc tggtggagtc tggaccggag atgagaaagc ccggggagtc tctgaaaatt    60
tcctgcaaga cttctggcta catatttagc gactactgga ctgcctgggt gcgccagctg   120
cccgggaagg gccttcagtg gatgggaatc atctattctg gtgactctga taccagatat   180
catccgtccg tccaaggcca cgtcaccatg tcaaccgaca gttccctcac caccgcctac   240
ctgcagtgga gcagcctgaa ggcctcggac accggcatat attactgtgc gcgccttgat   300
gcaagagttg atgctggatg caattagat tcgtggggcc aggggaccct ggtcaccgtc   360
tcttca                                                              366

<210> SEQ ID NO 118
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 118
gacatccagt tgacccagtc tccagattcc ctggctgtgt ctctgggcga gcgggccacc    60
atcaactgca gtccagcca gagtgttttc tccaggggaca caataaaaaa ctacctagct   120
tggtaccagc acaaatcagg gcagcctcct aagttgctct ttttctgggc gtccagtcgt   180
gaatctgggg tctcagaccg attcagcggc agcgggtctg gacagatttt cactctcacc   240
atcgacaacc tgcaggctga agatgtggca ctttattact gtcaacatta ttttaatact   300
ccccacaatt ttggccaggg gaccaagctg gagatcaaa                           339

```
<210> SEQ ID NO 119
<211> LENGTH: 121
<212> TYPE: PRT
<213> ORGANISM: Artificial Sequence
<220> FEATURE:
<223> OTHER INFORMATION: Combination of PCR-generated and human sequence

<400> SEQUENCE: 119

Gln Val Gln Leu Gln Gln Ser Gly Ala Glu Val Lys Lys Pro Gly Glu
1               5                   10                  15

Ser Leu Lys Ile Ser Cys Glu Ala Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Pro Phe
    50                  55                  60

Gln Gly Gln Val Thr Ile Thr Ala Asp Arg Ser Ile Thr Thr Ala Tyr
65                  70                  75                  80

Leu Glu Trp Ser Ser Leu Lys Ala Ser Asp Thr Ala Met Tyr Tyr Cys
                85                  90                  95

Ala Arg Val Gly Arg Pro Ser Lys Gly Gly Trp Phe Asp Pro Trp Gly
            100                 105                 110

Gln Gly Thr Leu Val Thr Val Ser Ser
        115                 120

<210> SEQ ID NO 120
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 120

Asp Ile Gln Met Thr Gln Ser Pro Asp Ser Leu Ala Val Ser Leu Gly
1               5                   10                  15

Glu Arg Ala Thr Ile Asn Cys Glu Ser Ser Gln Thr Leu Leu Tyr Ser
            20                  25                  30

Ser Asn Glu Lys Asn Tyr Leu Ala Trp Tyr Gln Gln Lys Pro Gly Gln
        35                  40                  45

Pro Pro Lys Leu Leu Ile Ser Trp Ala Ser Thr Pro Glu Ser Gly Val
    50                  55                  60

Pro Asp Arg Phe Ser Gly Ser Gly Ser Gly Thr Ser Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Ser Pro Tyr Thr Phe Gly Gln Gly Thr Arg Leu Glu Ile
            100                 105                 110

Lys

<210> SEQ ID NO 121
<211> LENGTH: 363
<212> TYPE: DNA
<213> ORGANISM: Artificial Sequence
<220> FEATURE:
<223> OTHER INFORMATION: Combination of PCR-generated and human sequence

<400> SEQUENCE: 121
caggtgcagc tacagcagtc aggagcagaa gtgaaaaagc ccggggagtc tctgaagatc     60
```

```
tcctgtgagg cctctggata cagcttcacc aattactgga tcggctgggt gcgccagatg    120
cccggtaaag gcctggagtg gatgggaatc atctatcctg gtgactctga caccagatac    180
agtccgccct tccaaggcca ggtcaccatc acagccgaca ggtccatcac caccgcctac    240
ttggagtgga gcagtctgaa ggcctcggac accgccatgt attactgtgc aagagttggg    300
agaccttcta aggaggctg gttcgacccc tggggccagg gaaccctggt caccgtctct    360
tca                                                                  363
```

<210> SEQ ID NO 122
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 122

```
gacatccaga tgacccagtc tccagactcc ctggctgtgt ctctgggcga gagggccacc    60
atcaactgtg agtccagcca gactctttta tacagttcca cgaaaagaa ctacctagct    120 tggtaccagc agaaaccagg acagcctcct aagttgctca tttcctgggc ttctaccccg    180
gaatccgggg tccctgaccg attcagtggc agtgggtctg ggacaagttt cactctcacc    240
atcagcagcc tgcaggctga ggatgtggca gtttattact gtcagcaata ttataacagt    300
ccatacactt ttggccaagg gacacgactg gagattaaa                           339
```

<210> SEQ ID NO 123
<211> LENGTH: 126
<212> TYPE: PRT
<213> ORGANISM: Artificial Sequence
<220> FEATURE:
<223> OTHER INFORMATION: Combination of PCR-generated and human sequence

<400> SEQUENCE: 123

```
Glu Val Gln Leu Leu Glu Ser Gly Gly Gly Leu Val Lys Pro Gly Gly
 1               5                  10                  15

Ser Leu Arg Leu Ser Cys Val Ala Ser Gly Ile Thr Phe Ser Asp Ser
             20                  25                  30

Tyr Met Ser Trp Ile Arg Gln Thr Pro Gly Lys Gly Leu Glu Trp Leu
         35                  40                  45

Ser Tyr Ile Ser Arg Ser Ser His Thr Asn Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Gly Glu Asp Thr Ala Val Tyr Tyr Cys
                 85                  90                  95

Ala Arg Val Gln Thr Thr Met Ile Glu Gly Lys Thr Lys Leu Asn Tyr
            100                 105                 110

Phe Asp Tyr Trp Gly Gln Gly Thr Gln Val Thr Val Ser Ser
        115                 120                 125
```

<210> SEQ ID NO 124
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 124

Asp Ile Gln Met Thr Gln Ser Pro Asp Ser Leu Ala Val Ser Leu Gly

```
            1               5                  10                 15
Glu Arg Val Thr Ile Thr Cys Glu Ser Ser His Ser Leu Leu Tyr Arg
                20                  25                  30

Ser Asn Asn Arg Asn Tyr Leu Ala Trp Tyr Gln Gln Lys Pro Arg Gln
                35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Val Tyr Tyr Cys Gln Gln
                85                  90                  95

Phe Tyr Thr Thr Pro Tyr Thr Phe Gly Gln Gly Thr Lys Val Glu Ile
                100                 105                 110

Lys
```

<210> SEQ ID NO 125
<211> LENGTH: 378
<212> TYPE: DNA
<213> ORGANISM: Artificial Sequence
<220> FEATURE:
<223> OTHER INFORMATION: Combination of PCR-generated and human sequence

<400> SEQUENCE: 125

```
gaggtgcagc tgttggagtc tgggggaggc ttggtcaagc ctggagggtc cctgagactc      60
tcctgtgtcg cctctggaat caccttcagt gactcctaca tgagctggat ccgccagact     120
ccagggaagg ggctagagtg gctttcatac attagtcgta gtagttctca cacaaattac     180
gcagactctg tgaagggccg attcaccatc tccagagaca acgccaagaa ttcactatat     240
ctccaaatga atagcctgag aggcgaggac acggctgtgt attactgtgc gagagtccag     300
acaactatga tagaagggaa aacgaaactt aactactttg actactgggg ccagggaacc     360
caggtcaccg tctcctca                                                   378
```

<210> SEQ ID NO 126
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 126

```
gacatccaga tgacccagtc tccagactcc ctggctgtgt ctctgggcga gagggtcacc      60
atcacctgcg agtccagcca gtctttta cacaggtcca acaataggaa ctacttagct      120
tggtaccagc aaaaaccaag acagcctcct aagttgctca tttactgggc atctacccgg     180
gagtccgggg tcccagaccg attcagcggc agcgggtctg agacagattt cactctcacc     240
atcagcagcc tgcgggctga agatgtggcg gtatattact gtcaacaatt ttatactact     300
ccttacactt ttggccaagg gaccaaggtg gagatcaaa                            339
```

<210> SEQ ID NO 127
<211> LENGTH: 126
<212> TYPE: PRT
<213> ORGANISM: Artificial Sequence
<220> FEATURE:
<223> OTHER INFORMATION: Combination of PCR-generated and human sequence

<400> SEQUENCE: 127

Glu Val Gln Leu Val Gln Ser Gly Gly Gly Leu Val Lys Pro Gly Gly

```
                1               5                  10                  15
            Ser Leu Arg Leu Ser Cys Val Ala Ser Gly Ile Thr Phe Ser Asp Ser
                            20                  25                  30
            Tyr Met Ser Trp Ile Arg Gln Thr Pro Gly Lys Gly Leu Glu Trp Leu
                            35                  40                  45
            Ser Tyr Ile Ser Arg Ser Ser His Thr Asn Tyr Ala Asp Ser Val
                        50                  55                  60
            Lys Gly Arg Phe Thr Ile Ser Arg Asp Asn Ala Lys Asn Ser Leu Tyr
            65                  70                  75                  80
            Leu Gln Met Asn Ser Leu Arg Gly Glu Asp Thr Ala Val Tyr Tyr Cys
                            85                  90                  95
            Ala Arg Val Gln Thr Thr Met Ile Glu Gly Lys Thr Lys Leu Asn Tyr
                            100                 105                 110
            Phe Asp Tyr Trp Gly Gln Gly Thr Leu Val Thr Val Ser Ser
                            115                 120                 125

<210> SEQ ID NO 128
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 128

Ala Ile Gln Leu Thr Gln Ser Pro Asp Ser Leu Ala Val Ser Leu Gly
1               5                  10                  15
Glu Arg Val Thr Ile Ser Cys Glu Ser Ser His Ser Leu Leu Tyr Arg
                20                  25                  30
Ser Asn Asn Lys Asn Tyr Leu Ala Trp Tyr Gln Gln Lys Pro Arg Gln
                35                  40                  45
Pro Pro Lys Leu Leu Ile Tyr Trp Ala Ser Thr Arg Glu Ser Gly Val
            50                  55                  60
Pro Asp Arg Phe Ser Gly Ser Gly Ser Glu Thr Asp Phe Thr Leu Thr
65                  70                  75                  80
Ile Ser Ser Leu Arg Ala Glu Asp Val Ala Val Tyr Tyr Cys Gln Gln
                85                  90                  95
Phe Tyr Thr Thr Pro Tyr Thr Phe Gly Gln Gly Thr Lys Leu Glu Ile
                100                 105                 110
Lys

<210> SEQ ID NO 129
<211> LENGTH: 378
<212> TYPE: DNA
<213> ORGANISM: Artificial Sequence
<220> FEATURE:
<223> OTHER INFORMATION: Combination of PCR-generated and human sequence

<400> SEQUENCE: 129
gaggtgcagc tggtgcagtc tggggaggc ttggtcaagc ctggagggtc cctgagactc      60
tcctgtgtcg cctctggaat caccttcagt gactcctaca tgagctggat ccgccagact     120
ccagggaagg gctagagtg ctttcatac attagtcgta gtagttctca cacaaattac       180
gcagactctg tgaagggccg attcaccatc tccagagaca acgccaagaa ttcactatat     240
ctccaaatga atagcctgag aggcgaggac acggctgtgt attactgtgc gagagtccag     300
acaactatga tagaagggaa aacgaaactt aactactttg actactgggg ccagggaacc     360
ctggtcaccg tctcctca                                                   378
```

<210> SEQ ID NO 130
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 130

```
gccatccagt tgacccagtc tccagactcc ctggctgtgt ctctgggcga gagggtcacc    60
atcagctgcg agtccagcca cagtcttta tacaggtcca acaataagaa ctacttagct   120
tggtaccagc agaaaccaag acagcctcct aagttgctca tttactgggc atctacccgg   180
gagtccgggg tcccagaccg attcagcggc agcgggtctg agacagattt cactctcacc   240
atcagcagcc tgcgggctga agatgtggca gtgtattact gtcaacaatt ttatactact   300
ccttacactt ttggccaggg gaccaagctg gagatcaaa                          339
```

<210> SEQ ID NO 131
<211> LENGTH: 122
<212> TYPE: PRT
<213> ORGANISM: Artificial Sequence
<220> FEATURE:
<223> OTHER INFORMATION: Combination of PCR-generated and human sequence

<400> SEQUENCE: 131

```
Gln Leu Val Gln Ser Glu Gly Gly Leu Ala Glu Pro Gly Gly Ser Leu
  1               5                  10                  15
Arg Leu Ser Cys Ala Ala Ser Gly Phe Thr Phe Thr Lys Ala Trp Met
                 20                  25                  30
Ser Trp Val Arg Gln Thr Pro Gly Arg Gly Leu Glu Trp Leu Gly Arg
             35                  40                  45
Ile Lys Ser Lys Val Asp Gly Glu Thr Thr Asp Tyr Ala Ala Pro Val
 50                  55                  60
Arg Gly Arg Phe Thr Ile Ser Arg Asp Asp Ser Lys Ser Thr Val Tyr
 65                  70                  75                  80
Leu Gln Met Thr Gly Leu Arg Thr Glu Asp Thr Gly Val Tyr Phe Cys
                 85                  90                  95
Thr Thr Leu Ile His Cys Asp Leu Ser Ala Cys Leu Pro His Phe Trp
            100                 105                 110
Gly Arg Gly Thr Leu Val Thr Val Ser Ser
            115                 120
```

<210> SEQ ID NO 132
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 132

```
Glu Ile Val Leu Thr Gln Ser Pro Asp Ser Leu Ala Val Ser Leu Gly
  1               5                  10                  15
Glu Arg Val Thr Ile Ser Cys Glu Ser Ser His Ser Leu Leu Tyr Arg
                 20                  25                  30
Ser Asn Asn Lys Asn Tyr Leu Ala Trp Tyr Gln Gln Lys Pro Arg Gln
             35                  40                  45
Pro Pro Lys Leu Leu Ile Tyr Trp Ala Ser Thr Arg Glu Ser Gly Val
 50                  55                  60
```

```
Pro Asp Arg Phe Ser Gly Ser Gly Ser Glu Thr Asp Phe Thr Leu Thr
 65                  70                  75                  80

Ile Ser Ser Leu Arg Ala Glu Asp Val Ala Val Tyr Tyr Cys Gln Gln
                 85                  90                  95

Phe Tyr Thr Thr Pro Tyr Thr Phe Gly Gln Gly Thr Lys Leu Glu Ile
            100                 105                 110

Lys
```

```
<210> SEQ ID NO 133
<211> LENGTH: 378
<212> TYPE: DNA
<213> ORGANISM: Artificial Sequence
<220> FEATURE:
<223> OTHER INFORMATION: Combination of PCR-generated and human sequence

<400> SEQUENCE: 133
gaggtgcagc tggtgcagtc tgggggaggc ttggtcaagc ctggagggtc cctgagactc      60
tcctgtgtcg cctctggaat caccttcagt gactcctaca tgagctggat ccgccagact     120
ccagggaagg ggctagagtg gctttcatac attagtcgta gtagttctca cacaaattac     180
gcagactctg tgaagggccg attcaccatc tccagagaca cgccaagaa ttcactatat      240 ctccaaatga atagcctgag aggcgaggac acggctgtgt attactgtgc gagagtccag     300
acaactatga tagaagggaa aacgaaactt aactactttg actactgggg ccagggaacc     360
ctggtcaccg tctcctca                                                   378
```

```
<210> SEQ ID NO 134
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 134
gaaattgtgt tgacgcagtc tccagactcc ctggctgtgt ctctgggcga gagggtcacc      60
atcagctgcg agtccagcca cagtctttta tacaggtcca acaataagaa ctacttagct     120
tggtaccagc agaaaccaag acagcctcct aagttgctca tttactgggc atctacccgg     180
gagtccgggg tcccagaccg attcagcggc agcgggtctg agacagattt cactctcacc     240
atcagcagcc tgcgggctga agatgtggca gtgtattact gtcaacaatt ttatactact     300
ccttacactt ttggccaggg gaccaagctg gagatcaaa                             339
```

```
<210> SEQ ID NO 135
<211> LENGTH: 124
<212> TYPE: PRT
<213> ORGANISM: Artificial Sequence
<220> FEATURE:
<223> OTHER INFORMATION: Combination of PCR-generated and human sequence

<400> SEQUENCE: 135

Gln Val Gln Leu Val Gln Ser Gly Gly Glu Val Lys Lys Pro Gly Glu
 1               5                  10                  15

Ser Leu Lys Ile Ser Cys Lys Gly Ser Gly Tyr Ser Phe Ser Asn Tyr
                 20                  25                  30

Trp Ile Ala Trp Val Arg Gln Met Pro Gly Lys Gly Leu Glu Cys Met
             35                  40                  45

Gly Ile Ile Tyr Pro Gly Asp Ser Asp Thr Thr Tyr Ser Pro Ser Phe
         50                  55                  60
```

```
Gln Gly Gln Val Thr Ile Ser Ala Asp Lys Ser Val Ser Thr Thr Tyr
 65                  70                  75                  80

Leu Gln Trp Ser Ser Leu Lys Ala Ser Asp Ser Ala Met Tyr Tyr Cys
                 85                  90                  95

Ala Arg Leu Pro Arg Thr Asp Gly Asp Asn Ser Ile Gly Tyr Phe Glu
            100                 105                 110

Tyr Trp Gly Gln Gly Thr Met Val Thr Val Ser Ser
            115                 120
```

<210> SEQ ID NO 136
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 136

```
Glu Ile Val Leu Thr Gln Ser Pro Ala Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Ser Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Phe Thr Phe Gly Gln Gly Thr Arg Leu Glu Ile
            100                 105                 110

Lys
```

<210> SEQ ID NO 137
<211> LENGTH: 372
<212> TYPE: DNA
<213> ORGANISM: Artificial Sequence
<220> FEATURE:
<223> OTHER INFORMATION: Combination of PCR-generated and human sequence

<400> SEQUENCE: 137

```
caggtgcagc tggtgcagtc tggaggagag gtgaaaaagc cggggagtc tctgaagatc      60
tcctgtaagg gttctgggta ctcctttagt aactactgga tcgcctgggt gcgccagatg    120
cccgggaaag gcctggagtg catgggaatc atctatcctg gtgactctga taccacatac    180
agcccgtcct tccaaggcca ggtcaccatt tctgccgaca gtccgtcag taccacctac    240
ctacaatgga gcagcctgaa ggcctcggac agcgccatgt attattgtgc gaggctaccc    300
cgtacagatg gcgacaattc catcggctac tttgaatatt ggggccaggg aaccatggtc    360
accgtctctt ca                                                         372
```

<210> SEQ ID NO 138
<211> LENGTH: 345
<212> TYPE: DNA
<213> ORGANISM: Artificial Sequence
<220> FEATURE:
<223> OTHER INFORMATION: Combination of PCR-generated and human sequence

<400> SEQUENCE: 138

```
gaaattgtgt tgacacagtc tccagcctcc ctggctgtgt ctctgggcga gagggccacc    60
atcaactgca agtccagcca gagtgtttta tacagctcca acagtgagaa ctacttagct   120
tggtatcagc agaaaccagg acagcctccc aagttgctca tttactgggc gtctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
ccattcactt tcggccaagg gacacgactg gagattaaac gtaag               345
```

<210> SEQ ID NO 139
<211> LENGTH: 118
<212> TYPE: PRT
<213> ORGANISM: Artificial Sequence
<220> FEATURE:
<223> OTHER INFORMATION: Combination of PCR-generated and human sequence

<400> SEQUENCE: 139

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Thr Thr Thr Ile Tyr Tyr Ala Asp Ser Val
    50                  55                  60

Lys Gly Arg Phe Thr Ile Ser Arg Asp Asn Val Lys Asn Ser Leu Tyr
65                  70                  75                  80

Leu Gln Met His Ser Leu Arg Ala Glu Asp Thr Ala Val Tyr Tyr Cys
                85                  90                  95

Val Pro Ala Pro Arg Leu Gly Gly Ser Tyr Thr Tyr Trp Gly Gln Gly
            100                 105                 110

Thr Leu Val Thr Val Ser
        115
```

<210> SEQ ID NO 140
<211> LENGTH: 108
<212> TYPE: PRT
<213> ORGANISM: Artificial Sequence
<220> FEATURE:
<223> OTHER INFORMATION: Combination of PCR-generated and human sequence

<400> SEQUENCE: 140

```
Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Leu Thr Phe Gly Gly Gly Thr Lys Val Glu Ile Lys
            100                 105
```

<210> SEQ ID NO 141

```
<211> LENGTH: 357
<212> TYPE: DNA
<213> ORGANISM: Artificial Sequence
<220> FEATURE:
<223> OTHER INFORMATION: Combination of PCR-generated and human sequence

<400> SEQUENCE: 141
gaggtgcagc tggtggagtc tgggggaggc ttggtacagc ctggggggtc cctgagactc      60
tcctgtgcag cctctggatt caccttcagt agttatagca tgaactgggt ccgccaggct     120
ccagggaagg ggctggagtg ggtttcatac attagtagta gtactactac catatactac     180
gcagactctg tgaagggccg attcaccatc tccagggaca atgtcaagaa ctctctgtat     240
ctgcaaatgc acagcctgag agccgaggac acggctgtgt attactgtgt cccggccccc     300
cggttgggtg ggagctacac ttactggggc cagggaaccc tggtcaccgt ctcctca       357

<210> SEQ ID NO 142
<211> LENGTH: 324
<212> TYPE: DNA
<213> ORGANISM: Artificial Sequence
<220> FEATURE:
<223> OTHER INFORMATION: Combination of PCR-generated and human sequence

<400> SEQUENCE: 142
gacatccaga tgacccagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggca cctcaccgct cactttcggc     300
ggagggacca aggtggaaat caaa                                            324

<210> SEQ ID NO 143
<211> LENGTH: 119
<212> TYPE: PRT
<213> ORGANISM: Artificial Sequence
<220> FEATURE:
<223> OTHER INFORMATION: Combination of PCR-generated and human sequence

<400> SEQUENCE: 143

Glu Val Gln Leu Val Glu Ser Gly Gly Asp Leu Val Lys Pro Gly Gly
1               5                   10                  15

Ser Leu Arg Leu Ser Cys Ala Ala Ser Gly Phe Val Phe Thr Asp Ala
            20                  25                  30

Trp Met Ser Trp Val Arg Gln Ser Pro Gly Lys Gly Pro Glu Trp Leu
        35                  40                  45

Gly Arg Ile Lys Ser Lys Asn Val Gly Glu Thr Thr Asp Tyr Ala Glu
    50                  55                  60

His Val Arg Gly Arg Phe Thr Ile Ala Arg Asp Asp Ser Asn Arg Thr
65                  70                  75                  80

Leu Tyr Leu Gln Met Ser Asn Leu Lys Ile Asp Asp Thr Ala Val Tyr
                85                  90                  95

Tyr Cys Thr Thr Gly Leu Gly Gly Thr Tyr Gly Trp Gly Arg Gly
            100                 105                 110

Thr Arg Val Thr Val Ser Ser
        115

<210> SEQ ID NO 144
<211> LENGTH: 108
```

```
<212> TYPE: PRT
<213> ORGANISM: Artificial Sequence
<220> FEATURE:
<223> OTHER INFORMATION: Combination of PCR-generated and human sequence

<400> SEQUENCE: 144

Glu Ile Val Leu Thr Gln Ser Pro Leu Ser Leu Pro Ala Thr Leu Gly
1               5                   10                  15

Gln Pro Ala Ser Ile Ser Cys Arg Ser Ser Ala Gly Leu Arg Asn Asn
            20                  25                  30

Asp Gly Asp Ile Leu Leu Ser Trp Phe His Gln Arg Pro Gly Gln Ser
        35                  40                  45

Pro Arg Arg Leu Phe Tyr Arg Val Ser Arg Arg Asp Ser Gly Val Pro
    50                  55                  60

Asp Arg Phe Asn Gly Ser Gly Ser Ala Thr Asp Phe Thr Leu Arg Ile
65                  70                  75                  80

Asn Ser Val Glu Ala Glu Asp Val Gly Ile Tyr Tyr Cys Met Arg Gly
                85                  90                  95

Pro Tyr Trp Gly Gln Gly Thr Arg Leu Glu Ile Lys
            100                 105

<210> SEQ ID NO 145
<211> LENGTH: 357
<212> TYPE: DNA
<213> ORGANISM: Artificial Sequence
<220> FEATURE:
<223> OTHER INFORMATION: Combination of PCR-generated and human sequence

<400> SEQUENCE: 145
gaggtgcagc tggtggagtc tgggggagac ttggtaaagc ctggggggtc ccttagactc      60
tcctgtgcag cctctggatt cgttttcact gacgcctgga tgagctgggt ccgccagagt     120
cccgggaagg ggccggagtg gcttggccgt atcaaaagta aaaatgtcgg tgagacaaca     180
gactacgctg aacacgtgag aggcagattt accatcgcaa gagatgattc aaccgcact     240 ctatatctac aaatgagcaa cctgaaaatc gacgacacag ccgtctatta ttgtaccact     300
ggactgggag gagggaccta cggatggggc cggggaaccc gggtcaccgt ctcttca       357

<210> SEQ ID NO 146
<211> LENGTH: 324
<212> TYPE: DNA
<213> ORGANISM: Artificial Sequence
<220> FEATURE:
<223> OTHER INFORMATION: Combination of PCR-generated and human sequence

<400> SEQUENCE: 146
gaaattgtgt tgacacagtc tccactctcc ctgcccgcca cccttggaca gccggcctcc      60
atctcctgca ggtcgagtgc aggcctccga acaacgatg gtgacatcct cttgagttgg     120
tttcatcagc ggccaggcca gtctccgagg cgcctatttt atagagtttc taggcgtgac     180
tctggagtcc cagacagatt caacggcagt gggtcagcca ctgatttcac actgagaatc     240
aattctgtgg aggctgaaga tgttggcatt tactactgca tgcgaggacc atattgggc    300 caagggacac gactggagat taaa                                            324

<210> SEQ ID NO 147
<211> LENGTH: 119
<212> TYPE: PRT
<213> ORGANISM: Artificial Sequence
<220> FEATURE:
<223> OTHER INFORMATION: Combination of PCR-generated and human sequence
```

<400> SEQUENCE: 147

Gln Val Gln Leu Val Glu Ser Gly Gly Gly Leu Val Gln Pro Gly Glu
1               5                   10                  15

Ser Leu Arg Leu Ser Cys Val Ala Ser Gly Phe Asn Phe Ser Ile Tyr
            20                  25                  30

Glu Met Asn Trp Val Arg Gln Ala Pro Gly Lys Gly Leu Glu Trp Val
        35                  40                  45

Ser Tyr Ile Thr Asn Arg Gly Ser Thr Ile Tyr Tyr Ala Asp Ser Val
50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Ile Gly Ala Arg Val Phe Asp Val Trp Gly Gln Gly
            100                 105                 110

Thr Met Val Thr Val Ser Ser
            115

<210> SEQ ID NO 148
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 148

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Thr Leu Leu Tyr Lys
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Thr Thr Ala Leu Thr Phe Gly Gly Gly Thr Lys Val Glu Ile
            100                 105                 110

Lys

<210> SEQ ID NO 149
<211> LENGTH: 357
<212> TYPE: DNA
<213> ORGANISM: Artificial Sequence
<220> FEATURE:
<223> OTHER INFORMATION: Combination of PCR-generated and human sequence

<400> SEQUENCE: 149
caggtacagc tggtggagtc tgggggaggc ttggtacagc ctggagagtc cctgagactc      60
tcctgtgtag cctctggatt caacttcagt atttatgaga tgaattgggt ccgccaggct     120
ccagggaagg ggctggagtg ggtttcatac attaccaatc gaggtagtac catatactac     180
gcagactctg tgaagggccg attcaccatc tccaggaca acgccagaa ctcactgtat      240 ctgcaaatga acagcctgag agccgaagac acggctgttt attactgtgc gaaccccgt     300 ataggagctc gtgtatttga tgtctggggc caagggacaa tggtcaccgt ctcctca      357

<210> SEQ ID NO 150
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 150
gacatccagt tgacccagtc tccagactcc ctggctgtgt ctctgggcga gagggccacc      60
atcaactgca gtccagcca gactctttta tacaagtcca acaatgagaa ctacttagct     120
tggtaccagc agaaaccagg acagcctcca aagctgctca tttactgggc atctactcgg     180
gaatccgggg tccctgaccg attcagtggc agcgggtctg ggacagattt cactctcacc     240
atcagcagcc tgcaggctga ggatgtggca gtttactact gtcagcaata ttttactact     300
gcgctcactt tcggcggagg gaccaaggtg gagatcaaa                            339

<210> SEQ ID NO 151
<211> LENGTH: 121
<212> TYPE: PRT
<213> ORGANISM: Artificial Sequence
<220> FEATURE:
<223> OTHER INFORMATION: Combination of PCR-generated and human sequence

<400> SEQUENCE: 151

Gln Val Gln Leu Val Glu Ser Gly Ala Val Val Lys Lys Pro Gly Glu
1               5                   10                  15

Ser Leu Lys Ile Ser Cys Glu Ala Ser Gly Tyr Met Phe Leu Asp His
            20                  25                  30

Trp Ile Gly Trp Val Arg Gln Met Pro Gly Lys Gly Leu Glu Trp Met
        35                  40                  45

Gly Ile Ile Phe Pro Glu Asp Ser Asp Thr Arg Tyr Ser Gly Ser Phe
    50                  55                  60

Glu Gly Gln Val Thr Ile Ser Ala Asp Arg Ser Val Asn Thr Val Tyr
65                  70                  75                  80

Leu Glu Trp Ser Ser Leu Lys Ala Ser Asp Thr Ala Met Tyr Tyr Cys
                85                  90                  95

Ala Arg Val Ser Val Val Arg Lys Gly Gly Trp Phe Asp Pro Trp Gly
            100                 105                 110

Gln Gly Thr Leu Val Thr Val Ser Ser
        115                 120

<210> SEQ ID NO 152
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 152

Ala Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Thr
            20                  25                  30

Ser Asn Asn Lys Asn Tyr Leu Ala Trp Tyr Gln Gln Lys Pro Gly Gln
        35                  40                  45

Thr Pro Lys Leu Leu Ile Ile Trp Ala Ser Thr Arg Glu Ser Gly Val

```
                  50                  55                  60
Pro Asp Arg Phe Thr Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Asn Ser Pro Tyr Thr Phe Gly Gln Gly Thr Arg Leu Glu Ile
            100                 105                 110

Lys

<210> SEQ ID NO 153
<211> LENGTH: 363
<212> TYPE: DNA
<213> ORGANISM: Artificial Sequence
<220> FEATURE:
<223> OTHER INFORMATION: Combination of PCR-generated and human sequence

<400> SEQUENCE: 153
caggtgcagc tggtgcagtc tggagcagtg gtgaaaaagc cgggggagtc tctgaagatc      60
tcctgtgagg cttctggata catgttcctc gatcactgga tcggctgggt gcgccagatg     120
cccgggaaag gcctggagtg gatgggaatc atctttcctg aggactctga taccagatat     180
agtgggtcct tcgaaggcca ggtcaccatc tcagccgaca ggtccgtcaa caccgtctac     240
ctggagtgga gcagcctgaa ggcctcggac accgccatgt attattgtgc gagagtctca     300
gtagttcgta aggggggctg gttcgaccca tggggccagg gaaccacggt caccgtctcc     360
tca                                                                   363

<210> SEQ ID NO 154
<211> LENGTH: 339
<212> TYPE: DNA
<213> ORGANISM: Artificial Sequence
<220> FEATURE:
<223> OTHER INFORMATION: Combination of PCR-generated and human sequence
<220> FEATURE:
<221> NAME/KEY: misc_feature
<222> LOCATION: (5)..(6)
<223> OTHER INFORMATION: n is a, c, g, or t

<400> SEQUENCE: 154
gaaanncaac tgacgcagtc tccagactcc ctggctgtgt ctctgggcga gagggccacc      60
atcaactgca gtccagcca gagtcttta tacacctcca acaataagaa ctacttagct      120
tggtaccagc agaaaccagg acagactcct aaactgctca ttatctgggc ctctacccga     180
gaatccgggg tccctgaccg attcactggc agcgggtctg ggacagattt cactctcacc     240
atcagcagcc tgcaggctga agatgtggca gtttattact gtcagcaata ttataatagt     300
ccgtacactt ttggccaagg gacacgactg gagattaaa                            339

<210> SEQ ID NO 155
<211> LENGTH: 121
<212> TYPE: PRT
<213> ORGANISM: Artificial Sequence
<220> FEATURE:
<223> OTHER INFORMATION: Combination of PCR-generated and human sequence

<400> SEQUENCE: 155

Gln Val Gln Leu Val Glu Ser Gly Ala Glu Leu Lys Lys Pro Gly Glu
  1               5                  10                  15

Ser Leu Lys Ile Ser Cys Glu Ala Ser Gly Tyr Ile Phe Ala Asp His
             20                  25                  30
```

```
Trp Ile Gly Trp Val Arg Gln Met Pro Gly Lys Gly Leu Glu Trp Met
             35                  40                  45

Gly Ile Ile Phe Pro Gly Asp Ser Asp Ile Arg Tyr Ser Pro Ser Phe
 50                  55                  60

Glu Gly Gln Val Thr Ile Ser Val Asp Arg Ser Val Ser Thr Ala Phe
65                  70                  75                  80

Leu Gln Trp Ser Ser Leu Lys Ala Ser Asp Thr Ala Met Tyr Phe Cys
                 85                  90                  95

Ala Arg Val Ala Val Arg Lys Gly Gly Trp Phe Asp Ser Trp Gly
            100                 105                 110

Gln Gly Thr Arg Val Thr Val Ser Ser
            115                 120
```

<210> SEQ ID NO 156
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 156

```
Glu Ile Val Met Thr Gln Ser Pro Glu Ser Leu Ala Val Ser Leu Gly
1               5                   10                  15

Glu Arg Ala Thr Ile Asn Cys Lys Ser Thr Gln Ser Leu Leu Trp Ser
             20                  25                  30

Ala Asn Asn Lys Asn Tyr Leu Ala Trp Tyr Arg Gln Lys Pro Arg Gln
         35                  40                  45

Thr Pro Glu Leu Leu Ile Thr Trp Ala Ser Thr Arg Glu Ser Gly Val
 50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                 85                  90                  95

Tyr Tyr Asn Ser Pro Tyr Thr Phe Gly Gln Gly Thr Arg Leu Glu Ile
            100                 105                 110

Lys
```

<210> SEQ ID NO 157
<211> LENGTH: 363
<212> TYPE: DNA
<213> ORGANISM: Artificial Sequence
<220> FEATURE:
<223> OTHER INFORMATION: Combination of PCR-generated and human sequence

<400> SEQUENCE: 157

```
caggtacagc tggtggagtc tgagcagaa ctgaaaaagc cgggggagtc tctgaagatc      60
tcctgtgagg catctggata catctttgcc gatcactgga tcggctgggt gcgccagatg    120
cccgggaaag gcctggagtg gatgggaatc atctttcctg gtgactctga tatcagatat    180
agtccgtcct tcgaaggcca ggtcaccatc tcagtcgaca ggtccgtcag taccgccttc    240
ctgcagtgga gcagcctgaa ggcctcggac accgccatgt atttttgtgc gagagtcgca    300
gtagtgcgta aagggggctg gttcgactcc tggggccagg aacccgggt caccgtctcc     360 tca                                                                  363
```

<210> SEQ ID NO 158
<211> LENGTH: 339
<212> TYPE: DNA

<213> ORGANISM: Artificial Sequence
<220> FEATURE:
<223> OTHER INFORMATION: Combination of PCR-generated and human sequence

<400> SEQUENCE: 158

```
gaaattgtga tgacccagtc tccagagtcc ctggctgtgt ctctgggcga gagggccacc    60
atcaactgca agtccaccca gagtctttta tggagcgcca acaacaagaa ctacttagct   120
tggtaccggc agaaaccacg acagactcct gaactgctca ttcgtgggc ttccacccgg    180
gaatccgggg tccctgaccg attcagtggc agcgggtctg ggacagattt cactctcacc   240
atcaccagcc tgcaggctga agatgtggca gtttattatt gtcaacaata ttataatagt   300
ccgtacactt ttggccaagg gacacgactg gagattaaa                          339
```

<210> SEQ ID NO 159
<211> LENGTH: 126
<212> TYPE: PRT
<213> ORGANISM: Artificial Sequence
<220> FEATURE:
<223> OTHER INFORMATION: Combination of PCR-generated and human sequence

<400> SEQUENCE: 159

```
Gln Val Gln Leu Val Gln Ser Gly Ala Glu Val Lys Lys Pro Trp Glu
1               5                   10                  15
Ser Leu Lys Ile Ser Cys Leu Ala Ser Gly Tyr Asp Phe Ala Ser Tyr
            20                  25                  30
Trp Ile Gly Trp Val Arg Gln Met Pro Gly Lys Gly Leu Glu Trp Val
        35                  40                  45
Gly Ile Ile Tyr Pro Asp Asp Ser Asp Thr Arg Tyr Asn Ala Ser Leu
    50                  55                  60
Glu Gly Arg Val Thr Met Ser Val Asp Thr Ser Thr Asn Thr Ala Tyr
65                  70                  75                  80
Leu Gln Trp Thr Ser Leu Lys Val Ser Asp Thr Gly Met Tyr Tyr Cys
                85                  90                  95
Ala Arg Arg Asp Arg Asn Cys Ser Gly Thr Thr Cys Tyr Pro Arg Trp
            100                 105                 110
Phe Asp Ser Trp Gly Gln Gly Thr Leu Val Thr Val Ser Ser
        115                 120                 125
```

<210> SEQ ID NO 160
<211> LENGTH: 113
<212> TYPE: PRT
<213> ORGANISM: Artificial Sequence
<220> FEATURE:
<223> OTHER INFORMATION: Combination of PCR-generated and human sequence

<400> SEQUENCE: 160

```
Glu Ile Val Leu Thr Gln Ser Pro Asp Phe Leu Ala Val Ser Leu Gly
1               5                   10                  15
Glu Arg Ala Thr Ile Asn Cys Lys Ser Ser Gln Ser Leu Phe Tyr Ser
            20                  25                  30
Gly Asn Ser Lys Asp Phe Leu Ala Trp Tyr Gln Gln Lys Pro Gly Gln
        35                  40                  45
Pro Pro Arg Leu Leu Val Tyr Trp Ala Ser Thr Arg Asp Ser Gly Val
    50                  55                  60
Pro Glu Arg Phe Ser Gly Ser Gly Ser Gly Thr Asp Phe Thr Leu Thr
65                  70                  75                  80
Ile Ser Arg Leu Gln Ala Glu Asp Val Ala Leu Tyr Tyr Cys His Gln
                85                  90                  95
```

Tyr His Ser Thr Pro Leu Ser Phe Gly Gly Gly Thr Lys Val Glu Ile
            100                 105                 110
Lys

<210> SEQ ID NO 161
<211> LENGTH: 378
<212> TYPE: DNA
<213> ORGANISM: Artificial Sequence
<220> FEATURE:
<223> OTHER INFORMATION: Combination of PCR-generated and human sequence

<400> SEQUENCE: 161
caggtgcagc tggtgcagtc tggggcagag gtgaaaaagc cgtgggagtc tctgaagatc    60
tcctgtttgg cttctggata cgactttgcc tcctactgga tcggctgggt gcgccagatg   120
cccgggaaag gcctggagtg ggtggggatc atctatcctg atgactctga taccagatac   180
aatgcgtcac tagaaggccg ggtcaccatg tcagtcgaca cgtccaccaa taccgcctac   240
ctgcagtgga ccagcctgaa ggtctcggac accggcatgt attactgtgc gagacgggat   300
cgcaattgta gtgggactac gtgttatccg aggtggttcg actcctgggg ccagggaacc   360
ctggtcaccg tctcttca                                                 378

<210> SEQ ID NO 162
<211> LENGTH: 339
<212> TYPE: DNA
<213> ORGANISM: Artificial Sequence
<220> FEATURE:
<223> OTHER INFORMATION: Combination of PCR-generated and human sequence

<400> SEQUENCE: 162
gaaattgtgc tgactcagtc tccagacttc ctggctgtgt ctctgggcga gagggccacc    60
atcaactgca gtccagcca gagtctttc tacagcggca acagtaagga cttcttagct   120
tggtaccagc agaaaccagg acagcctcct cgcttgctcg tttactgggc atctacccgg   180
gattccgggg tccctgagcg attcagtggc agcgggtctg ggacagattt tactctcacc   240
atcagccgcc tgcaggctga agatgtggct ctttattact gtcaccaata tcatagtact   300
cctctctctt tcggcggagg gaccaaggtg gaaatcaaa                          339

<210> SEQ ID NO 163
<211> LENGTH: 5
<212> TYPE: PRT
<213> ORGANISM: Homo sapiens

<400> SEQUENCE: 163

Ser Tyr Trp Met His
1               5

<210> SEQ ID NO 164
<211> LENGTH: 17
<212> TYPE: PRT
<213> ORGANISM: Homo sapiens

<400> SEQUENCE: 164

Arg Ile Asn Ser Asp Gly Ser Asp Thr Asn Tyr Ala Asp Ser Val Lys
1               5                   10                  15

Gly

<210> SEQ ID NO 165
<211> LENGTH: 9

```
<212> TYPE: PRT
<213> ORGANISM: Homo sapiens

<400> SEQUENCE: 165

Gly Arg Ser Tyr Gly Phe Phe Asp Tyr
1               5

<210> SEQ ID NO 166
<211> LENGTH: 12
<212> TYPE: PRT
<213> ORGANISM: Homo sapiens

<400> SEQUENCE: 166

Arg Ala Ser Gln Ile Ile Ser Ser Asn Tyr Leu Ala
1               5                   10

<210> SEQ ID NO 167
<211> LENGTH: 7
<212> TYPE: PRT
<213> ORGANISM: Homo sapiens

<400> SEQUENCE: 167

Gly Ala Ser Ser Arg Ala Thr
1               5

<210> SEQ ID NO 168
<211> LENGTH: 9
<212> TYPE: PRT
<213> ORGANISM: Homo sapiens

<400> SEQUENCE: 168

Gln Gln Tyr Gly Thr Ser Pro Arg Thr
1               5

<210> SEQ ID NO 169
<211> LENGTH: 5
<212> TYPE: PRT
<213> ORGANISM: Homo sapiens

<400> SEQUENCE: 169

Thr Tyr Gly Met His
1               5

<210> SEQ ID NO 170
<211> LENGTH: 17
<212> TYPE: PRT
<213> ORGANISM: Homo sapiens

<400> SEQUENCE: 170

Val Ile Trp Phe Asp Gly Asn Asn Lys Tyr Tyr Ala Asp Ser Val Lys
1               5                   10                  15

Gly

<210> SEQ ID NO 171
<211> LENGTH: 15
<212> TYPE: PRT
<213> ORGANISM: Homo sapiens

<400> SEQUENCE: 171

Asp Trp Trp Glu Ala Gly Cys Arg Pro Cys Tyr Phe Phe Asp Tyr
1               5                   10                  15

<210> SEQ ID NO 172
<211> LENGTH: 17
```

<212> TYPE: PRT
<213> ORGANISM: Homo sapiens

<400> SEQUENCE: 172

Lys Ser Ser Gln Ser Val Leu Tyr Ser Ser Asn Asn Lys Asn Tyr Leu
1               5                   10                  15

Ala

<210> SEQ ID NO 173
<211> LENGTH: 7
<212> TYPE: PRT
<213> ORGANISM: Homo sapiens

<400> SEQUENCE: 173

Trp Ala Ser Thr Arg Glu Ser
1               5

<210> SEQ ID NO 174
<211> LENGTH: 9
<212> TYPE: PRT
<213> ORGANISM: Homo sapiens

<400> SEQUENCE: 174

Gln Gln Tyr Tyr Ser Pro Pro Leu Thr
1               5

<210> SEQ ID NO 175
<211> LENGTH: 5
<212> TYPE: PRT
<213> ORGANISM: Homo sapiens

<400> SEQUENCE: 175

Asp Tyr Trp Met Ser
1               5

<210> SEQ ID NO 176
<211> LENGTH: 17
<212> TYPE: PRT
<213> ORGANISM: Homo sapiens

<400> SEQUENCE: 176

Asn Ile Asn Gln Asp Gly Ser Ala Ala Tyr Tyr Val Asp Ser Val Arg
1               5                   10                  15

Gly

<210> SEQ ID NO 177
<211> LENGTH: 18
<212> TYPE: PRT
<213> ORGANISM: Homo sapiens

<400> SEQUENCE: 177

Asp Ala His Tyr Tyr Asp Arg Asn Arg Asn Asn Tyr Tyr Tyr Tyr Phe
1               5                   10                  15

Asp Phe

<210> SEQ ID NO 178
<211> LENGTH: 11
<212> TYPE: PRT
<213> ORGANISM: Homo sapiens

<400> SEQUENCE: 178

Arg Ala Ser Gln Ser Val Gly Ala Asn Leu Ala
1               5                   10

```
<210> SEQ ID NO 179
<211> LENGTH: 7
<212> TYPE: PRT
<213> ORGANISM: Homo sapiens

<400> SEQUENCE: 179

Ser Ala Ser Thr Arg Ala Thr
1               5

<210> SEQ ID NO 180
<211> LENGTH: 9
<212> TYPE: PRT
<213> ORGANISM: Homo sapiens

<400> SEQUENCE: 180

Gln Gln Tyr Asn Asn Trp Pro Arg Thr
1               5

<210> SEQ ID NO 181
<211> LENGTH: 7
<212> TYPE: PRT
<213> ORGANISM: Homo sapiens

<400> SEQUENCE: 181

Ser Gly Asn Tyr Tyr Trp Ser
1               5

<210> SEQ ID NO 182
<211> LENGTH: 16
<212> TYPE: PRT
<213> ORGANISM: Homo sapiens

<400> SEQUENCE: 182

Arg Met Ser Ser Ser Gly Ser Thr Asn Tyr Asn Pro Ser Leu Lys Ser
1               5                   10                  15

<210> SEQ ID NO 183
<211> LENGTH: 17
<212> TYPE: PRT
<213> ORGANISM: Homo sapiens

<400> SEQUENCE: 183

Glu Ser Gly Ser Ser Trp Gln Asn His Tyr Tyr Tyr Tyr Gly Met Asp
1               5                   10                  15

Val

<210> SEQ ID NO 184
<211> LENGTH: 9
<212> TYPE: PRT
<213> ORGANISM: Homo sapiens

<400> SEQUENCE: 184

Gln Gln Tyr Tyr Ser Thr Pro Leu Thr
1               5

<210> SEQ ID NO 185
<211> LENGTH: 5
<212> TYPE: PRT
<213> ORGANISM: Homo sapiens

<400> SEQUENCE: 185

Asn Tyr Ala Met Ser
1               5
```

<210> SEQ ID NO 186
<211> LENGTH: 16
<212> TYPE: PRT
<213> ORGANISM: Homo sapiens

<400> SEQUENCE: 186

Gly Ile Ser Ser Asp Gly Asn Thr Phe Tyr Ala Asp Ser Val Lys Gly
1               5                   10                  15

<210> SEQ ID NO 187
<211> LENGTH: 15
<212> TYPE: PRT
<213> ORGANISM: Homo sapiens

<400> SEQUENCE: 187

Glu Ser Gly Arg Trp Gly Gly Gly Thr Leu Tyr Gly Ala His Tyr
1               5                   10                  15

<210> SEQ ID NO 188
<211> LENGTH: 17
<212> TYPE: PRT
<213> ORGANISM: Homo sapiens

<400> SEQUENCE: 188

Lys Ser Ser Gln Ser Leu Leu Tyr Asn Ser Asn Asn Lys Asn Tyr Leu
1               5                   10                  15

Thr

<210> SEQ ID NO 189
<211> LENGTH: 9
<212> TYPE: PRT
<213> ORGANISM: Homo sapiens

<400> SEQUENCE: 189

Gln Gln Tyr Tyr Ser Ser Pro Leu Thr
1               5

<210> SEQ ID NO 190
<211> LENGTH: 5
<212> TYPE: PRT
<213> ORGANISM: Homo sapiens

<400> SEQUENCE: 190

Asp Tyr Asn Val His
1               5

<210> SEQ ID NO 191
<211> LENGTH: 17
<212> TYPE: PRT
<213> ORGANISM: Homo sapiens

<400> SEQUENCE: 191

Arg Ile Ser Pro Asn Ser Gly Gly Thr Lys Tyr Ala Gln Lys Phe Gln
1               5                   10                  15

Gly

<210> SEQ ID NO 192
<211> LENGTH: 12
<212> TYPE: PRT
<213> ORGANISM: Homo sapiens

<400> SEQUENCE: 192

Gly His Cys Asp Gly Thr Thr Cys Ser Arg Ala Tyr
1               5                  10

<210> SEQ ID NO 193
<211> LENGTH: 16
<212> TYPE: PRT
<213> ORGANISM: Homo sapiens

<400> SEQUENCE: 193

Arg Ser Ser Gln Ser Leu Leu His Arg Ser Gly His Lys Tyr Leu His
1               5                  10                  15

<210> SEQ ID NO 194
<211> LENGTH: 7
<212> TYPE: PRT
<213> ORGANISM: Homo sapiens

<400> SEQUENCE: 194

Leu Gly Ser Asn Arg Ala Ser
1               5

<210> SEQ ID NO 195
<211> LENGTH: 9
<212> TYPE: PRT
<213> ORGANISM: Homo sapiens

<400> SEQUENCE: 195

Met Gln Thr Leu Gln Thr Pro Trp Thr
1               5

<210> SEQ ID NO 196
<211> LENGTH: 5
<212> TYPE: PRT
<213> ORGANISM: Homo sapiens

<400> SEQUENCE: 196

Gly Tyr Tyr Leu His
1               5

<210> SEQ ID NO 197
<211> LENGTH: 17
<212> TYPE: PRT
<213> ORGANISM: Homo sapiens

<400> SEQUENCE: 197

Trp Val Asn Pro Arg Ser Gly Gly Thr Ser Tyr Pro Pro Lys Phe Gln
1               5                  10                  15

Gly

<210> SEQ ID NO 198
<211> LENGTH: 11
<212> TYPE: PRT
<213> ORGANISM: Homo sapiens

<400> SEQUENCE: 198

Gly Arg Ile Pro Asp Val Thr Ala Phe Asp Ile
1               5                  10

<210> SEQ ID NO 199
<211> LENGTH: 17
<212> TYPE: PRT
<213> ORGANISM: Homo sapiens

<400> SEQUENCE: 199

```
Lys Ser Ser Glu Ser Leu Leu Tyr Asp Ser Asn Asn Lys Asn Tyr Leu
1               5                   10                  15

Ala

<210> SEQ ID NO 200
<211> LENGTH: 9
<212> TYPE: PRT
<213> ORGANISM: Homo sapiens

<400> SEQUENCE: 200

Gln Gln Tyr Phe Ser Thr Pro Trp Thr
1               5

<210> SEQ ID NO 201
<211> LENGTH: 5
<212> TYPE: PRT
<213> ORGANISM: Homo sapiens

<400> SEQUENCE: 201

Asp Tyr Trp Thr Ala
1               5

<210> SEQ ID NO 202
<211> LENGTH: 17
<212> TYPE: PRT
<213> ORGANISM: Homo sapiens

<400> SEQUENCE: 202

Ile Ile Tyr Ser Gly Asp Ser Asp Thr Arg Tyr His Pro Ser Val Gln
1               5                   10                  15

Gly

<210> SEQ ID NO 203
<211> LENGTH: 13
<212> TYPE: PRT
<213> ORGANISM: Homo sapiens

<400> SEQUENCE: 203

Leu Asp Ala Arg Val Asp Ala Gly Trp Gln Leu Asp Ser
1               5                   10

<210> SEQ ID NO 204
<211> LENGTH: 17
<212> TYPE: PRT
<213> ORGANISM: Homo sapiens

<400> SEQUENCE: 204

Lys Ser Ser Gln Ser Val Phe Ser Arg Asp Asn Asn Lys Asn Tyr Leu
1               5                   10                  15

Ala

<210> SEQ ID NO 205
<211> LENGTH: 7
<212> TYPE: PRT
<213> ORGANISM: Homo sapiens

<400> SEQUENCE: 205

Trp Ala Ser Ser Arg Glu Ser
1               5

<210> SEQ ID NO 206
<211> LENGTH: 9
<212> TYPE: PRT
```

<213> ORGANISM: Homo sapiens

<400> SEQUENCE: 206

Gln His Tyr Phe Asn Thr Pro His Asn
1               5

<210> SEQ ID NO 207
<211> LENGTH: 5
<212> TYPE: PRT
<213> ORGANISM: Homo sapiens

<400> SEQUENCE: 207

Asn Tyr Trp Ile Gly
1               5

<210> SEQ ID NO 208
<211> LENGTH: 17
<212> TYPE: PRT
<213> ORGANISM: Homo sapiens

<400> SEQUENCE: 208

Ile Ile Tyr Pro Gly Asp Ser Asp Thr Arg Tyr Ser Pro Pro Phe Gln
1               5                   10                  15

Gly

<210> SEQ ID NO 209
<211> LENGTH: 12
<212> TYPE: PRT
<213> ORGANISM: Homo sapiens

<400> SEQUENCE: 209

Val Gly Arg Pro Ser Lys Gly Gly Trp Phe Asp Pro
1               5                   10

<210> SEQ ID NO 210
<211> LENGTH: 17
<212> TYPE: PRT
<213> ORGANISM: Homo sapiens

<400> SEQUENCE: 210

Glu Ser Ser Gln Thr Leu Leu Tyr Ser Ser Asn Glu Lys Asn Tyr Leu
1               5                   10                  15

Ala

<210> SEQ ID NO 211
<211> LENGTH: 7
<212> TYPE: PRT
<213> ORGANISM: Homo sapiens

<400> SEQUENCE: 211

Trp Ala Ser Thr Pro Glu Ser
1               5

<210> SEQ ID NO 212
<211> LENGTH: 9
<212> TYPE: PRT
<213> ORGANISM: Homo sapiens

<400> SEQUENCE: 212

Gln Gln Tyr Tyr Asn Ser Pro Tyr Thr
1               5

<210> SEQ ID NO 213

```
<211> LENGTH: 5
<212> TYPE: PRT
<213> ORGANISM: Homo sapiens

<400> SEQUENCE: 213

Asp Ser Tyr Met Ser
1               5

<210> SEQ ID NO 214
<211> LENGTH: 17
<212> TYPE: PRT
<213> ORGANISM: Homo sapiens

<400> SEQUENCE: 214

Tyr Ile Ser Arg Ser Ser Ser His Thr Asn Tyr Ala Asp Ser Val Lys
1               5                  10                  15

Gly

<210> SEQ ID NO 215
<211> LENGTH: 17
<212> TYPE: PRT
<213> ORGANISM: Homo sapiens

<400> SEQUENCE: 215

Val Gln Thr Thr Met Ile Glu Gly Lys Thr Lys Leu Asn Tyr Phe Asp
1               5                  10                  15

Tyr

<210> SEQ ID NO 216
<211> LENGTH: 17
<212> TYPE: PRT
<213> ORGANISM: Homo sapiens

<400> SEQUENCE: 216

Glu Ser Ser His Ser Leu Leu Tyr Arg Ser Asn Asn Arg Asn Tyr Leu
1               5                  10                  15

Ala

<210> SEQ ID NO 217
<211> LENGTH: 9
<212> TYPE: PRT
<213> ORGANISM: Homo sapiens

<400> SEQUENCE: 217

Gln Gln Phe Tyr Thr Thr Pro Tyr Thr
1               5

<210> SEQ ID NO 218
<211> LENGTH: 17
<212> TYPE: PRT
<213> ORGANISM: Homo sapiens

<400> SEQUENCE: 218

Glu Ser Ser His Ser Leu Leu Tyr Arg Ser Asn Asn Lys Asn Tyr Leu
1               5                  10                  15

Ala

<210> SEQ ID NO 219
<211> LENGTH: 5
<212> TYPE: PRT
<213> ORGANISM: Homo sapiens

<400> SEQUENCE: 219
```

Lys Ala Trp Met Ser
1               5

<210> SEQ ID NO 220
<211> LENGTH: 19
<212> TYPE: PRT
<213> ORGANISM: Homo sapiens

<400> SEQUENCE: 220

Arg Ile Lys Ser Lys Val Asp Gly Glu Thr Thr Asp Tyr Ala Ala Pro
1               5                   10                  15

Val Arg Gly

<210> SEQ ID NO 221
<211> LENGTH: 13
<212> TYPE: PRT
<213> ORGANISM: Homo sapiens

<400> SEQUENCE: 221

Leu Ile His Cys Asp Leu Ser Ala Cys Leu Pro His Phe
1               5                   10

<210> SEQ ID NO 222
<211> LENGTH: 5
<212> TYPE: PRT
<213> ORGANISM: Homo sapiens

<400> SEQUENCE: 222

Asn Tyr Trp Ile Ala
1               5

<210> SEQ ID NO 223
<211> LENGTH: 17
<212> TYPE: PRT
<213> ORGANISM: Homo sapiens

<400> SEQUENCE: 223

Ile Ile Tyr Pro Gly Asp Ser Asp Thr Thr Tyr Ser Pro Ser Phe Gln
1               5                   10                  15

Gly

<210> SEQ ID NO 224
<211> LENGTH: 15
<212> TYPE: PRT
<213> ORGANISM: Homo sapiens

<400> SEQUENCE: 224

Leu Pro Arg Thr Asp Gly Asp Asn Ser Ile Gly Tyr Phe Glu Tyr
1               5                   10                  15

<210> SEQ ID NO 225
<211> LENGTH: 17
<212> TYPE: PRT
<213> ORGANISM: Homo sapiens

<400> SEQUENCE: 225

Lys Ser Ser Gln Ser Val Leu Tyr Ser Ser Asn Ser Glu Asn Tyr Leu
1               5                   10                  15

Ala

<210> SEQ ID NO 226
<211> LENGTH: 9

```
<212> TYPE: PRT
<213> ORGANISM: Homo sapiens

<400> SEQUENCE: 226

Gln Gln Tyr Tyr Ser Thr Pro Phe Thr
1               5

<210> SEQ ID NO 227
<211> LENGTH: 5
<212> TYPE: PRT
<213> ORGANISM: Homo sapiens

<400> SEQUENCE: 227

Ser Tyr Ser Met Asn
1               5

<210> SEQ ID NO 228
<211> LENGTH: 17
<212> TYPE: PRT
<213> ORGANISM: Homo sapiens

<400> SEQUENCE: 228

Tyr Ile Ser Ser Ser Thr Thr Thr Ile Tyr Tyr Ala Asp Ser Val Lys
1               5                   10                  15

Gly

<210> SEQ ID NO 229
<211> LENGTH: 12
<212> TYPE: PRT
<213> ORGANISM: Homo sapiens

<400> SEQUENCE: 229

Val Pro Ala Pro Arg Leu Gly Gly Ser Tyr Thr Tyr
1               5                   10

<210> SEQ ID NO 230
<211> LENGTH: 12
<212> TYPE: PRT
<213> ORGANISM: Homo sapiens

<400> SEQUENCE: 230

Arg Ala Ser Gln Ser Val Ser Ser Ser Tyr Leu Ala
1               5                   10

<210> SEQ ID NO 231
<211> LENGTH: 9
<212> TYPE: PRT
<213> ORGANISM: Homo sapiens

<400> SEQUENCE: 231

Gln Gln Tyr Gly Thr Ser Pro Leu Thr
1               5

<210> SEQ ID NO 232
<211> LENGTH: 5
<212> TYPE: PRT
<213> ORGANISM: Homo sapiens

<400> SEQUENCE: 232

Asp Ala Trp Met Ser
1               5

<210> SEQ ID NO 233
<211> LENGTH: 19
```

```
<212> TYPE: PRT
<213> ORGANISM: homo sapiens

<400> SEQUENCE: 233

Arg Ile Lys Ser Lys Asn Val Gly Glu Thr Thr Asp Tyr Ala Glu His
1               5                   10                  15

Val Arg Gly

<210> SEQ ID NO 234
<211> LENGTH: 8
<212> TYPE: PRT
<213> ORGANISM: homo sapiens

<400> SEQUENCE: 234

Gly Leu Gly Gly Gly Thr Tyr Gly
1               5

<210> SEQ ID NO 235
<211> LENGTH: 16
<212> TYPE: PRT
<213> ORGANISM: Homo sapiens

<400> SEQUENCE: 235

Arg Ser Ser Ala Gly Leu Arg Asn Asn Asp Gly Asp Ile Leu Leu Ser
1               5                   10                  15

<210> SEQ ID NO 236
<211> LENGTH: 7
<212> TYPE: PRT
<213> ORGANISM: homo sapiens

<400> SEQUENCE: 236

Arg Val Ser Arg Arg Asp Ser
1               5

<210> SEQ ID NO 237
<211> LENGTH: 5
<212> TYPE: PRT
<213> ORGANISM: homo sapiens

<400> SEQUENCE: 237

Met Arg Gly Pro Tyr
1               5

<210> SEQ ID NO 238
<211> LENGTH: 5
<212> TYPE: PRT
<213> ORGANISM: Homo sapiens

<400> SEQUENCE: 238

Ile Tyr Glu Met Asn
1               5

<210> SEQ ID NO 239
<211> LENGTH: 17
<212> TYPE: PRT
<213> ORGANISM: Homo sapiens

<400> SEQUENCE: 239

Tyr Ile Thr Asn Arg Gly Ser Thr Ile Tyr Tyr Ala Asp Ser Val Lys
1               5                   10                  15

Gly
```

```
<210> SEQ ID NO 240
<211> LENGTH: 10
<212> TYPE: PRT
<213> ORGANISM: Homo sapiens

<400> SEQUENCE: 240

Pro Arg Ile Gly Ala Arg Val Phe Asp Val
1               5                   10

<210> SEQ ID NO 241
<211> LENGTH: 17
<212> TYPE: PRT
<213> ORGANISM: Homo sapiens

<400> SEQUENCE: 241

Lys Ser Ser Gln Thr Leu Leu Tyr Lys Ser Asn Asn Glu Asn Tyr Leu
1               5                   10                  15

Ala

<210> SEQ ID NO 242
<211> LENGTH: 9
<212> TYPE: PRT
<213> ORGANISM: Homo sapiens

<400> SEQUENCE: 242

Gln Gln Tyr Phe Thr Thr Ala Leu Thr
1               5

<210> SEQ ID NO 243
<211> LENGTH: 5
<212> TYPE: PRT
<213> ORGANISM: Homo sapiens

<400> SEQUENCE: 243

Asp His Trp Ile Gly
1               5

<210> SEQ ID NO 244
<211> LENGTH: 17
<212> TYPE: PRT
<213> ORGANISM: Homo sapiens

<400> SEQUENCE: 244

Ile Ile Phe Pro Glu Asp Ser Asp Thr Arg Tyr Ser Gly Ser Phe Glu
1               5                   10                  15

Gly

<210> SEQ ID NO 245
<211> LENGTH: 12
<212> TYPE: PRT
<213> ORGANISM: Homo sapiens

<400> SEQUENCE: 245

Val Ser Val Val Arg Lys Gly Gly Trp Phe Asp Pro
1               5                   10

<210> SEQ ID NO 246
<211> LENGTH: 17
<212> TYPE: PRT
<213> ORGANISM: Homo sapiens

<400> SEQUENCE: 246

Lys Ser Ser Gln Ser Leu Leu Tyr Thr Ser Asn Asn Lys Asn Tyr Leu
1               5                   10                  15
```

Ala

<210> SEQ ID NO 247
<211> LENGTH: 17
<212> TYPE: PRT
<213> ORGANISM: Homo sapiens

<400> SEQUENCE: 247

Ile Ile Phe Pro Gly Asp Ser Asp Ile Arg Tyr Ser Pro Ser Phe Glu
1               5                   10                  15

Gly

<210> SEQ ID NO 248
<211> LENGTH: 12
<212> TYPE: PRT
<213> ORGANISM: Homo sapiens

<400> SEQUENCE: 248

Val Ala Val Val Arg Lys Gly Gly Trp Phe Asp Ser
1               5                   10

<210> SEQ ID NO 249
<211> LENGTH: 17
<212> TYPE: PRT
<213> ORGANISM: Homo sapiens

<400> SEQUENCE: 249

Lys Ser Thr Gln Ser Leu Leu Trp Ser Ala Asn Asn Lys Asn Tyr Leu
1               5                   10                  15

Ala

<210> SEQ ID NO 250
<211> LENGTH: 5
<212> TYPE: PRT
<213> ORGANISM: Homo sapiens

<400> SEQUENCE: 250

Ser Tyr Trp Ile Gly
1               5

<210> SEQ ID NO 251
<211> LENGTH: 17
<212> TYPE: PRT
<213> ORGANISM: Homo sapiens

<400> SEQUENCE: 251

Ile Ile Tyr Pro Asp Asp Ser Asp Thr Arg Tyr Asn Ala Ser Leu Glu
1               5                   10                  15

Gly

<210> SEQ ID NO 252
<211> LENGTH: 17
<212> TYPE: PRT
<213> ORGANISM: Homo sapiens

<400> SEQUENCE: 252

Arg Asp Arg Asn Cys Ser Gly Thr Thr Cys Tyr Pro Arg Trp Phe Asp
1               5                   10                  15

Ser

<210> SEQ ID NO 253

```
<211> LENGTH: 17
<212> TYPE: PRT
<213> ORGANISM: Homo sapiens

<400> SEQUENCE: 253

Lys Ser Ser Gln Ser Leu Phe Tyr Ser Gly Asn Ser Lys Asp Phe Leu
1               5                   10                  15

Ala

<210> SEQ ID NO 254
<211> LENGTH: 7
<212> TYPE: PRT
<213> ORGANISM: Homo sapiens

<400> SEQUENCE: 254

Trp Ala Ser Thr Arg Asp Ser
1               5

<210> SEQ ID NO 255
<211> LENGTH: 9
<212> TYPE: PRT
<213> ORGANISM: Homo sapiens

<400> SEQUENCE: 255

His Gln Tyr His Ser Thr Pro Leu Ser
1               5

<210> SEQ ID NO 256
<211> LENGTH: 296
<212> TYPE: DNA
<213> ORGANISM: Homo sapiens

<400> SEQUENCE: 256
gaggtgcagc tggtggagtc cggggggaggc ttagttcagc ctgggggtc  cctgagactc      60 tcctgtgcag cctctggatt caccttcagt agctactgga tgcactgggt ccgccaagct     120
ccagggaagg ggctggtgtg ggtctcacgt attaatagtg atgggagtag cacaagctac     180
gcggactccg tgaagggccg attcaccatc tccagagaca acgccaagaa cacgctgtat     240
ctgcaaatga acagtctgag agccgaggac acggctgtgt attactgtgc aagaga        296

<210> SEQ ID NO 257
<211> LENGTH: 107
<212> TYPE: PRT
<213> ORGANISM: Homo sapiens

<400> SEQUENCE: 257

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Asp Thr Asn Tyr Ala Asp Ser Val
    50                  55                  60

Lys Gly Arg Phe Thr Phe Ser Arg Asp Asn Ala Lys Asn Thr Leu Tyr
65                  70                  75                  80

Leu Gln Met Thr Ser Leu Arg Ala Glu Asp Thr Ala Ile Tyr Tyr Cys
                85                  90                  95

Thr Arg Gly Arg Ser Tyr Gly Phe Phe Asp Tyr
                100                 105
```

<210> SEQ ID NO 258
<211> LENGTH: 288
<212> TYPE: DNA
<213> ORGANISM: Homo sapiens

<400> SEQUENCE: 258

| | | | | |
|---|---|---|---|---|
| gaaattgtgt tgacgcagtc tccagccacc ctgtctttgt ctccagggga aagagccacc | 60 |
| ctctcctgca gggccagtca gagtgttagc agcagctact tagcctggta ccagcagaaa | 120 |
| cctggccagg ctcccaggct cctcatctat gatgcatcca gcagggccac tggcatccca | 180 |
| gacaggttca gtggcagtgg gtctgggaca gacttcactc tcaccatcag cagactggag | 240 |
| cctgaagatt ttgcagtcta ttactgtcag cagcgtagca actggcat | 288 |

<210> SEQ ID NO 259
<211> LENGTH: 98
<212> TYPE: PRT
<213> ORGANISM: Homo sapiens

<400> SEQUENCE: 259

Glu Ile Val Leu Thr Gln Ser Pro Asp Thr Leu Ser Leu Ser Pro Gly
1               5                   10                  15

Glu Arg Ala Thr Leu Ser Cys Arg Ala Ser Gln Ile Ile Ser Ser Asn
            20                  25                  30

Tyr Leu Ala Trp Tyr Gln Gln Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Ala Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Arg Thr

<210> SEQ ID NO 260
<211> LENGTH: 296
<212> TYPE: DNA
<213> ORGANISM: Homo sapiens

<400> SEQUENCE: 260

| | | | | |
|---|---|---|---|---|
| caggtgcagc tggtggagtc tgggggaggc gtggtccagc ctgggaggtc cctgagactc | 60 |
| tcctgtgcag cgtctggatt caccttcagt agctatggca tgcactgggt ccgccaggct | 120 |
| ccaggcaagg ggctggagtg ggtggcagtt atatggtatg atggaagtaa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagaga | 296 |

<210> SEQ ID NO 261
<211> LENGTH: 113
<212> TYPE: PRT
<213> ORGANISM: Homo sapiens

<400> SEQUENCE: 261

Gln Val Gln Leu Val Glu Ser Arg Gly Gly Val Val Gln Pro Gly Thr
1               5                   10                  15

Ser Leu Arg Leu Ser Cys Lys Ala Ser Gly Phe Thr Phe Ser Thr Tyr
            20                  25                  30

Gly Met His Trp Val Arg Gln Ala Pro Gly Lys Ala Leu Glu Trp Val
            35                  40                  45

Ala Val Ile Trp Phe Asp Gly Asn Asn Lys Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Gly Glu Asp Thr Ala Val Tyr Tyr Cys
                 85                  90                  95

Ala Arg Asp Trp Trp Glu Ala Gly Cys Arg Pro Cys Tyr Phe Phe Asp
            100                 105                 110

Tyr

<210> SEQ ID NO 262
<211> LENGTH: 305
<212> TYPE: DNA
<213> ORGANISM: Homo sapiens

<400> SEQUENCE: 262
gacatcgtga tgacccagtc tccagactcc ctggctgtgt ctctgggcga gagggccacc    60
atcaactgca gtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctcc                                                               305

<210> SEQ ID NO 263
<211> LENGTH: 103
<212> TYPE: PRT
<213> ORGANISM: Homo sapiens

<400> SEQUENCE: 263

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Pro Pro Leu Thr
            100

<210> SEQ ID NO 264
<211> LENGTH: 296
<212> TYPE: DNA
<213> ORGANISM: Homo sapiens

<400> SEQUENCE: 264
gaggtgcagc tggtggagtc tgggggaggc ttggtccagc ctgggggtgtc cctgagactc    60 tcctgtgcag cctctggatt caccttcagt agctatgcta tgcactgggt ccgccaggct   120
ccagggaagg gactggaata tgtttcagct attagtagta tgggggtag cacatattat   180

```
gcaaactctg tgaagggcag attcaccatc tccagagaca attccaagaa cacgctgtat      240
cttcaaatgg gcagcctgag agctgaggac atggctgtgt attactgtgc gagaga          296
```

<210> SEQ ID NO 265
<211> LENGTH: 116
<212> TYPE: PRT
<213> ORGANISM: Homo sapiens

<400> SEQUENCE: 265

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Ala Ala Tyr Tyr Val Asp Ser Val
    50                  55                  60

Arg Gly Arg Phe Thr Ile Ser Arg Asp Ser Ala Glu Asn Ser Leu Asn
65                  70                  75                  80

Leu Gln Met Asn Ser Leu Arg Ala Glu Asp Thr Ala Val Tyr Tyr Cys
                85                  90                  95

Ala Lys Asp Ala His Tyr Tyr Asp Arg Asn Arg Asn Asn Tyr Tyr Tyr
            100                 105                 110

Tyr Phe Asp Phe
        115
```

<210> SEQ ID NO 266
<211> LENGTH: 287
<212> TYPE: DNA
<213> ORGANISM: Homo sapiens

<400> SEQUENCE: 266

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctcc                   287
```

<210> SEQ ID NO 267
<211> LENGTH: 97
<212> TYPE: PRT
<213> ORGANISM: Homo sapiens

<400> SEQUENCE: 267

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ala Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
```

Thr

<210> SEQ ID NO 268
<211> LENGTH: 291
<212> TYPE: DNA
<213> ORGANISM: Homo sapiens

<400> SEQUENCE: 268

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gaccgcggac gcggccgtgt attactgtgc g              291
```

<210> SEQ ID NO 269
<211> LENGTH: 116
<212> TYPE: PRT
<213> ORGANISM: Homo sapiens

<400> SEQUENCE: 269

Gln Val Gln Leu Gln Glu Ser Gly Pro Gly Leu Val Asn Pro Ser Gln
1               5                   10                  15

Thr Leu Ser Leu Thr Cys Thr Val Ser Gly Gly Ser Ile Ser Ser Gly
            20                  25                  30

Asn Tyr Tyr Trp Ser Trp Ile Arg Gln Pro Ala Gly Lys Gly Leu Glu
        35                  40                  45

Trp Ile Gly Arg Met Ser Ser Gly Ser Thr Asn Tyr Asn Pro Ser
    50                  55                  60

Leu Lys Ser Arg Val Thr Met Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Ser Gly Ser Ser Trp Gln Asn His Tyr Tyr Tyr Tyr
            100                 105                 110

Gly Met Asp Val
        115

<210> SEQ ID NO 270
<211> LENGTH: 103
<212> TYPE: PRT
<213> ORGANISM: Homo sapiens

<400> SEQUENCE: 270

Asp Ile Val Met Thr Gln Ser Pro Asp Ser Leu Ala Val Ser Leu Gly
1               5                   10                  15

Glu Arg Ala Asn Ile Asn Cys Lys Ser Ser Gln Ser Val Leu Tyr Ser
            20                  25                  30

Ser Asn Asn Lys Asn Tyr Leu Ala Trp Tyr Gln Gln Lys Ser Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr
            100

<210> SEQ ID NO 271
<211> LENGTH: 296
<212> TYPE: DNA
<213> ORGANISM: Homo sapiens

<400> SEQUENCE: 271
gaggtgcagc tggtggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcaaatga acagcctgag agccgaggac acggccgtat attactgtgc gaaaga       296

<210> SEQ ID NO 272
<211> LENGTH: 112
<212> TYPE: PRT
<213> ORGANISM: Homo sapiens

<400> SEQUENCE: 272

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Gly Ile Ser Ser Asp Gly Asn Thr Phe Tyr Ala Asp Ser Val Lys
    50                  55                  60

Gly Arg Phe Thr Val Ser Arg Asp Asn Ser Lys Asn Thr Leu Tyr Leu
65                  70                  75                  80

Gln Val Asn Ser Leu Arg Ala Asp Asp Thr Ala Val Tyr Tyr Cys Ala
                85                  90                  95

Lys Glu Ser Gly Arg Trp Gly Gly Gly Thr Leu Tyr Gly Ala His Tyr
            100                 105                 110

<210> SEQ ID NO 273
<211> LENGTH: 103
<212> TYPE: PRT
<213> ORGANISM: Homo sapiens

<400> SEQUENCE: 273

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Asn
            20                  25                  30

Ser Asn Asn Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ser Pro Leu Thr
            100

<210> SEQ ID NO 274
<211> LENGTH: 296
<212> TYPE: DNA
<213> ORGANISM: Homo sapiens

<400> SEQUENCE: 274
caggtgcagc tggtgcagtc tggggctgag gtgaagaagc ctggggcctc agtgaaggtc        60
tcctgcaagg cttctggata caccttcacc ggctactata tgcactgggt gcgacaggcc       120
cctggacaag gcttgagtg gatgggatgg atcaaccta acagtggtgg cacaaactat         180
gcacagaagt tccagggcag ggtcaccatg accaggaca cgtccatcag cacagcctac        240
atggagctga gcaggctgag atctgacgac acggccgtgt attactgtgc gagaga          296

<210> SEQ ID NO 275
<211> LENGTH: 110
<212> TYPE: PRT
<213> ORGANISM: Homo sapiens

<400> SEQUENCE: 275

Gln Val Gln Leu Val Gln Ser Gly Ala Glu Val Lys Lys Pro Gly Ala
1               5                   10                  15

Pro Val Lys Val Ser Cys Glu Thr Ser Gly Tyr Arg Phe Ser Asp Tyr
            20                  25                  30

Asn Val His Trp Val Arg Gln Ala Pro Gly Gln Gly Pro Glu Trp Ile
        35                  40                  45

Gly Arg Ile Ser Pro Asn Ser Gly Gly Thr Lys Tyr Ala Gln Lys Phe
    50                  55                  60

Gln Gly Arg Val Thr Met Thr Arg Asp Met Ser Met Asn Thr Ala Tyr
65                  70                  75                  80

Met Glu Leu Ser Gly Leu Arg Ser Asp Asp Thr Ala Val Tyr Tyr Cys
                85                  90                  95

Val Arg Gly His Cys Asp Gly Thr Thr Cys Ser Arg Ala Tyr
            100                 105                 110

<210> SEQ ID NO 276
<211> LENGTH: 302
<212> TYPE: DNA
<213> ORGANISM: Homo sapiens

<400> SEQUENCE: 276
gatattgtga tgactcagtc tccactctcc ctgcccgtca cccctggaga gccggcctcc        60
atctcctgca ggtctagtca gagcctcctg catagtaatg gatacaacta tttggattgg       120
tacctgcaga agccagggca gtctccacag ctcctgatct atttgggttc taatcgggcc       180
tccggggtcc ctgacaggtt cagtggcagt ggatcaggca cagattttac actgaaaatc       240
agcagagtgg aggctgagga tgttggggtt tattactgca tgcaagctct acaaactcct       300
cc                                                                     302

<210> SEQ ID NO 277
<211> LENGTH: 102
<212> TYPE: PRT
<213> ORGANISM: Homo sapiens

<400> SEQUENCE: 277

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Arg
                20                  25                  30

Ser Gly His Lys Tyr Leu His Trp Tyr Leu Gln Arg Pro Gly Gln Ser
            35                  40                  45

Pro Gln Val Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Thr
                85                  90                  95

Leu Gln Thr Pro Trp Thr
            100

<210> SEQ ID NO 278
<211> LENGTH: 296
<212> TYPE: DNA
<213> ORGANISM: Homo sapiens

<400> SEQUENCE: 278
caggtccagc ttgtgcagtc tggggctgag gtgaagaagc ctggggcctc agtgaaggtt      60
tcctgcaagg cttctggata caccttcact agctatgcta tgcattgggt gcgccaggcc     120
cccggacaaa ggcttgagtg gatgggatgg atcaacgctg caatggtaa cacaaaatat      180 tcacagaagt tccagggcag agtcaccatt accaggaca catccgcgag cacagcctac      240
atggagctga gcagcctgag atctgaagac acggctgtgt attactgtgc gagaga         296

<210> SEQ ID NO 279
<211> LENGTH: 109
<212> TYPE: PRT
<213> ORGANISM: Homo sapiens

<400> SEQUENCE: 279

Gln Val Gln Leu Val Gln Ser Gly Ala Glu Val Lys Lys Pro Gly Ala
1               5                   10                  15

Ser Val Lys Val Ser Cys Thr Ala Ser Gly Tyr Thr Phe Thr Gly Tyr
                20                  25                  30

Tyr Leu His Trp Val Arg Gln Ala Pro Gly Gln Gly Leu Glu Trp Met
            35                  40                  45

Gly Trp Val Asn Pro Arg Ser Gly Gly Thr Ser Tyr Pro Pro Lys Phe
        50                  55                  60

Gln Gly Arg Val Thr Met Thr Arg Asp Thr Ser Ile Asn Thr Ala Tyr
65                  70                  75                  80

Met Asp Leu Thr Trp Leu Thr Ser Asp Thr Ala Val Tyr Tyr Cys
                85                  90                  95

Ala Val Gly Arg Ile Pro Asp Val Thr Ala Phe Asp Ile
            100                 105

<210> SEQ ID NO 280
<211> LENGTH: 103
<212> TYPE: PRT
<213> ORGANISM: Homo sapiens

<400> SEQUENCE: 280

Asp Ile Val Met Thr Gln Ser Pro Asp Ser Leu Ala Val Ser Leu Gly
1               5                   10                  15

Glu Arg Ala Thr Ile Asn Cys Lys Ser Ser Glu Ser Leu Leu Tyr Asp
                20                  25                  30

```
Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Glu Thr Asp Phe Thr Leu Thr
 65                  70                  75                  80

Ile Ser Ser Leu Gln Ala Glu Asp Val Ala Val Tyr His Cys Gln Gln
                 85                  90                  95

Tyr Phe Ser Thr Pro Trp Thr
                100
```

<210> SEQ ID NO 281
<211> LENGTH: 296
<212> TYPE: DNA
<213> ORGANISM: Homo sapiens

<400> SEQUENCE: 281

```
gaggtgcagc tggtgcagtc tggagcagag gtgaaaaagc ccggggagtc tctgaagatc     60
tcctgtaagg gttctggata cagctttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca gtccatcag caccgcctac    240
ctgcagtgga gcagcctgaa ggcctcggac accgccatgt attactgtgc gagaca       296
```

<210> SEQ ID NO 282
<211> LENGTH: 111
<212> TYPE: PRT
<213> ORGANISM: Homo sapiens

<400> SEQUENCE: 282

```
Glu Val Gln Leu Val Gln Ser Gly Pro Glu Met Arg Lys Pro Gly Glu
 1               5                  10                  15

Ser Leu Lys Ile Ser Cys Lys Thr Ser Gly Tyr Ile Phe Ser Asp Tyr
                 20                  25                  30

Trp Thr Ala Trp Val Arg Gln Leu Pro Gly Lys Gly Leu Gln Trp Met
             35                  40                  45

Gly Ile Ile Tyr Ser Gly Asp Ser Asp Thr Arg Tyr His Pro Ser Val
 50                  55                  60

Gln Gly His Val Thr Met Ser Asp Ser Ser Leu Thr Thr Ala Tyr
 65                  70                  75                  80

Leu Gln Trp Ser Ser Leu Lys Ala Ser Asp Thr Gly Ile Tyr Tyr Cys
                 85                  90                  95

Ala Arg Leu Asp Ala Arg Val Asp Ala Gly Trp Gln Leu Asp Ser
                100                 105                 110
```

<210> SEQ ID NO 283
<211> LENGTH: 103
<212> TYPE: PRT
<213> ORGANISM: Homo sapiens

<400> SEQUENCE: 283

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Phe Ser Arg
                 20                  25                  30

Asp Asn Asn Lys Asn Tyr Leu Ala Trp Tyr Gln His Lys Ser Gly Gln
             35                  40                  45
```

```
Pro Pro Lys Leu Leu Phe Phe Trp Ala Ser Ser Arg Glu Ser Gly Val
        50                  55                  60

Ser Asp Arg Phe Ser Gly Ser Gly Ser Gly Thr Asp Phe Thr Leu Thr
 65                  70                  75                  80

Ile Asp Asn Leu Gln Ala Glu Asp Val Ala Leu Tyr Tyr Cys Gln His
                    85                  90                  95

Tyr Phe Asn Thr Pro His Asn
                100
```

<210> SEQ ID NO 284
<211> LENGTH: 110
<212> TYPE: PRT
<213> ORGANISM: Homo sapiens

<400> SEQUENCE: 284

```
Glu Val Gln Leu Val Gln Ser Gly Ala Glu Val Lys Lys Pro Gly Glu
 1               5                  10                  15

Ser Leu Lys Ile Ser Cys Glu Ala Ser Gly Tyr Ser Phe Thr Asn Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Pro Phe
        50                  55                  60

Gln Gly Gln Val Thr Ile Thr Ala Asp Arg Ser Ile Thr Thr Ala Tyr
 65                  70                  75                  80

Leu Glu Trp Ser Ser Leu Lys Ala Ser Asp Thr Ala Met Tyr Tyr Cys
                85                  90                  95

Ala Arg Val Gly Arg Pro Ser Lys Gly Gly Trp Phe Asp Pro
                100                 105                 110
```

<210> SEQ ID NO 285
<211> LENGTH: 103
<212> TYPE: PRT
<213> ORGANISM: Homo sapiens

<400> SEQUENCE: 285

```
Asp Ile Val Met Thr Gln Ser Pro Asp Ser Leu Ala Val Ser Leu Gly
 1               5                  10                  15

Glu Arg Ala Thr Ile Asn Cys Glu Ser Ser Gln Thr Leu Leu Tyr Ser
                20                  25                  30

Ser Asn Glu Lys Asn Tyr Leu Ala Trp Tyr Gln Gln Lys Pro Gly Gln
            35                  40                  45

Pro Pro Lys Leu Leu Ile Ser Trp Ala Ser Thr Pro Glu Ser Gly Val
        50                  55                  60

Pro Asp Arg Phe Ser Gly Ser Gly Ser Gly Thr Ser Phe Thr Leu Thr
 65                  70                  75                  80

Ile Ser Ser Leu Gln Ala Glu Asp Val Ala Val Tyr Tyr Cys Gln Gln
                    85                  90                  95

Tyr Tyr Asn Ser Pro Tyr Thr
                100
```

<210> SEQ ID NO 286
<211> LENGTH: 296
<212> TYPE: DNA
<213> ORGANISM: Homo sapiens

<400> SEQUENCE: 286
caggtgcagc tggtggagtc tgggggaggc ttggtcaagc ctggagggtc cctgagactc     60

```
tcctgtgcag cctctggatt caccttcagt gactactaca tgagctggat ccgccaggct    120
ccagggaagg ggctggagtg ggtttcatac attagtagta gtagtagtta cacaaactac    180
gcagactctg tgaagggccg attcaccatc tccagagaca acgccaagaa ctcactgtat    240
ctgcaaatga acagcctgag agccgaggac acggctgtgt attactgtgc gagaga        296
```

<210> SEQ ID NO 287
<211> LENGTH: 115
<212> TYPE: PRT
<213> ORGANISM: Homo sapiens

<400> SEQUENCE: 287

Gln Val Gln Leu Val Glu Ser Gly Gly Gly Leu Val Lys Pro Gly Gly
1               5                   10                  15

Ser Leu Arg Leu Ser Cys Val Ala Ser Gly Ile Thr Phe Ser Asp Ser
            20                  25                  30

Tyr Met Ser Trp Ile Arg Gln Thr Pro Gly Lys Gly Leu Glu Trp Leu
        35                  40                  45

Ser Tyr Ile Ser Arg Ser Ser Ser His Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                85                  90                  95

Ala Arg Val Gln Thr Thr Met Ile Glu Gly Lys Thr Lys Leu Asn Tyr
            100                 105                 110

Phe Asp Tyr
        115

<210> SEQ ID NO 288
<211> LENGTH: 103
<212> TYPE: PRT
<213> ORGANISM: Homo sapiens

<400> SEQUENCE: 288

Asp Ile Val Met Thr Gln Ser Pro Asp Ser Leu Ala Val Ser Leu Gly
1               5                   10                  15

Glu Arg Val Thr Ile Thr Cys Glu Ser Ser His Ser Leu Leu Tyr Arg
            20                  25                  30

Ser Asn Asn Arg Asn Tyr Leu Ala Trp Tyr Gln Gln Lys Pro Arg Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Val Tyr Tyr Cys Gln Gln
                85                  90                  95

Phe Tyr Thr Thr Pro Tyr Thr
            100

<210> SEQ ID NO 289
<211> LENGTH: 115
<212> TYPE: PRT
<213> ORGANISM: Homo sapiens

<400> SEQUENCE: 289

Gln Val Gln Leu Val Glu Ser Gly Gly Gly Leu Val Lys Pro Gly Gly

```
              1               5                  10                 15
Ser Leu Arg Leu Ser Cys Val Ala Ser Gly Ile Thr Phe Ser Asp Ser
                    20                  25                 30

Tyr Met Ser Trp Ile Arg Gln Thr Pro Gly Lys Gly Leu Glu Trp Leu
            35                  40                  45

Ser Tyr Ile Ser Arg Ser Ser His Thr Asn Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Gly Glu Asp Thr Ala Val Tyr Tyr Cys
                    85                  90                  95

Ala Arg Val Gln Thr Thr Met Ile Glu Gly Lys Thr Lys Leu Asn Tyr
                100                 105                 110

Phe Asp Tyr
        115
```

<210> SEQ ID NO 290
<211> LENGTH: 103
<212> TYPE: PRT
<213> ORGANISM: Homo sapiens

<400> SEQUENCE: 290

```
Asp Ile Val Met Thr Gln Ser Pro Asp Ser Leu Ala Val Ser Leu Gly
1               5                   10                  15

Glu Arg Val Thr Ile Ser Cys Glu Ser Ser His Ser Leu Leu Tyr Arg
                20                  25                  30

Ser Asn Asn Lys Asn Tyr Leu Ala Trp Tyr Gln Gln Lys Pro Arg Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Val Tyr Tyr Cys Gln Gln
                85                  90                  95

Phe Tyr Thr Thr Pro Tyr Thr
                100
```

<210> SEQ ID NO 291
<211> LENGTH: 302
<212> TYPE: DNA
<213> ORGANISM: Homo sapiens

<400> SEQUENCE: 291

```
gaggtgcagc tggtggagtc tgggggaggc ttggtaaagc ctgggggtc ccttagactc      60 tcctgtgcag cctctggatt cactttcagt aacgcctgga tgagctgggt ccgccaggct    120
ccagggaagg ggctggagtg ggttggccgt attaaaagca aaactgatgg tgggacaaca    180
gactacgctg cacccgtgaa aggcagattc accatctcaa gagatgattc aaaaaacacg    240
ctgtatctgc aaatgaacag cctgaaaacc gaggacacag ccgtgtatta ctgtaccaca    300
ga                                                                   302
```

<210> SEQ ID NO 292
<211> LENGTH: 111
<212> TYPE: PRT
<213> ORGANISM: Homo sapiens

<400> SEQUENCE: 292

```
Gln Leu Val Glu Ser Gly Gly Leu Ala Glu Pro Gly Gly Ser Leu
1               5                   10                  15

Arg Leu Ser Cys Ala Ala Ser Gly Phe Thr Phe Thr Lys Ala Trp Met
            20                  25                  30

Ser Trp Val Arg Gln Thr Pro Gly Arg Gly Leu Glu Trp Leu Gly Arg
            35                  40                  45

Ile Lys Ser Lys Val Asp Gly Glu Thr Thr Asp Tyr Ala Ala Pro Val
50                  55                  60

Arg Gly Arg Phe Thr Ile Ser Arg Asp Asp Ser Lys Ser Thr Val Tyr
65                  70                  75                  80

Leu Gln Met Thr Gly Leu Arg Thr Glu Asp Thr Gly Val Tyr Phe Cys
            85                  90                  95

Thr Thr Leu Ile His Cys Asp Leu Ser Ala Cys Leu Pro His Phe
            100                 105                 110

<210> SEQ ID NO 293
<211> LENGTH: 103
<212> TYPE: PRT
<213> ORGANISM: Homo sapiens

<400> SEQUENCE: 293

Asp Ile Val Met Thr Gln Ser Pro Asp Ser Leu Ala Val Ser Leu Gly
1               5                   10                  15

Glu Arg Val Thr Ile Ser Cys Glu Ser Ser His Ser Leu Leu Tyr Arg
            20                  25                  30

Ser Asn Asn Lys Asn Tyr Leu Ala Trp Tyr Gln Gln Lys Pro Arg Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Glu Thr Asp Phe Thr Leu Thr
65                  70                  75                  80

Ile Ser Ser Leu Arg Ala Glu Asp Val Ala Val Tyr Tyr Cys Gln Gln
            85                  90                  95

Phe Tyr Thr Thr Pro Tyr Thr
            100

<210> SEQ ID NO 294
<211> LENGTH: 294
<212> TYPE: DNA
<213> ORGANISM: Homo sapiens

<400> SEQUENCE: 294
gaggtgcagc tggtgcagtc tggagcagag gtgaaaaagc cgggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgc gaga           294

<210> SEQ ID NO 295
<211> LENGTH: 113
<212> TYPE: PRT
<213> ORGANISM: Homo sapiens

<400> SEQUENCE: 295

Glu Val Gln Leu Val Gln Ser Gly Gly Glu Val Lys Lys Pro Gly Glu
1               5                   10                  15
```

Ser Leu Lys Ile Ser Cys Lys Gly Ser Gly Tyr Ser Phe Ser Asn Tyr
            20                  25                  30

Trp Ile Ala Trp Val Arg Gln Met Pro Gly Lys Gly Leu Glu Cys Met
        35                  40                  45

Gly Ile Ile Tyr Pro Gly Asp Ser Asp Thr Thr Tyr Ser Pro Ser Phe
    50                  55                  60

Gln Gly Gln Val Thr Ile Ser Ala Asp Lys Ser Val Ser Thr Thr Tyr
65                  70                  75                  80

Leu Gln Trp Ser Ser Leu Lys Ala Ser Asp Ser Ala Met Tyr Tyr Cys
                85                  90                  95

Ala Arg Leu Pro Arg Thr Asp Gly Asp Asn Ser Ile Gly Tyr Phe Glu
            100                 105                 110

Tyr

<210> SEQ ID NO 296
<211> LENGTH: 103
<212> TYPE: PRT
<213> ORGANISM: Homo sapiens

<400> SEQUENCE: 296

Asp Ile Val Met Thr Gln Ser Pro Ala Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr
            100

<210> SEQ ID NO 297
<211> LENGTH: 296
<212> TYPE: DNA
<213> ORGANISM: Homo sapiens

<400> SEQUENCE: 297
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg ggtttcatac attagtagta gtagtagtac catatactac     180
gcagactctg tgaagggccg attcaccatc tccagagaca atgccaagaa ctcactgtat     240
ctgcaaatga acagcctgag agccgaggac acggctgtgt attactgtgc gagaga         296

<210> SEQ ID NO 298
<211> LENGTH: 108
<212> TYPE: PRT
<213> ORGANISM: Homo sapiens

<400> SEQUENCE: 298

Glu Val Gln Leu Val Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Thr Thr Thr Ile Tyr Tyr Ala Asp Ser Val
    50                  55                  60

Lys Gly Arg Phe Thr Ile Ser Arg Asp Asn Val Lys Asn Ser Leu Tyr
65                  70                  75                  80

Leu Gln Met His Ser Leu Arg Ala Glu Asp Thr Ala Val Tyr Tyr Cys
                85                  90                  95

Val Pro Ala Pro Arg Leu Gly Gly Ser Tyr Thr Tyr
            100                 105
```

<210> SEQ ID NO 299
<211> LENGTH: 290
<212> TYPE: DNA
<213> ORGANISM: Homo sapiens

<400> SEQUENCE: 299

```
gaaattgtgt tgacgcagtc tccaggcacc ctgtctttgt ctccagggga aagagccacc      60
ctctcctgca gggccagtca gagtgttagc agcagctact tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatggta gctcacctcc                290
```

<210> SEQ ID NO 300
<211> LENGTH: 98
<212> TYPE: PRT
<213> ORGANISM: Homo sapiens

<400> SEQUENCE: 300

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Thr Ser Pro
                85                  90                  95

Leu Thr
```

<210> SEQ ID NO 301
<211> LENGTH: 302
<212> TYPE: DNA
<213> ORGANISM: Homo sapiens

<400> SEQUENCE: 301

```
gaggtgcagc tggtggagtc tgggggagcc ttggtaaagc ctgggggtc ccttagactc       60
tcctgtgcag cctctggatt cactttcagt aacgcctgga tgagctgggt ccgccaggct     120
ccagggaagg ggctggagtg ggttggccgt attaaaagca aaactgatgg tgggacaaca     180
gactacgctg cacccgtgaa aggcagattc accatctcaa gagatgattc aaaaaacacg     240
```

-continued

```
ctgtatctgc aaatgaacag cctgaaaacc gaggacacag ccgtgtatta ctgtaccaca    300
ga                                                                  302
```

<210> SEQ ID NO 302
<211> LENGTH: 108
<212> TYPE: PRT
<213> ORGANISM: Homo sapiens

<400> SEQUENCE: 302

| Glu | Val | Gln | Leu | Val | Glu | Ser | Gly | Gly | Asp | Leu | Val | Lys | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Val | Phe | Thr | Asp | Ala |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ser | Pro | Gly | Lys | Gly | Pro | Glu | Trp | Leu |
|---|---|---|---|---|---|---|---|---|---|---|---|---|---|---|---|
| | | 35 | | | | | 40 | | | | | 45 | | | |

| Gly | Arg | Ile | Lys | Ser | Lys | Asn | Val | Gly | Glu | Thr | Thr | Asp | Tyr | Ala | Glu |
|---|---|---|---|---|---|---|---|---|---|---|---|---|---|---|---|
| | 50 | | | | | 55 | | | | | 60 | | | | |

| His | Val | Arg | Gly | Arg | Phe | Thr | Ile | Ala | Arg | Asp | Ser | Asn | Arg | Thr |
|---|---|---|---|---|---|---|---|---|---|---|---|---|---|---|
| 65 | | | | | 70 | | | | | 75 | | | | | 80 |

| Leu | Tyr | Leu | Gln | Met | Ser | Asn | Leu | Lys | Ile | Asp | Asp | Thr | Ala | Val | Tyr |
|---|---|---|---|---|---|---|---|---|---|---|---|---|---|---|---|
| | | | | 85 | | | | | 90 | | | | | 95 | |

| Tyr | Cys | Thr | Thr | Gly | Leu | Gly | Gly | Gly | Thr | Tyr | Gly |
|---|---|---|---|---|---|---|---|---|---|---|---|
| | | | 100 | | | | | 105 | | | |

<210> SEQ ID NO 303
<211> LENGTH: 302
<212> TYPE: DNA
<213> ORGANISM: Homo sapiens

<400> SEQUENCE: 303

```
gatgttgtga tgactcagtc tccactctcc ctgcccgtca cccttggaca gccggcctcc    60
atctcctgca ggtctagtca aagcctcgta tacagtgatg aaacacccta cttgaattgg    120
tttcagcaga ggccaggcca atctccaagg cgcctaattt ataaggtttc taaccgggac    180
tctggggtcc cagacagatt cagcggcagt gggtcaggca ctgatttcac actgaaaatc    240
agcagggtgg aggctgagga tgttggggtt tattactgca tgcaaggtac acactggcct    300
cc                                                                  302
```

<210> SEQ ID NO 304
<211> LENGTH: 98
<212> TYPE: PRT
<213> ORGANISM: Homo sapiens

<400> SEQUENCE: 304

| Asp | Val | Val | Met | Thr | Gln | Ser | Pro | Leu | Ser | Leu | Pro | Ala | Thr | Leu | Gly |
|---|---|---|---|---|---|---|---|---|---|---|---|---|---|---|---|
| 1 | | | | 5 | | | | | 10 | | | | | 15 | |

| Gln | Pro | Ala | Ser | Ile | Ser | Cys | Arg | Ser | Ser | Ala | Gly | Leu | Arg | Asn | Asn |
|---|---|---|---|---|---|---|---|---|---|---|---|---|---|---|---|
| | | | 20 | | | | | 25 | | | | | 30 | | |

| Asp | Gly | Asp | Ile | Leu | Leu | Ser | Trp | Phe | His | Gln | Arg | Pro | Gly | Gln | Ser |
|---|---|---|---|---|---|---|---|---|---|---|---|---|---|---|---|
| | | 35 | | | | | 40 | | | | | 45 | | | |

| Pro | Arg | Arg | Leu | Phe | Tyr | Arg | Val | Ser | Arg | Arg | Asp | Ser | Gly | Val | Pro |
|---|---|---|---|---|---|---|---|---|---|---|---|---|---|---|---|
| | 50 | | | | | 55 | | | | | 60 | | | | |

| Asp | Arg | Phe | Asn | Gly | Ser | Gly | Ser | Ala | Thr | Phe | Thr | Leu | Arg | Ile |
|---|---|---|---|---|---|---|---|---|---|---|---|---|---|---|
| 65 | | | | | 70 | | | | | 75 | | | | | 80 |

| Asn | Ser | Val | Glu | Ala | Glu | Asp | Val | Gly | Ile | Tyr | Tyr | Cys | Met | Arg | Gly |
|---|---|---|---|---|---|---|---|---|---|---|---|---|---|---|---|
| | | | | 85 | | | | | 90 | | | | | 95 | |

Pro Tyr

<210> SEQ ID NO 305
<211> LENGTH: 296
<212> TYPE: DNA
<213> ORGANISM: Homo sapiens

<400> SEQUENCE: 305

```
gaggtgcagc tggtggagtc tgggggaggc ttggtacagc ctggagggtc cctgagactc      60
tcctgtgcag cctctggatt caccttcagt agttatgaaa tgaactgggt ccgccaggct     120
ccagggaagg ggctggagtg ggtttcatac attagtagta gtggtagtac catatactac     180
gcagactctg tgaagggccg attcaccatc tccagagaca acgccaagaa ctcactgtat     240
ctgcaaatga acagcctgag agccgaggac acggctgttt attactgtgc gagaga         296
```

<210> SEQ ID NO 306
<211> LENGTH: 108
<212> TYPE: PRT
<213> ORGANISM: Homo sapiens

<400> SEQUENCE: 306

Glu Val Gln Leu Val Glu Ser Gly Gly Gly Leu Val Gln Pro Gly Glu
1               5                   10                  15

Ser Leu Arg Leu Ser Cys Val Ala Ser Gly Phe Asn Phe Ser Ile Tyr
            20                  25                  30

Glu Met Asn Trp Val Arg Gln Ala Pro Gly Lys Gly Leu Glu Trp Val
        35                  40                  45

Ser Tyr Ile Thr Asn Arg Gly Ser Thr Ile Tyr Tyr Ala Asp Ser Val
    50                  55                  60

Lys Gly Arg Phe Thr Ile Ser Arg Asp Asn Ala Gln Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Ile Gly Ala Arg Val Phe Asp Val
            100                 105

<210> SEQ ID NO 307
<211> LENGTH: 103
<212> TYPE: PRT
<213> ORGANISM: Homo sapiens

<400> SEQUENCE: 307

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Leu Tyr Lys
            20                  25                  30

Ser Asn Asn Glu Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Thr Thr Ala Leu Thr
            100

<210> SEQ ID NO 308
<211> LENGTH: 296
<212> TYPE: DNA
<213> ORGANISM: Homo sapiens

<400> SEQUENCE: 308

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct ccaaggcca ggtcaccatc tcagccgaca gtccatcag caccgcctac    240 ctgcagtgga gcagcctgaa ggcctcggac accgccatgt attactgtgc gagaca      296
```

<210> SEQ ID NO 309
<211> LENGTH: 110
<212> TYPE: PRT
<213> ORGANISM: Homo sapiens

<400> SEQUENCE: 309

Glu Val Gln Leu Val Gln Ser Gly Ala Val Lys Lys Pro Gly Glu
1               5                   10                  15

Ser Leu Lys Ile Ser Cys Glu Ala Ser Gly Tyr Met Phe Leu Asp His
                20                  25                  30

Trp Ile Gly Trp Val Arg Gln Met Pro Gly Lys Gly Leu Glu Trp Met
        35                  40                  45

Gly Ile Ile Phe Pro Glu Asp Ser Asp Thr Arg Tyr Ser Gly Ser Phe
    50                  55                  60

Glu Gly Gln Val Thr Ile Ser Ala Asp Arg Ser Val Asn Thr Val Tyr
65                  70                  75                  80

Leu Glu Trp Ser Ser Leu Lys Ala Ser Asp Thr Ala Met Tyr Tyr Cys
                85                  90                  95

Ala Arg Val Ser Val Val Arg Lys Gly Gly Trp Phe Asp Pro
            100                 105                 110

<210> SEQ ID NO 310
<211> LENGTH: 103
<212> TYPE: PRT
<213> ORGANISM: Homo sapiens

<400> SEQUENCE: 310

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Thr
                20                  25                  30

Ser Asn Asn Lys Asn Tyr Leu Ala Trp Tyr Gln Gln Lys Pro Gly Gln
        35                  40                  45

Thr Pro Lys Leu Leu Ile Ile Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Ser Pro Tyr Thr
            100

<210> SEQ ID NO 311
<211> LENGTH: 110

<212> TYPE: PRT
<213> ORGANISM: Homo sapiens

<400> SEQUENCE: 311

Glu Val Gln Leu Val Gln Ser Gly Ala Glu Leu Lys Lys Pro Gly Glu
1               5                   10                  15

Ser Leu Lys Ile Ser Cys Glu Ala Ser Gly Tyr Ile Phe Ala Asp His
            20                  25                  30

Trp Ile Gly Trp Val Arg Gln Met Pro Gly Lys Gly Leu Glu Trp Met
        35                  40                  45

Gly Ile Ile Phe Pro Gly Asp Ser Asp Ile Arg Tyr Ser Pro Ser Phe
    50                  55                  60

Glu Gly Gln Val Thr Ile Ser Val Asp Arg Ser Val Ser Thr Ala Phe
65                  70                  75                  80

Leu Gln Trp Ser Ser Leu Lys Ala Ser Asp Thr Ala Met Tyr Phe Cys
                85                  90                  95

Ala Arg Val Ala Val Val Arg Lys Gly Gly Trp Phe Asp Ser
            100                 105                 110

<210> SEQ ID NO 312
<211> LENGTH: 103
<212> TYPE: PRT
<213> ORGANISM: Homo sapiens

<400> SEQUENCE: 312

Asp Ile Val Met Thr Gln Ser Pro Glu Ser Leu Ala Val Ser Leu Gly
1               5                   10                  15

Glu Arg Ala Thr Ile Asn Cys Lys Ser Thr Gln Ser Leu Leu Trp Ser
            20                  25                  30

Ala Asn Asn Lys Asn Tyr Leu Ala Trp Tyr Arg Gln Lys Pro Arg Gln
        35                  40                  45

Thr Pro Glu Leu Leu Ile Thr Trp Ala Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

Tyr Tyr Asn Ser Pro Tyr Thr
            100

<210> SEQ ID NO 313
<211> LENGTH: 115
<212> TYPE: PRT
<213> ORGANISM: Homo sapiens

<400> SEQUENCE: 313

Glu Val Gln Leu Val Gln Ser Gly Ala Glu Val Lys Lys Pro Trp Glu
1               5                   10                  15

Ser Leu Lys Ile Ser Cys Leu Ala Ser Gly Tyr Asp Phe Ala Ser Tyr
            20                  25                  30

Trp Ile Gly Trp Val Arg Gln Met Pro Gly Lys Gly Leu Glu Trp Val
        35                  40                  45

Gly Ile Ile Tyr Pro Asp Asp Ser Asp Thr Arg Tyr Asn Ala Ser Leu
    50                  55                  60

Glu Gly Arg Val Thr Met Ser Val Asp Thr Ser Thr Asn Thr Ala Tyr
65                  70                  75                  80

Leu Gln Trp Thr Ser Leu Lys Val Ser Asp Thr Gly Met Tyr Tyr Cys

```
                    85                  90                  95

Ala Arg Arg Asp Arg Asn Cys Ser Gly Thr Thr Cys Tyr Pro Arg Trp
            100                 105                 110

Phe Asp Ser
        115

<210> SEQ ID NO 314
<211> LENGTH: 103
<212> TYPE: PRT
<213> ORGANISM: Homo sapiens

<400> SEQUENCE: 314

Asp Ile Val Met Thr Gln Ser Pro Asp Phe Leu Ala Val Ser Leu Gly
1               5                   10                  15

Glu Arg Ala Thr Ile Asn Cys Lys Ser Ser Gln Ser Leu Phe Tyr Ser
            20                  25                  30

Gly Asn Ser Lys Asp Phe Leu Ala Trp Tyr Gln Gln Lys Pro Gly Gln
        35                  40                  45

Pro Pro Arg Leu Leu Val Tyr Trp Ala Ser Thr Arg Asp Ser Gly Val
    50                  55                  60

Pro Glu Arg Phe Ser Gly Ser Gly Ser Gly Thr Asp Phe Thr Leu Thr
65                  70                  75                  80

Ile Ser Arg Leu Gln Ala Glu Asp Val Ala Leu Tyr Tyr Cys His Gln
                85                  90                  95

Tyr His Ser Thr Pro Leu Ser
            100

<210> SEQ ID NO 315
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 315

Arg Ser Gly Tyr Ser Ser Pro Gly Ser Pro Gly Thr Pro Gly Ser Arg
1               5                   10                  15

Ser Arg Thr

<210> SEQ ID NO 316
<211> LENGTH: 19
<212> TYPE: PRT
<213> ORGANISM: Artificial Sequence
<220> FEATURE:
<223> OTHER INFORMATION: synthetic construct

<400> SEQUENCE: 316

Arg Ser Gly Tyr Ser Ser Pro Gly Ser Pro Gly Thr Pro Gly Ser Arg
1               5                   10                  15

Ser Arg Thr

<210> SEQ ID NO 317
<211> LENGTH: 18
<212> TYPE: PRT
```

```
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 317

Gly Thr Pro Gly Ser Arg Ser Arg Thr Pro Ser Leu Pro Thr Pro Pro
1               5                   10                  15

Thr Arg

<210> SEQ ID NO 318
<211> LENGTH: 18
<212> TYPE: PRT
<213> ORGANISM: Artificial Sequence
<220> FEATURE:
<223> OTHER INFORMATION: synthetic construct

<400> SEQUENCE: 318

Gly Thr Pro Gly Ser Arg Ser Arg Thr Pro Ser Leu Pro Thr Pro Pro
1               5                   10                  15

Thr Arg

<210> SEQ ID NO 319
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 319

Pro Gly Ser Pro Gly Thr Pro Gly Ser Arg Ser Arg Thr Pro Ser Leu
1               5                   10                  15

Pro Thr

<210> SEQ ID NO 320
<211> LENGTH: 18
<212> TYPE: PRT
<213> ORGANISM: Artificial Sequence
<220> FEATURE:
<223> OTHER INFORMATION: synthetic construct

<400> SEQUENCE: 320

Pro Gly Ser Pro Gly Thr Pro Gly Ser Arg Ser Arg Thr Pro Ser Leu
1               5                   10                  15

Pro Thr

<210> SEQ ID NO 321
<211> LENGTH: 68
<212> TYPE: PRT
<213> ORGANISM: Artificial Sequence
<220> FEATURE:
<223> OTHER INFORMATION: synthetic construct

<400> SEQUENCE: 321

Gly Glu Pro Pro Lys Ser Gly Asp Arg Ser Gly Tyr Ser Ser Pro Gly
```

```
                1               5                   10                  15
Ser Pro Gly Thr Pro Gly Ser Arg Ser Arg Thr Pro Ser Leu Pro Thr
            20                  25                  30

Pro Pro Thr Arg Glu Pro Lys Lys Val Ala Val Arg Thr Pro Pro
            35                  40                  45

Lys Ser Pro Ser Ser Ala Lys Ser Arg Leu Gln Thr Ala Pro Val Pro
    50                  55                  60

Met Pro Asp Leu
65
```

<210> SEQ ID NO 322
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 322

```
Glu Pro Gly Ser Glu Thr Ser Asp Ala Lys Ser Thr Pro Thr Ala Glu
1               5                   10                  15

Asp Val Thr
```

<210> SEQ ID NO 323
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 323

```
Pro Gly Ser Glu Thr Ser Asp Ala Lys Ser Thr Pro Thr Ala Glu Asp
1               5                   10                  15

Val Thr Ala Pro
            20
```

<210> SEQ ID NO 324
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 324

Ser Glu Thr Ser Asp Ala Lys Ser Thr Pro Thr Ala Glu Asp Val Thr
1               5                   10                  15

Ala Pro

<210> SEQ ID NO 325
<211> LENGTH: 62
<212> TYPE: PRT
<213> ORGANISM: Artificial Sequence
<220> FEATURE:
<223> OTHER INFORMATION: synthetic construct

<400> SEQUENCE: 325

Gly Leu Lys Glu Ser Pro Leu Gln Thr Pro Thr Glu Asp Gly Ser Glu
1               5                   10                  15

Glu Pro Gly Ser Glu Thr Ser Asp Ala Lys Ser Thr Pro Thr Ala Glu
                20                  25                  30

Asp Val Thr Ala Pro Leu Val Asp Glu Gly Ala Pro Gly Lys Gln Ala
            35                  40                  45

Ala Ala Gln Pro His Thr Glu Ile Pro Glu Gly Thr Thr Ala
        50                  55                  60

<210> SEQ ID NO 326
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 326

Arg His Leu Ser Asn Val Ser Ser Thr Gly Ser Ile Asp Met Val Asp
1               5                   10                  15

Ser Pro Gln Leu Ala Thr Leu Ala
                20

<210> SEQ ID NO 327
<211> LENGTH: 53
<212> TYPE: PRT
<213> ORGANISM: Artificial Sequence
<220> FEATURE:
<223> OTHER INFORMATION: synthetic construct

<400> SEQUENCE: 327

Gly Ala Glu Ile Val Tyr Lys Ser Pro Val Val Ser Gly Asp Thr Ser
1               5                   10                  15

Pro Arg His Leu Ser Asn Val Ser Ser Thr Gly Ser Ile Asp Met Val
                20                  25                  30

Asp Ser Pro Gln Leu Ala Thr Leu Ala Asp Glu Val Ser Ala Ser Leu
            35                  40                  45

Ala Lys Gln Gly Leu
        50

<210> SEQ ID NO 328
<211> LENGTH: 25
<212> TYPE: PRT
<213> ORGANISM: Artificial Sequence
<220> FEATURE:

<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 328

Arg Glu Pro Lys Lys Val Ala Val Val Arg Thr Pro Pro Lys Ser Pro
1               5                   10                  15

Ser Ser Ala Lys Ser Arg Leu Gln Thr
            20                  25

<210> SEQ ID NO 329
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 329

Val Val Arg Thr Pro Pro Lys Ser Pro Ser Ser Ala Lys Ser Arg Leu
1               5                   10                  15

Gln Thr

<210> SEQ ID NO 330
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 330

Lys Val Ala Val Val Arg Thr Pro Pro Lys Ser Pro Ser Ser Ala Lys
1               5                   10                  15

Ser Arg Leu Gln Thr
            20

<210> SEQ ID NO 331
<211> LENGTH: 71
<212> TYPE: PRT
<213> ORGANISM: Artificial Sequence
<220> FEATURE:
<223> OTHER INFORMATION: synthetic construct

<400> SEQUENCE: 331

His Val Pro Gly Gly Gly Ser Val Gln Ile Val Tyr Lys Pro Val Asp
1               5                   10                  15

Leu Ser Lys Val Thr Ser Lys Cys Gly Ser Leu Gly Asn Ile His His
            20                  25                  30

Lys Pro Gly Gly Gly Gln Val Glu Val Lys Ser Glu Lys Leu Asp Phe
        35                  40                  45

Lys Asp Arg Val Gln Ser Lys Ile Gly Ser Leu Asp Asn Ile Thr His
 50                  55                  60

Val Pro Gly Gly Gly Asn Lys
 65                  70

<210> SEQ ID NO 332
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (6)..(6)
<223> OTHER INFORMATION: PHOSPHORYLATION

<400> SEQUENCE: 332

Lys Ser Lys Ile Gly Ser Thr Glu Asn Leu Lys His Gln Pro Gly Gly
 1               5                  10                  15

<210> SEQ ID NO 333
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 333

Lys Lys Val Ala Val Val Arg Thr Pro Pro Lys Ser Pro Ser Ser Ala
 1               5                  10                  15

Lys Ser

<210> SEQ ID NO 334
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 334

Glu Pro Pro Lys Ser Gly Asp Arg Ser Gly Tyr Ser Ser Pro Gly Ser
 1               5                  10                  15

Pro Gly Thr Pro Gly Ser Arg Ser Arg Thr
                 20                  25

<210> SEQ ID NO 335
<211> LENGTH: 18
<212> TYPE: PRT
<213> ORGANISM: Artificial Sequence
<220> FEATURE:
<223> OTHER INFORMATION: synthetic construct
<220> FEATURE:

```
<221> NAME/KEY: Phosphorylation
<222> LOCATION: (11)..(12)
<223> OTHER INFORMATION: Phosphorylation of serine at amino acid 11
<220> FEATURE:
<221> NAME/KEY: MOD_RES
<222> LOCATION: (11)..(11)
<223> OTHER INFORMATION: PHOSPHORYLATION

<400> SEQUENCE: 335

Pro Pro Lys Ser Gly Asp Arg Ser Gly Tyr Ser Ser Pro Gly Ser Pro
1               5                   10                  15

Gly Thr

<210> SEQ ID NO 336
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 336

Pro Pro Lys Ser Gly Asp Arg Ser Gly Tyr Ser Ser Pro Gly Ser Pro
1               5                   10                  15

Gly Thr Pro

<210> SEQ ID NO 337
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 337

Pro Pro Lys Ser Gly Asp Arg Ser Gly Tyr Ser Ser Pro Gly Ser Pro
1               5                   10                  15

Gly Thr Pro Gly Ser Arg
            20

<210> SEQ ID NO 338
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 338
```

-continued

Pro Pro Lys Ser Gly Asp Arg Ser Gly Tyr Ser Ser Pro Gly Ser Pro
1               5                   10                  15

Gly Thr Pro Gly Ser Arg Ser Arg Thr
            20                  25

<210> SEQ ID NO 339
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 339

Pro Lys Ser Gly Asp Arg Ser Gly Tyr Ser Ser Pro Gly Ser Pro Gly
1               5                   10                  15

Thr Pro

<210> SEQ ID NO 340
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 340

Pro Lys Ser Gly Asp Arg Ser Gly Tyr Ser Ser Pro Gly Ser Pro Gly
1               5                   10                  15

Thr Pro Gly Ser Arg
            20

<210> SEQ ID NO 341
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 341

Pro Lys Ser Gly Asp Arg Ser Gly Tyr Ser Ser Pro Gly Ser Pro Gly
1               5                   10                  15

Thr Pro Gly Ser Arg Ser Arg Thr
            20

<210> SEQ ID NO 342
<211> LENGTH: 20
<212> TYPE: PRT
<213> ORGANISM: Artificial Sequence
<220> FEATURE:
<223> OTHER INFORMATION: synthetic construct

<400> SEQUENCE: 342

Lys Ser Gly Asp Arg Ser Gly Tyr Ser Ser Pro Gly Ser Pro Gly Thr
1               5                   10                  15

Pro Gly Ser Arg
            20

<210> SEQ ID NO 343
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)

<400> SEQUENCE: 343

Gly Asp Arg Ser Gly Tyr Ser Ser Pro Gly Ser Pro Gly Thr Pro Gly
1               5                   10                  15

Ser Arg

<210> SEQ ID NO 344
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 344

Gly Asp Arg Ser Gly Tyr Ser Ser Pro Gly Ser Pro Gly Thr Pro Gly
1               5                   10                  15

Ser Arg Ser Arg Thr
            20

<210> SEQ ID NO 345
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 345

Gly Asp Arg Ser Gly Tyr Ser Ser Pro Gly Ser Pro Gly Thr Pro Gly
1               5                   10                  15

Ser Arg Ser Arg Thr Pro Ser Leu
            20

<210> SEQ ID NO 346

```
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 346

Gly Asp Arg Ser Gly Tyr Ser Ser Pro Gly Ser Pro Gly Thr Pro Gly
1               5                   10                  15

Ser Arg Ser Arg Thr Pro Ser Leu Pro Thr
            20                  25

<210> SEQ ID NO 347
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 347

Ser Gly Tyr Ser Ser Pro Gly Ser Pro Gly Thr Pro Gly Ser Arg Ser
1               5                   10                  15

Arg Thr

<210> SEQ ID NO 348
<211> LENGTH: 21
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 348

Ser Gly Tyr Ser Ser Pro Gly Ser Pro Gly Thr Pro Gly Ser Arg Ser
1               5                   10                  15

Arg Thr Pro Ser Leu
            20

<210> SEQ ID NO 349
<211> LENGTH: 23
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (16)..(16)
```

<223> OTHER INFORMATION: PHOSPHORYLATION

<400> SEQUENCE: 349

Ser Gly Tyr Ser Ser Pro Gly Ser Pro Gly Thr Pro Gly Ser Arg Ser
1               5                   10                  15

Arg Thr Pro Ser Leu Pro Thr
            20

<210> SEQ ID NO 350
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 350

Ser Gly Tyr Ser Ser Pro Gly Ser Pro Gly Thr Pro Gly Ser Arg Ser
1               5                   10                  15

Arg Thr Pro Ser Leu Pro Thr Pro Pro
            20                  25

<210> SEQ ID NO 351
<211> LENGTH: 20
<212> TYPE: PRT
<213> ORGANISM: Artificial Sequence
<220> FEATURE:
<223> OTHER INFORMATION: synthetic construct

<400> SEQUENCE: 351

Ser Gly Tyr Ser Ser Pro Gly Ser Pro Gly Thr Pro Gly Ser Arg Ser
1               5                   10                  15

Arg Thr Pro Ser
            20

<210> SEQ ID NO 352
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 352

Ser Ser Pro Gly Ser Pro Gly Thr Pro Gly Ser Arg Ser Arg Thr Pro
1               5                   10                  15

Ser Leu

<210> SEQ ID NO 353
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)

```
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 353

Ser Ser Pro Gly Ser Pro Gly Thr Pro Gly Ser Arg Ser Arg Thr Pro
1               5                   10                  15

Ser Leu Pro Thr
            20

<210> SEQ ID NO 354
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 354

Ser Ser Pro Gly Ser Pro Gly Thr Pro Gly Ser Arg Ser Arg Thr Pro
1               5                   10                  15

Ser Leu Pro Thr Pro Pro
            20

<210> SEQ ID NO 355
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 355

Ser Ser Pro Gly Ser Pro Gly Thr Pro Gly Ser Arg Ser Arg Thr Pro
1               5                   10                  15

Ser Leu Pro Thr Pro Pro Thr Arg
            20

<210> SEQ ID NO 356
<211> LENGTH: 20
<212> TYPE: PRT
<213> ORGANISM: Artificial Sequence
<220> FEATURE:
<223> OTHER INFORMATION: synthetic construct

<400> SEQUENCE: 356

Ser Ser Pro Gly Ser Pro Gly Thr Pro Gly Ser Arg Ser Arg Thr Pro
1               5                   10                  15

Ser Leu Pro Thr
            20
```

```
<210> SEQ ID NO 357
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 357

Pro Gly Ser Pro Gly Thr Pro Gly Ser Arg Ser Arg Thr Pro Ser Leu
1               5                   10                  15

Pro Thr Pro Pro
            20

<210> SEQ ID NO 358
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (15)..(15)
<223> OTHER INFORMATION: PHOSPHORYLATION

<400> SEQUENCE: 358

Pro Gly Ser Pro Gly Thr Pro Gly Ser Arg Ser Arg Thr Pro Ser Leu
1               5                   10                  15

Pro Thr Pro Pro Thr Arg
            20

<210> SEQ ID NO 359
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 359

Pro Gly Ser Pro Gly Thr Pro Gly Ser Arg Ser Arg Thr Pro Ser Leu
1               5                   10                  15

Pro Thr Pro Pro Thr Arg Glu Pro Lys
            20                  25

<210> SEQ ID NO 360
<211> LENGTH: 18
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (11)..(11)
<223> OTHER INFORMATION: PHOSPHORYLATION

<400> SEQUENCE: 360

Ser Pro Arg His Leu Ser Asn Val Ser Thr Gly Ser Ile Asp Met
1               5                   10                  15

Val Asp

<210> SEQ ID NO 361
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 361

Ser Pro Arg His Leu Ser Asn Val Ser Thr Gly Ser Ile Asp Met
1               5                   10                  15

Val Asp Ser Pro Gln Leu Ala Thr Leu Ala
            20                  25

<210> SEQ ID NO 362
<211> LENGTH: 19
<212> TYPE: PRT
<213> ORGANISM: Artificial Sequence
<220> FEATURE:
<223> OTHER INFORMATION: synthetic construct

<400> SEQUENCE: 362

Pro Arg His Leu Ser Asn Val Ser Ser Thr Gly Ser Ile Asp Met Val
1               5                   10                  15

Asp Ser Pro

<210> SEQ ID NO 363
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 363

Arg His Leu Ser Asn Val Ser Ser Thr Gly Ser Ile Asp Met Val Asp
1               5                   10                  15

Ser Pro

<210> SEQ ID NO 364
<211> LENGTH: 20
<212> TYPE: PRT
<213> ORGANISM: Artificial Sequence
<220> FEATURE:
<223> OTHER INFORMATION: synthetic construct

<400> SEQUENCE: 364
```

Ser Asn Val Ser Ser Thr Gly Ser Ile Asp Met Val Asp Ser Pro Gln
1               5                   10                  15

Leu Ala Thr Leu
            20

<210> SEQ ID NO 365
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 365

Ser Ser Thr Gly Ser Ile Asp Met Val Asp Ser Pro Gln Leu Ala Thr
1               5                   10                  15

Leu Ala

<210> SEQ ID NO 366
<211> LENGTH: 23
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 366

Ser Ser Thr Gly Ser Ile Asp Met Val Asp Ser Pro Gln Leu Ala Thr
1               5                   10                  15

Leu Ala Asp Glu Val Ser Ala
            20

<210> SEQ ID NO 367
<211> LENGTH: 68
<212> TYPE: PRT
<213> ORGANISM: Artificial Sequence
<220> FEATURE:
<223> OTHER INFORMATION: synthetic construct

<400> SEQUENCE: 367

Gly Glu Pro Pro Lys Ser Gly Asp Arg Ser Gly Tyr Ser Ser Pro Gly
1               5                   10                  15

Ser Pro Gly Thr Pro Gly Ser Arg Ser Arg Thr Pro Ser Leu Pro Thr
            20                  25                  30

Pro Pro Thr Arg Glu Pro Lys Lys Val Ala Val Val Arg Thr Pro Pro
                35                  40                  45

Lys Ser Pro Ser Ser Ala Lys Ser Arg Leu Gln Thr Ala Pro Val Pro
    50                  55                  60

Met Pro Asp Leu
65

<210> SEQ ID NO 368
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 368

Arg Glu Pro Lys Lys Val Ala Val Val Arg Thr Pro Pro Lys Ser Pro
1               5                   10                  15

Ser Ser

<210> SEQ ID NO 369
<211> LENGTH: 22
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (15)..(15)
<223> OTHER INFORMATION: PHOSPHORYLATION

<400> SEQUENCE: 369

Arg Glu Pro Lys Lys Val Ala Val Val Arg Thr Pro Pro Lys Ser Pro
1               5                   10                  15

Ser Ser Ala Lys Ser Arg
            20

<210> SEQ ID NO 370
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 370

Arg Glu Pro Lys Lys Val Ala Val Val Arg Thr Pro Pro Lys Ser Pro
1               5                   10                  15

Ser Ser Ala Lys Ser Arg Leu Gln
            20

<210> SEQ ID NO 371
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 371

Lys Val Ala Val Val Arg Thr Pro Pro Lys Ser Pro Ser Ser Ala Lys
1               5                   10                  15

Ser Arg

<210> SEQ ID NO 372

```
<211> LENGTH: 20
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (13)..(13)
<223> OTHER INFORMATION: PHOSPHORYLATION

<400> SEQUENCE: 372

Lys Val Ala Val Val Arg Thr Pro Pro Lys Ser Pro Ser Ser Ala Lys
 1               5                  10                  15

Ser Arg Leu Gln
            20

<210> SEQ ID NO 373
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 373

Ala Val Val Arg Thr Pro Pro Lys Ser Pro Ser Ser Ala Lys Ser Arg
 1               5                  10                  15

Leu Gln

<210> SEQ ID NO 374
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION

<400> SEQUENCE: 374

Ala Val Val Arg Thr Pro Pro Lys Ser Pro Ser Ser Ala Lys Ser Arg
 1               5                  10                  15

Leu Gln Thr

<210> SEQ ID NO 375
<211> LENGTH: 20
<212> TYPE: PRT
<213> ORGANISM: Artificial Sequence
<220> FEATURE:
<223> OTHER INFORMATION: synthetic construct

<400> SEQUENCE: 375

His Val Pro Gly Gly Gly Ser Val Gln Ile Val Tyr Lys Pro Val Asp
 1               5                  10                  15

Leu Ser Lys Val
            20
```

```
<210> SEQ ID NO 376
<211> LENGTH: 20
<212> TYPE: PRT
<213> ORGANISM: Artificial Sequence
<220> FEATURE:
<223> OTHER INFORMATION: synthetic construct

<400> SEQUENCE: 376

Val Tyr Lys Pro Val Asp Leu Ser Lys Val Thr Ser Lys Cys Gly Ser
1               5                   10                  15

Leu Gly Asn Ile
            20

<210> SEQ ID NO 377
<211> LENGTH: 20
<212> TYPE: PRT
<213> ORGANISM: Artificial Sequence
<220> FEATURE:
<223> OTHER INFORMATION: synthetic construct

<400> SEQUENCE: 377

Thr Ser Lys Cys Gly Ser Leu Gly Asn Ile His His Lys Pro Gly Gly
1               5                   10                  15

Gly Gln Val Glu
            20

<210> SEQ ID NO 378
<211> LENGTH: 20
<212> TYPE: PRT
<213> ORGANISM: Artificial Sequence
<220> FEATURE:
<223> OTHER INFORMATION: synthetic construct

<400> SEQUENCE: 378

His His Lys Pro Gly Gly Gly Gln Val Glu Val Lys Ser Glu Lys Leu
1               5                   10                  15

Asp Phe Lys Asp
            20

<210> SEQ ID NO 379
<211> LENGTH: 20
<212> TYPE: PRT
<213> ORGANISM: Artificial Sequence
<220> FEATURE:
<223> OTHER INFORMATION: synthetic construct

<400> SEQUENCE: 379

Val Lys Ser Glu Lys Leu Asp Phe Lys Asp Arg Val Gln Ser Lys Ile
1               5                   10                  15

Gly Ser Leu Asp
            20

<210> SEQ ID NO 380
<211> LENGTH: 21
<212> TYPE: PRT
<213> ORGANISM: Artificial Sequence
<220> FEATURE:
<223> OTHER INFORMATION: synthetic construct

<400> SEQUENCE: 380

Arg Val Gln Ser Lys Ile Gly Ser Leu Asp Asn Ile Thr His Val Pro
1               5                   10                  15

Gly Gly Gly Asn Lys
```

20

<210> SEQ ID NO 381
<211> LENGTH: 20
<212> TYPE: PRT
<213> ORGANISM: Artificial Sequence
<220> FEATURE:
<223> OTHER INFORMATION: synthetic construct

<400> SEQUENCE: 381

Gly Leu Lys Glu Ser Pro Leu Gln Thr Pro Thr Glu Asp Gly Ser Glu
1               5                   10                  15

Glu Pro Gly Ser
            20

<210> SEQ ID NO 382
<211> LENGTH: 20
<212> TYPE: PRT
<213> ORGANISM: Artificial Sequence
<220> FEATURE:
<223> OTHER INFORMATION: synthetic construct

<400> SEQUENCE: 382

Thr Glu Asp Gly Ser Glu Glu Pro Gly Ser Glu Thr Ser Asp Ala Lys
1               5                   10                  15

Ser Thr Pro Thr
            20

<210> SEQ ID NO 383
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 383

Glu Pro Gly Ser Glu Thr Ser Asp Ala Lys Ser Thr Pro Thr Ala Glu
1               5                   10                  15

Asp Val

<210> SEQ ID NO 384
<211> LENGTH: 20
<212> TYPE: PRT
<213> ORGANISM: Artificial Sequence
<220> FEATURE:
<223> OTHER INFORMATION: synthetic construct

<400> SEQUENCE: 384

Glu Thr Ser Asp Ala Lys Ser Thr Pro Thr Ala Glu Asp Val Thr Ala
1               5                   10                  15

Pro Leu Val Asp
            20

<210> SEQ ID NO 385
<211> LENGTH: 20
<212> TYPE: PRT
<213> ORGANISM: Artificial Sequence
<220> FEATURE:
<223> OTHER INFORMATION: synthetic construct

<400> SEQUENCE: 385

```
Ala Glu Asp Val Thr Ala Pro Leu Val Asp Glu Gly Ala Pro Gly Lys
1               5                   10                  15

Gln Ala Ala Ala
            20

<210> SEQ ID NO 386
<211> LENGTH: 22
<212> TYPE: PRT
<213> ORGANISM: Artificial Sequence
<220> FEATURE:
<223> OTHER INFORMATION: synthetic construct

<400> SEQUENCE: 386

Glu Gly Ala Pro Gly Lys Gln Ala Ala Ala Gln Pro His Thr Glu Ile
1               5                   10                  15

Pro Glu Gly Thr Thr Ala
            20

<210> SEQ ID NO 387
<211> LENGTH: 20
<212> TYPE: PRT
<213> ORGANISM: Artificial Sequence
<220> FEATURE:
<223> OTHER INFORMATION: synthetic construct

<400> SEQUENCE: 387

Gly Asp Arg Ser Gly Tyr Ser Ser Pro Gly Ser Pro Gly Thr Pro Gly
1               5                   10                  15

Ser Arg Ser Arg
            20

<210> SEQ ID NO 388
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 388

Ala Pro Pro Lys Ser Gly Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 389
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 389
```

Glu Ala Pro Lys Ser Gly Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 390
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 390

Glu Pro Ala Lys Ser Gly Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 391
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 391

Glu Pro Pro Ala Ser Gly Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 392
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 392

Glu Pro Pro Lys Ala Gly Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 393
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 393

Glu Pro Pro Lys Ser Ala Asp Arg Ser Gly Tyr Ser Ser Pro Gly Ser
1               5                   10                  15

Pro Gly Thr Pro Gly Ser Arg Ser Arg Thr
            20                  25

<210> SEQ ID NO 394
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 394

Glu Pro Pro Lys Ser Gly Ala Arg Ser Gly Tyr Ser Ser Pro Gly Ser
1               5                   10                  15

Pro Gly Thr Pro Gly Ser Arg Ser Arg Thr
            20                  25

<210> SEQ ID NO 395
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 395

Glu Pro Pro Lys Ser Gly Asp Ala Ser Gly Tyr Ser Ser Pro Gly Ser
1               5                   10                  15

Pro Gly Thr Pro Gly Ser Arg Ser Arg Thr
            20                  25

<210> SEQ ID NO 396
<211> LENGTH: 26
<212> TYPE: PRT
<213> ORGANISM: Artificial Sequence
<220> FEATURE:
<223> OTHER INFORMATION: synthetic construct

```
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 396

Glu Pro Pro Lys Ser Gly Asp Arg Ala Gly Tyr Ser Ser Pro Gly Ser
1               5                   10                  15

Pro Gly Thr Pro Gly Ser Arg Ser Arg Thr
            20                  25

<210> SEQ ID NO 397
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 397

Glu Pro Pro Lys Ser Gly Asp Arg Ser Ala Tyr Ser Ser Pro Gly Ser
1               5                   10                  15

Pro Gly Thr Pro Gly Ser Arg Ser Arg Thr
            20                  25

<210> SEQ ID NO 398
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 398

Glu Pro Pro Lys Ser Gly Asp Arg Ser Gly Ala Ser Ser Pro Gly Ser
1               5                   10                  15

Pro Gly Thr Pro Gly Ser Arg Ser Arg Thr
            20                  25

<210> SEQ ID NO 399
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
```

<223> OTHER INFORMATION: PHOSPHORYLATION

<400> SEQUENCE: 399

Glu Pro Pro Lys Ser Gly Asp Arg Ser Gly Tyr Ala Ser Pro Gly Ser
1               5                   10                  15

Pro Gly Thr Pro Gly Ser Arg Ser Arg Thr
            20                  25

<210> SEQ ID NO 400
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 400

Glu Pro Pro Lys Ser Gly Asp Arg Ser Gly Tyr Ser Ala Pro Gly Ser
1               5                   10                  15

Pro Gly Thr Pro Gly Ser Arg Ser Arg Thr
            20                  25

<210> SEQ ID NO 401
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 401

Glu Pro Pro Lys Ser Gly Asp Arg Ser Gly Tyr Ser Ser Ala Gly Ser
1               5                   10                  15

Pro Gly Thr Pro Gly Ser Arg Ser Arg Thr
            20                  25

<210> SEQ ID NO 402
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 402

Glu Pro Pro Lys Ser Gly Asp Arg Ser Gly Tyr Ser Ser Pro Ala Ser
1               5                   10                  15

Pro Gly Thr Pro Gly Ser Arg Ser Arg Thr
            20                  25

<210> SEQ ID NO 403
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (19)..(19)
<223> OTHER INFORMATION: PHOSPHORYLATION

<400> SEQUENCE: 403

Glu Pro Pro Lys Ser Gly Asp Arg Ser Gly Tyr Ser Ser Pro Gly Ala
1               5                   10                  15

Pro Gly Thr Pro Gly Ser Arg Ser Arg Thr
            20                  25

<210> SEQ ID NO 404
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 404

Glu Pro Pro Lys Ser Gly Asp Arg Ser Gly Tyr Ser Ser Pro Gly Ser
1               5                   10                  15

Ala Gly Thr Pro Gly Ser Arg Ser Arg Thr
            20                  25

<210> SEQ ID NO 405
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 405

Glu Pro Pro Lys Ser Gly Asp Arg Ser Gly Tyr Ser Ser Pro Gly Ser
1               5                   10                  15

Pro Ala Thr Pro Gly Ser Arg Ser Arg Thr
            20                  25

<210> SEQ ID NO 406
<211> LENGTH: 26
<212> TYPE: PRT
<213> ORGANISM: Artificial Sequence
<220> FEATURE:
<223> OTHER INFORMATION: synthetic construct
<220> FEATURE:

```
<221> NAME/KEY: MOD_RES
<222> LOCATION: (16)..(16)
<223> OTHER INFORMATION: PHOSPHORYLATION

<400> SEQUENCE: 406

Glu Pro Pro Lys Ser Gly Asp Arg Ser Gly Tyr Ser Ser Pro Gly Ser
1               5                   10                  15

Pro Gly Ala Pro Gly Ser Arg Ser Arg Thr
            20                  25

<210> SEQ ID NO 407
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 407

Glu Pro Pro Lys Ser Gly Asp Arg Ser Gly Tyr Ser Ser Pro Gly Ser
1               5                   10                  15

Pro Gly Thr Ala Gly Ser Arg Ser Arg Thr
            20                  25

<210> SEQ ID NO 408
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 408

Glu Pro Pro Lys Ser Gly Asp Arg Ser Gly Tyr Ser Ser Pro Gly Ser
1               5                   10                  15

Pro Gly Thr Pro Ala Ser Arg Ser Arg Thr
            20                  25

<210> SEQ ID NO 409
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 409

Glu Pro Pro Lys Ser Gly Asp Arg Ser Gly Tyr Ser Ser Pro Gly Ser
```

```
1               5                   10                  15
Pro Gly Thr Pro Gly Ala Arg Ser Arg Thr
            20                  25

<210> SEQ ID NO 410
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 410

Glu Pro Pro Lys Ser Gly Asp Arg Ser Gly Tyr Ser Ser Pro Gly Ser
1               5                   10                  15

Pro Gly Thr Pro Gly Ser Ala Ser Arg Thr
            20                  25

<210> SEQ ID NO 411
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 411

Glu Pro Pro Lys Ser Gly Asp Arg Ser Gly Tyr Ser Ser Pro Gly Ser
1               5                   10                  15

Pro Gly Thr Pro Gly Ser Arg Ala Arg Thr
            20                  25

<210> SEQ ID NO 412
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 412

Glu Pro Pro Lys Ser Gly Asp Arg Ser Gly Tyr Ser Ser Pro Gly Ser
1               5                   10                  15

Pro Gly Thr Pro Gly Ser Arg Ser Ala Thr
            20                  25

<210> SEQ ID NO 413
```

```
<211> LENGTH: 26
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 413

Glu Pro Pro Lys Ser Gly Asp Arg Ser Gly Tyr Ser Ser Pro Gly Ser
1               5                   10                  15
Pro Gly Thr Pro Gly Ser Arg Ser Arg Ala
            20                  25

<210> SEQ ID NO 414
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 414

Ala His Leu Ser Asn Val Ser Ser Thr Gly Ser Ile Asp Met Val Asp
1               5                   10                  15
Ser Pro Gln Leu Ala Thr Leu Ala
            20

<210> SEQ ID NO 415
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 415

Arg Ala Leu Ser Asn Val Ser Ser Thr Gly Ser Ile Asp Met Val Asp
1               5                   10                  15
Ser Pro Gln Leu Ala Thr Leu Ala
            20

<210> SEQ ID NO 416
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
```

```
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 416

Arg His Ala Ser Asn Val Ser Ser Thr Gly Ser Ile Asp Met Val Asp
1               5                   10                  15

Ser Pro Gln Leu Ala Thr Leu Ala
            20

<210> SEQ ID NO 417
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 417

Arg His Leu Ala Asn Val Ser Ser Thr Gly Ser Ile Asp Met Val Asp
1               5                   10                  15

Ser Pro Gln Leu Ala Thr Leu Ala
            20

<210> SEQ ID NO 418
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 418

Arg His Leu Ser Ala Val Ser Ser Thr Gly Ser Ile Asp Met Val Asp
1               5                   10                  15

Ser Pro Gln Leu Ala Thr Leu Ala
            20

<210> SEQ ID NO 419
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION
```

<400> SEQUENCE: 419

Arg His Leu Ser Asn Ala Ser Ser Thr Gly Ser Ile Asp Met Val Asp
1               5                   10                  15

Ser Pro Gln Leu Ala Thr Leu Ala
            20

<210> SEQ ID NO 420
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 420

Arg His Leu Ser Asn Val Ala Ser Thr Gly Ser Ile Asp Met Val Asp
1               5                   10                  15

Ser Pro Gln Leu Ala Thr Leu Ala
            20

<210> SEQ ID NO 421
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 421

Arg His Leu Ser Asn Val Ser Ala Thr Gly Ser Ile Asp Met Val Asp
1               5                   10                  15

Ser Pro Gln Leu Ala Thr Leu Ala
            20

<210> SEQ ID NO 422
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 422

Arg His Leu Ser Asn Val Ser Ser Ala Gly Ser Ile Asp Met Val Asp
1               5                   10                  15

Ser Pro Gln Leu Ala Thr Leu Ala
            20

```
<210> SEQ ID NO 423
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 423

Arg His Leu Ser Asn Val Ser Ser Thr Ala Ser Ile Asp Met Val Asp
1               5                   10                  15

Ser Pro Gln Leu Ala Thr Leu Ala
            20

<210> SEQ ID NO 424
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (17)..(17)
<223> OTHER INFORMATION: PHOSPHORYLATION

<400> SEQUENCE: 424

Arg His Leu Ser Asn Val Ser Ser Thr Gly Ala Ile Asp Met Val Asp
1               5                   10                  15

Ser Pro Gln Leu Ala Thr Leu Ala
            20

<210> SEQ ID NO 425
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 425

Arg His Leu Ser Asn Val Ser Ser Thr Gly Ser Ala Asp Met Val Asp
1               5                   10                  15

Ser Pro Gln Leu Ala Thr Leu Ala
            20

<210> SEQ ID NO 426
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
```

```
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 426

Arg His Leu Ser Asn Val Ser Ser Thr Gly Ser Ile Ala Met Val Asp
1               5                   10                  15

Ser Pro Gln Leu Ala Thr Leu Ala
            20

<210> SEQ ID NO 427
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 427

Arg His Leu Ser Asn Val Ser Ser Thr Gly Ser Ile Asp Ala Val Asp
1               5                   10                  15

Ser Pro Gln Leu Ala Thr Leu Ala
            20

<210> SEQ ID NO 428
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 428

Arg His Leu Ser Asn Val Ser Ser Thr Gly Ser Ile Asp Met Ala Asp
1               5                   10                  15

Ser Pro Gln Leu Ala Thr Leu Ala
            20

<210> SEQ ID NO 429
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 429
```

Arg His Leu Ser Asn Val Ser Ser Thr Gly Ser Ile Asp Met Val Ala
1               5                   10                  15

Ser Pro Gln Leu Ala Thr Leu Ala
            20

<210> SEQ ID NO 430
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 430

Arg His Leu Ser Asn Val Ser Ser Thr Gly Ser Ile Asp Met Val Asp
1               5                   10                  15

Ala Pro Gln Leu Ala Thr Leu Ala
            20

<210> SEQ ID NO 431
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 431

Arg His Leu Ser Asn Val Ser Ser Thr Gly Ser Ile Asp Met Val Asp
1               5                   10                  15

Ser Ala Gln Leu Ala Thr Leu Ala
            20

<210> SEQ ID NO 432
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 432

Arg His Leu Ser Asn Val Ser Ser Thr Gly Ser Ile Asp Met Val Asp
1               5                   10                  15

Ser Pro Ala Leu Ala Thr Leu Ala
            20

<210> SEQ ID NO 433
<211> LENGTH: 24
<212> TYPE: PRT

<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 433

Arg His Leu Ser Asn Val Ser Ser Thr Gly Ser Ile Asp Met Val Asp
1               5                   10                  15

Ser Pro Gln Ala Ala Thr Leu Ala
            20

<210> SEQ ID NO 434
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 434

Arg His Leu Ser Asn Val Ser Ser Thr Gly Ser Ile Asp Met Val Asp
1               5                   10                  15

Ser Pro Gln Leu Ala Ala Leu Ala
            20

<210> SEQ ID NO 435
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 435

Arg His Leu Ser Asn Val Ser Ser Thr Gly Ser Ile Asp Met Val Asp
1               5                   10                  15

Ser Pro Gln Leu Ala Thr Ala Ala
            20

<210> SEQ ID NO 436
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

```
<220> FEATURE:
<221> NAME/KEY: MOD_RES
<222> LOCATION: (18)..(18)
<223> OTHER INFORMATION: PHOSPHORYLATION

<400> SEQUENCE: 436

Arg Ala Pro Lys Lys Val Ala Val Val Arg Thr Pro Pro Lys Ser Pro
1               5                   10                  15

Ser Ser Ala Lys Ser Arg Leu Gln Thr
            20                  25

<210> SEQ ID NO 437
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 437

Arg Glu Ala Lys Lys Val Ala Val Val Arg Thr Pro Pro Lys Ser Pro
1               5                   10                  15

Ser Ser Ala Lys Ser Arg Leu Gln Thr
            20                  25

<210> SEQ ID NO 438
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 438

Arg Glu Pro Ala Lys Val Ala Val Val Arg Thr Pro Pro Lys Ser Pro
1               5                   10                  15

Ser Ser Ala Lys Ser Arg Leu Gln Thr
            20                  25

<210> SEQ ID NO 439
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 439
```

```
Arg Glu Pro Lys Ala Val Ala Val Val Arg Thr Pro Pro Lys Ser Pro
1               5                   10                  15

Pro Ser Ala Lys Ser Arg Leu Gln Thr
            20                  25

<210> SEQ ID NO 440
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 440

Arg Glu Pro Lys Lys Ala Ala Val Val Arg Thr Pro Pro Lys Ser Pro
1               5                   10                  15

Ser Ser Ala Lys Ser Arg Leu Gln Thr
            20                  25

<210> SEQ ID NO 441
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 441

Arg Glu Pro Lys Lys Val Ala Ala Val Arg Thr Pro Pro Lys Ser Pro
1               5                   10                  15

Ser Ser Ala Lys Ser Arg Leu Gln Thr
            20                  25

<210> SEQ ID NO 442
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 442

Arg Glu Pro Lys Lys Val Ala Val Ala Arg Thr Pro Pro Lys Ser Pro
1               5                   10                  15

Ser Ser Ala Lys Ser Arg Leu Gln Thr
            20                  25
```

```
<210> SEQ ID NO 443
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 443

Arg Glu Pro Lys Lys Val Ala Val Val Ala Thr Pro Pro Lys Ser Pro
1               5                   10                  15

Ser Ser Ala Lys Ser Arg Leu Gln Thr
            20                  25

<210> SEQ ID NO 444
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (18)..(18)
<223> OTHER INFORMATION: PHOSPHORYLATION

<400> SEQUENCE: 444

Arg Glu Pro Lys Lys Val Ala Val Val Arg Ala Pro Pro Lys Ser Pro
1               5                   10                  15

Ser Ser Ala Lys Ser Arg Leu Gln Thr
            20                  25

<210> SEQ ID NO 445
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 445

Arg Glu Pro Lys Lys Val Ala Val Val Arg Thr Ala Pro Lys Ser Pro
1               5                   10                  15

Ser Ser Ala Lys Ser Arg Leu Gln Thr
            20                  25

<210> SEQ ID NO 446
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
```

```
<221> NAME/KEY: MOD_RES
<222> LOCATION: (18)..(18)
<223> OTHER INFORMATION: PHOSPHORYLATION

<400> SEQUENCE: 446

Arg Glu Pro Lys Lys Val Ala Val Val Arg Thr Pro Pro Lys Ser Ala
1               5                   10                  15

Ser Ser Ala Lys Ser Arg Leu Gln Thr
            20                  25

<210> SEQ ID NO 447
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 447

Arg Glu Pro Lys Lys Val Ala Val Val Arg Thr Pro Pro Ala Ser Pro
1               5                   10                  15

Ser Ser Ala Lys Ser Arg Leu Gln Thr
            20                  25

<210> SEQ ID NO 448
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 448

Arg Glu Pro Lys Lys Val Ala Val Val Arg Thr Pro Pro Lys Ala Pro
1               5                   10                  15

Ser Ser Ala Lys Ser Arg Leu Gln Thr
            20                  25

<210> SEQ ID NO 449
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 449

Arg Glu Pro Lys Lys Val Ala Val Val Arg Thr Pro Pro Lys Ser Ala
```

```
                1               5                      10                      15
Ser Ser Ala Lys Ser Arg Leu Gln Thr
                20                      25

<210> SEQ ID NO 450
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 450

Arg Glu Pro Lys Lys Val Ala Val Val Arg Thr Pro Pro Lys Ser Pro
1               5                      10                      15

Ala Ser Ala Lys Ser Arg Leu Gln Thr
                20                      25

<210> SEQ ID NO 451
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION

<400> SEQUENCE: 451

Arg Glu Pro Lys Lys Val Ala Val Val Arg Thr Pro Pro Lys Ser Pro
1               5                      10                      15

Ser Ala Ala Lys Ser Arg Leu Gln Thr
                20                      25

<210> SEQ ID NO 452
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 452

Arg Glu Pro Lys Lys Val Ala Val Val Arg Thr Pro Pro Lys Ser Pro
1               5                      10                      15

Ser Ser Ala Ala Ser Arg Leu Gln Thr
                20                      25

<210> SEQ ID NO 453
<211> LENGTH: 25
<212> TYPE: PRT
<213> ORGANISM: Artificial Sequence
<220> FEATURE:
```

<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 453

Arg Glu Pro Lys Lys Val Ala Val Val Arg Thr Pro Pro Lys Ser Pro
1               5                   10                  15

Ser Ser Ala Lys Ala Arg Leu Gln Thr
            20                  25

<210> SEQ ID NO 454
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 454

Arg Glu Pro Lys Lys Val Ala Val Val Arg Thr Pro Pro Lys Ser Pro
1               5                   10                  15

Ser Ser Ala Lys Ser Ala Leu Gln Thr
            20                  25

<210> SEQ ID NO 455
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 455

Arg Glu Pro Lys Lys Val Ala Val Val Arg Thr Pro Pro Lys Ser Pro
1               5                   10                  15

Ser Ser Ala Lys Ser Arg Ala Gln Thr
            20                  25

<210> SEQ ID NO 456
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES

```
<222> LOCATION: (18)..(18)
<223> OTHER INFORMATION: PHOSPHORYLATION

<400> SEQUENCE: 456

Arg Glu Pro Lys Lys Val Ala Val Val Arg Thr Pro Pro Lys Ser Pro
1               5                   10                  15

Ser Ser Ala Lys Ser Arg Leu Ala Thr
            20                  25

<210> SEQ ID NO 457
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (11)..(11)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 457

Arg Glu Pro Lys Lys Val Ala Val Val Arg Thr Pro Pro Lys Ser Pro
1               5                   10                  15

Ser Ser Ala Lys Ser Arg Leu Gln Ala
            20                  25

<210> SEQ ID NO 458
<211> LENGTH: 25
<212> TYPE: PRT
<213> ORGANISM: Artificial Sequence
<220> FEATURE:
<223> OTHER INFORMATION: synthetic construct

<400> SEQUENCE: 458

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 459
<211> LENGTH: 25
<212> TYPE: PRT
<213> ORGANISM: Artificial Sequence
<220> FEATURE:
<223> OTHER INFORMATION: synthetic construct

<400> SEQUENCE: 459

Ala Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 460
<211> LENGTH: 25
<212> TYPE: PRT
<213> ORGANISM: Artificial Sequence
<220> FEATURE:
<223> OTHER INFORMATION: synthetic construct

<400> SEQUENCE: 460

His Ala Pro Gly Gly Gly Ser Val Gln Ile Val Tyr Lys Pro Val Asp
1               5                   10                  15
```

Leu Ser Lys Val Thr Ser Lys Cys Gly
            20                  25

<210> SEQ ID NO 461
<211> LENGTH: 25
<212> TYPE: PRT
<213> ORGANISM: Artificial Sequence
<220> FEATURE:
<223> OTHER INFORMATION: synthetic construct

<400> SEQUENCE: 461

His Val Ala Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 462
<211> LENGTH: 25
<212> TYPE: PRT
<213> ORGANISM: Artificial Sequence
<220> FEATURE:
<223> OTHER INFORMATION: synthetic construct

<400> SEQUENCE: 462

His Val Pro Ala Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 463
<211> LENGTH: 25
<212> TYPE: PRT
<213> ORGANISM: Artificial Sequence
<220> FEATURE:
<223> OTHER INFORMATION: synthetic construct

<400> SEQUENCE: 463

His Val Pro Gly Ala Gly Ser Val Gln Ile Val Tyr Lys Pro Val Asp
1               5                   10                  15

Leu Ser Lys Val Thr Ser Lys Cys Gly
            20                  25

<210> SEQ ID NO 464
<211> LENGTH: 25
<212> TYPE: PRT
<213> ORGANISM: Artificial Sequence
<220> FEATURE:
<223> OTHER INFORMATION: synthetic construct

<400> SEQUENCE: 464

His Val Pro Gly Gly Ala Ser Val Gln Ile Val Tyr Lys Pro Val Asp
1               5                   10                  15

Leu Ser Lys Val Thr Ser Lys Cys Gly
            20                  25

<210> SEQ ID NO 465
<211> LENGTH: 25
<212> TYPE: PRT
<213> ORGANISM: Artificial Sequence
<220> FEATURE:
<223> OTHER INFORMATION: synthetic construct

<400> SEQUENCE: 465

His Val Pro Gly Gly Gly Ala Val Gln Ile Val Tyr Lys Pro Val Asp

```
                1               5                  10                  15
Leu Ser Lys Val Thr Ser Lys Cys Gly
            20              25

<210> SEQ ID NO 466
<211> LENGTH: 25
<212> TYPE: PRT
<213> ORGANISM: Artificial Sequence
<220> FEATURE:
<223> OTHER INFORMATION: synthetic construct

<400> SEQUENCE: 466

His Val Pro Gly Gly Gly Ser Ala Gln Ile Val Tyr Lys Pro Val Asp
1               5                  10                  15

Leu Ser Lys Val Thr Ser Lys Cys Gly
            20              25

<210> SEQ ID NO 467
<211> LENGTH: 25
<212> TYPE: PRT
<213> ORGANISM: Artificial Sequence
<220> FEATURE:
<223> OTHER INFORMATION: synthetic construct

<400> SEQUENCE: 467

His Val Pro Gly Gly Gly Ser Val Ala Ile Val Tyr Lys Pro Val Asp
1               5                  10                  15

Leu Ser Lys Val Thr Ser Lys Cys Gly
            20              25

<210> SEQ ID NO 468
<211> LENGTH: 25
<212> TYPE: PRT
<213> ORGANISM: Artificial Sequence
<220> FEATURE:
<223> OTHER INFORMATION: synthetic construct

<400> SEQUENCE: 468

His Val Pro Gly Gly Gly Ser Val Gln Ala Val Tyr Lys Pro Val Asp
1               5                  10                  15

Leu Ser Lys Val Thr Ser Lys Cys Gly
            20              25

<210> SEQ ID NO 469
<211> LENGTH: 25
<212> TYPE: PRT
<213> ORGANISM: Artificial Sequence
<220> FEATURE:
<223> OTHER INFORMATION: synthetic construct

<400> SEQUENCE: 469

His Val Pro Gly Gly Gly Ser Val Gln Ile Ala Tyr Lys Pro Val Asp
1               5                  10                  15

Leu Ser Lys Val Thr Ser Lys Cys Gly
            20              25

<210> SEQ ID NO 470
<211> LENGTH: 25
<212> TYPE: PRT
<213> ORGANISM: Artificial Sequence
<220> FEATURE:
<223> OTHER INFORMATION: synthetic construct

<400> SEQUENCE: 470
```

His Val Pro Gly Gly Gly Ser Val Gln Ile Val Ala Lys Pro Val Asp
1               5                   10                  15

Leu Ser Lys Val Thr Ser Lys Cys Gly
            20                  25

<210> SEQ ID NO 471
<211> LENGTH: 25
<212> TYPE: PRT
<213> ORGANISM: Artificial Sequence
<220> FEATURE:
<223> OTHER INFORMATION: synthetic construct

<400> SEQUENCE: 471

His Val Pro Gly Gly Gly Ser Val Gln Ile Val Tyr Ala Pro Val Asp
1               5                   10                  15

Leu Ser Lys Val Thr Ser Lys Cys Gly
            20                  25

<210> SEQ ID NO 472
<211> LENGTH: 25
<212> TYPE: PRT
<213> ORGANISM: Artificial Sequence
<220> FEATURE:
<223> OTHER INFORMATION: synthetic construct

<400> SEQUENCE: 472

His Val Pro Gly Gly Gly Ser Val Gln Ile Val Tyr Lys Ala Val Asp
1               5                   10                  15

Leu Ser Lys Val Thr Ser Lys Cys Gly
            20                  25

<210> SEQ ID NO 473
<211> LENGTH: 25
<212> TYPE: PRT
<213> ORGANISM: Artificial Sequence
<220> FEATURE:
<223> OTHER INFORMATION: synthetic construct

<400> SEQUENCE: 473

His Val Pro Gly Gly Gly Ser Val Gln Ile Val Tyr Lys Pro Ala Asp
1               5                   10                  15

Leu Ser Lys Val Thr Ser Lys Cys Gly
            20                  25

<210> SEQ ID NO 474
<211> LENGTH: 25
<212> TYPE: PRT
<213> ORGANISM: Artificial Sequence
<220> FEATURE:
<223> OTHER INFORMATION: synthetic construct

<400> SEQUENCE: 474

His Val Pro Gly Gly Gly Ser Val Gln Ile Val Tyr Lys Pro Val Ala
1               5                   10                  15

Leu Ser Lys Val Thr Ser Lys Cys Gly
            20                  25

<210> SEQ ID NO 475
<211> LENGTH: 25
<212> TYPE: PRT
<213> ORGANISM: Artificial Sequence
<220> FEATURE:
<223> OTHER INFORMATION: synthetic construct

<400> SEQUENCE: 475

```
His Val Pro Gly Gly Gly Ser Val Gln Ile Val Tyr Lys Pro Val Asp
1               5                   10                  15

Ala Ser Lys Val Thr Ser Lys Cys Gly
            20                  25

<210> SEQ ID NO 476
<211> LENGTH: 25
<212> TYPE: PRT
<213> ORGANISM: Artificial Sequence
<220> FEATURE:
<223> OTHER INFORMATION: synthetic construct

<400> SEQUENCE: 476

His Val Pro Gly Gly Gly Ser Val Gln Ile Val Tyr Lys Pro Val Asp
1               5                   10                  15

Leu Ala Lys Val Thr Ser Lys Cys Gly
            20                  25

<210> SEQ ID NO 477
<211> LENGTH: 25
<212> TYPE: PRT
<213> ORGANISM: Artificial Sequence
<220> FEATURE:
<223> OTHER INFORMATION: synthetic construct

<400> SEQUENCE: 477

His Val Pro Gly Gly Gly Ser Val Gln Ile Val Tyr Lys Pro Val Asp
1               5                   10                  15

Leu Ser Ala Val Thr Ser Lys Cys Gly
            20                  25

<210> SEQ ID NO 478
<211> LENGTH: 25
<212> TYPE: PRT
<213> ORGANISM: Artificial Sequence
<220> FEATURE:
<223> OTHER INFORMATION: synthetic construct

<400> SEQUENCE: 478

His Val Pro Gly Gly Gly Ser Val Gln Ile Val Tyr Lys Pro Val Asp
1               5                   10                  15

Leu Ser Lys Ala Thr Ser Lys Cys Gly
            20                  25

<210> SEQ ID NO 479
<211> LENGTH: 25
<212> TYPE: PRT
<213> ORGANISM: Artificial Sequence
<220> FEATURE:
<223> OTHER INFORMATION: synthetic construct

<400> SEQUENCE: 479

His Val Pro Gly Gly Gly Ser Val Gln Ile Val Tyr Lys Pro Val Asp
1               5                   10                  15

Leu Ser Lys Val Ala Ser Lys Cys Gly
            20                  25

<210> SEQ ID NO 480
<211> LENGTH: 25
<212> TYPE: PRT
<213> ORGANISM: Artificial Sequence
<220> FEATURE:
<223> OTHER INFORMATION: synthetic construct
```

-continued

```
<400> SEQUENCE: 480

His Val Pro Gly Gly Gly Ser Val Gln Ile Val Tyr Lys Pro Val Asp
1               5                   10                  15

Leu Ser Lys Val Thr Ala Lys Cys Gly
            20                  25

<210> SEQ ID NO 481
<211> LENGTH: 25
<212> TYPE: PRT
<213> ORGANISM: Artificial Sequence
<220> FEATURE:
<223> OTHER INFORMATION: synthetic construct

<400> SEQUENCE: 481

His Val Pro Gly Gly Gly Ser Val Gln Ile Val Tyr Lys Pro Val Asp
1               5                   10                  15

Leu Ser Lys Val Thr Ser Ala Cys Gly
            20                  25

<210> SEQ ID NO 482
<211> LENGTH: 25
<212> TYPE: PRT
<213> ORGANISM: Artificial Sequence
<220> FEATURE:
<223> OTHER INFORMATION: synthetic construct

<400> SEQUENCE: 482

His Val Pro Gly Gly Gly Ser Val Gln Ile Val Tyr Lys Pro Val Asp
1               5                   10                  15

Leu Ser Lys Val Thr Ser Lys Ala Gly
            20                  25

<210> SEQ ID NO 483
<211> LENGTH: 25
<212> TYPE: PRT
<213> ORGANISM: Artificial Sequence
<220> FEATURE:
<223> OTHER INFORMATION: synthetic construct

<400> SEQUENCE: 483

His Val Pro Gly Gly Gly Ser Val Gln Ile Val Tyr Lys Pro Val Asp
1               5                   10                  15

Leu Ser Lys Val Thr Ser Lys Cys Ala
            20                  25

<210> SEQ ID NO 484
<211> LENGTH: 20
<212> TYPE: PRT
<213> ORGANISM: Artificial Sequence
<220> FEATURE:
<223> OTHER INFORMATION: synthetic construct

<400> SEQUENCE: 484

Ala Glu Asp Gly Ser Glu Glu Pro Gly Ser Glu Thr Ser Asp Ala Lys
1               5                   10                  15

Ser Thr Pro Thr
            20

<210> SEQ ID NO 485
<211> LENGTH: 20
<212> TYPE: PRT
<213> ORGANISM: Artificial Sequence
<220> FEATURE:
<223> OTHER INFORMATION: synthetic construct
```

```
<400> SEQUENCE: 485

Thr Ala Asp Gly Ser Glu Glu Pro Gly Ser Glu Thr Ser Asp Ala Lys
1               5                   10                  15

Ser Thr Pro Thr
            20

<210> SEQ ID NO 486
<211> LENGTH: 20
<212> TYPE: PRT
<213> ORGANISM: Artificial Sequence
<220> FEATURE:
<223> OTHER INFORMATION: synthetic construct

<400> SEQUENCE: 486

Thr Glu Ala Gly Ser Glu Glu Pro Gly Ser Glu Thr Ser Asp Ala Lys
1               5                   10                  15

Ser Thr Pro Thr
            20

<210> SEQ ID NO 487
<211> LENGTH: 20
<212> TYPE: PRT
<213> ORGANISM: Artificial Sequence
<220> FEATURE:
<223> OTHER INFORMATION: synthetic construct

<400> SEQUENCE: 487

Thr Glu Asp Ala Ser Glu Glu Pro Gly Ser Glu Thr Ser Asp Ala Lys
1               5                   10                  15

Ser Thr Pro Thr
            20

<210> SEQ ID NO 488
<211> LENGTH: 20
<212> TYPE: PRT
<213> ORGANISM: Artificial Sequence
<220> FEATURE:
<223> OTHER INFORMATION: synthetic construct

<400> SEQUENCE: 488

Thr Glu Asp Gly Ala Glu Glu Pro Gly Ser Glu Thr Ser Asp Ala Lys
1               5                   10                  15

Ser Thr Pro Thr
            20

<210> SEQ ID NO 489
<211> LENGTH: 20
<212> TYPE: PRT
<213> ORGANISM: Artificial Sequence
<220> FEATURE:
<223> OTHER INFORMATION: synthetic construct

<400> SEQUENCE: 489

Thr Glu Asp Gly Ser Ala Glu Pro Gly Ser Glu Thr Ser Asp Ala Lys
1               5                   10                  15

Ser Thr Pro Thr
            20

<210> SEQ ID NO 490
<211> LENGTH: 20
<212> TYPE: PRT
<213> ORGANISM: Artificial Sequence
<220> FEATURE:
```

<223> OTHER INFORMATION: synthetic construct

<400> SEQUENCE: 490

Thr Glu Asp Gly Ser Glu Ala Pro Gly Ser Glu Ser Asp Ala Lys
1               5                   10                  15

Ser Thr Pro Thr
            20

<210> SEQ ID NO 491
<211> LENGTH: 20
<212> TYPE: PRT
<213> ORGANISM: Artificial Sequence
<220> FEATURE:
<223> OTHER INFORMATION: synthetic construct

<400> SEQUENCE: 491

Thr Glu Asp Gly Ser Glu Glu Ala Gly Ser Thr Ser Asp Ala Lys
1               5                   10                  15

Ser Thr Pro Thr
            20

<210> SEQ ID NO 492
<211> LENGTH: 20
<212> TYPE: PRT
<213> ORGANISM: Artificial Sequence
<220> FEATURE:
<223> OTHER INFORMATION: synthetic construct

<400> SEQUENCE: 492

Thr Glu Asp Gly Ser Glu Glu Pro Ala Ser Glu Thr Ser Asp Ala Lys
1               5                   10                  15

Ser Thr Pro Thr
            20

<210> SEQ ID NO 493
<211> LENGTH: 20
<212> TYPE: PRT
<213> ORGANISM: Artificial Sequence
<220> FEATURE:
<223> OTHER INFORMATION: synthetic construct

<400> SEQUENCE: 493

Thr Glu Asp Gly Ser Glu Glu Pro Gly Ala Glu Thr Ser Asp Ala Lys
1               5                   10                  15

Ser Thr Pro Thr
            20

<210> SEQ ID NO 494
<211> LENGTH: 20
<212> TYPE: PRT
<213> ORGANISM: Artificial Sequence
<220> FEATURE:
<223> OTHER INFORMATION: synthetic construct

<400> SEQUENCE: 494

Thr Glu Asp Gly Ser Glu Glu Pro Gly Ser Ala Thr Ser Asp Ala Lys
1               5                   10                  15

Ser Thr Pro Thr
            20

<210> SEQ ID NO 495
<211> LENGTH: 20
<212> TYPE: PRT
<213> ORGANISM: Artificial Sequence
<220> FEATURE:
<223> OTHER INFORMATION: synthetic construct

<400> SEQUENCE: 495

Thr Glu Asp Gly Ser Glu Glu Pro Gly Ser Glu Ala Ser Asp Ala Lys
1               5                   10                  15

Ser Thr Pro Thr
            20

<210> SEQ ID NO 496
<211> LENGTH: 20
<212> TYPE: PRT
<213> ORGANISM: Artificial Sequence
<220> FEATURE:
<223> OTHER INFORMATION: synthetic construct

<400> SEQUENCE: 496

Thr Glu Asp Gly Ser Glu Glu Pro Gly Ser Glu Thr Ala Asp Ala Lys
1               5                   10                  15

Ser Thr Pro Thr
            20

<210> SEQ ID NO 497
<211> LENGTH: 20
<212> TYPE: PRT
<213> ORGANISM: Artificial Sequence
<220> FEATURE:
<223> OTHER INFORMATION: synthetic construct

<400> SEQUENCE: 497

Thr Glu Asp Gly Ser Glu Glu Pro Gly Ser Glu Thr Ser Ala Ala Lys
1               5                   10                  15

Ser Thr Pro Thr
            20

<210> SEQ ID NO 498
<211> LENGTH: 20
<212> TYPE: PRT
<213> ORGANISM: Artificial Sequence
<220> FEATURE:
<223> OTHER INFORMATION: synthetic construct

<400> SEQUENCE: 498

Thr Glu Asp Gly Ser Glu Glu Pro Gly Ser Glu Thr Ser Asp Ala Ala
1               5                   10                  15

Ser Thr Pro Thr
            20

<210> SEQ ID NO 499
<211> LENGTH: 20
<212> TYPE: PRT
<213> ORGANISM: Artificial Sequence
<220> FEATURE:
<223> OTHER INFORMATION: synthetic construct

<400> SEQUENCE: 499

Thr Glu Asp Gly Ser Glu Glu Pro Gly Ser Glu Thr Ser Asp Ala Lys
1               5                   10                  15

Ala Thr Pro Thr
            20

<210> SEQ ID NO 500
<211> LENGTH: 20
<212> TYPE: PRT

```
<213> ORGANISM: Artificial Sequence
<220> FEATURE:
<223> OTHER INFORMATION: synthetic construct

<400> SEQUENCE: 500

Thr Glu Asp Gly Ser Glu Glu Pro Gly Ser Glu Thr Ser Asp Ala Lys
1               5                   10                  15

Ser Ala Pro Thr
            20

<210> SEQ ID NO 501
<211> LENGTH: 20
<212> TYPE: PRT
<213> ORGANISM: Artificial Sequence
<220> FEATURE:
<223> OTHER INFORMATION: synthetic construct

<400> SEQUENCE: 501

Thr Glu Asp Gly Ser Glu Glu Pro Gly Ser Glu Thr Ser Asp Ala Lys
1               5                   10                  15

Ser Thr Ala Thr
            20

<210> SEQ ID NO 502
<211> LENGTH: 20
<212> TYPE: PRT
<213> ORGANISM: Artificial Sequence
<220> FEATURE:
<223> OTHER INFORMATION: synthetic construct

<400> SEQUENCE: 502

Thr Glu Asp Gly Ser Glu Glu Pro Gly Ser Glu Thr Ser Asp Ala Lys
1               5                   10                  15

Ser Thr Pro Ala
            20

<210> SEQ ID NO 503
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION

<400> SEQUENCE: 503

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 504
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (12)..(12)
<223> OTHER INFORMATION: PHOSPHORYLATION

<400> SEQUENCE: 504

His Val Pro Gly Gly Gly Ser Val Gln Ile Val Tyr Lys Pro Val Asp
```

```
                1               5                   10                  15

Leu Ser Lys Val Thr Ser Lys Cys Gly
            20                  25

<210> SEQ ID NO 505
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (18)..(18)
<223> OTHER INFORMATION: PHOSPHORYLATION

<400> SEQUENCE: 505

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 506
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (21)..(21)
<223> OTHER INFORMATION: PHOSPHORYLATION

<400> SEQUENCE: 506

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 507
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (22)..(22)
<223> OTHER INFORMATION: PHOSPHORYLATION

<400> SEQUENCE: 507

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 508
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (12)..(12)
```

<223> OTHER INFORMATION: PHOSPHORYLATION

<400> SEQUENCE: 508

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 509
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 509

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 510
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION

<400> SEQUENCE: 510

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 511
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (7)..(7)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION

<400> SEQUENCE: 511

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 512
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (18)..(18)
<223> OTHER INFORMATION: PHOSPHORYLATION

<400> SEQUENCE: 512

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 513
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION

<400> SEQUENCE: 513

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 514
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION

<400> SEQUENCE: 514

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 515
<211> LENGTH: 25
<212> TYPE: PRT

<213> ORGANISM: Artificial Sequence
<220> FEATURE:
<223> OTHER INFORMATION: synthetic construct
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (21)..(21)
<223> OTHER INFORMATION: PHOSPHORYLATION

<400> SEQUENCE: 515

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 516
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION

<400> SEQUENCE: 516

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 517
<211> LENGTH: 25
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (21)..(21)
<223> OTHER INFORMATION: PHOSPHORYLATION
<220> FEATURE:
<221> NAME/KEY: MOD_RES
<222> LOCATION: (22)..(22)
<223> OTHER INFORMATION: PHOSPHORYLATION

<400> SEQUENCE: 517

His Val Pro Gly Gly Gly Ser Val Gln Ile Val Tyr Lys Pro Val Asp
1               5                   10                  15

Leu Ser Lys Val Thr Ser Lys Cys Gly
            20                  25

<210> SEQ ID NO 518
<211> LENGTH: 24
<212> TYPE: PRT
<213> ORGANISM: Artificial Sequence
<220> FEATURE:
<223> OTHER INFORMATION: synthetic construct

<400> SEQUENCE: 518

Leu Gln Thr Pro Thr Glu Asp Gly Ser Glu Glu Pro Gly Ser Glu Thr

```
1               5                   10                  15

Ser Asp Ala Lys Ser Thr Pro Thr
            20

<210> SEQ ID NO 519
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (24)..(24)
<223> OTHER INFORMATION: PHOSPHORYLATION

<400> SEQUENCE: 519

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 520
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION

<400> SEQUENCE: 520

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 521
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: PHOSPHORYLATION

<400> SEQUENCE: 521

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 522
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (9)..(9)
<223> OTHER INFORMATION: PHOSPHORYLATION

<400> SEQUENCE: 522
```

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 523
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: PHOSPHORYLATION

<400> SEQUENCE: 523

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 524
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (21)..(21)
<223> OTHER INFORMATION: PHOSPHORYLATION

<400> SEQUENCE: 524

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 525
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (22)..(22)
<223> OTHER INFORMATION: PHOSPHORYLATION

<400> SEQUENCE: 525

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 526
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (17)..(17)
<223> OTHER INFORMATION: PHOSPHORYLATION

<400> SEQUENCE: 526

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 527
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 527

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 528
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 528

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 529
<211> LENGTH: 24
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (17)..(17)
<223> OTHER INFORMATION: PHOSPHORYLATION

<400> SEQUENCE: 529

Leu Gln Thr Pro Thr Glu Asp Gly Ser Glu Glu Pro Gly Ser Glu Thr
1               5                   10                  15

Ser Asp Ala Lys Ser Thr Pro Thr
            20

<210> SEQ ID NO 530
<211> LENGTH: 23
<212> TYPE: DNA
<213> ORGANISM: Artificial Sequence
<220> FEATURE:
<223> OTHER INFORMATION: synthetic construct

<400> SEQUENCE: 530
tctccgccgg tgagtctcga ggc                                          23

<210> SEQ ID NO 531
<211> LENGTH: 26
<212> TYPE: DNA
<213> ORGANISM: Artificial Sequence
<220> FEATURE:
<223> OTHER INFORMATION: synthetic construct

<400> SEQUENCE: 531
tgtccctgga tgcaggctac tctagg                                       26

<210> SEQ ID NO 532
<211> LENGTH: 24
<212> TYPE: DNA
<213> ORGANISM: Artificial Sequence
<220> FEATURE:
<223> OTHER INFORMATION: synthetic construct

<400> SEQUENCE: 532
agagtagcct gcatccaggg acag                                         24

<210> SEQ ID NO 533
<211> LENGTH: 30
<212> TYPE: DNA
<213> ORGANISM: Artificial Sequence
<220> FEATURE:
<223> OTHER INFORMATION: synthetic construct

<400> SEQUENCE: 533
tctagatcat ttaccaggag agtgggagag                                   30

<210> SEQ ID NO 534
<211> LENGTH: 34
<212> TYPE: DNA
<213> ORGANISM: Artificial Sequence
<220> FEATURE:
<223> OTHER INFORMATION: synthetic construct

<400> SEQUENCE: 534
tctcctggta aatgatctag agtttaaacc gctg                              34

<210> SEQ ID NO 535
<211> LENGTH: 25
<212> TYPE: PRT
<213> ORGANISM: Artificial Sequence
<220> FEATURE:
<223> OTHER INFORMATION: synthetic construct

<400> SEQUENCE: 535

Ala Thr Gly Gly Cys Cys Cys Ala Cys Thr Ala Cys Gly Thr Gly Ala
1               5                   10                  15

Ala Cys Cys Ala Thr Cys Ala Cys Cys
            20                  25